(12) United States Patent
Petaipimol et al.

(10) Patent No.: US 12,150,991 B2
(45) Date of Patent: Nov. 26, 2024

(54) PHARMACEUTICAL COMPOSITIONS COMPRISING ANTI-HUMAN TSLP RECEPTOR ANTIBODIES AND METHODS OF USING THE SAME

(71) Applicant: UPSTREAM BIO, INC., Waltham, MA (US)

(72) Inventors: Parika Petaipimol, Waltham, MA (US); Robert Patrick Gearing, Waltham, MA (US); Bingquan Wang, Boston, MA (US); Geng Li, Shanghai (CN); Jeremy Guo, Palo Alto, CA (US)

(73) Assignee: UPSTREAM BIO, INC., Waltham, MA (US)

( * ) Notice: Subject to any disclaimer, the term of this patent is extended or adjusted under 35 U.S.C. 154(b) by 0 days.

(21) Appl. No.: 18/503,245

(22) Filed: Nov. 7, 2023

(65) Prior Publication Data
US 2024/0173405 A1    May 30, 2024

Related U.S. Application Data

(63) Continuation-in-part of application No. PCT/CN2022/130252, filed on Nov. 7, 2022.

(60) Provisional application No. 63/591,238, filed on Oct. 18, 2023, provisional application No. 63/508,564, filed on Jun. 16, 2023.

(51) Int. Cl.
| | | |
|---|---|---|
| *A61K 39/395* | (2006.01) | |
| *A61K 47/18* | (2017.01) | |
| *A61K 47/22* | (2006.01) | |
| *A61P 11/06* | (2006.01) | |
| *A61P 37/08* | (2006.01) | |
| *C07K 16/28* | (2006.01) | |
| *A61K 39/00* | (2006.01) | |

(52) U.S. Cl.
CPC ...... *A61K 39/39591* (2013.01); *A61K 47/183* (2013.01); *A61K 47/22* (2013.01); *A61P 11/06* (2018.01); *A61P 37/08* (2018.01); *C07K 16/2866* (2013.01); *A61K 2039/505* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,731,953 B2 | 6/2010 | Leonard et al. | |
| 8,344,110 B2 | 1/2013 | Saris et al. | |
| 8,758,747 B2 | 6/2014 | Kallmeyer et al. | |
| 9,328,171 B2 | 5/2016 | Sato et al. | |
| 9,908,941 B2 | 3/2018 | Sato et al. | |
| 10,994,011 B2 | 5/2021 | Ikeda et al. | |
| 11,712,472 B2* | 8/2023 | Ikeda | A61K 47/12 424/133.1 |
| 2003/0180287 A1 | 9/2003 | Gombotz et al. | |
| 2007/0172475 A1 | 7/2007 | Matheus et al. | |
| 2007/0243185 A1 | 10/2007 | Gombotz et al. | |
| 2008/0286280 A1 | 11/2008 | Kallmeyer et al. | |
| 2009/0074747 A1 | 3/2009 | Dong et al. | |
| 2009/0286312 A1 | 11/2009 | Dong et al. | |
| 2010/0086559 A1 | 4/2010 | Gombotz et al. | |
| 2010/0285011 A1 | 11/2010 | Morichika et al. | |
| 2011/0020369 A1 | 1/2011 | De Waal Malefyt et al. | |
| 2012/0020960 A1 | 1/2012 | Palucka et al. | |
| 2012/0020988 A1 | 1/2012 | Auer et al. | |
| 2012/0027756 A1 | 2/2012 | Dong et al. | |
| 2012/0148587 A1 | 6/2012 | Gombotz et al. | |
| 2013/0344088 A1 | 12/2013 | Cosenza et al. | |
| 2014/0248274 A1 | 9/2014 | Kallmeyer et al. | |
| 2014/0377264 A1 | 12/2014 | Gombotz et al. | |
| 2016/0046720 A1* | 2/2016 | Sato | A61P 11/06 435/69.6 |
| 2016/0208005 A1 | 7/2016 | Sato et al. | |
| 2017/0051039 A1 | 2/2017 | Gombotz et al. | |
| 2019/0111129 A1* | 4/2019 | Ikeda | A61K 9/0019 |
| 2019/0144523 A1 | 5/2019 | Gombotz et al. | |
| 2020/0147213 A1 | 5/2020 | Sharma et al. | |
| 2022/0023422 A1 | 1/2022 | Ikeda et al. | |

FOREIGN PATENT DOCUMENTS

| | | |
|---|---|---|
| CN | 102159204 A | 8/2011 |
| CN | 108430507 A | 8/2018 |
| CN | 112292146 A | 1/2021 |
| EP | 2238985 A1 | 10/2010 |
| JP | 2007522157 A | 8/2007 |
| JP | 2009523426 A | 6/2009 |
| JP | 2010530233 A | 9/2010 |
| JP | 2011511638 A | 4/2011 |

(Continued)

OTHER PUBLICATIONS

Almagro et al., Front. Immunol., 8:1751, doi: 10.3389/fimmu.2017.01751 (Year: 2018).*

(Continued)

*Primary Examiner* — Jessica H Roark
(74) *Attorney, Agent, or Firm* — Goodwin Procter LLP

(57) ABSTRACT

Pharmaceutical compositions of anti-TSLP-R antibodies, and uses thereof, are provided herein. The pharmaceutical compositions can comprise for example, an anti-TSLP-R antibody, or antigen-binding fragment thereof, a pharmaceutically acceptable buffer, an excipient, and a surfactant, or other compositions as provided for herein.

18 Claims, 18 Drawing Sheets

Specification includes a Sequence Listing.

(56) References Cited

FOREIGN PATENT DOCUMENTS

| | | | |
|---|---|---|---|
| JP | 2015521593 A | 7/2015 |
| KR | 10-2009-0009204 A | 1/2009 |
| RU | 2390353 C2 | 5/2010 |
| RU | 2497544 C2 | 11/2013 |
| TW | 201536806 A | 10/2015 |
| WO | 2003072060 A2 | 9/2003 |
| WO | 2004091658 A1 | 10/2004 |
| WO | 2007112146 A2 | 10/2007 |
| WO | 2008155365 A1 | 12/2008 |
| WO | 2009084659 A1 | 7/2009 |
| WO | 2009100324 A1 | 8/2009 |
| WO | 2010032220 A1 | 3/2010 |
| WO | 2010106812 A1 | 9/2010 |
| WO | 2012007495 A1 | 1/2012 |
| WO | 2012151199 A1 | 11/2012 |
| WO | 2013186700 A1 | 12/2013 |
| WO | 2014031718 A1 | 2/2014 |
| WO | 2014068021 A1 | 5/2014 |
| WO | 2014143909 A1 | 9/2014 |
| WO | 2015020193 A1 | 2/2015 |
| WO | 2017104778 A1 | 6/2017 |
| WO | 2018193471 A1 | 10/2018 |
| WO | 2019198100 A1 | 10/2019 |
| WO | 2019198101 A1 | 10/2019 |

OTHER PUBLICATIONS

International Search Report and Written Opinion for PCT/CN2022/130252 dated Jul. 21, 2023.
Arakwaka, "Role of Arginine in Development of Biopharmaceuticals," Yakagaku Zasshi, The Pharmaceutical Society of Japan, 2010, vol. 130, No. 6, pp. 793-800.
Daugherty et al., "Formulating and Delivery Issues for Monoclonal Antibody Therapeutics," AdvDrug Deliv. Rev. (May 22, 2006) vol. 58, No. 5-6, pp. 668-706.
Donavan T. Cheng et al., "Thymic Stromal Lymphopoietin Receptor Blockade Reduces Allergic Inflammation in a Cynomolgus Monkey Model of Asthma," J Allergy Clin Immunol, Aug. 2013, pp. 455-462.
International Preliminary Report on Patentability for PCT/JP2014/071008 dated Feb. 9, 2016, 10 pages.
International Preliminary Report on Patentability for PCT/JP2016/087480 dated Jun. 19, 2018, 16 pages.
International Search Report and Written Opinion for PCT/US2023/078873 dated Apr. 9, 2024.
International Search Report and Written Opinion issued for PCT/JP2014/071008, mailed on Oct. 28, 2014, 8 pgs.
International Search Report and Written Opinion issued Feb. 21, 2017, in PCT/JP2016/087480 filed Dec. 16, 2016.
Jorgensen et al., "Recent Trends in Stabilising Peptides and Proteins in Pharmaceutical Formulation—Considerations in the Choice of Excipients," Expert Opinion on Drug Delivery (2009) vol. 6, No. 11, pp. 1219-1230.
Wang et al., "Antibody Structure, Instability, and Formulation," Journal of Pharmaceutical Sciences (Jan. 2007); vol. 98, No. 1, p. 1-26.

* cited by examiner

\* = therapeutic threshold (0.3 µg/mL TRAB-1)

- ••• = 1.0 μg/ml-Conservative estimate based half-log increase from pre-clinical data
- $IC_{90}$ = 0.300 μg/ml- $IC_{90}$ from pre-clinical data
- $EC_{90}$ = 0.139 μg/ml-$EC_{90}$ FeNO from MAD
- $EC_{80}$ = 0.062 μg/ml-$EC_{80}$ FeNO from MAD
- $EC_{50}$ = 0.015 μg/ml-$EC_{50}$ FeNO from MAD 20 mg Q12W maintains exposure above $EC_{50}$ through dosing interval 100 mg Q12W maintains exposure above $EC_{90}$ through dosing interval

```
···  =  1.0 µg/ml-Conservative estimate based
         half-log increase from pre-clinical data
IC₉₀ = 0.300 µg/ml- IC₉₀ from pre-clinical data
EC₉₀ = 0.139 µg/ml-EC₉₀ FeNO from MAD
EC₈₀ = 0.062 µg/ml-EC₈₀ FeNO from MAD
EC₅₀ = 0.015 µg/ml-EC₅₀ FeNO from MAD
```

400 mg Q24W maintains exposure above EC₈₀ through dosing interval

PHARMACEUTICAL COMPOSITIONS COMPRISING ANTI-HUMAN TSLP RECEPTOR ANTIBODIES AND METHODS OF USING THE SAME

CROSS-REFERENCE TO RELATED APPLICATIONS

This application is a continuation-in-part of, and claims priority to PCT Application No. PCT/CN2022/130252, filed Nov. 7, 2022, and this application claims priority to U.S. Provisional Application No. 63/508,564, filed Jun. 16, 2023 and U.S. 63/591,238, filed Oct. 18, 2023, each of which is hereby incorporated by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Nov. 3, 2023, is named "UPS-003WO2_SL.XML" and is 14,288 bytes in size.

FIELD

The embodiments provided herein relate to antibodies, and fragments thereof, that bind to the thymic stromal lymphopoietin receptor (TSLP-R), and pharmaceutical compositions comprising the same.

BACKGROUND

Thymic stromal lymphopoietin (TSLP) is a cytokine derived from epithelium cells that is produced in response to pro-inflammatory stimuli, and it is involved in dendritic cell mediated Th2 cell activation and interacts with the TSLP receptor (TSLP-R). It has been reported that TSLP-mediated activation of the dendritic cells through the TSLP-R is involved in various disease pathologies, including allergic inflammation and chronic obstructive pulmonary disease, autoimmune diseases and rheumatic diseases, cancer, coronary artery disease, and myocardial infarction. Accordingly, a monoclonal antibody that specifically binds to human TSLP-R and inhibits the action of human TSLP through human TSLP-R is useful for preventing and treating various diseases in which human TSLP and human TSLP-R are involved in the disease pathology. A need exists for improved formulations of pharmaceutical compositions that contain antibodies, and fragments thereof, that are specific for TSLP-R. A need also exists for methods of treating TSLP mediated pathologies using pharmaceutical compositions that contain antibodies, and fragments thereof, that are specific for TSLP-R. The present embodiments address these need as well as others.

SUMMARY

The disclosed embodiments are directed towards antibodies, or antibody fragments thereof, that specifically bind to TSLP-R, and pharmaceutical compositions that contain antibodies, and fragments thereof, that are specific for TSLP-R.

Embodiments provided herein are directed to pharmaceutical compositions comprising anti-TSLP-R antibodies, or antigen-binding fragments thereof. In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) an excipient at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) glycine, or a pharmaceutically acceptable salt thereof, at a concentration of about 100 mmol/L to about 200 mmol/L; and (iv) polysorbate 80 at a concentration of about 0.01% to about 0.2% (w/v).

In some embodiments, the pharmaceutical composition comprises: (i) an anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) arginine, or a pharmaceutically acceptable salt thereof, at a concentration of about 100 mmol/L to about 150 mmol/L; and (iv) polysorbate 80 at a concentration of about 0.01% to about 0.2% (w/v).

In some embodiments, the pharmaceutical composition comprises: (i) anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) proline, or a pharmaceutically acceptable salt thereof, at a concentration of about 100 mmol/L to about 220 mmol/L; and (iv) polysorbate 80 at a concentration of about 0.01% to about 0.2% (w/v).

In some embodiments, the pharmaceutical composition comprises: (i) anti-TSLP-R antibody, or antigen-binding fragment thereof, at a concentration of about 180 mg/mL to about 220 mg/mL; (ii) histidine buffer at a concentration of about 18 mmol/L to about 22 mmol/L; (iii) glycine, or a pharmaceutically acceptable salt thereof, at a concentration of about 160 mmol/L to about 200 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) glycine, or a pharmaceutically acceptable salt thereof, at a concentration of about 160 mmol/L to about 200 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 180 mg/mL to about 220 mg/mL; (ii) histidine buffer at a concentration of about 18 mmol/L to about 22 mmol/L; (iii) arginine, or a pharmaceutically acceptable salt thereof, at a concentration of about 105 mmol/L to 135 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) arginine, or a pharmaceutically acceptable salt thereof, at a concentration of about 105 mmol/L to 135 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 180 mg/mL to about 220 mg/mL; (ii) histidine buffer at a concentration of about 18 mmol/L to about 22 mmol/L; (iii) proline, or a pharmaceutically acceptable salt thereof, at a concentration of about 160 mmol/L to about 200 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) proline, or a pharmaceutically acceptable salt thereof, at a concentration of about 160 mmol/L to about 200 mmol/L; (iv) polysorbate 80 at a concentration of about 0.01% to about 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 130 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 200 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; and optionally:
(ii) a pharmaceutically acceptable buffer at a concentration of about 5 mmol/L to about 100 mmol/L; (iii) an excipient at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, a pharmaceutical dosage form of the pharmaceutical composition is provided herein. In some embodiments, the pharmaceutical dosage form comprises the pharmaceutical composition in a container.

In some embodiments, a kit is provided herein. In some embodiments, the kit comprises the pharmaceutical composition as disclosed herein and instructions for use. In some embodiments, the kit additionally comprises a pharmaceutical dosage form of the pharmaceutical composition, wherein the pharmaceutical dosage form comprises the pharmaceutical composition in a container. In some embodiments, the container is a pre-filled syringe, a plastic vial, or a glass vial.

In some embodiments, a method of treating a disease in a subject in need thereof is provided. In some embodiments, the method comprises administering a therapeutically effective amount of the pharmaceutical composition or the pharmaceutical dosage form of the pharmaceutical composition as disclosed herein.

In some embodiments, a method of treating and reducing the severity of a disease in a subject in need thereof is provided. In some embodiments, the method comprises administering a therapeutically effective amount of the pharmaceutical composition or the pharmaceutical dosage form of the pharmaceutical composition.

In some embodiments, a method of delaying the onset of a disease in a subject in need thereof is provided. In some embodiments, the method comprises administering a therapeutically effective amount of the pharmaceutical composition or the pharmaceutical dosage form of the pharmaceutical composition.

In some embodiments, a method of preventing a disease in a subject in need thereof is provided. In some embodiments, the method comprises administering a therapeutically effective amount of the pharmaceutical composition or the pharmaceutical dosage form of the pharmaceutical composition.

In some embodiments, a method of increasing the internalization of TSLP-R on a cell is provided. In some embodiments, the method comprises contacting the cell with the pharmaceutical composition or the pharmaceutical dosage form of the pharmaceutical composition.

In some embodiments, a method of inhibiting TSLP-R on a cell is provided. In some embodiments, the method comprises contacting the cell with the pharmaceutical composition or the pharmaceutical dosage form of the pharmaceutical composition.

In some embodiments, a method of inhibiting TSLP-R by at least 95%, 96%, 97%, 98%, or 99% or by 100% in a subject in need thereof is provided. In some embodiments, the method comprises administering the pharmaceutical composition or the pharmaceutical dosage form of the pharmaceutical composition.

BRIEF DESCRIPTION OF THE DRAWINGS

FIG. 1A: Chart depicting cell proliferation rates in Ba/F3 cells transfected with human TSLP-R/IL-7Rα and treated with either TRAB-1 antibody, tezepelumab antibody, or IgG antibody, plotted as a function of the concentration of the antibody concentration. FIG. 1B: Bar graph depicting CCL17 (ng/mL) production in dendritic cells treated with TRAB-1 antibody, tezepelumab antibody, or IgG antibody, plotted as a function of the concentration of the antibody concentration.

FIG. 2A: Graph depicting mean serum concentration over time, as a function of dose and route of administration of TRAB-1. IV=intravenous; SC=subcutaneous. FIG. 2B: Graph depicting predicted mean serum concentration of TRAB-1 over time, as a function of dose of TRAB-1 administered subcutaneously every 4 weeks. FIG. 2C: Graph depicting predicted mean serum concentration of TRAB-1 over time, as a function of dose of TRAB-1 administered subcutaneously every 12 weeks.

FIG. 3A: Graph depicting eosinophil concentrations in healthy volunteers treated with greater than or equal to 20 mg (0.3 mg/kg) of TRAB-1, as a function of time. Groups were selected based on eosinophil concentrations at day 0: <150 cells/µL; and >150 cells/11E FIG. 3B: Graph depicting eosinophil concentrations in healthy volunteers treated with greater than or equal to 20 mg (0.3 mg/kg) of TRAB-1, as a function of time, compared to the placebo group. Groups were selected based on eosinophil concentrations at day 0: <150 cells/µL (n=17); 150-200 cells/µL (n=3); 200-300 cells/µL (n=5); and >300 cell/µL (n=5).

FIG. 4A: Pharmacokinetics curves depicting serum mean TRAB-1 as a function of time in healthy volunteers treated with 2 mg, 7 mg, 20 mg, 70 mg, 210 mg, or 700 mg of TRAB-1. FIG. 4B: Pharmacodynamics curves depicting eosinophils as a function of time in healthy volunteers treated with 2 mg and 7 mg, or 20 mg and 70 mg of TRAB-1.

FIG. 7A: Graph depicting mean blood eosinophil concentration (cells/µL) over time. Error bars represent the standard error of the mean. FIG. 7B: Graph depicting changes in mean blood eosinophil concentrations (cells/µL), compared to baseline levels, over time. Error bars represent the standard error of the mean. The dashed line represents the known maximum therapeutic response for tezepelumab (Ly et al., J Clin Pharm 2021). FIG. 7C: Graph depicting percent change in mean blood eosinophil concentrations, compared to baseline levels, over time. Error bars represent the standard error of the mean. The dashed line represents the known maximum therapeutic response for tezepelumab (Ly et al., J Clin Pharm 2021).

FIG. 8A: Graph depicting mean FeNO (ppb) over time. Error bars represent the standard error of the mean. FIG. 8B: Graph depicting changes in mean FeNO (ppb), compared to baseline levels, over time. Error bars represent the standard error of the mean. The dashed line represents the known maximum therapeutic response for tezepelumab (Ly et al., J Clin Pharm 2021. Jul.; 61(7):901-912). FIG. 8C: Graph depicting percent change in mean FeNO, compared to baseline levels, over time, for Group 1, Group 2, Group 3, and Group 4. Error bars represent the standard error of the mean. The dashed line represents the known maximum therapeutic response for tezepelumab (Ly et al., J Clin Pharm 2021. Jul.; 61(7):901-912). FIG. 8D: Graph depicting percent change in mean FeNO, compared to baseline levels, over time, for Group 1 and Group 4. Error bars represent the standard error of the mean.

FIG. 9A: Pharmacokinetic/pharmacodynamic models are depicted for TRAB-1 serum concentration in patients treated with 25 mg or 100 mg of TRAB-1 every 12 weeks (FIG. 9A) or 400 mg of TRAB-1 every 24 weeks (FIG. 9B). The threshold concentrations of TRAB-1 needed for a 50% response (EC50), 80% response (EC80), and 90% response (EC90) on FeNO, based on the MAD study, are marked. The IC90 value representing the predicted trough concentration based on the SAD study of approximately 0.3 µg/mL is additionally marked.

DETAILED DESCRIPTION

Figure 1A:
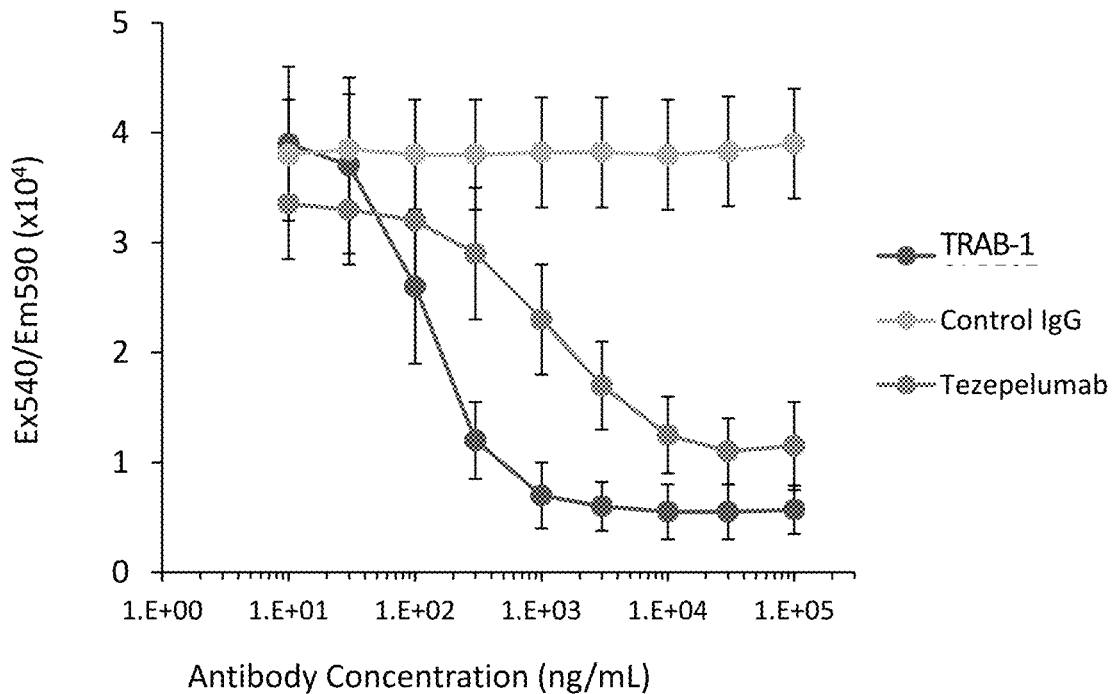
FIGS. 1A-1B: Data depicting that TRAB-1 produces potent suppression of TSLP/TSLP-R-mediated responses in vitro.

Provided herein are antibodies, or antigen-binding fragments thereof, that bind and modulate the activity of TSLP-R.

It is to be understood that the embodiments described herein are not limited to particular formulations, compositions and experimental conditions disclosed, as such formulations, compositions, and experimental conditions may vary. It is also to be understood that the terminology used herein is only for the purpose of describing particular embodiments, and it is not intended to be limiting.

Furthermore, the formulations, compositions, and experimental conditions described herein, unless otherwise indicated, use conventional molecular and cellular biological and immunological techniques known within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Unless defined otherwise, all technical and scientific terms have the same meaning as it is commonly understood by one of ordinary skill in the art to which the embodiments disclosed belong. Certain terms are discussed below, or elsewhere in the specification, to provide additional guidance to the practitioner in describing the methods of the disclosure and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in the specification, including examples of any terms discussed herein, is illustrative only, and in no way limits the scope and meaning of the disclosure or any exemplified term. Likewise, the disclosure is not limited to its preferred embodiments.

Unless otherwise required by context, singular terms shall include pluralities, and plural terms shall include the singular.

That the disclosure may be more readily understood, select terms are defined.

The articles "a," "an," and "the" are used herein to refer to one or to more than one (i.e., to at least one) of the grammatical object of the article. By way of example, "an animal" means one animal or more than one animal.

As used herein, the adverbs "about" or "approximately" mean that the numerical value is approximate and small variations would not significantly affect the practice of the disclosed embodiments. Where a numerical limitation is used, unless indicated otherwise by the context, "about" means the numerical value can vary by ±5% and remain within the scope of the disclosed embodiments. Thus, about 100 means 95 to 105.

As used herein, the irregular verb "has" and its conjugates, and the verbs "comprise," "include," "contain" and their conjugates, mean "including but not limited to." As used herein, the term "including but not limited to" is inclusive or open-ended and does not exclude additional, unrecited elements or method steps. While various compositions, and methods are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized antibodies, fully human antibodies, chimeric antibodies, and camelized single domain antibodies. Another word for antibody is "immunoglobulin." An antibody can immunospecifically bind to one or more epitope or antigen-binding site. As used herein, the assignment of amino acids to each domain within an antibody is in accordance with the Kabat numbering system.

As used herein, unless otherwise indicated, "antibody fragment" or "antigen-binding fragment" refers to antigen-binding fragments of antibodies, i.e., antibody fragments that retain the ability to bind specifically to the antigen bound by the full-length antibody, e.g., fragments that retain one or more CDR regions. Examples of antibody binding fragments include, but are not limited to, Fab, Fab', F(ab')2, and Fv fragments; diabodies; linear antibodies; single-chain antibody molecules, e.g., sc-Fv; nanobodies and multispecific antibody fragments.

The term "antigen" as used herein means any molecule that has the ability to generate antibodies either directly or indirectly. An "antigen" can also refer to the binding partner of an antibody, or fragment thereof. Included within the definition of "antigen" is a protein-encoding nucleic acid.

The terms "epitope" and "antigen-binding site" are meant to refer to that portion of any molecule capable of being recognized by and bound by an antibody, or fragment thereof, at one or more of the Ab's antigen-binding regions. Epitopes usually consist of chemically active surface groupings of molecules such as amino acids or sugar side chains and have specific three-dimensional structural characteristics as well as specific charge characteristics. Examples of epitopes include, but are not limited to, the residues described herein that form TSLP-R epitopes.

As used herein, the terms "specific binding," "immunospecific binding," "binds immune-specifically," and the like are used interchangeably to refer to an antibody, or fragment thereof, binding to a predetermined antigen (e.g., TSLP-R) or epitope present on the antigen. The extent of specific binding between an antibody, or fragment thereof, and its antigen can be quantified by a dissociation constant (KD), which is an equilibrium constant that measures the propensity of a complex to dissociate into smaller components. A typical KD for an antibody bound to an antigen is between about 10-9 M and about 10-6 M or less. An antibody can be defined as "specific for" a predetermined antigen if the KD between said antibody and said predetermined antigen is at least two-fold the KD between said antibody to a non-specific antigen (e.g., BSA, casein, or another non-specific polypeptide). If the KD between an antibody and a predetermined antigen is at about 10-9 M or greater, then the antibody can be said to have "high specific binding" the predetermined antigen. Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which are herein incorporated by reference in their entirety entirely.

The terms "purified" or "isolated" means altered or removed from the natural state. When in reference to an antibody, or fragment thereof, the terms refer to an antibody, or fragment thereof, that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80% to 90% (w/w) pure, at least 90% to 95% pure (w/w), at least 95% pure (w/w), at least 96% pure (w/w), at least 97% pure (w/w), at least 98% pure (w/w), at least 99% pure (w/w), or 100% (w/w) pure.

As used herein, the term "encoding" refers to the inherent property of specific sequences of nucleotides in a polynucleotide, such as a gene, a cDNA, or an mRNA or viral RNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "homolog" means protein sequences having between 40% and 100% sequence homology or identity to a reference sequence. Percent identity between two peptide chains can be determined by pair wise alignment using the default settings of the AlignX module of Vector NTI v.9.0.0 (Invitrogen Corp., Carslbad, Calif.).

Anti-TSLP-R Antibodies

Reference in the present disclosure may be made to TSLP and the TSLP-R. An alternative name for the TSLP-R is cytokine receptor like factor 2 (CRLF2).

TSLP is a cytokine produced in and secreted from epithelium cells in response to pro-inflammatory stimuli. Without wishing to be bound to a particular theory, TSLP enhances the allergic inflammatory response through the activation of dendritic cells and mast cells. TSLP activates dendritic cells by binding to TSLP-R/IL7R-α heterodimers composed of one TSLP-R and one IL-7 receptor α-chain (IL7R-α). The dendritic cells activated by TSLP express inflammatory cytokines that induce the differentiation of naive T cells into Th2 cells and additionally attract Th2 cells to inflammation sites (Nat. Immunol., 2002, Vol. 7, p. 673 to 680; Int. Immunol., 1999, Vol. 11, p. 81 to 88). The inflammatory responses mediated by TSLP-activated dendritic cells are reported to be involved with multiple disease pathologies, including allergic inflammatory diseases such as asthma and systemic sclerosis (Nat. Immunol., 2005, Vol. 6, p. 1047 to 1053). Loss of TSLP-R has been associated with suppression of Th2 cytokines and suppression of IgE production in the blood in a TSLP-R knockout mouse model, and the usage of anti-TSLP-R antibodies in a mouse model of asthma has additionally been associated with improvement of respiratory function (J. Exp. Med., 2005, Vol. 202, p. 829 to 839, and Clin. Immunol., 2008, Vol. 129. p. 202 to 210). Accordingly, antibodies, and antibody fragments thereof, that specifically bind to and inhibit TSLP-R are hypothesized to be useful for preventing and treating various diseases in which TSLP and TSLP-R are involved in disease pathology.

In general, the basic antibody structural unit comprises a tetramer. Each tetramer includes two identical pairs of polypeptide chains, each pair having one "light" (about 25 kDa) and one "heavy" chain (about 50-70 kDa).

Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively.

The amino-terminal portion of each chain includes a variable region of about 100 to 110 or more amino acids that is primarily responsible for antigen recognition. The variable regions of a light chain and a heavy chain are abbreviated as $V_L$ and $V_H$, respectively.

The variable regions of each chain are followed by one or more constant region of about 100 to 110 or more amino acids per constant region. The constant regions are identical in all antibodies, or antigen-binding fragments thereof, of the same isotype, but differ between different isotypes. The light chain contains one constant region, which is abbreviated as $C_L$. Heavy chains contain multiple constant regions that can be abbreviated as $C_H1$, $C_H2$, $C_H3$, etc. The carboxy-terminal portion of the heavy chain may define a constant region primarily responsible for effector function.

Within light and heavy chains, the variable and constant regions are joined by a "J" region of about 12 or more amino acids, with the heavy chain also including a "D" region of about ten more amino acids. See generally, Fundamental Immunology Ch. 7 (Paul, W., ed., 2nd ed. Raven Press, N.Y. (1989).

The variable regions of each light/heavy chain pair form the antigen-binding domain or site. Thus, in general, an intact antibody has two binding sites. Except in bifunctional or bispecific antibodies, the two binding sites are, in general, the same.

As used herein, the terms "complementarity determining region," abbreviated as "CDR," or "hypervariable region" refer to the amino acid residues of an antibody, or fragment thereof, that are responsible for antigen-binding. A CDR can comprise a "hypervariable loop" within a folded antibody, or fragment thereof. Typically, the variable domains of both the heavy and light chains comprise three CDRs, located within relatively conserved framework regions (FR). As used herein, the term "framework" or "FR" residues refers to those variable domain residues other than the hypervariable region residues defined herein as CDR residues.

The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. For example, as used herein, three CDRs within a light chain are abbreviated as CDRL1, CDRL2, and CDRL3, with CDRL1 representing the CDR closest to the N terminal of the light chain and CDRL3 representing the CDR closest to the C terminal of the light chain. Similarly, as used herein, the CDRs within a heavy chain that contains three CDRs are abbreviated as CDRH1, CDRH2, and CDRH3. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

CDRs provide the majority of contact residues for the binding of the anti-TSLP-R antibody, or antigen-binding fragment thereof, to the antigen or epitope. CDRs of interest can be derived from variable heavy and light chain sequences from a donor antibody, or fragment thereof, and include analogs of the naturally occurring CDRs, which analogs also share or retain the same antigen-binding specificity and/or neutralizing ability as the donor antibody, or fragment thereof, from which they were derived.

The "Fv region" comprises the variable regions from both the light and heavy chains, i.e., the Fv region comprises VL and VH. As used herein, the term "Fv domain" is used interchangeably with "Fv region." Generally, the Fv region further comprises a polypeptide linker between the VH and VL domains which enables the scFv to form the desired structure for antigen-binding. The term "single-chain Fv" or "scFv" antibody refers to antibody fragments comprising the VH and VL domains of an antibody, or fragment thereof, wherein these domains are present in a single polypeptide chain. For a review of scFv, see Pluckthun (1994) The Pharmacology Of Monoclonal Antibodies, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

As used herein, the term "Fab region" or "Fab domain" is used to refer to the region of an antibody, or fragment thereof, that is comprised of one light chain and the variable regions and $C_H1$ of one heavy chain. The Fab region typically comprises $V_L$, $C_L$, $V_H$, and $C_H1$. A "Fab fragment" is an antibody fragment that is comprised of one light chain and the $C_H1$ and variable regions of one heavy chain. The heavy chain of a Fab region cannot form a disulfide bond with another heavy chain molecule. A "Fab' fragment" contains one Fab region ($V_L$, $C_L$, $V_H$, and $C_H1$), wherein the heavy chain also contains the region between the $C_H1$ and $C_H2$ domains, such that an interchain disulfide bond can be formed between the two heavy chains of two Fab' fragments to form a F(ab')2 molecule. A "F(ab')2 fragment" contains two Fab' fragments (two light chains and two heavy chains containing a portion of the constant region between the $C_H1$ and $C_H2$ domains), wherein an interchain disulfide bond is formed between the two heavy chains. A F(ab')2 fragment thus is composed of two Fab' fragments that are held together by a disulfide bond between the two heavy chains.

As used herein, the term "Fc region" is used interchangeably with "Fc domain," which is defined as the region of an antibody, or fragment thereof, that contains two heavy chains held together by two or more disulfide bonds and hydrophobic interactions. An Fc domain typically comprises the $C_H2$ and $C_H3$ domains for each heavy chain. The two heavy chain fragments are held together by two or more disulfide bonds and by hydrophobic interactions of the $C_H3$ domains.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens. As used herein, the term "diabodies" refers to small antibody fragments with two antigen-binding domains, wherein the fragments comprise a heavy chain variable domain (VH) connected to a light chain variable domain (VL) in the same polypeptide chain (VH-VL or VL-VH). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibodies, fragments thereof, and variants thereof, generally see Holliger and Hudson (2005) Nat. Biotechnol. 23:1126-1136.

A "bivalent antibody" comprises two antigen-binding sites. In some instances, the two binding sites have the same antigen specificities. In some instances, the two binding sites have different antigen specificities, in which case the antibody is a bispecific antibody. The terms "bispecific antibody" and "multispecific antibody" refers to any antibody that binds immunospecifically to two or more different binding sites that have different antigen specificities.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) Proc. Natl. Acad. Sci. USA 81: 6851-6855). Typically, the variable domains are obtained from an antibody from an experimental animal (the "parental antibody"), such as a rodent, and the constant domain sequences are obtained from human antibodies, so that the resulting chimeric antibody is less likely to elicit an adverse immune response in a human subject than the parental (e.g., rodent) antibody.

As used herein, the term "humanized antibody" refers to forms of antibodies that contain sequences from both human and non-human (e.g., murine, rat) antibodies. In general, a humanized antibody, or fragment thereof, will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody, or fragment thereof, may optionally comprise at least a portion of a human immunoglobulin constant region (Fc).

"Parental antibodies" are antibodies obtained by exposure of an immune system to an antigen prior to modification of the antibodies for an intended use, such as humanization of an antibody for use as a human therapeutic antibody, or fragment thereof.

The term "monoclonal antibody," as used herein, refers to population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies, or antigen-binding fragments thereof, having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, monoclonal antibodies to be used in accordance with the present disclosure may be made by the hybridoma method first described by Kohler et al. (1975) Nature 256: 495, or may be made by recombinant DNA methods (see, e.g., U.S. Pat. No. 4,816,567). The monoclonal antibodies may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody display libraries or antigen-binding protein display libraries can be found in the literature. Thus, the epitopes described herein can be used to screen for other antibodies that can be used therapeutically, diagnostically, or as research tools.

The phrases "an antibody recognizing TSLP-R" and "an antibody specific for TSLP-R" are used interchangeably herein with the term "an antibody which binds specifically to TSLP-R." The term also includes antibodies that are specific for CRLF2. In some embodiments, the pharmaceutical composition comprising the anti-TSLP-R antibody is designated TRAB-1.

In some embodiments, an antibody, or antigen-binding fragment thereof, is provided, wherein the antibody, or antigen-binding fragment thereof, is specific for TSLP-R. In some embodiments, the anti-TSLP-R antibody, or antigen-binding fragment thereof, is used to detect the presence of an antigen. In some embodiments, the antigen is TSLP-R. In some embodiments, the antibody, or fragment thereof, contains a variable region that binds specifically to TSLP-R. In some embodiments, antibody, or fragment thereof, binds specifically to one or more antigen-binding site within TSLP-R. In some embodiments, the antibody, or fragment thereof, binds to amino acids of an epitope of the TSLP-R. In some embodiments, the antibody, or fragment thereof, binds to the one or more epitope, wherein the one or more epitope is an antigen-binding site within TSLP-R. In some embodiments, the present anti-TSLP-R antibody, or antigen-binding fragment thereof, can be used in any device or method to detect the presence of the antigen.

In some embodiments, the anti-TSLP-R antibody, or antigen-binding fragment thereof, binds specifically to one or more TSLP-R binding site wherein the KD between the antibody, or fragment thereof, and the one or more TSLP-R binding site is at least twice the KD between the antibody, or fragment thereof, and a non-specific antigen. In some embodiments, the non-specific antigen can include, but is not limited to, BSA, casein, or any other polypeptide that binds to the anti-TSLP-R antibody, or antigen-binding fragment thereof, in a non-specific manner. In some embodiments, the antibody, or fragment thereof, binds to its antigen (TSLP-R) with an affinity that is at least two-fold greater, at least ten times greater, at least 20-times greater, or at least 100-times greater than the affinity with any other antigen. The degree of specificity necessary for an anti-TSLP-R antibody, or antigen-binding fragment thereof, may depend on the intended use of the antibody, or fragment thereof, and at any rate is defined by its suitability for use for an intended purpose.

In some embodiments, the anti-TSLP-R antibody, or antigen-binding fragment thereof, binds specifically to one or more TSLP-R binding site wherein the KD between the anti-TSLP-R antibody, or antigen-binding fragment thereof, and the one or more TSLP-R binding site is at least $10^{-6}$, $10^{-7}$, $10^{-8}$, $10^{-9}$, $10^{-10}$, $10^{-11}$, $10^{-12}$, or $10^{-13}$ M. In some embodiments, the anti-TSLP-R antibody, or antigen-binding fragment thereof, is highly specific for one or more TSLP-R binding site, wherein the KD is at least about $10^{-9}$ M. In some embodiments, the anti-TSLP-R antibody, or antigen-binding fragment thereof, is highly specific for one or more TSLP-R binding site, wherein the KD is at least about $10^{-12}$ M.

In some embodiments, the antigen is the TSLP-R protein expressed on the surface of a cell. In some embodiments, the cell is an intact cell. In some embodiments, the cell is not an intact cell. An intact cell is a cell that has not been lysed or broken open with the use of detergents or other reagents. A cell that has been treated with detergents or other reagents that breaks up the cellular membrane or punches holes in a cellular membrane is not an intact cell. For example, methods are provided herein for generating an antibody, or fragment thereof, that binds to a TSLP-R protein, the method comprising culturing a cell comprising a nucleic acid molecule encoding the TSLP-R antibody, or fragment thereof.

In some embodiments, the anti-TSLP-R antibody comprises at least two light chains and at least two heavy chains. In some embodiments, the anti-TSLP-R antibody comprises a tetramer. In some embodiments, the tetramer comprises two light chains and two heavy chains. In some embodiments, the anti-TSLP-R antibody comprises one or more tetramers. In some embodiments, the anti-TSLP-R antibody comprises two, five, or more tetramers. In some embodiments, the anti-TSLP-R antibody, or antigen-binding fragment thereof, is of IgM, IgD, IgG, IgA, or IgE isotype, or any combination thereof.

In some embodiments, the anti-TSLP-R antibody fragment comprises a monomer or an oligomer. In some embodiments, the oligomer comprises two, three, four, five, or more monomers. In some embodiments, the monomer comprises an intact light chain or portion thereof, or an intact heavy chain or portion thereof. In some embodiments, the oligomer comprises two or more monomers, wherein the two or more monomers comprise one or more intact light chain, light chain portion, intact heavy chain, heavy chain portion, or a combination thereof.

In some embodiments, the anti-TSLP-R antibody, or antigen-binding fragment thereof, comprises one or more chains comprising a kappa light chain, lambda light chain, mu heavy chain, delta heavy chain, gamma heavy chain, alpha heavy chain, epsilon heavy chain, or a combination thereof. In some embodiments, the anti-TSLP-R antibody fragment comprises intact chains, portions of chains, or a combination of intact chains and chain portions. In some embodiments, the one or more intact heavy chains, or portion thereof, comprises 1, 2, 3, or 4 constant regions. In some embodiments, the constant region comprises a $C_H1$, $C_H2$, $C_H3$, or $C_H4$ constant region, or any combination thereof.

In some embodiments, the anti-TSLP-R antibody, or antigen-binding fragment thereof, comprises one or more antibody region, wherein the one or more antibody region is V L, $V_H$, $C_L$, $C_H1$, $C_H2$, $C_H3$, or $C_H4$, or any combination thereof. In some embodiments, the anti-TSLP-R antibody, or antigen-binding fragment thereof, comprises one or more linker, wherein the N-terminus of the linker is covalently bound to a VL, VH, CL, $C_H1$, $C_H2$, $C_H3$, or $C_H4$, and the C-terminus of the linker is covalently bound to a VL, VH, CL, $C_H1$, $C_H2$, $C_H3$, or $C_H4$. In some embodiments, the anti-TSLP-R antibody, or antigen-binding fragment thereof, additionally comprises a "J" region. In some embodiments, the anti-TSLP-R antibody, or antigen-binding fragment thereof, additionally comprises a "D" region.

In some embodiments, the anti-TSLP-R antibody, or antigen-binding fragment thereof, comprises one or more amino acid sequences as provided herein. In some embodiments, the anti-TSLP-R antibody, or antigen-binding fragment thereof, comprises an antigen-binding domain that comprises one or more amino acid sequences as provided herein. In some embodiments, the anti-TSLP-R antibody, or fragment thereof, or antigenic binding fragment thereof, has, at least 50, 60, 70, 80, 90, 91, 92, 93, 94, 95, 96, 97, 98, or 99% homology or identity to a sequence described herein.

In some embodiments, the antibody comprises one or more peptides having the sequences as listed in Table 1, or a variant thereof.

TABLE 1

| AB ID NO. | LC Sequence | HC Sequence |
|---|---|---|
| TRAB-1 | DIQMTQSPSSLSASV GDRVTITCRASQDIS NYLAWFQQKPGKAPK SLIYTASSLQSGVPS KFSGSGSGTDFTLTI SSLOPEDFATYYCQQ YNLYPPTFGQGTKVE IKRTVAAPSVFIFPP SDEQLKSGTASVVCL | EVQLLESGGGLVQPG GSLRLSCAASGFTFR SSAMHWVRQAPGKGL KWVSSVSGSGAGTYY ADSVKGRFTISRDNP KNTLYLQMNSLRAED TAVYYCVKEGGSRGF DYWGQGTLVTVSSAS TKGPSVFPLAPSSKS |

TABLE 1-continued

| AB ID NO. | LC Sequence | HC Sequence |
|---|---|---|
| | LNNFYPREAKVQWKV DNALQSGNSQESVTE QDSKDSTYSLSSTLT LSKADYEKHKVYACE VTHQGLSSPVTKSFN RGEC (SEQ ID NO: 3) | TSGGTAALGCLVKDY FPEPVTVSWNSGALT SGVHTFPAVLQSSGL YSLSSVVTVPSSSLG TQTYICNVNHKPSNT KVDKKVEPKSCDKTH TCPPCPAPELLGGPS VFLFPPKPKDTLMIS RTPEVTCVVVDVSHE DPEVKFNWYVDGVEV HNAKTKPREEQYNST YRVVSVLTVLHQDWL NGKEYKCKVSNKALP APIEKTISKAKGQPR EPQVYTLPPSRDELT KNQVSLTCLVKGFYP SDIAVEWESNGQPEN NYKTTPPVLDSDGSF FLYSKLTVDKSRWQQ GNVFSCSVMHEALHN HYTQKSLSLSPGK (SEQ ID NO: 1) |

In some embodiments, the anti-TSLP-R antibody, or antigen-binding fragment thereof, comprises one or more heavy chain (HC). In some embodiments, the anti-TSLP-R antibody, or antigen-binding fragment thereof, comprises one or more heavy chain having the amino acid sequence of SEQ ID NO: 1. In some embodiments, the anti-TSLP-R antibody, or antigen-binding fragment thereof, comprises two heavy chains having the amino acid sequence of SEQ ID NO: 1. In some embodiments, the anti-TSLP-R antibody, or antigen-binding fragment thereof, comprises a heavy chain encoded by the nucleotide sequence of SEQ ID NO: 2:

(SEQ ID NO: 2)
gaggtgcagctgttggagtctgggggaggcttggtacagc cggggggtccctgagactctcctgtgcagcctctggatt cacctttcgcagctctgccatgcattgggtccgccaggct ccagggaagggactgaaatgggtctcaagtgttagtggca gtggtgctggaacatactacgcagactccgtgaagggccg gttcaccatctccagagacaatcccaagaatacactgtat ctgcaaatgaacagtctgagagccgaggacacggccgtat attattgtgtgaaagaaggggcagccggggttttgacta ctggggccagggaaccctggtcaccgtctcctcagcctcc accaagggcccatcggtcttcccctggcaccctcctcca agagcacctctggggcacagcggccctgggctgcctggt caaggactacttccccgaaccggtgacggtgtcgtggaac tcaggcgccctgaccagcggcgtgcacaccttcccggctg tcctacagtcctcaggactctactcccttagtagcgtggt gaccgtgccctccagcagcttgggcacccagacctacatc tgcaacgtgaatcacaagcccagcaacaccaaggtggaca agaaagttgagcccaaatcttgtgacaaaactcacacatg cccaccgtgcccagcacctgaactcctggggggaccgtca gtcttcctcttccccccaaaacccaaggacaccctcatga -continued

```
tctcccggaccoctgaggtcacatgcgtggtggtggacgt gagccacgaagaccctgaggtcaagttcaactggtacgtg gacggcgtggaggtgcataatgccaagacaaagccgcggg aggagcagtacaacagcacgtaccgtgtggtcagcgtcct caccgtcctgcaccaggactggctgaatggcaaggagtac aagtgcaaggtctccaacaaagccctcccagcccccatcg agaaaaccatctccaaagccaaagggcagccccgagaacc acaggtgtacaccctgcccccatcccgggatgagctgacc aagaaccaggtcagcctgacctgcctggtcaaaggcttct atcccagcgacatcgccgtggagtgggagagcaatgggca gccggagaacaactacaagaccacgcctcccgtgctggac tccgacggctccttcttcctctacagcaagctcaccgtgg acaagagcaggtggcagcaggggaacgtcttctcatgctc cgtgatgcatgaggctctgcacaaccactacacgcagaag agcctctccctgtctccgggtaaatga
```

In some embodiments, the anti-TSLP-R antibody, or antigen-binding fragment thereof, comprises a heavy chain having the amino acid sequence of SEQ ID NO: 1, encoded by the nucleotide sequence of SEQ ID NO: 2.

In some embodiments, the anti-TSLP-R antibody, or antigen-binding fragment thereof, comprises one or more light chain (LC). In some embodiments, the anti-TSLP-R antibody, or antigen-binding fragment thereof, comprises one or more light chain having the amino acid sequence of SEQ ID NO: 3. In some embodiments, the anti-TSLP-R antibody, or antigen-binding fragment thereof, comprises two light chains having the amino acid sequence of SEQ ID NO: 3.

In some embodiments, the anti-TSLP-R antibody, or antigen-binding fragment thereof, comprises a light chain encoded by the nucleotide sequence of SEQ ID NO: 4:

```
                                    (SEQ ID NO: 4)
gacatccagatgacccagtctccatcctcactgtctgcat ctgtaggagacagagtcaccatcacttgtcggcgagtca ggacattagcaattatttagcctggtttcagcagaaacca gggaaagcccctaagtccctgatctatactgcatccagtt tgcaaagtgggtcccatcaaagttcagcggcagtggatc tgggacagatttcactctcaccatcagcagcctgcagcct gaagattttgcaacttattactgccaacagtataatcttt atcctccgacgttcggccaagggaccaaggtggaaatcaa acggactgtggctgcaccatctgtcttcatcttcccgcca tctgatgagcagttgaaatctggaactgcctctgttgtgt gcctgctgaataacttctatcccagagaggccaaagtaca gtggaaggtggataacgccctccaatcgggtaactcccag gagagtgtcacagagcaggacagcaaggacagcacctaca
```

-continued

```
gcctcagcagcaccctgacgctgagcaaagcagactacga gaaacacaaagtctacgcctgcgaagtcacccatcagggc ctgagctcgcccgtcacaaagagcttcaacaggggagagt gttag
```

In some embodiments, the anti-TSLP-R antibody, or antigen-binding fragment thereof, comprises one or more heavy chain having the amino acid sequence of SEQ ID NO: 1 encoded by the nucleotide sequence of SEQ ID NO: 2, and one or more light chain having the amino acid sequence of SEQ ID NO: 3 encoded by the nucleotide sequence of SEQ ID NO: 4. In some embodiments, the anti-TSLP-R antibody, or antigen-binding fragment thereof, comprises two heavy chains having the amino acid sequence of SEQ ID NO: 1 encoded by the nucleotide sequence of SEQ ID NO: 2, and two light chains having the amino acid sequence of SEQ ID NO: 3 encoded by the nucleotide sequence of SEQ ID NO: 4. In some embodiments, the anti-TSLP-R antibody, or antigen-binding fragment thereof, comprises a light chain having the amino acid sequence of SEQ ID NO: 3, encoded by the nucleotide sequence of SEQ ID NO: 4.

In some embodiments, the anti-TSLP-R antibody, or antigen-binding fragment thereof, comprises a heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, the anti-TSLP-R antibody, or antigen-binding fragment thereof, comprises a light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, the anti-TSLP-R antibody, or antigen-binding fragment thereof, comprises a heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1; and a light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the anti-TSLP-R antibody, or antigen-binding fragment thereof, comprises one or more variable heavy chain (VH) polypeptide. In some embodiments, the anti-TSLP-R antibody, or antigen-binding fragment thereof, comprises one or more variable light chain (VL) polypeptide. In some embodiments, the antibody heavy chain sequence comprises the variable heavy chain of the antibody, and the antibody light chain sequence comprises the variable light chain of the antibody. In some embodiments, the anti-TSLP-R antibody, or antigen-binding fragment thereof, comprises a variable heavy chain polypeptide VH and the variable light chain polypeptide VL, having the sequences shown in Table 2.

TABLE 2

| AB ID NO. | V_L Sequence | V_H Sequence |
|---|---|---|
| TRAB-1 | DIQMTQSPSSLSASV GDRVTITCRASQDIS NYLAWFQQKPGKAPK SLIYTASSLQSGVPS KFSGSGSGTDFTLTI SSLQPEDFATYYCQQ YNLYPPTFGQGTKVE IK (SEQ ID NO: 6) | EVQLLESGGGLVQPG GSLRLSCAASGFTFR SSAMHWVRQAPGKGL KWVSSVSGSGAGTYY ADSVKGRFTISRDNP KNTLYLQMNSLRAED TAVYYCVKEGGSRGF DYWGQGTLVTVSS (SEQ ID NO: 5) |

TABLE 3

| Ab ID No | LCDR1 | LCDR2 | LCDR3 | HCDR1 | HCDR2 | HCDR3 |
|---|---|---|---|---|---|---|
| TRAB-1 | RASQD ISNY LA (SEQ ID NO: 10) | TASS LQS (SEQ ID NO: 11) | QQYNL YPPT (SEQ ID NO: 12) | SSAMH (SEQ ID NO: 7) | SVSG SGAGT YYAD SVKG (SEQ ID NO: 8) | EGGS RGFDY (SEQ ID NO: 9) |

In some embodiments, the anti-TSLP-R antibody, or antigen-binding fragment thereof, comprises a variable heavy chain polypeptide having an amino acid sequence of SEQ ID NO: 5.

In some embodiments, the anti-TSLP-R antibody, or antigen-binding fragment thereof, comprises a variable light chain polypeptide having the amino acid sequence of SEQ ID NO: 6.

In some embodiments, the anti-TSLP-R antibody, or antigen-binding fragment thereof, comprises a variable heavy chain polypeptide having the amino acid sequence of SEQ ID NO: 5, and a variable light chain polypeptide having the amino acid sequence of SEQ ID NO: 6.

In some embodiments, the anti-TSLP-R antibody, or antigen-binding fragment thereof, comprises a variable heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5. In some embodiments, the anti-TSLP-R antibody, or antigen-binding fragment thereof, comprises a variable light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6. In some embodiments, the anti-TSLP-R antibody, or antigen-binding fragment thereof, comprises a variable heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5; and a variable light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6.

In some embodiments, an antibody, or antigen-binding fragment thereof, is provided, wherein the antibody, or antibody fragment comprises a CDR polypeptide selected from Table 3. As used herein, the terms LCDR1, LCDR2, and LCDR3 refer to the CDR1, CDR2, and CDR3 of the light chain. As used herein, the terms HCDR1, HCDR2, and HCDR3 refer to the CDR1, CDR2, and CDR3 of the heavy chain. In some embodiments, the anti-TSLP-R antibody, or the anti-TSLP-R antibody fragment thereof, contains one or more CDR regions. In some embodiments, the anti-TSLP-R antibody, or anti-TSLP-R antibody fragment thereof, contains one or more CDR region with a sequence chosen from Table 3.

In some embodiments, the anti-TSLP-R antibody, or the antigen-binding fragment thereof, comprises a heavy chain HCDR1, HCDR2, and HCDR3 comprising the amino acid sequence of SEQ ID NO: 7, 8, and 9, respectively. In some embodiments, the anti-TSLP-R antibody, or the fragment thereof, comprises a heavy chain comprising a HCDR1 amino acid sequence of SEQ ID NO: 7; a HCDR2 amino acid sequence of SEQ ID NO: 8; and a HCDR3 amino acid sequence of SEQ ID NO: 9. In some embodiments, the anti-TSLP-R antibody, or the fragment thereof, comprises a heavy chain comprising a HCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 7; a HCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8; and a HCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 9.

In some embodiments, the anti-TSLP-R antibody, or antigen-binding fragment thereof, comprises a heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1, provided that the heavy chain polypeptide comprises a HCDR1 amino acid sequence of SEQ ID NO: 7; a HCDR2 amino acid sequence of SEQ ID NO: 8; and a HCDR3 amino acid sequence of SEQ ID NO: 9.

In some embodiments, the anti-TSLP-R antibody, or the antigen-binding fragment thereof, comprises a variable heavy chain HCDR1, HCDR2, and HCDR3 comprising the amino acid sequence of SEQ ID NO: 7, 8, and 9, respectively. In some embodiments, the anti-TSLP-R antibody, or the fragment thereof, comprises a variable heavy chain comprising a HCDR1 amino acid sequence of SEQ ID NO: 7; a HCDR2 amino acid sequence of SEQ ID NO: 8; and a HCDR3 amino acid sequence of SEQ ID NO: 9. In some embodiments, the anti-TSLP-R antibody, or the fragment thereof, comprises a variable heavy chain comprising a HCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 7; a HCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8; and a HCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 9.

In some embodiments, the anti-TSLP-R antibody, or the antigen-binding fragment thereof, comprises a light chain LCDR1, LCDR2, and LCDR3 comprising the amino acid sequence of SEQ ID NO: 10, 11, and 12, respectively. In some embodiments, the anti-TSLP-R antibody, or the fragment thereof, comprises a light chain comprising a LCDR1 amino acid sequence of SEQ ID NO: 10; a LCDR2 amino acid sequence of SEQ ID NO: 11; and a LCDR3 amino acid sequence of SEQ ID NO: 12. In some embodiments, the anti-TSLP-R antibody, or the fragment thereof, comprises a light chain comprising a LCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 10; a LCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 11; and a LCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 12.

In some embodiments, the anti-TSLP-R antibody, or antigen-binding fragment thereof, comprises a light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3, provided that the light chain polypeptide comprises a LCDR1 amino acid sequence of SEQ ID NO: 10; a LCDR2 amino acid sequence of SEQ ID NO: 11; and a LCDR3 amino acid sequence of SEQ ID NO: 12.

In some embodiments, the anti-TSLP-R antibody, or the antigen-binding fragment thereof, comprises a variable light chain LCDR1, LCDR2, and LCDR3 comprising the amino acid sequence of SEQ ID NO: 10, 11, and 12, respectively. In some embodiments, the anti-TSLP-R antibody, or the fragment thereof, comprises a variable light chain comprising a LCDR1 amino acid sequence of SEQ ID NO: 10; a LCDR2 amino acid sequence of SEQ ID NO: 11; and a LCDR3 amino acid sequence of SEQ ID NO: 12. In some embodiments, the anti-TSLP-R antibody, or the fragment thereof, comprises a variable light chain comprising a LCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 10; a LCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 11; and a LCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 12.

In some embodiments, the anti-TSLP-R antibody, or the antigen-binding fragment thereof, comprises a heavy chain HCDR1, HCDR2, and HCDR3 comprising the amino acid sequence of SEQ ID NO: 7, 8, and 9, respectively; and a light chain LCDR1, LCDR2, and LCDR3 comprising the amino acid sequence of SEQ ID NO: 10, 11, and 12, respectively. In some embodiments, the anti-TSLP-R antibody, or the fragment thereof, comprises a heavy chain comprising a HCDR1 amino acid sequence of SEQ ID NO: 7; a HCDR2 amino acid sequence of SEQ ID NO: 8; and a HCDR3 amino acid sequence of SEQ ID NO: 9; and a light chain comprising a LCDR1 amino acid sequence of SEQ ID NO: 10; a LCDR2 amino acid sequence of SEQ ID NO: 11; and a LCDR3 amino acid sequence of SEQ ID NO: 12. In some embodiments, the anti-TSLP-R antibody, or the fragment thereof, comprises a heavy chain comprising a HCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 7; a HCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8; and a HCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 9; and a light chain comprising a LCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 10; a LCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 11; and a LCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 12.

In some embodiments, the anti-TSLP-R antibody, or antigen-binding fragment thereof, comprises a heavy chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1, provided that the heavy chain polypeptide comprises a HCDR1 amino acid sequence of SEQ ID NO: 7; a HCDR2 amino acid sequence of SEQ ID NO: 8; and a HCDR3 amino acid sequence of SEQ ID NO: 9; and a light chain polypeptide having an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3, provided that the light chain polypeptide comprises a LCDR1 amino acid sequence of SEQ ID NO: 10; a LCDR2 amino acid sequence of SEQ ID NO: 11; and a LCDR3 amino acid sequence of SEQ ID NO: 12.

In some embodiments, the anti-TSLP-R antibody, or the antigen-binding fragment thereof, comprises a variable heavy chain HCDR1, HCDR2, and HCDR3 comprising the amino acid sequence of SEQ ID NO: 7, 8, and 9, respectively; and a variable light chain LCDR1, LCDR2, and LCDR3 comprising the amino acid sequence of SEQ ID NO: 10, 11, and 12, respectively. In some embodiments, the anti-TSLP-R antibody, or the fragment thereof, comprises a variable heavy chain comprising a HCDR1 amino acid sequence of SEQ ID NO: 7; a HCDR2 amino acid sequence of SEQ ID NO: 8; and a HCDR3 amino acid sequence of SEQ ID NO: 9; and a variable light chain comprising a LCDR1 amino acid sequence of SEQ ID NO: 10; a LCDR2 amino acid sequence of SEQ ID NO: 11; and a LCDR3 amino acid sequence of SEQ ID NO: 12. In some embodiments, the anti-TSLP-R antibody, or the fragment thereof, comprises a variable heavy chain comprising a HCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 7; a HCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8; and a HCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 9; and a variable light chain comprising a LCDR1 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO: 10; a LCDR2 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 11; and a LCDR3 amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 12.

In some embodiments, the anti-TSLP-R antibody, or antigen-binding fragment thereof, has conservative substitutions as compared to a sequence described herein. Exemplary conservative substitutions are illustrated in Table 4 and are encompassed within the scope of the disclosed subject matter. In some embodiments, the conservative substitution may reside in the framework regions, or in antigen-binding sites, as long they do not adversely affect the properties of the antibody, or fragment thereof. In some embodiments, substitutions may be made to improve the properties or the antibody, or fragment thereof, for example the stability or affinity. In some embodiments, conservative substitutions will produce molecules having functional and chemical characteristics similar to those molecules into which such modifications are made. Exemplary amino acid substitutions are shown in the table below.

TABLE 4

Exemplary Conservative Substitutions

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |

TABLE 4-continued

Exemplary Conservative Substitutions

| Original Residue | Exemplary Conservative Substitutions |
|---|---|
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. In some embodiments, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

In some embodiments, "derivatives" of the antibodies, are provided. The term "derivatives" includes those proteins encoded by truncated or modified genes to yield molecular species functionally resembling the immunoglobulin or immunoglobulin fragments. In some embodiments, the modifications can include, but are not limited to, addition of genetic sequences coding for cytotoxic proteins such as plant and bacterial toxins. In some embodiments, the modification can also include a reporter protein, such as a fluorescent or chemiluminescent tag. In some embodiments, the fragments and derivatives can be produced in any manner.

In some embodiments, the anti-TSLP-R antibody, or antigen-binding fragment thereof, can include, but is not limited to, a monoclonal, polyclonal, bispecific, humanized, fully human, chimeric, or a single-domain antibody, or fragment thereof, or any combination thereof.

In some embodiments, the anti-TSLP-R antibody fragment can include, but is not limited to, a Fab, Fab', F(ab')2, Fv fragment, diabody, linear antibody, single chain antibody, sc-Fv, nanobody, or multispecific antibody fragment, or any combination thereof.

In some embodiments, the anti-TSLP-R antibody, or fragment thereof, is isolated. In some embodiments, the anti-TSLP-R antibody, or fragment thereof, is at least 70%, 75%, 80%, 85%, 90%, 95%, 96%, 97%, 98%, 99%, 99.5%, 99.9%, or 100% (w/w) pure. In some embodiments, the anti-TSLP-R antibody, or fragment thereof, is at least 70%-80%, 75%-80%, 75%-85%, 80%-85%, 80%-90%, 85%-90%, 85%-95%, or 90%-95% pure. In some embodiments, the anti-TSLP-R antibody, or fragment thereof, is at least 70% to at least 80% pure. In some embodiments, the anti-TSLP-R antibody, or fragment thereof, is at least 75% to at least 80% pure. In some embodiments, the anti-TSLP-R antibody, or fragment thereof, is at least 75% to at least 85% pure. In some embodiments, the anti-TSLP-R antibody, or fragment thereof, is at least 80% to at least 85% pure. In some embodiments, the anti-TSLP-R antibody, or fragment thereof, is at least 80% to at least 90% pure. In some embodiments, the anti-TSLP-R antibody, or fragment thereof, is at least 85% to at least 90% pure. In some embodiments, the anti-TSLP-R antibody, or fragment thereof, is at least 85% to at least 95% pure. In some embodiments, the anti-TSLP-R antibody, or fragment thereof, is at least 90% to at least 95% pure. In some embodiments, the anti-TSLP-R antibody, or fragment thereof, is at least 95% to at least 99% pure.

In some embodiments, the anti-TSLP-R antibody, or fragment thereof, binds specifically to one or more TSLP-R protein, wherein the one or more TSLP-R protein can include, but is not limited to primates such as humans or monkeys, mice, rats, other rodents, rabbits, dogs, cats, swine, cattle, sheep, or horses, or any combination thereof. In some embodiments, the anti-TSLP-R antibody, or fragment thereof, binds specifically to human TSLP-R. In some embodiments, the anti-TSLP-R antibody, or fragment thereof, binds specifically to murine TSLP-R. In some embodiments, the anti-TSLP-R antibody, or fragment thereof, binds specifically to one TSLP-R protein that is human in origin, and at least one additional TSLP-R protein that is another species in origin, wherein the another species of origin can include, but are not limited to, primates such as monkeys, mice, rats, other rodents, rabbits, dogs, cats, swine, cattle, sheep, or horses, or any combination thereof. In some embodiments, the anti-TSLP-R antibody, or fragment thereof, binds specifically to one TSLP-R protein that is murine in origin, and at least one additional TSLP-R protein that is another species in origin, wherein the another species of origin can include, but are not limited to, primates such as humans or monkeys, rats, other rodents, rabbits, dogs, cats, swine, cattle, sheep, or horses, or any combination thereof.

In some embodiments, the anti-TSLP-R antibody, or antigen-binding fragment thereof, is a MAb which binds to TSLP-R. In some embodiments, the anti-TSLP-R antibody, or antigen-binding fragment thereof, is a human IgG. In some embodiments, the anti-TSLP-R antibody, or antigen-binding fragment thereof, is a variant of human IgG. A "variant of human IgG" refers to an antibody that has been modified to be a human IgG or fragment thereof, when the starting antibody is not a human IgG antibody, or fragment thereof. In some embodiments, the sequences of the antibodies, or antigen-binding fragments thereof, can be modified to yield human IgG antibodies, or antigen-binding fragments thereof. In some embodiments, the conversion of the sequences provided herein can be modified to yield other types of antibodies, or antigen-binding fragments thereof. In some embodiments, the CDRs can also be linked to other antibodies, or antigen-binding fragments thereof, that bind to TSLP-R. In some embodiments, the CDRs can also be linked to other proteins or molecules to create an antibody, or fragment thereof, that binds to TSLP-R.

In some embodiments, the variable regions of the anti-TSLP-R antibody, or antigen-binding fragment thereof, as described herein can be combined with any type of constant region including a human constant region or murine constant region. In some embodiments, the constant region comprises a mutation at position at an amino acid residue relative to a wild-type human IgG constant domain, numbered according to the EU numbering index of Kabat. In some embodiments, the mutation increases the half-life of the anti-TSLP-R antibody, or antigen-binding fragment thereof, as compared to the half-life of an IgG having the wild-type human IgG constant domain.

In some embodiments, the antibodies, or fragments thereof, comprise an Fc region. In some embodiments, the Fc region comprises a mutation that extends the half-life of the anti-TSLP-R antibody, or antigen-binding fragment thereof, when linked to the Fc region. In some embodiments, the Fc domain comprises a mutation such as those described in US2007041972A1, EP2235059B1, U.S. Pat. Nos. 7,670,600, 8,394,925, and Mueller et al, Mol Immunol 1997 April; 34(6):441-52, each of which is incorporated by reference in its entirety. The numbering referenced herein refers to the Kabat numbering system for the Fc region.

As described herein, it is also intended that an antibody, or fragment thereof, of the present disclosure can include conservative or non-conservative amino acid substitutions, which can also be referred to as "conservative variants" or "function conserved variants" of the antibody, or fragment thereof, that do not substantially alter its biological activity. In some embodiments, a variant antibody, or fragment thereof, or antigen-binding fragment of the antibodies, thereof, provided herein retains at least 10% of its TSLP-R binding activity (when compared to a parental antibody, or fragment thereof, that is modified) when that activity is expressed on a molar basis. In some embodiments, a variant antibody, or fragment thereof, provided herein, retains at least 20%, 50%, 70%, 80%, 90%, 95% or 100% or more of the TSLP-R binding affinity as the parental antibody, or fragment thereof.

In some embodiments, a variant antibody, or fragment thereof, provided herein, retains at least 20% or more of the TSLP-R binding affinity as the parental antibody, or fragment thereof. In some embodiments, a variant antibody, or fragment thereof, provided herein, retains at least 50% or more of the TSLP-R binding affinity as the parental antibody, or fragment thereof. In some embodiments, a variant antibody, or fragment thereof, provided herein, retains at least 70% or more of the TSLP-R binding affinity as the parental antibody, or fragment thereof. In some embodiments, a variant antibody, or fragment thereof, provided herein, retains at least 80% or more of the TSLP-R binding affinity as the parental antibody, or fragment thereof. In some embodiments, a variant antibody, or fragment thereof, provided herein, retains at least 90% or more of the TSLP-R binding affinity as the parental antibody, or fragment thereof. In some embodiments, a variant antibody, or fragment thereof, provided herein, retains at least 95% or more of the TSLP-R binding affinity as the parental antibody, or fragment thereof. In some embodiments, a variant antibody, or fragment thereof, provided herein, retains at least 100% of the TSLP-R binding affinity as the parental antibody, or fragment thereof.

The antibodies provided for herein may also be conjugated to a chemical moiety. The chemical moiety may be, inter alia, a polymer, a radionuclide, or a cytotoxic factor. In some embodiments, this can be referred to as an antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylen-etriaminpentaacetic acid (DTPA)). Examples of chemical moieties include, but are not limited to, anti-mitotics, such as calicheamicins (e.g., ozogamicin), monomethyl auristatin E, mertansine, and the like. Other examples include, but are not limited to, biologically active anti-microtubule agents, alkylating agents, and DNA minor groove binding agents. Other examples of are provided herein and below. The chemical moiety can be linked to the antibody through a linking group (maleimide), a cleavable linker, such as a cathepsin cleavable linkers (valine-citrulline), and in some embodiments, one or more spacers (e.g., para-aminobenzyl-carbamate). Without being bound to any particular theory, once the antibody conjugate binds TSLP-R it can be internalized and the chemical moiety can kill the cell or otherwise inhibit its growth.

The antibodies and antigen-binding fragments of the present disclosure may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies, and antibody fragments thereof, may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, 152Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, Pseudomonas aeruginosa exotoxin A chain, ricin A chain, abrin A chain, modeccin A chain, alpha-sarcin, Aleurites fordii proteins and compounds (e.g., fatty acids), dianthin proteins, Phytoiacca americana proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody molecules of the present disclosure to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Pharmaceutical Compositions

The term "composition" as used herein means a product which results from the mixing or combining of more than one element or ingredient.

The term "carrier" as used herein encompasses carriers, excipients, and diluents, meaning a material, composition, or vehicle, such as a liquid or solid filler, diluent, excipient, solvent or encapsulating material involved in carrying or transporting a pharmaceutical, cosmetic or other agent across a tissue layer.

The phrase "pharmaceutically acceptable" is employed herein to refer to those agents of interest/compounds, salts, compositions, pharmaceutical dosage forms, etc., which are, within the scope of sound medical judgment, suitable for use in contact with the tissues of human beings and/or other mammals without excessive toxicity, irritation, allergic response, or other problem or complication, commensurate with a reasonable benefit/risk ratio. In some embodiments, pharmaceutically acceptable means approved by a regulatory agency of the federal or a state government, or listed in the U.S. Pharmacopeia or other generally recognized pharmacopeia for use in animals (e.g., mammals), and more particularly, in humans.

The term "stable" as used herein means to have stability against, for example, heat, light, temperature, and/or humidity.

The term "excipient" refers to a pharmacologically inactive substance formulated with an antibody, or antigen-binding fragment thereof, as described herein.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) an excipient at a concentration of about 1 mmol/L to about 600 mmol/L; and (iv) a surfactant at a concentration of about 0.001% to about 1% (w/v).

In some embodiments, a pharmaceutical composition is provided, wherein the pharmaceutical composition comprises anti-TSLP-R antibody, or one or more antigen-binding fragment thereof. In some embodiments, a pharmaceutical composition is provided, wherein the pharmaceutical composition comprises the anti-TSLP-R antibody, or one or more antigen-binding fragment thereof, as disclosed herein.

In some embodiments, the pharmaceutical composition comprises an anti-TSLP-R antibody, or fragment thereof, wherein the anti-TSLP-R antibody, or antigen-binding fragment thereof, comprises: (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

In some embodiments, the pharmaceutical composition comprises an anti-TSLP-R antibody, or fragment thereof, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

In some embodiments, the pharmaceutical composition comprises an anti-TSLP-R antibody, or antigen-binding fragment thereof, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises an anti-TSLP-R antibody, or antigen-binding fragment thereof, wherein the anti-TSLP-R antibody, or fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises an anti-TSLP-R antibody, or antigen-binding fragment thereof, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises the anti-TSLP-R antibody, or antigen-binding fragment thereof, wherein the anti-TSLP-R antibody, or fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5; and (ii) a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises an anti-TSLP-R antibody, or antigen-binding fragment thereof, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises an anti-TSLP-R antibody, or antigen-binding fragment thereof, wherein the anti-TSLP-R antibody, or fragment thereof, comprises a variable heavy chain polypeptide having a sequence of SEQ ID NO: 5.

In some embodiments, the pharmaceutical composition comprises an anti-TSLP-R antibody, or antigen-binding fragment thereof, wherein the anti-TSLP-R antibody, or fragment thereof, comprises a variable light chain polypeptide having a sequence of SEQ ID NO: 6.

In some embodiments, the pharmaceutical composition comprises the anti-TSLP-R antibody, or antigen-binding fragment thereof, wherein the anti-TSLP-R antibody, or fragment thereof, comprises: (i) a variable heavy chain polypeptide having a sequence of SEQ ID NO: 5; and (ii) a variable light chain polypeptide having a sequence of SEQ ID NO: 6.

In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 1000 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 900 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 800 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 700 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 600 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 500 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 400 mg/mL. In some embodiments, the pharmaceutical composition comprises an anti-TSLP-R antibody, or antigen-binding fragment thereof, wherein the antibody, or antigen-binding fragment thereof, is present at a concentration from about 1 mg/mL to about 300 mg/mL. In some embodiments, the pharmaceutical composition comprises an anti-TSLP-R antibody, or antigen-binding fragment thereof, wherein the antibody, or antigen-binding fragment thereof, is present at a concentration from about 50 mg/mL to about 250 mg/mL. In some embodiments, the pharmaceutical composition comprises an anti-TSLP-R antibody, or antigen-binding fragment thereof, wherein the antibody, or antigen-binding fragment thereof, is present at a concentration from about 100 mg/mL to about 200 mg/mL. In some embodiments, the pharmaceutical composition comprises an anti-TSLP-R antibody, or antigen-binding fragment thereof, wherein the antibody, or antigen-binding fragment thereof, is present at a concentration from about 150 mg/mL to about 200 mg/mL.

In some embodiments, the pharmaceutical composition comprises an anti-TSLP-R antibody, or antigen-binding fragment thereof, wherein the antibody, or antigen-binding fragment thereof, is present at a concentration of about 25 mg/mL. In some embodiments, the pharmaceutical composition comprises an anti-TSLP-R antibody, or antigen-binding fragment thereof, wherein the antibody, or antigen-binding fragment thereof, is present at a concentration of about 50 mg/mL. In some embodiments, the pharmaceutical composition comprises an anti-TSLP-R antibody, or antigen-binding fragment thereof, wherein the antibody, or antigen-binding fragment thereof, is present at a concentration of about 100 mg/mL. In some embodiments, the pharmaceutical composition comprises an anti-TSLP-R antibody, or antigen-binding fragment thereof, wherein the antibody, or antigen-binding fragment thereof, is present at a concentration of about 125 mg/mL. In some embodiments, the pharmaceutical composition comprises an anti-TSLP-R antibody, or antigen-binding fragment thereof, wherein the antibody, or antigen-binding fragment thereof, is present at a concentration of about 150 mg/mL. In some embodiments, the pharmaceutical composition comprises an anti-TSLP-R antibody, or antigen-binding fragment thereof, wherein the antibody, or antigen-binding fragment thereof, is present at a concentration of about 155 mg/mL. In some embodiments, the pharmaceutical composition comprises an anti-TSLP-R antibody, or antigen-binding fragment thereof, wherein the antibody, or antigen-binding fragment thereof, is present at a concentration of about 160 mg/mL. In some embodiments, the pharmaceutical composition comprises an anti-TSLP-R antibody, or antigen-binding fragment thereof, wherein the antibody, or antigen-binding fragment thereof, is present at a concentration of about 165 mg/mL. In some embodiments, the pharmaceutical composition comprises an anti-TSLP-R antibody, or antigen-binding fragment thereof, wherein the antibody, or antigen-binding fragment thereof, is present at a concentration of about 170 mg/mL. In some embodiments, the pharmaceutical composition comprises an anti-TSLP-R antibody, or antigen-binding fragment thereof, wherein the antibody, or antigen-binding fragment thereof, is present at a concentration of about 175 mg/mL. In some embodiments, the pharmaceutical composition comprises an anti-TSLP-R antibody, or antigen-binding fragment thereof, wherein the antibody, or antigen-binding fragment thereof, is present at a concentration of about 180 mg/mL. In some embodiments, the pharmaceutical composition comprises an anti-TSLP-R antibody, or antigen-binding fragment thereof, wherein the antibody, or antigen-binding fragment thereof, is present at a concentration of about 185 mg/mL. In some embodiments, the pharmaceutical composition comprises an anti-TSLP-R antibody, or antigen-binding fragment thereof, wherein the antibody, or antigen-binding fragment thereof, is present at a concentration of about 190 mg/mL. In some embodiments, the pharmaceutical composition comprises an anti-TSLP-R antibody, or antigen-binding fragment thereof, wherein the antibody, or antigen-binding fragment thereof, is present at a concentration of about 195 mg/mL. In some embodiments, the pharmaceutical composition comprises an anti-TSLP-R antibody, or antigen-binding fragment thereof, wherein the antibody, or antigen-binding fragment thereof, is present at a concentration of about 200 mg/mL. In some embodiments, the pharmaceutical composition comprises an anti-TSLP-R antibody, or antigen-binding fragment thereof, wherein the antibody, or antigen-binding fragment thereof, is present at a concentration of about 205 mg/mL. In some embodiments, the pharmaceutical composition comprises an anti-TSLP-R antibody, or antigen-binding fragment thereof, wherein the antibody, or antigen-binding fragment thereof, is present at a concentration of about 210 mg/mL. In some embodiments, the pharmaceutical composition comprises an anti-TSLP-R antibody, or antigen-binding fragment thereof, wherein the antibody, or antigen-binding fragment thereof, is present at a concentration of about 215 mg/mL. In some embodiments, the pharmaceutical composition comprises an anti-TSLP-R antibody, or antigen-binding fragment thereof, wherein the antibody, or antigen-binding fragment thereof, is present at a concentration of about 220 mg/mL. In some embodiments, the pharmaceutical composition comprises an anti-TSLP-R antibody, or antigen-binding fragment thereof, wherein the antibody, or antigen-binding fragment thereof, is present at a concentration of about 225 mg/mL. In some embodiments, the pharmaceutical composition comprises an anti-TSLP-R antibody, or antigen-binding fragment thereof, wherein the antibody, or antigen-binding fragment thereof, is present at a concentration of about 230 mg/mL. In some embodiments, the pharmaceutical composition comprises an anti-TSLP-R antibody, or antigen-binding fragment thereof, wherein the antibody, or antigen-binding fragment thereof, is present at a concentration of about 235 mg/mL. In some embodiments, the pharmaceutical composition comprises an anti-TSLP-R antibody, or antigen-binding fragment thereof, wherein the antibody, or antigen-binding fragment thereof, is present at a concentration of about 240 mg/mL. In some embodiments, the pharmaceutical composition comprises an anti-TSLP-R antibody, or antigen-binding fragment thereof, wherein the antibody, or antigen-binding fragment thereof, is present at a concentration of about 245 mg/mL. In some embodiments, the pharmaceutical composition comprises an anti-TSLP-R antibody, or antigen-binding fragment thereof, wherein the antibody, or antigen-binding fragment thereof, is present at a concentration of about 250 mg/mL. In some embodiments, the pharmaceutical composition comprises an anti-TSLP-R antibody, or antigen-binding fragment thereof, wherein the antibody, or antigen-binding fragment thereof, is present at a concentration of about 255 mg/mL. In some embodiments, the pharmaceutical composition comprises an anti-TSLP-R antibody, or antigen-binding fragment thereof, wherein the antibody, or antigen-binding fragment thereof, is present at a concentration of about 260 mg/mL. In some embodiments, the pharmaceutical composition comprises an anti-TSLP-R antibody, or antigen-binding fragment thereof, wherein the antibody, or antigen-binding fragment thereof, is present at a concentration of about 265 mg/mL. In some embodiments, the pharmaceutical composition comprises an anti-TSLP-R antibody, or antigen-binding fragment thereof, wherein the antibody, or antigen-binding fragment thereof, is present at a concentration of about 270 mg/mL. In some embodiments, the pharmaceutical composition comprises an anti-TSLP-R antibody, or antigen-binding fragment thereof, wherein the antibody, or antigen-binding fragment thereof, is present at a concentration of about 275 mg/mL. In some embodiments, the pharmaceutical composition comprises an anti-TSLP-R antibody, or antigen-binding fragment thereof, wherein the antibody, or antigen-binding fragment thereof, is present at a concentration of about 280 mg/mL. In some embodiments, the pharmaceutical composition comprises an anti-TSLP-R antibody, or antigen-binding fragment thereof, wherein the antibody, or antigen-binding fragment thereof, is present at a concentration of about 285 mg/mL. In some embodiments, the pharmaceutical composition comprises an anti-TSLP-R antibody, or antigen-binding fragment thereof, wherein the antibody, or antigen-binding fragment thereof, is present at a concentration of about 290 mg/mL. In some embodiments, the pharmaceutical composition comprises an anti-TSLP-R antibody, or antigen-binding fragment thereof, wherein the antibody, or antigen-binding fragment thereof, is present at a concentration of about 300 mg/mL. In some embodiments, the pharmaceutical composition comprises an anti-TSLP-R antibody, or antigen-binding fragment thereof, wherein the antibody, or antigen-binding fragment thereof, is present at a concentration of about 325 mg/mL. In some embodiments, the pharmaceutical composition comprises an anti-TSLP-R antibody, or antigen-binding fragment thereof, wherein the antibody, or antigen-binding fragment thereof, is present at a concentration of about 350 mg/mL. In some embodiments, the pharmaceutical composition comprises an anti-TSLP-R antibody, or antigen-binding fragment thereof, wherein the antibody, or antigen-binding fragment thereof, is present at a concentration of about 375 mg/mL. In some embodiments, the pharmaceutical composition comprises an anti-TSLP-R antibody, or antigen-binding fragment thereof, wherein the antibody, or antigen-binding fragment thereof, is present at a concentration of about 400 mg/mL. In some embodiments, the pharmaceutical composition comprises an anti-TSLP-R antibody, or antigen-binding fragment thereof, wherein the antibody, or antigen-binding fragment thereof, is present at a concentration of about 425 mg/mL. In some embodiments, the pharmaceutical composition comprises an anti-TSLP-R antibody, or antigen-binding fragment thereof, wherein the antibody, or antigen-binding fragment thereof, is present at a concentration of about 450 mg/mL. In some embodiments, the pharmaceutical composition comprises an anti-TSLP-R antibody, or antigen-binding fragment thereof, wherein the antibody, or antigen-binding fragment thereof, is present at a concentration of about 475 mg/mL. In some embodiments, the pharmaceutical composition comprises an anti-TSLP-R antibody, or antigen-binding fragment thereof, wherein the antibody, or antigen-binding fragment thereof, is present at a concentration of about 500 mg/mL. In some embodiments, the pharmaceutical composition comprises an anti-TSLP-R antibody, or antigen-binding fragment thereof, wherein the antibody, or antigen-binding fragment thereof, is present at a concentration of about 525 mg/mL. In some embodiments, the pharmaceutical composition comprises an anti-TSLP-R antibody, or antigen-binding fragment thereof, wherein the antibody, or antigen-binding fragment thereof, is present at a concentration of about 550 mg/mL. In some embodiments, the pharmaceutical composition comprises an anti-TSLP-R antibody, or antigen-binding fragment thereof, wherein the antibody, or antigen-binding fragment thereof, is present at a concentration of about 575 mg/mL. In some embodiments, the pharmaceutical composition comprises an anti-TSLP-R antibody, or antigen-binding fragment thereof, wherein the antibody, or antigen-binding fragment thereof, is present at a concentration of about 600 mg/mL. In some embodiments, the pharmaceutical composition comprises an anti-TSLP-R antibody, or antigen-binding fragment thereof, wherein the antibody, or antigen-binding fragment thereof, is present at a concentration of about 700 mg/mL. In some embodiments, the pharmaceutical composition comprises an anti-TSLP-R antibody, or antigen-binding fragment thereof, wherein the antibody, or antigen-binding fragment thereof, is present at a concentration of about 800 mg/mL. In some embodiments, the pharmaceutical composition comprises an anti-TSLP-R antibody, or antigen-binding fragment thereof, wherein the antibody, or antigen-binding fragment thereof, is present at a concentration of about 900 mg/mL. In some embodiments, the pharmaceutical composition comprises an anti-TSLP-R antibody, or antigen-binding fragment thereof, wherein the antibody, or antigen-binding fragment thereof, is present at a concentration of about 1000 mg/mL.

In some embodiments, the pharmaceutical composition comprises an anti-TSLP-R antibody, or the antigen-binding fragment thereof, wherein the antibody, or antigen-binding fragment thereof, is present at a concentration of about 200 mg/mL or less.

In some embodiments, the pharmaceutical composition comprises an anti-TSLP-R antibody, or antigen-binding fragment thereof, wherein the antibody, or antigen-binding fragment thereof, is present at a dose of about 0.01 mg/kg to about 15 mg/kg. In some embodiments, the pharmaceutical composition comprises an anti-TSLP-R antibody, or antigen-binding fragment thereof, wherein the antibody, or antigen-binding fragment thereof, is present at a dose of about 0.02 mg/kg to about 15 mg/kg. In some embodiments, the pharmaceutical composition comprises an anti-TSLP-R antibody, or antigen-binding fragment thereof, wherein the antibody, or antigen-binding fragment thereof, is present at a dose of about 0.03 mg/kg to about 10 mg/kg.

In some embodiments, the pharmaceutical composition comprises an anti-TSLP-R antibody, or antigen-binding fragment thereof, wherein the antibody, or antigen-binding fragment thereof, is present at a dose of 0.01 mg/kg to 15 mg/kg. some embodiments, the pharmaceutical composition comprises an anti-TSLP-R antibody, or antigen-binding fragment thereof, wherein the antibody, or antigen-binding fragment thereof, is present at a dose of 0.02 mg/kg to 15 mg/kg. some embodiments, the pharmaceutical composition comprises an anti-TSLP-R antibody, or antigen-binding fragment thereof, wherein the antibody, or antigen-binding fragment thereof, is present at a dose of 0.03 mg/kg to 10 mg/kg.

In some embodiments, the pharmaceutical composition comprises an anti-TSLP-R antibody, or antigen-binding fragment thereof, wherein the antibody, or antigen-binding fragment thereof, is present in an amount of about 10 mg to about 700 mg. In some embodiments, the pharmaceutical composition comprises an anti-TSLP-R antibody, or antigen-binding fragment thereof, wherein the antibody, or antigen-binding fragment thereof, is present in an amount of about 25 mg to about 600 mg.

In some embodiments, the pharmaceutical composition comprises an anti-TSLP-R antibody, or antigen-binding fragment thereof, wherein the antibody, or antigen-binding fragment thereof, is present in an amount of 10 mg to 700 mg. In some embodiments, the pharmaceutical composition comprises an anti-TSLP-R antibody, or antigen-binding fragment thereof, wherein the antibody, or antigen-binding fragment thereof, is present in an amount of 25 mg to 600 mg.

In some embodiments, the pharmaceutical composition comprises an anti-TSLP-R antibody, or antigen-binding fragment thereof, wherein the antibody, or antigen-binding fragment thereof, is present at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3.0 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4.0 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5.0 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6.0 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7.0 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8.0 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9.0 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10.0 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11.0 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12.0 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13.0 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14.0 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15.0 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, or about 15.9 mg/kg.

In some embodiments, the pharmaceutical composition comprises an anti-TSLP-R antibody, or antigen-binding fragment thereof, wherein the antibody, or antigen-binding fragment thereof, is present at a dose of 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11.0 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12.0 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13.0 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14.0 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15.0 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, or 15.9 mg/kg.

In some embodiments, the pharmaceutical composition comprises an anti-TSLP-R antibody, or antigen-binding fragment thereof, wherein the antibody, or antigen-binding fragment thereof, is present in an amount of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, or about 700 mg.

In some embodiments, the pharmaceutical composition comprises an anti-TSLP-R antibody, or antigen-binding fragment thereof, wherein the antibody, or antigen-binding fragment thereof, is present in an amount of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, or 700 mg.

In some embodiments, the pharmaceutical composition comprises an anti-TSLP-R antibody, or antigen-binding fragment thereof, wherein the antibody, or antigen-binding fragment thereof, is present in an amount of 25 mg, 50 mg, 100 mg, 150 mg, 200 mg, 250 mg, or 300 mg. In some embodiments, the pharmaceutical composition comprises an anti-TSLP-R antibody, or antigen-binding fragment thereof, wherein the antibody, or antigen-binding fragment thereof, is present in an amount of about 200 mg, about 250 mg, about 300 mg, about 350 mg, about 400 mg, about 500 mg, or about 600 mg.

In some embodiments, the pharmaceutical composition comprises an anti-TSLP-R antibody, or antigen-binding fragment thereof, present at a dose of about 0.03 mg/kg to about 10 mg/kg, is present in an amount of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, or 700 mg.

In some embodiments, the pharmaceutical composition comprises an anti-TSLP-R antibody, or antigen-binding fragment thereof, present at a dose of about 0.03 mg/kg to about 10 mg/kg, is present in an amount of 25 mg, 50 mg, 100 mg, 150 mg, 200 mg, 250 mg, or 300 mg.

In some embodiments, the pharmaceutical composition comprises an anti-TSLP-R antibody, or antigen-binding fragment thereof, present at a dose of about 0.03 mg/kg to about 10 mg/kg, is present in an amount of about 200 mg, about 250 mg, about 300 mg, about 350 mg, about 400 mg, about 500 mg, or about 600 mg.

In some embodiments, to prepare pharmaceutical or sterile compositions of the anti-TSLP-R antibodies, or fragments thereof, provided herein, the antibody, or antigen-binding fragment thereof, provided herein are admixed with a pharmaceutically acceptable carrier or excipient. See, e.g., *Remington's Pharmaceutical Sciences and U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) Excipient Toxicity and Safety, Marcel Dekker, Inc., New York, NY). In some embodiments, NaCl or sucrose is added to the anti-TSLP-R antibody composition for tonicity. Additional agents, such as polysorbate 20 or polysorbate 80, may be added to enhance stability.

In some embodiments, the pharmaceutical compositions can further comprise one or more pharmaceutically acceptable carriers, including, e.g., ion exchangers, alumina, aluminum stearate, lecithin, serum proteins, such as human serum albumin, buffer substances such as phosphates, acetates, succinates, sucrose, glycine, arginine, proline, histidine, glutamate, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, sodium acetate, sodium succinate, sodium phosphate, histidine hydrochloride, glycine hydrochloride, arginine hydrochloride, proline hydrochloride, glutamate hydrochloride, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol, or a combination thereof.

In some embodiments, the pharmaceutical compositions described herein comprise a buffer (e.g., histidine, acetate, phosphate, or citrate buffer) and/or a stabilizer agent (e.g., human albumin), etc., or a combination thereof. In some embodiments, the buffer is used to buffer the pH. In some embodiments, the pH of the pharmaceutical composition is from about 4.4 to about 7.6. In some embodiments, the pH of the pharmaceutical composition is from about 5.0 to about 6.5. In some embodiments, the pH of the pharmaceutical composition if about 5.0, 5.1, 5.2, 5.3, 5.4, 5.5, 5.6, 5.7, 5.8, 5.9, 6.0, 6.1, 6.2, 6.3, 6.4, or 6.5. In some embodiments, the pH of the pharmaceutical composition is about 5.0. In some embodiments, the pH of the pharmaceutical composition is about 5.1. In some embodiments, the pH of the pharmaceutical composition is about 5.2. In some embodiments, the pH of the pharmaceutical composition is about 5.3. In some embodiments, the pH of the pharmaceutical composition is about 5.4. In some embodiments, the pH of the pharmaceutical composition is about 5.5. In some embodiments, the pH of the pharmaceutical composition is about 5.6. In some embodiments, the pH of the pharmaceutical composition is about 5.7. In some embodiments, the pH of the pharmaceutical composition is about 5.8. In some embodiments, the pH of the pharmaceutical composition is about 5.9. In some embodiments, the pH of the pharmaceutical composition is about 6.0. In some embodiments, the pH of the pharmaceutical composition is about 6.1. In some embodiments, the pH of the pharmaceutical composition is about 6.2. In some embodiments, the pH of the pharmaceutical composition is about 6.3. In some embodiments, the pH of the pharmaceutical composition is about 6.4. In some embodiments, the pH of the pharmaceutical composition is about 6.5.

In some embodiments, the pharmaceutical composition comprises a pharmaceutically acceptable buffer, wherein the pharmaceutically acceptable buffer is phosphoric acid buffer, citric acid buffer, acetic acid buffer, succinic acid buffer, citrate buffer, ascorbic acid buffer, glutamic acid buffer, lactic acid buffer, maleic acid buffer, trometamol buffer, and gluconic acid buffer, acetate buffer, succinate buffer, phosphate buffer, histidine buffer or any combination thereof.

In some embodiments, the pharmaceutical composition comprises a citric acid buffer. In some embodiments, the pharmaceutical composition comprises an acetic acid buffer. In some embodiments, the pharmaceutical composition comprises a succinic acid buffer. In some embodiments, the pharmaceutical composition comprises a citrate buffer. In some embodiments, the pharmaceutical composition comprises an ascorbic acid buffer. In some embodiments, the pharmaceutical composition comprises a glutamic acid buffer. In some embodiments, the pharmaceutical composition comprises a lactic acid buffer. In some embodiments, the pharmaceutical composition comprises a maleic acid buffer. In some embodiments, the pharmaceutical composition comprises a trometamol acid buffer. In some embodiments, the pharmaceutical composition comprises a gluconic acid buffer. In some embodiments, the pharmaceutical composition comprises an acetate buffer. In some embodiments, the pharmaceutical composition comprises a succinate buffer. In some embodiments, the pharmaceutical composition comprises a phosphate buffer. In some embodiments, the pharmaceutical composition comprises a histidine buffer.

In some embodiments, the pharmaceutically acceptable buffer is about 5 mmol/L phosphoric acid buffer to about 100 mmol/L phosphoric acid buffer. In some embodiments, the pharmaceutically acceptable buffer is about 10 mmol/L to about 70 mmol/L phosphoric acid buffer. In some embodiments, the pharmaceutically acceptable buffer is about 10 mmol/L to about 50 mmol/L phosphoric acid buffer. In some embodiments, the pharmaceutically acceptable buffer is about 5 mmol/L to about 60 mmol/L phosphoric acid buffer. In some embodiments, the pharmaceutically acceptable buffer is about 10 mmol/L to about 40 mmol/L phosphoric acid buffer. In some embodiments, the pharmaceutically acceptable buffer is about 15 mmol/L to about 30 mmol/L phosphoric acid buffer. In some embodiments, 15 mmol/L to about 25 mmol/L phosphoric acid buffer.

In some embodiments, the pharmaceutically acceptable buffer is about 5 mmol/L phosphoric acid buffer. In some embodiments, the pharmaceutically acceptable buffer is about 10 mmol/L phosphoric acid buffer. In some embodiments, the pharmaceutically acceptable buffer is about 15 mmol/L phosphoric acid buffer. In some embodiments, the pharmaceutically acceptable buffer is about 20 mmol/L phosphoric acid buffer. In some embodiments, the pharmaceutically acceptable buffer is about 25 mmol/L phosphoric acid buffer. In some embodiments, the pharmaceutically acceptable buffer is about 30 mmol/L phosphoric acid buffer. In some embodiments, the pharmaceutically acceptable buffer is about 35 mmol/L phosphoric acid buffer. In some embodiments, the pharmaceutically acceptable buffer is about 40 mmol/L phosphoric acid buffer. In some embodiments, the pharmaceutically acceptable buffer is about 45 mmol/L phosphoric acid buffer. In some embodiments, the pharmaceutically acceptable buffer is about 50 mmol/L phosphoric acid buffer. In some embodiments, the pharmaceutically acceptable buffer is about 55 mmol/L phosphoric acid buffer. In some embodiments, the pharmaceutically acceptable buffer is about 60 mmol/L phosphoric acid buffer. In some embodiments, the pharmaceutically acceptable buffer is about 75 mmol/L phosphoric acid buffer. In some embodiments, the pharmaceutically acceptable buffer is about 80 mmol/L phosphoric acid buffer. In some embodiments, the pharmaceutically acceptable buffer is about 85 mmol/L phosphoric acid buffer. In some embodiments, the pharmaceutically acceptable buffer is about 90 mmol/L phosphoric acid buffer. In some embodiments, the pharmaceutically acceptable buffer is about 95 mmol/L phosphoric acid buffer. In some embodiments, the pharmaceutically acceptable buffer is about 100 mmol/L phosphoric acid buffer.

In some embodiments, the pharmaceutically acceptable buffer is about 5 mmol/L citric acid buffer to about 100 mmol/L citric acid buffer. In some embodiments, the pharmaceutically acceptable buffer is about 10 mmol/L to about 70 mmol/L citric acid buffer. In some embodiments, the pharmaceutically acceptable buffer is about 10 mmol/L to about 50 mmol/L citric acid buffer. In some embodiments, the pharmaceutically acceptable buffer is about 5 mmol/L to about 60 mmol/L citric acid buffer. In some embodiments, the pharmaceutically acceptable buffer is about 10 mmol/L to about 40 mmol/L citric acid buffer. In some embodiments, the pharmaceutically acceptable buffer is about 15 mmol/L to about 30 mmol/L citric acid buffer. In some embodiments, 15 mmol/L to about 25 mmol/L citric acid buffer.

In some embodiments, the pharmaceutically acceptable buffer is about 5 mmol/L citric acid buffer. In some embodiments, the pharmaceutically acceptable buffer is about 10 mmol/L citric acid buffer. In some embodiments, the pharmaceutically acceptable buffer is about 15 mmol/L citric acid buffer. In some embodiments, the pharmaceutically acceptable buffer is about 20 mmol/L citric acid buffer. In some embodiments, the pharmaceutically acceptable buffer is about 25 mmol/L citric acid buffer. In some embodiments, the pharmaceutically acceptable buffer is about 30 mmol/L citric acid buffer. In some embodiments, the pharmaceutically acceptable buffer is about 35 mmol/L citric acid buffer. In some embodiments, the pharmaceutically acceptable buffer is about 40 mmol/L citric acid buffer. In some embodiments, the pharmaceutically acceptable buffer is about 45 mmol/L citric acid buffer. In some embodiments, the pharmaceutically acceptable buffer is about 50 mmol/L citric acid buffer. In some embodiments, the pharmaceutically acceptable buffer is about 55 mmol/L citric acid buffer. In some embodiments, the pharmaceutically acceptable buffer is about 60 mmol/L citric acid buffer. In some embodiments, the pharmaceutically acceptable buffer is about 75 mmol/L citric acid buffer. In some embodiments, the pharmaceutically acceptable buffer is about 80 mmol/L citric acid buffer. In some embodiments, the pharmaceutically acceptable buffer is about 85 mmol/L citric acid buffer. In some embodiments, the pharmaceutically acceptable buffer is about 90 mmol/L citric acid buffer. In some embodiments, the pharmaceutically acceptable buffer is about 95 mmol/L citric acid buffer. In some embodiments, the pharmaceutically acceptable buffer is about 100 mmol/L citric acid buffer.

In some embodiments, the pharmaceutically acceptable buffer is about 5 mmol/L acetic acid buffer to about 100 mmol/L acetic acid buffer. In some embodiments, the pharmaceutically acceptable buffer is about 10 mmol/L to about 70 mmol/L acetic acid buffer. In some embodiments, the pharmaceutically acceptable buffer is about 10 mmol/L to about 50 mmol/L acetic acid buffer. In some embodiments, the pharmaceutically acceptable buffer is about 5 mmol/L to about 60 mmol/L acetic acid buffer. In some embodiments, the pharmaceutically acceptable buffer is about 10 mmol/L to about 40 mmol/L acetic acid buffer. In some embodiments, the pharmaceutically acceptable buffer is about 15 mmol/L to about 30 mmol/L acetic acid buffer. In some embodiments, 15 mmol/L to about 25 mmol/L acetic acid buffer.

In some embodiments, the pharmaceutically acceptable buffer is about 5 mmol/L acetic acid buffer. In some embodiments, the pharmaceutically acceptable buffer is about 10 mmol/L acetic acid buffer. In some embodiments, the pharmaceutically acceptable buffer is about 15 mmol/L acetic acid buffer. In some embodiments, the pharmaceutically acceptable buffer is about 20 mmol/L acetic acid buffer. In some embodiments, the pharmaceutically acceptable buffer is about 25 mmol/L acetic acid buffer. In some embodiments, the pharmaceutically acceptable buffer is about 30 mmol/L acetic acid buffer. In some embodiments, the pharmaceutically acceptable buffer is about 35 mmol/L acetic acid buffer. In some embodiments, the pharmaceutically acceptable buffer is about 40 mmol/L acetic acid buffer. In some embodiments, the pharmaceutically acceptable buffer is about 45 mmol/L acetic acid buffer. In some embodiments, the pharmaceutically acceptable buffer is about 50 mmol/L acetic acid buffer. In some embodiments, the pharmaceutically acceptable buffer is about 55 mmol/L acetic acid buffer. In some embodiments, the pharmaceutically acceptable buffer is about 60 mmol/L acetic acid buffer. In some embodiments, the pharmaceutically acceptable buffer is about 75 mmol/L acetic acid buffer. In some embodiments, the pharmaceutically acceptable buffer is about 80 mmol/L acetic acid buffer. In some embodiments, the pharmaceutically acceptable buffer is about 85 mmol/L acetic acid buffer. In some embodiments, the pharmaceutically acceptable buffer is about 90 mmol/L acetic acid buffer. In some embodiments, the pharmaceutically acceptable buffer is about 95 mmol/L acetic acid buffer. In some embodiments, the pharmaceutically acceptable buffer is about 100 mmol/L acetic acid buffer.

In some embodiments, the pharmaceutically acceptable buffer is about 5 mmol/L succinic acid buffer to about 100 mmol/L succinic acid buffer. In some embodiments, the pharmaceutically acceptable buffer is about 10 mmol/L to about 70 mmol/L succinic acid buffer. In some embodiments, the pharmaceutically acceptable buffer is about 10 mmol/L to about 50 mmol/L succinic acid buffer. In some embodiments, the pharmaceutically acceptable buffer is about 5 mmol/L to about 60 mmol/L succinic acid buffer. In some embodiments, the pharmaceutically acceptable buffer is about 10 mmol/L to about 40 mmol/L succinic acid buffer. In some embodiments, the pharmaceutically acceptable buffer is about 15 mmol/L to about 30 mmol/L succinic acid buffer. In some embodiments, 15 mmol/L to about 25 mmol/L succinic acid buffer.

In some embodiments, the pharmaceutically acceptable buffer is about 5 mmol/L succinic acid buffer. In some embodiments, the pharmaceutically acceptable buffer is about 10 mmol/L succinic acid buffer. In some embodiments, the pharmaceutically acceptable buffer is about 15 mmol/L succinic acid buffer. In some embodiments, the pharmaceutically acceptable buffer is about 20 mmol/L succinic acid buffer. In some embodiments, the pharmaceutically acceptable buffer is about 25 mmol/L succinic acid buffer. In some embodiments, the pharmaceutically acceptable buffer is about 30 mmol/L succinic acid buffer. In some embodiments, the pharmaceutically acceptable buffer is about 35 mmol/L succinic acid buffer. In some embodiments, the pharmaceutically acceptable buffer is about 40 mmol/L succinic acid buffer. In some embodiments, the pharmaceutically acceptable buffer is about 45 mmol/L succinic acid buffer. In some embodiments, the pharmaceutically acceptable buffer is about 50 mmol/L succinic acid buffer. In some embodiments, the pharmaceutically acceptable buffer is about 55 mmol/L succinic acid buffer. In some embodiments, the pharmaceutically acceptable buffer is about 60 mmol/L succinic acid buffer. In some embodiments, the pharmaceutically acceptable buffer is about 75 mmol/L succinic acid buffer. In some embodiments, the pharmaceutically acceptable buffer is about 80 mmol/L succinic acid buffer. In some embodiments, the pharmaceutically acceptable buffer is about 85 mmol/L succinic acid buffer. In some embodiments, the pharmaceutically acceptable buffer is about 90 mmol/L succinic acid buffer. In some embodiments, the pharmaceutically acceptable buffer is about 95 mmol/L succinic acid buffer. In some embodiments, the pharmaceutically acceptable buffer is about 100 mmol/L succinic acid buffer.

In some embodiments, the pharmaceutically acceptable buffer about 5 mmol/L citrate buffer to about 100 mmol/L citrate buffer. In some embodiments, the pharmaceutically acceptable buffer is about 10 mmol/L to about 70 mmol/L citrate buffer. In some embodiments, the pharmaceutically acceptable buffer is about 10 mmol/L to about 50 mmol/L citrate buffer. In some embodiments, the pharmaceutically acceptable buffer is about 5 mmol/L to about 60 mmol/L citrate buffer. In some embodiments, the pharmaceutically acceptable buffer is about 10 mmol/L to about 40 mmol/L citrate buffer. In some embodiments, the pharmaceutically acceptable buffer is about 15 mmol/L to about 30 mmol/L citrate buffer. In some embodiments, 15 mmol/L to about 25 mmol/L citrate buffer.

In some embodiments, the pharmaceutically acceptable buffer is about 5 mmol/L citrate buffer. In some embodiments, the pharmaceutically acceptable buffer is about 10 mmol/L citrate buffer. In some embodiments, the pharmaceutically acceptable buffer is about 15 mmol/L citrate buffer. In some embodiments, the pharmaceutically acceptable buffer is about 20 mmol/L citrate buffer. In some embodiments, the pharmaceutically acceptable buffer is about 25 mmol/L citrate buffer. In some embodiments, the pharmaceutically acceptable buffer is about 30 mmol/L citrate buffer. In some embodiments, the pharmaceutically acceptable buffer is about 35 mmol/L citrate buffer. In some embodiments, the pharmaceutically acceptable buffer is about 40 mmol/L citrate buffer. In some embodiments, the pharmaceutically acceptable buffer is about 45 mmol/L citrate buffer. In some embodiments, the pharmaceutically acceptable buffer is about 50 mmol/L citrate buffer. In some embodiments, the pharmaceutically acceptable buffer is about 55 mmol/L citrate buffer. In some embodiments, the pharmaceutically acceptable buffer is about 60 mmol/L citrate buffer. In some embodiments, the pharmaceutically acceptable buffer is about 75 mmol/L citrate buffer. In some embodiments, the pharmaceutically acceptable buffer is about 80 mmol/L citrate buffer. In some embodiments, the pharmaceutically acceptable buffer is about 85 mmol/L citrate buffer. In some embodiments, the pharmaceutically acceptable buffer is about 90 mmol/L citrate buffer. In some embodiments, the pharmaceutically acceptable buffer is about 95 mmol/L citrate buffer. In some embodiments, the pharmaceutically acceptable buffer is about 100 mmol/L citrate buffer.

In some embodiments, the pharmaceutically acceptable buffer is about 5 mmol/L ascorbic acid buffer to about 100 mmol/L ascorbic acid buffer. In some embodiments, the pharmaceutically acceptable buffer is about 10 mmol/L to about 70 mmol/L ascorbic acid buffer. In some embodiments, the pharmaceutically acceptable buffer is about 10 mmol/L to about 50 mmol/L ascorbic acid buffer. In some embodiments, the pharmaceutically acceptable buffer is about 5 mmol/L to about 60 mmol/L ascorbic acid buffer. In some embodiments, the pharmaceutically acceptable buffer is about 10 mmol/L to about 40 mmol/L ascorbic acid buffer. In some embodiments, the pharmaceutically acceptable buffer is about 15 mmol/L to about 30 mmol/L ascorbic acid buffer. In some embodiments, 15 mmol/L to about 25 mmol/L ascorbic acid buffer.

In some embodiments, the pharmaceutically acceptable buffer is about 5 mmol/L ascorbic acid buffer. In some embodiments, the pharmaceutically acceptable buffer is about 10 mmol/L ascorbic acid buffer. In some embodiments, the pharmaceutically acceptable buffer is about 15 mmol/L ascorbic acid buffer. In some embodiments, the pharmaceutically acceptable buffer is about 20 mmol/L ascorbic acid buffer. In some embodiments, the pharmaceutically acceptable buffer is about 25 mmol/L ascorbic acid buffer. In some embodiments, the pharmaceutically acceptable buffer is about 30 mmol/L ascorbic acid buffer. In some embodiments, the pharmaceutically acceptable buffer is about 35 mmol/L ascorbic acid buffer. In some embodiments, the pharmaceutically acceptable buffer is about 40 mmol/L ascorbic acid buffer. In some embodiments, the pharmaceutically acceptable buffer is about 45 mmol/L ascorbic acid buffer. In some embodiments, the pharmaceutically acceptable buffer is about 50 mmol/L ascorbic acid buffer. In some embodiments, the pharmaceutically acceptable buffer is about 55 mmol/L ascorbic acid buffer. In some embodiments, the pharmaceutically acceptable buffer is about 60 mmol/L ascorbic acid buffer. In some embodiments, the pharmaceutically acceptable buffer is about 75 mmol/L ascorbic acid buffer. In some embodiments, the pharmaceutically acceptable buffer is about 80 mmol/L ascorbic acid buffer. In some embodiments, the pharmaceutically acceptable buffer is about 85 mmol/L ascorbic acid buffer. In some embodiments, the pharmaceutically acceptable buffer is about 90 mmol/L ascorbic acid buffer. In some embodiments, the pharmaceutically acceptable buffer is about 95 mmol/L ascorbic acid buffer. In some embodiments, the pharmaceutically acceptable buffer is about 100 mmol/L ascorbic acid buffer.

In some embodiments, the pharmaceutically acceptable buffer is about 5 mmol/L glutamic acid buffer to about 100 mmol/L glutamic acid buffer. In some embodiments, the pharmaceutically acceptable buffer is about 10 mmol/L to about 70 mmol/L glutamic acid buffer. In some embodiments, the pharmaceutically acceptable buffer is about 10 mmol/L to about 50 mmol/L glutamic acid buffer. In some embodiments, the pharmaceutically acceptable buffer is about 5 mmol/L to about 60 mmol/L glutamic acid buffer. In some embodiments, the pharmaceutically acceptable buffer is about 10 mmol/L to about 40 mmol/L glutamic acid buffer. In some embodiments, the pharmaceutically acceptable buffer is about 15 mmol/L to about 30 mmol/L glutamic acid buffer. In some embodiments, 15 mmol/L to about 25 mmol/L glutamic acid buffer.

In some embodiments, the pharmaceutically acceptable buffer is about 5 mmol/L glutamic acid buffer. In some embodiments, the pharmaceutically acceptable buffer is about 10 mmol/L glutamic acid buffer. In some embodiments, the pharmaceutically acceptable buffer is about 15 mmol/L glutamic acid buffer. In some embodiments, the pharmaceutically acceptable buffer is about 20 mmol/L glutamic acid buffer. In some embodiments, the pharmaceutically acceptable buffer is about 25 mmol/L glutamic acid buffer. In some embodiments, the pharmaceutically acceptable buffer is about 30 mmol/L glutamic acid buffer. In some embodiments, the pharmaceutically acceptable buffer is about 35 mmol/L glutamic acid buffer. In some embodiments, the pharmaceutically acceptable buffer is about 40 mmol/L glutamic acid buffer. In some embodiments, the pharmaceutically acceptable buffer is about 45 mmol/L glutamic acid buffer. In some embodiments, the pharmaceutically acceptable buffer is about 50 mmol/L glutamic acid buffer. In some embodiments, the pharmaceutically acceptable buffer is about 55 mmol/L glutamic acid buffer. In some embodiments, the pharmaceutically acceptable buffer is about 60 mmol/L glutamic acid buffer. In some embodiments, the pharmaceutically acceptable buffer is about 75 mmol/L glutamic acid buffer. In some embodiments, the pharmaceutically acceptable buffer is about 80 mmol/L glutamic acid buffer. In some embodiments, the pharmaceutically acceptable buffer is about 85 mmol/L glutamic acid buffer. In some embodiments, the pharmaceutically acceptable buffer is about 90 mmol/L glutamic acid buffer. In some embodiments, the pharmaceutically acceptable buffer is about 95 mmol/L glutamic acid buffer. In some embodiments, the pharmaceutically acceptable buffer is about 100 mmol/L glutamic acid buffer.

In some embodiments, the pharmaceutically acceptable buffer is about 5 mmol/L lactic acid buffer to about 100 mmol/L lactic acid buffer. In some embodiments, the pharmaceutically acceptable buffer is about 10 mmol/L to about 70 mmol/L lactic acid buffer. In some embodiments, the pharmaceutically acceptable buffer is about 10 mmol/L to about 50 mmol/L lactic acid buffer. In some embodiments, the pharmaceutically acceptable buffer is about 5 mmol/L to about 60 mmol/L lactic acid buffer. In some embodiments, the pharmaceutically acceptable buffer is about 10 mmol/L to about 40 mmol/L lactic acid buffer. In some embodiments, the pharmaceutically acceptable buffer is about 15 mmol/L to about 30 mmol/L lactic acid buffer. In some embodiments, 15 mmol/L to about 25 mmol/L lactic acid buffer.

In some embodiments, the pharmaceutically acceptable buffer is about 5 mmol/L lactic acid buffer. In some embodiments, the pharmaceutically acceptable buffer is about 10 mmol/L lactic acid buffer. In some embodiments, the pharmaceutically acceptable buffer is about 15 mmol/L lactic acid buffer. In some embodiments, the pharmaceutically acceptable buffer is about 20 mmol/L lactic acid buffer. In some embodiments, the pharmaceutically acceptable buffer is about 25 mmol/L lactic acid buffer. In some embodiments, the pharmaceutically acceptable buffer is about 30 mmol/L lactic acid buffer. In some embodiments, the pharmaceutically acceptable buffer is about 35 mmol/L lactic acid buffer. In some embodiments, the pharmaceutically acceptable buffer is about 40 mmol/L lactic acid buffer. In some embodiments, the pharmaceutically acceptable buffer is about 45 mmol/L lactic acid buffer. In some embodiments, the pharmaceutically acceptable buffer is about 50 mmol/L lactic acid buffer. In some embodiments, the pharmaceutically acceptable buffer is about 55 mmol/L lactic acid buffer. In some embodiments, the pharmaceutically acceptable buffer is about 60 mmol/L lactic acid buffer. In some embodiments, the pharmaceutically acceptable buffer is about 75 mmol/L lactic acid buffer. In some embodiments, the pharmaceutically acceptable buffer is about 80 mmol/L lactic acid buffer. In some embodiments, the pharmaceutically acceptable buffer is about 85 mmol/L lactic acid buffer. In some embodiments, the pharmaceutically acceptable buffer is about 90 mmol/L lactic acid buffer. In some embodiments, the pharmaceutically acceptable buffer is about 95 mmol/L lactic acid buffer. In some embodiments, the pharmaceutically acceptable buffer is about 100 mmol/L lactic acid buffer.

In some embodiments, the pharmaceutically acceptable buffer is about 5 mmol/L maleic acid buffer to about 100 mmol/L maleic acid buffer. In some embodiments, the pharmaceutically acceptable buffer is about 10 mmol/L to about 70 mmol/L maleic acid buffer. In some embodiments, the pharmaceutically acceptable buffer is about 10 mmol/L to about 50 mmol/L maleic acid buffer. In some embodiments, the pharmaceutically acceptable buffer is about 5 mmol/L to about 60 mmol/L maleic acid buffer. In some embodiments, the pharmaceutically acceptable buffer is about 10 mmol/L to about 40 mmol/L maleic acid buffer. In some embodiments, the pharmaceutically acceptable buffer is about 15 mmol/L to about 30 mmol/L maleic acid buffer. In some embodiments, 15 mmol/L to about 25 mmol/L maleic acid buffer.

In some embodiments, the pharmaceutically acceptable buffer is about 5 mmol/L maleic acid buffer. In some embodiments, the pharmaceutically acceptable buffer is about 10 mmol/L maleic acid buffer. In some embodiments, the pharmaceutically acceptable buffer is about 15 mmol/L maleic acid buffer. In some embodiments, the pharmaceutically acceptable buffer is about 20 mmol/L maleic acid buffer. In some embodiments, the pharmaceutically acceptable buffer is about 25 mmol/L maleic acid buffer. In some embodiments, the pharmaceutically acceptable buffer is about 30 mmol/L maleic acid buffer. In some embodiments, the pharmaceutically acceptable buffer is about 35 mmol/L maleic acid buffer. In some embodiments, the pharmaceutically acceptable buffer is about 40 mmol/L maleic acid buffer. In some embodiments, the pharmaceutically acceptable buffer is about 45 mmol/L maleic acid buffer. In some embodiments, the pharmaceutically acceptable buffer is about 50 mmol/L maleic acid buffer. In some embodiments, the pharmaceutically acceptable buffer is about 55 mmol/L maleic acid buffer. In some embodiments, the pharmaceutically acceptable buffer is about 60 mmol/L maleic acid buffer. In some embodiments, the pharmaceutically acceptable buffer is about 75 mmol/L maleic acid buffer. In some embodiments, the pharmaceutically acceptable buffer is about 80 mmol/L maleic acid buffer. In some embodiments, the pharmaceutically acceptable buffer is about 85 mmol/L maleic acid buffer. In some embodiments, the pharmaceutically acceptable buffer is about 90 mmol/L maleic acid buffer. In some embodiments, the pharmaceutically acceptable buffer is about 95 mmol/L maleic acid buffer. In some embodiments, the pharmaceutically acceptable buffer is about 100 mmol/L maleic acid buffer.

In some embodiments, the pharmaceutically acceptable buffer is about 5 mmol/L trometamol buffer to about 100 mmol/L trometamol buffer. In some embodiments, the pharmaceutically acceptable buffer is about 10 mmol/L to about 70 mmol/L trometamol buffer. In some embodiments, the pharmaceutically acceptable buffer is about 10 mmol/L to about 50 mmol/L trometamol buffer. In some embodiments, the pharmaceutically acceptable buffer is about 5 mmol/L to about 60 mmol/L trometamol buffer. In some embodiments, the pharmaceutically acceptable buffer is about 10 mmol/L to about 40 mmol/L trometamol buffer. In some embodiments, the pharmaceutically acceptable buffer is about 15 mmol/L to about 30 mmol/L trometamol buffer. In some embodiments, 15 mmol/L to about 25 mmol/L trometamol buffer.

In some embodiments, the pharmaceutically acceptable buffer is about 5 mmol/L trometamol buffer. In some embodiments, the pharmaceutically acceptable buffer is about 10 mmol/L trometamol buffer. In some embodiments, the pharmaceutically acceptable buffer is about 15 mmol/L trometamol buffer. In some embodiments, the pharmaceutically acceptable buffer is about 20 mmol/L trometamol buffer. In some embodiments, the pharmaceutically acceptable buffer is about 25 mmol/L trometamol buffer. In some embodiments, the pharmaceutically acceptable buffer is about 30 mmol/L trometamol buffer. In some embodiments, the pharmaceutically acceptable buffer is about 35 mmol/L trometamol buffer. In some embodiments, the pharmaceutically acceptable buffer is about 40 mmol/L trometamol buffer. In some embodiments, the pharmaceutically acceptable buffer is about 45 mmol/L trometamol buffer. In some embodiments, the pharmaceutically acceptable buffer is about 50 mmol/L trometamol buffer. In some embodiments, the pharmaceutically acceptable buffer is about 55 mmol/L trometamol buffer. In some embodiments, the pharmaceutically acceptable buffer is about 60 mmol/L trometamol buffer. In some embodiments, the pharmaceutically acceptable buffer is about 75 mmol/L trometamol buffer. In some embodiments, the pharmaceutically acceptable buffer is about 80 mmol/L trometamol buffer. In some embodiments, the pharmaceutically acceptable buffer is about 85 mmol/L trometamol buffer. In some embodiments, the pharmaceutically acceptable buffer is about 90 mmol/L trometamol buffer. In some embodiments, the pharmaceutically acceptable buffer is about 95 mmol/L trometamol buffer. In some embodiments, the pharmaceutically acceptable buffer is about 100 mmol/L trometamol buffer.

In some embodiments, the pharmaceutically acceptable buffer is about 5 mmol/L gluconic acid buffer to about 100 mmol/L gluconic acid buffer. In some embodiments, the pharmaceutically acceptable buffer is about 10 mmol/L to about 70 mmol/L gluconic acid buffer. In some embodiments, the pharmaceutically acceptable buffer is about 10 mmol/L to about 50 mmol/L gluconic acid buffer. In some embodiments, the pharmaceutically acceptable buffer is about 5 mmol/L to about 60 mmol/L gluconic acid buffer. In some embodiments, the pharmaceutically acceptable buffer is about 10 mmol/L to about 40 mmol/L gluconic acid buffer. In some embodiments, the pharmaceutically acceptable buffer is about 15 mmol/L to about 30 mmol/L gluconic acid buffer. In some embodiments, 15 mmol/L to about 25 mmol/L gluconic acid buffer.

In some embodiments, the pharmaceutically acceptable buffer is about 5 mmol/L gluconic acid buffer. In some embodiments, the pharmaceutically acceptable buffer is about 10 mmol/L gluconic acid buffer. In some embodiments, the pharmaceutically acceptable buffer is about 15 mmol/L gluconic acid buffer. In some embodiments, the pharmaceutically acceptable buffer is about 20 mmol/L gluconic acid buffer. In some embodiments, the pharmaceutically acceptable buffer is about 25 mmol/L gluconic acid buffer. In some embodiments, the pharmaceutically acceptable buffer is about 30 mmol/L gluconic acid buffer. In some embodiments, the pharmaceutically acceptable buffer is about 35 mmol/L gluconic acid buffer. In some embodiments, the pharmaceutically acceptable buffer is about 40 mmol/L gluconic acid buffer. In some embodiments, the pharmaceutically acceptable buffer is about 45 mmol/L gluconic acid buffer. In some embodiments, the pharmaceutically acceptable buffer is about 50 mmol/L gluconic acid buffer. In some embodiments, the pharmaceutically acceptable buffer is about 55 mmol/L gluconic acid buffer. In some embodiments, the pharmaceutically acceptable buffer is about 60 mmol/L gluconic acid buffer. In some embodiments, the pharmaceutically acceptable buffer is about 75 mmol/L gluconic acid buffer. In some embodiments, the pharmaceutically acceptable buffer is about 80 mmol/L gluconic acid buffer. In some embodiments, the pharmaceutically acceptable buffer is about 85 mmol/L gluconic acid buffer. In some embodiments, the pharmaceutically acceptable buffer is about 90 mmol/L gluconic acid buffer. In some embodiments, the pharmaceutically acceptable buffer is about 95 mmol/L gluconic acid buffer. In some embodiments, the pharmaceutically acceptable buffer is about 100 mmol/L gluconic acid buffer.

In some embodiments, the pharmaceutically acceptable buffer is about 5 mmol/L acetate buffer to about 100 mmol/L acetate buffer. In some embodiments, the pharmaceutically acceptable buffer is about 10 mmol/L to about 70 mmol/L acetate buffer. In some embodiments, the pharmaceutically acceptable buffer is about 10 mmol/L to about 50 mmol/L acetate buffer. In some embodiments, the pharmaceutically acceptable buffer is about 5 mmol/L to about 60 mmol/L acetate buffer. In some embodiments, the pharmaceutically acceptable buffer is about 10 mmol/L to about 40 mmol/L acetate buffer. In some embodiments, the pharmaceutically acceptable buffer is about 15 mmol/L to about 30 mmol/L acetate buffer. In some embodiments, 15 mmol/L to about 25 mmol/L acetate buffer.

In some embodiments, the pharmaceutically acceptable buffer is about 5 mmol/L acetate buffer. In some embodiments, the pharmaceutically acceptable buffer is about 10 mmol/L acetate buffer. In some embodiments, the pharmaceutically acceptable buffer is about 15 mmol/L acetate buffer. In some embodiments, the pharmaceutically acceptable buffer is about 20 mmol/L acetate buffer. In some embodiments, the pharmaceutically acceptable buffer is about 25 mmol/L acetate buffer. In some embodiments, the pharmaceutically acceptable buffer is about 30 mmol/L acetate buffer. In some embodiments, the pharmaceutically acceptable buffer is about 35 mmol/L acetate buffer. In some embodiments, the pharmaceutically acceptable buffer is about 40 mmol/L acetate buffer. In some embodiments, the pharmaceutically acceptable buffer is about 45 mmol/L acetate buffer. In some embodiments, the pharmaceutically acceptable buffer is about 50 mmol/L acetate buffer. In some embodiments, the pharmaceutically acceptable buffer is about 55 mmol/L acetate buffer. In some embodiments, the pharmaceutically acceptable buffer is about 60 mmol/L acetate buffer. In some embodiments, the pharmaceutically acceptable buffer is about 75 mmol/L acetate buffer. In some embodiments, the pharmaceutically acceptable buffer is about 80 mmol/L acetate buffer. In some embodiments, the pharmaceutically acceptable buffer is about 85 mmol/L acetate buffer. In some embodiments, the pharmaceutically acceptable buffer is about 90 mmol/L acetate buffer. In some embodiments, the pharmaceutically acceptable buffer is about 95 mmol/L acetate buffer. In some embodiments, the pharmaceutically acceptable buffer is about 100 mmol/L acetate buffer.

In some embodiments, the pharmaceutical composition comprises a pharmaceutically acceptable buffer, wherein the pharmaceutically acceptable buffer is an acetate buffer, wherein the acetate buffer can be, but is not limited to, sodium acetate, potassium acetate, or magnesium acetate, or any combination thereof. In some embodiments, the pharmaceutical composition comprises a sodium acetate buffer. In some embodiments, the pharmaceutical composition comprises a potassium acetate buffer. In some embodiments, the pharmaceutical composition comprises a magnesium acetate buffer.

In some embodiments, the pharmaceutically acceptable buffer is about 5 mmol/L potassium acetate buffer to about 100 mmol/L potassium acetate buffer. In some embodiments, the pharmaceutically acceptable buffer is about 10 mmol/L to about 70 mmol/L potassium acetate buffer. In some embodiments, the pharmaceutically acceptable buffer is about 10 mmol/L to about 50 mmol/L potassium acetate buffer. In some embodiments, the pharmaceutically acceptable buffer is about 5 mmol/L to about 60 mmol/L potassium acetate buffer. In some embodiments, the pharmaceutically acceptable buffer is about 10 mmol/L to about 40 mmol/L potassium acetate buffer. In some embodiments, the pharmaceutically acceptable buffer is about 15 mmol/L to about 30 mmol/L potassium acetate buffer. In some embodiments, 15 mmol/L to about 25 mmol/L potassium acetate buffer.

In some embodiments, the pharmaceutically acceptable buffer is about 5 mmol/L potassium acetate buffer. In some embodiments, the pharmaceutically acceptable buffer is about 10 mmol/L potassium acetate buffer. In some embodiments, the pharmaceutically acceptable buffer is about 15 mmol/L potassium acetate buffer. In some embodiments, the pharmaceutically acceptable buffer is about 20 mmol/L potassium acetate buffer. In some embodiments, the pharmaceutically acceptable buffer is about 25 mmol/L potassium acetate buffer. In some embodiments, the pharmaceutically acceptable buffer is about 30 mmol/L potassium acetate buffer. In some embodiments, the pharmaceutically acceptable buffer is about 35 mmol/L potassium acetate buffer. In some embodiments, the pharmaceutically acceptable buffer is about 40 mmol/L potassium acetate buffer. In some embodiments, the pharmaceutically acceptable buffer is about 45 mmol/L potassium acetate buffer. In some embodiments, the pharmaceutically acceptable buffer is about 50 mmol/L potassium acetate buffer. In some embodiments, the pharmaceutically acceptable buffer is about 55 mmol/L potassium acetate buffer. In some embodiments, the pharmaceutically acceptable buffer is about 60 mmol/L potassium acetate buffer. In some embodiments, the pharmaceutically acceptable buffer is about 75 mmol/L potassium acetate buffer. In some embodiments, the pharmaceutically acceptable buffer is about 80 mmol/L potassium acetate buffer. In some embodiments, the pharmaceutically acceptable buffer is about 85 mmol/L potassium acetate buffer. In some embodiments, the pharmaceutically acceptable buffer is about 90 mmol/L potassium acetate buffer. In some embodiments, the pharmaceutically acceptable buffer is about 95 mmol/L potassium acetate buffer. In some embodiments, the pharmaceutically acceptable buffer is about 100 mmol/L potassium acetate buffer.

In some embodiments, the pharmaceutically acceptable buffer is about 5 mmol/L magnesium acetate buffer to about 100 mmol/L magnesium acetate buffer. In some embodiments, the pharmaceutically acceptable buffer is about 10 mmol/L to about 70 mmol/L magnesium acetate buffer. In some embodiments, the pharmaceutically acceptable buffer is about 10 mmol/L to about 50 mmol/L magnesium acetate buffer. In some embodiments, the pharmaceutically acceptable buffer is about 5 mmol/L to about 60 mmol/L magnesium acetate buffer. In some embodiments, the pharmaceutically acceptable buffer is about 10 mmol/L to about 40 mmol/L magnesium acetate buffer. In some embodiments, the pharmaceutically acceptable buffer is about 15 mmol/L to about 30 mmol/L magnesium acetate buffer. In some embodiments, 15 mmol/L to about 25 mmol/L magnesium acetate buffer.

In some embodiments, the pharmaceutically acceptable buffer is about 5 mmol/L magnesium acetate buffer. In some embodiments, the pharmaceutically acceptable buffer is about 10 mmol/L magnesium acetate buffer. In some embodiments, the pharmaceutically acceptable buffer is about 15 mmol/L magnesium acetate buffer. In some embodiments, the pharmaceutically acceptable buffer is about 20 mmol/L magnesium acetate buffer. In some embodiments, the pharmaceutically acceptable buffer is about 25 mmol/L magnesium acetate buffer. In some embodiments, the pharmaceutically acceptable buffer is about 30 mmol/L magnesium acetate buffer. In some embodiments, the pharmaceutically acceptable buffer is about 35 mmol/L magnesium acetate buffer. In some embodiments, the pharmaceutically acceptable buffer is about 40 mmol/L magnesium acetate buffer. In some embodiments, the pharmaceutically acceptable buffer is about 45 mmol/L magnesium acetate buffer. In some embodiments, the pharmaceutically acceptable buffer is about 50 mmol/L magnesium acetate buffer. In some embodiments, the pharmaceutically acceptable buffer is about 55 mmol/L magnesium acetate buffer. In some embodiments, the pharmaceutically acceptable buffer is about 60 mmol/L magnesium acetate buffer. In some embodiments, the pharmaceutically acceptable buffer is about 75 mmol/L magnesium acetate buffer. In some embodiments, the pharmaceutically acceptable buffer is about 80 mmol/L magnesium acetate buffer. In some embodiments, the pharmaceutically acceptable buffer is about 85 mmol/L magnesium acetate buffer. In some embodiments, the pharmaceutically acceptable buffer is about 90 mmol/L magnesium acetate buffer. In some embodiments, the pharmaceutically acceptable buffer is about 95 mmol/L magnesium acetate buffer. In some embodiments, the pharmaceutically acceptable buffer is about 100 mmol/L magnesium acetate buffer.

In some embodiments, the pharmaceutically acceptable buffer is about 5 mmol/L sodium acetate buffer to about 100 mmol/L sodium acetate buffer. In some embodiments, the pharmaceutically acceptable buffer is about 10 mmol/L to about 70 mmol/L sodium acetate buffer. In some embodiments, the pharmaceutically acceptable buffer is about 10 mmol/L to about 50 mmol/L sodium acetate buffer. In some embodiments, the pharmaceutically acceptable buffer is about 5 mmol/L to about 60 mmol/L sodium acetate buffer. In some embodiments, the pharmaceutically acceptable buffer is about 10 mmol/L to about 40 mmol/L sodium acetate buffer. In some embodiments, the pharmaceutically acceptable buffer is about 15 mmol/L to about 30 mmol/L sodium acetate buffer. In some embodiments, 15 mmol/L to about 25 mmol/L sodium acetate buffer.

In some embodiments, the pharmaceutically acceptable buffer is about 5 mmol/L sodium acetate buffer. In some embodiments, the pharmaceutically acceptable buffer is about 10 mmol/L sodium acetate buffer. In some embodiments, the pharmaceutically acceptable buffer is about 15 mmol/L sodium acetate buffer. In some embodiments, the pharmaceutically acceptable buffer is about 20 mmol/L sodium acetate buffer. In some embodiments, the pharmaceutically acceptable buffer is about 25 mmol/L sodium acetate buffer. In some embodiments, the pharmaceutically acceptable buffer is about 30 mmol/L sodium acetate buffer. In some embodiments, the pharmaceutically acceptable buffer is about 35 mmol/L sodium acetate buffer. In some embodiments, the pharmaceutically acceptable buffer is about 40 mmol/L sodium acetate buffer. In some embodiments, the pharmaceutically acceptable buffer is about 45 mmol/L sodium acetate buffer. In some embodiments, the pharmaceutically acceptable buffer is about 50 mmol/L sodium acetate buffer. In some embodiments, the pharmaceutically acceptable buffer is about 55 mmol/L sodium acetate buffer. In some embodiments, the pharmaceutically acceptable buffer is about 60 mmol/L sodium acetate buffer. In some embodiments, the pharmaceutically acceptable buffer is about 75 mmol/L sodium acetate buffer. In some embodiments, the pharmaceutically acceptable buffer is about 80 mmol/L sodium acetate buffer. In some embodiments, the pharmaceutically acceptable buffer is about 85 mmol/L sodium acetate buffer. In some embodiments, the pharmaceutically acceptable buffer is about 90 mmol/L sodium acetate buffer. In some embodiments, the pharmaceutically acceptable buffer is about 95 mmol/L sodium acetate buffer. In some embodiments, the pharmaceutically acceptable buffer is about 100 mmol/L sodium acetate buffer.

In some embodiments, the pharmaceutically acceptable buffer is about 5 mmol/L succinate buffer to about 100 mmol/L succinate buffer. In some embodiments, the pharmaceutically acceptable buffer is about 10 mmol/L to about 70 mmol/L succinate buffer. In some embodiments, the pharmaceutically acceptable buffer is about 10 mmol/L to about 50 mmol/L succinate buffer. In some embodiments, the pharmaceutically acceptable buffer is about 5 mmol/L to about 60 mmol/L succinate buffer. In some embodiments, the pharmaceutically acceptable buffer is about 10 mmol/L to about 40 mmol/L succinate buffer. In some embodiments, the pharmaceutically acceptable buffer is about 15 mmol/L to about 30 mmol/L succinate buffer. In some embodiments, 15 mmol/L to about 25 mmol/L succinate buffer.

In some embodiments, the pharmaceutically acceptable buffer is about 5 mmol/L succinate buffer. In some embodiments, the pharmaceutically acceptable buffer is about 10 mmol/L succinate buffer. In some embodiments, the pharmaceutically acceptable buffer is about 15 mmol/L succinate buffer. In some embodiments, the pharmaceutically acceptable buffer is about 20 mmol/L succinate buffer. In some embodiments, the pharmaceutically acceptable buffer is about 25 mmol/L succinate buffer. In some embodiments, the pharmaceutically acceptable buffer is about 30 mmol/L succinate buffer. In some embodiments, the pharmaceutically acceptable buffer is about 35 mmol/L succinate buffer. In some embodiments, the pharmaceutically acceptable buffer is about 40 mmol/L succinate buffer. In some embodiments, the pharmaceutically acceptable buffer is about 45 mmol/L succinate buffer. In some embodiments, the pharmaceutically acceptable buffer is about 50 mmol/L succinate buffer. In some embodiments, the pharmaceutically acceptable buffer is about 55 mmol/L succinate buffer. In some embodiments, the pharmaceutically acceptable buffer is about 60 mmol/L succinate buffer. In some embodiments, the pharmaceutically acceptable buffer is about 75 mmol/L succinate buffer. In some embodiments, the pharmaceutically acceptable buffer is about 80 mmol/L succinate buffer. In some embodiments, the pharmaceutically acceptable buffer is about 85 mmol/L succinate buffer. In some embodiments, the pharmaceutically acceptable buffer is about 90 mmol/L succinate buffer. In some embodiments, the pharmaceutically acceptable buffer is about 95 mmol/L succinate buffer. In some embodiments, the pharmaceutically acceptable buffer is about 100 mmol/L succinate buffer.

In some embodiments, the succinate buffer is about 5 mmol/L sodium succinate buffer to about 100 mmol/L sodium succinate buffer. In some embodiments, the pharmaceutically acceptable buffer is about 10 mmol/L to about 70 mmol/L sodium succinate buffer. In some embodiments, the pharmaceutically acceptable buffer is about 10 mmol/L to about 50 mmol/L sodium succinate buffer. In some embodiments, the pharmaceutically acceptable buffer is about 5 mmol/L to about 60 mmol/L sodium succinate buffer. In some embodiments, the pharmaceutically acceptable buffer is about 10 mmol/L to about 40 mmol/L sodium succinate buffer. In some embodiments, the pharmaceutically acceptable buffer is about 15 mmol/L to about 30 mmol/L sodium succinate buffer. In some embodiments, 15 mmol/L to about 25 mmol/L sodium succinate buffer.

In some embodiments, the pharmaceutically acceptable buffer is about 5 mmol/L sodium succinate buffer. In some embodiments, the pharmaceutically acceptable buffer is about 10 mmol/L sodium succinate buffer. In some embodiments, the pharmaceutically acceptable buffer is about 15 mmol/L sodium succinate buffer. In some embodiments, the pharmaceutically acceptable buffer is about 20 mmol/L sodium succinate buffer. In some embodiments, the pharmaceutically acceptable buffer is about 25 mmol/L sodium succinate buffer. In some embodiments, the pharmaceutically acceptable buffer is about 30 mmol/L sodium succinate buffer. In some embodiments, the pharmaceutically acceptable buffer is about 35 mmol/L sodium succinate buffer. In some embodiments, the pharmaceutically acceptable buffer is about 40 mmol/L sodium succinate buffer. In some embodiments, the pharmaceutically acceptable buffer is about 45 mmol/L sodium succinate buffer. In some embodiments, the pharmaceutically acceptable buffer is about 50 mmol/L sodium succinate buffer. In some embodiments, the pharmaceutically acceptable buffer is about 55 mmol/L sodium succinate buffer. In some embodiments, the pharmaceutically acceptable buffer is about 60 mmol/L sodium succinate buffer. In some embodiments, the pharmaceutically acceptable buffer is about 75 mmol/L sodium succinate buffer. In some embodiments, the pharmaceutically acceptable buffer is about 80 mmol/L sodium succinate buffer. In some embodiments, the pharmaceutically acceptable buffer is about 85 mmol/L sodium succinate buffer. In some embodiments, the pharmaceutically acceptable buffer is about 90 mmol/L sodium succinate buffer. In some embodiments, the pharmaceutically acceptable buffer is about 95 mmol/L sodium succinate buffer. In some embodiments, the pharmaceutically acceptable buffer is about 100 mmol/L sodium succinate buffer.

In some embodiments, the pharmaceutically acceptable buffer is about 5 mmol/L phosphate buffer to about 100 mmol/L phosphate buffer. In some embodiments, the pharmaceutically acceptable buffer is about 10 mmol/L to about 70 mmol/L phosphate buffer. In some embodiments, the pharmaceutically acceptable buffer is about 10 mmol/L to about 50 mmol/L phosphate buffer. In some embodiments, the pharmaceutically acceptable buffer is about 5 mmol/L to about 60 mmol/L phosphate buffer. In some embodiments, the pharmaceutically acceptable buffer is about 10 mmol/L to about 40 mmol/L phosphate buffer. In some embodiments, the pharmaceutically acceptable buffer is about 15 mmol/L to about 30 mmol/L phosphate buffer. In some embodiments, 15 mmol/L to about 25 mmol/L phosphate buffer.

In some embodiments, the pharmaceutically acceptable buffer is about 5 mmol/L phosphate buffer. In some embodiments, the pharmaceutically acceptable buffer is about 10 mmol/L phosphate buffer. In some embodiments, the pharmaceutically acceptable buffer is about 15 mmol/L phosphate buffer. In some embodiments, the pharmaceutically acceptable buffer is about 20 mmol/L phosphate buffer. In some embodiments, the pharmaceutically acceptable buffer is about 25 mmol/L phosphate buffer. In some embodiments, the pharmaceutically acceptable buffer is about 30 mmol/L phosphate buffer. In some embodiments, the pharmaceutically acceptable buffer is about 35 mmol/L phosphate buffer. In some embodiments, the pharmaceutically acceptable buffer is about 40 mmol/L phosphate buffer. In some embodiments, the pharmaceutically acceptable buffer is about 45 mmol/L phosphate buffer. In some embodiments, the pharmaceutically acceptable buffer is about 50 mmol/L phosphate buffer. In some embodiments, the pharmaceutically acceptable buffer is about 55 mmol/L phosphate buffer. In some embodiments, the pharmaceutically acceptable buffer is about 60 mmol/L phosphate buffer. In some embodiments, the pharmaceutically acceptable buffer is about 75 mmol/L phosphate buffer. In some embodiments, the pharmaceutically acceptable buffer is about 80 mmol/L phosphate buffer. In some embodiments, the pharmaceutically acceptable buffer is about 85 mmol/L phosphate buffer. In some embodiments, the pharmaceutically acceptable buffer is about 90 mmol/L phosphate buffer. In some embodiments, the pharmaceutically acceptable buffer is about 95 mmol/L phosphate buffer. In some embodiments, the pharmaceutically acceptable buffer is about 100 mmol/L phosphate buffer.

In some embodiments, the phosphate buffer is sodium phosphate. In some embodiments, the pharmaceutically acceptable buffer is about 5 mmol/L sodium phosphate buffer to about 100 mmol/L sodium phosphate buffer. In some embodiments, the pharmaceutically acceptable buffer is about 10 mmol/L to about 70 mmol/L sodium phosphate buffer. In some embodiments, the pharmaceutically acceptable buffer is about 10 mmol/L to about 50 mmol/L sodium phosphate buffer. In some embodiments, the pharmaceutically acceptable buffer is about 5 mmol/L to about 60 mmol/L sodium phosphate buffer. In some embodiments, the pharmaceutically acceptable buffer is about 10 mmol/L to about 40 mmol/L sodium phosphate buffer. In some embodiments, the pharmaceutically acceptable buffer is about 15 mmol/L to about 30 mmol/L sodium phosphate buffer. In some embodiments, 15 mmol/L to about 25 mmol/L sodium phosphate buffer.

In some embodiments, the pharmaceutically acceptable buffer is about 5 mmol/L sodium phosphate buffer. In some embodiments, the pharmaceutically acceptable buffer is about 10 mmol/L sodium phosphate buffer. In some embodiments, the pharmaceutically acceptable buffer is about 15 mmol/L sodium phosphate buffer. In some embodiments, the pharmaceutically acceptable buffer is about 20 mmol/L sodium phosphate buffer. In some embodiments, the pharmaceutically acceptable buffer is about 25 mmol/L sodium phosphate buffer. In some embodiments, the pharmaceutically acceptable buffer is about 30 mmol/L sodium phosphate buffer. In some embodiments, the pharmaceutically acceptable buffer is about 35 mmol/L sodium phosphate buffer. In some embodiments, the pharmaceutically acceptable buffer is about 40 mmol/L sodium phosphate buffer. In some embodiments, the pharmaceutically acceptable buffer is about 45 mmol/L sodium phosphate buffer. In some embodiments, the pharmaceutically acceptable buffer is about 50 mmol/L sodium phosphate buffer. In some embodiments, the pharmaceutically acceptable buffer is about 55 mmol/L sodium phosphate buffer. In some embodiments, the pharmaceutically acceptable buffer is about 60 mmol/L sodium phosphate buffer. In some embodiments, the pharmaceutically acceptable buffer is about 75 mmol/L sodium phosphate buffer. In some embodiments, the pharmaceutically acceptable buffer is about 80 mmol/L sodium phosphate buffer. In some embodiments, the pharmaceutically acceptable buffer is about 85 mmol/L sodium phosphate buffer. In some embodiments, the pharmaceutically acceptable buffer is about 90 mmol/L sodium phosphate buffer. In some embodiments, the pharmaceutically acceptable buffer is about 95 mmol/L sodium phosphate buffer. In some embodiments, the pharmaceutically acceptable buffer is about 100 mmol/L sodium phosphate buffer.

In some embodiments, the pharmaceutically acceptable buffer is about 5 mmol/L to about 100 mmol/L histidine buffer. In some embodiments, the pharmaceutically acceptable buffer is about 10 mmol/L to about 70 mmol/L histidine buffer. In some embodiments, the pharmaceutically acceptable buffer is about 10 mmol/L to about 50 mmol/L histidine buffer. In some embodiments, the pharmaceutically acceptable buffer is about 5 mmol/L to about 60 mmol/L histidine buffer. In some embodiments, the pharmaceutically acceptable buffer is about 10 mmol/L to about 40 mmol/L histidine buffer. In some embodiments, the pharmaceutically acceptable buffer is about 15 mmol/L to about 30 mmol/L histidine buffer. In some embodiments, 15 mmol/L to about 25 mmol/L histidine buffer.

In some embodiments, the pharmaceutically acceptable buffer is about 5 mmol/L histidine buffer. In some embodiments, the pharmaceutically acceptable buffer is about 10 mmol/L histidine buffer. In some embodiments, the pharmaceutically acceptable buffer is about 15 mmol/L histidine buffer. In some embodiments, the pharmaceutically acceptable buffer is about 20 mmol/L histidine buffer. In some embodiments, the pharmaceutically acceptable buffer is about 25 mmol/L histidine buffer. In some embodiments, the pharmaceutically acceptable buffer is about 30 mmol/L histidine buffer. In some embodiments, the pharmaceutically acceptable buffer is about 35 mmol/L histidine buffer. In some embodiments, the pharmaceutically acceptable buffer is about 40 mmol/L histidine buffer. In some embodiments, the pharmaceutically acceptable buffer is about 45 mmol/L histidine buffer. In some embodiments, the pharmaceutically acceptable buffer is about 50 mmol/L histidine buffer. In some embodiments, the pharmaceutically acceptable buffer is about 55 mmol/L histidine buffer. In some embodiments, the pharmaceutically acceptable buffer is about 60 mmol/L histidine buffer. In some embodiments, the pharmaceutically acceptable buffer is about 75 mmol/L histidine buffer. In some embodiments, the pharmaceutically acceptable buffer is about 80 mmol/L histidine buffer. In some embodiments, the pharmaceutically acceptable buffer is about 85 mmol/L histidine buffer. In some embodiments, the pharmaceutically acceptable buffer is about 90 mmol/L histidine buffer. In some embodiments, the pharmaceutically acceptable buffer is about 95 mmol/L histidine buffer. In some embodiments, the pharmaceutically acceptable buffer is about 100 mmol/L histidine buffer.

One of the major stresses that proteins (e.g., antibodies) may encounter is interfacial stress (e.g., from air/water interfaces in liquid compositions, or ice/water interfaces during freezing/thawing). Surfactants are typically used to stabilize proteins in biopharmaceutical compositions while under stress or long-term storage to prevent or minimize aggregation and/or particle formation. Examples of a surfactant include, but are not limited to, anionic surfactants (e.g., ammonium lauryl sulfate, sodium lauryl sulfate, sodium laureth sulfate, sodium myreth sulfate, diocytl sodium sulfosuccinate, perfluorooctanesulfonate, perfluorobutanesulfonate, alkyl-aryl ether phosphates, alkyl ether phosphates, carboxylates, sodium lauroyl sarcosinate, perfluorononanoate, perfluorooctanoate); cationic surfactants (e.g., octenidine dihydrochloride, cetrimonium bromide, cetylpyridinium chloride, benzalkonium chloride, benzethonium chloride, dimethyldioctadecylammonium chloride, and dioctadecyldimethylammonium bromide); zwitterionic (amphoteric) surfactants (e.g., 3-[(3-cholamidopropyl)dimethylammonio]-1-propanesulfonate, cocamidopropyl hydroxysultaine, phosphatidylserine, phosphatidylethanolamine, phosphatidylcholine, sphingomyelins, lauryldimethylamine oxide and myristamine oxide); non-ionic surfactants (e.g., polysorbates or Brij series); ethoxylates (e.g., fatty alcohol ethoxylate (e.g., octaethylene glycol monododecyl ether and pentaethylene glycol monododecyl ether), alkylphenolethoxylates (e.g., nonoxynols and Triton X-100); fatty acid ethoxylates, ethoxylated amines and/or fatty acid amides (e.g., poly ethoxylated tallow amine, cocamide monoethanol amine, and cocamide diethanolamine); terminally blocked ethoxylates (e.g., pol oxamers); fatty acid esters of polyhydroxy compounds; fatty acid esters of glycerol (e.g., glycerol monostearate and glycerol monolaurate); fatty acid esters of sorbitol (e.g., Spans such as sorbitan monolaurate, sorbitan monostearate, and sorbitan tristearate, and Tweens such as Tween 20, Tween 40, Tween 60, and Tween 80); fatty acid esters of sucrose; alkyl poly glucosides (e.g., decyl glucoside, lauryl glucoside, and octyl glucoside); of a combination thereof.

In some embodiments, the pharmaceutical composition comprises a surfactant, wherein the surfactant is a polysorbate or a poloxamer.

In some embodiments, the pharmaceutical composition comprises a polysorbate, wherein the polysorbate is polysorbate 20 (PS20) or polysorbate 80 (PS80).

PS80 is also known as polyoxyethylene (20) sorbitan monooleate, and is represented by the formula:

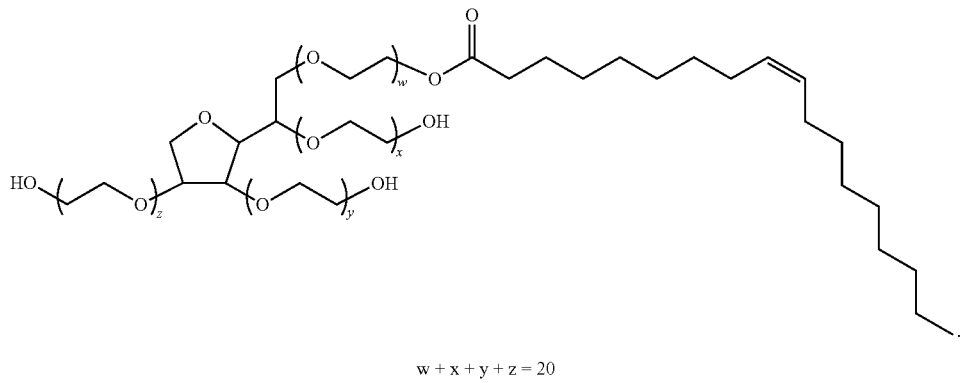

w + x + y + z = 20

PS20 is also known as polyoxyethylene (20) sorbitan monolaurate, and is represented by the formula:

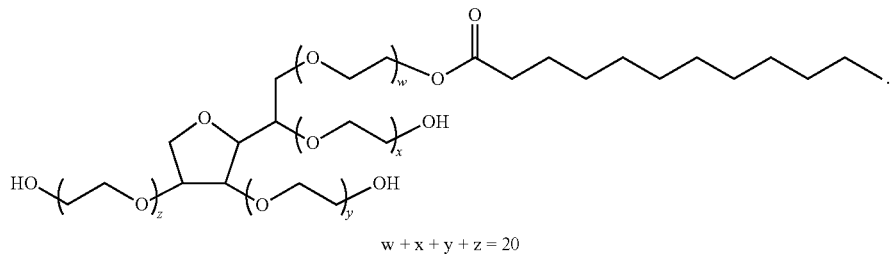

w + x + y + z = 20

In some embodiments, the surfactant is a poloxamer. Poloxamers are nonionic triblock copolymers composed of a central hydrophobic chain of polyoxypropylene (polypropylene oxide) flanked by two hydrophilic chains of polyoxyethylene (poly(ethylene oxide)). In some embodiments, the pharmaceutical composition comprises a poloxamer, wherein the poloxamer is poloxamer 188, poloxamer 407, poloxamer 184, poloxamer 124, or a combination thereof. In some embodiments, the pharmaceutical composition comprises poloxamer 188. In some embodiments, the pharmaceutical composition comprises poloxamer 407. In some embodiments, the pharmaceutical composition comprises poloxamer 184. In some embodiments, the pharmaceutical composition comprises poloxamer 124.

In some embodiments, the pharmaceutical composition comprises a surfactant, wherein the surfactant is present at a concentration of about 0.001% (w/v) to about 1% (w/v). In some embodiments, the pharmaceutical composition comprises a surfactant, wherein the surfactant is present at a concentration of about 0.01% (w/v) to about 0.5% (w/v). In some embodiments, the pharmaceutical composition comprises a surfactant, wherein the surfactant is present at a concentration of about 0.01% (w/v) to about 0.1% (w/v). In some embodiments, the pharmaceutical composition comprises a surfactant, wherein the surfactant is present at a concentration of about 0.02% (w/v) to about 0.05% (w/v).

In some embodiments, the pharmaceutical composition comprises a surfactant, wherein the surfactant is present at a concentration of about 0.01% (w/v). In some embodiments, the pharmaceutical composition comprises a surfactant, wherein the surfactant is present at a concentration of about 0.02% (w/v). In some embodiments, the pharmaceutical composition comprises a surfactant, wherein the surfactant is present at a concentration of about 0.03% (w/v). In some embodiments, the pharmaceutical composition comprises a surfactant, wherein the surfactant is present at a concentration of about 0.04% (w/v). In some embodiments, the pharmaceutical composition comprises a surfactant, wherein the surfactant is present at a concentration of about 0.05% (w/v). In some embodiments, the pharmaceutical composition comprises a surfactant, wherein the surfactant is present at a concentration of about 0.1% (w/v). In some embodiments, the pharmaceutical composition comprises a surfactant, wherein the surfactant is present at a concentration of about 0.15% (w/v). In some embodiments, the pharmaceutical composition comprises a surfactant, wherein the surfactant is present at a concentration of about 0.2% (w/v).

In some embodiments, PS20 is present at a concentration of about 0.01% (w/v). In some embodiments, PS20 is present at a concentration of about 0.02% (w/v). In some embodiments, PS20 is present at a concentration of about 0.03% (w/v). In some embodiments, PS20 is present at a concentration of about 0.04% (w/v). In some embodiments, PS20 is present at a concentration of about 0.05% (w/v). In some embodiments, PS20 is present at a concentration of about 0.05% (w/v). In some embodiments, PS20 is present at a concentration of about 0.1% (w/v). In some embodiments, PS20 is present at a concentration of about 0.15% (w/v). In some embodiments, PS20 is present at a concentration of about 0.2% (w/v).

In some embodiments, PS80 is present at a concentration of about 0.01% (w/v). In some embodiments, PS80 is present at a concentration of about 0.02% (w/v). In some embodiments, PS80 is present at a concentration of about 0.03% (w/v). In some embodiments, PS80 is present at a concentration of about 0.04% (w/v). In some embodiments, PS80 is present at a concentration of about 0.05% (w/v). In some embodiments, PS80 is present at a concentration of about 0.1% (w/v). In some embodiments, PS80 is present at a concentration of about 0.15% (w/v). In some embodiments, PS80 is present at a concentration of about 0.2% (w/v).

In some embodiments, poloxamer 188 is present at a concentration of about 0.01% (w/v). In some embodiments, poloxamer 188 is present at a concentration of about 0.02% (w/v). In some embodiments, poloxamer 188 is present at a concentration of about 0.03% (w/v). In some embodiments, poloxamer 188 is present at a concentration of about 0.04% (w/v). In some embodiments, poloxamer 188 is present at a concentration of about 0.05% (w/v). In some embodiments, poloxamer 188 is present at a concentration of about 0.05% (w/v). In some embodiments, poloxamer 188 is present at a concentration of about 0.1% (w/v). In some embodiments, poloxamer 188 is present at a concentration of about 0.15% (w/v). In some embodiments, poloxamer 188 is present at a concentration of about 0.2% (w/v).

In some embodiments, poloxamer 407 is present at a concentration of about 0.01% (w/v). In some embodiments, poloxamer 407 is present at a concentration of about 0.02% (w/v). In some embodiments, poloxamer 407 is present at a concentration of about 0.03% (w/v). In some embodiments, poloxamer 407 is present at a concentration of about 0.04% (w/v). In some embodiments, poloxamer 407 is present at a concentration of about 0.05% (w/v). In some embodiments, poloxamer 407 is present at a concentration of about 0.05% (w/v). In some embodiments, poloxamer 407 is present at a concentration of about 0.1% (w/v). In some embodiments, poloxamer 407 is present at a concentration of about 0.15% (w/v). In some embodiments, poloxamer 407 is present at a concentration of about 0.2% (w/v).

In some embodiments, poloxamer 184 is present at a concentration of about 0.01% (w/v). In some embodiments, poloxamer 184 is present at a concentration of about 0.02% (w/v). In some embodiments, poloxamer 184 is present at a concentration of about 0.03% (w/v). In some embodiments, poloxamer 184 is present at a concentration of about 0.04% (w/v). In some embodiments, poloxamer 184 is present at a concentration of about 0.05% (w/v). In some embodiments, poloxamer 184 is present at a concentration of about 0.05% (w/v). In some embodiments, poloxamer 184 is present at a concentration of about 0.1% (w/v). In some embodiments, poloxamer 184 is present at a concentration of about 0.15% (w/v). In some embodiments, poloxamer 184 is present at a concentration of about 0.2% (w/v).

In some embodiments, poloxamer 124 is present at a concentration of about 0.01% (w/v). In some embodiments, poloxamer 124 is present at a concentration of about 0.02% (w/v). In some embodiments, poloxamer 124 is present at a concentration of about 0.03% (w/v). In some embodiments, poloxamer 124 is present at a concentration of about 0.04% (w/v). In some embodiments, poloxamer 124 is present at a concentration of about 0.05% (w/v). In some embodiments, poloxamer 124 is present at a concentration of about 0.05% (w/v). In some embodiments, poloxamer 124 is present at a concentration of about 0.1% (w/v). In some embodiments, poloxamer 124 is present at a concentration of about 0.15% (w/v). In some embodiments, poloxamer 124 is present at a concentration of about 0.2% (w/v).

In some embodiments, the pharmaceutical composition comprises an excipient. In some embodiments, the pharmaceutical composition comprises an excipient, wherein the excipient is present at a concentration of about 1 mmol/L to about 600 mmol/L. In some embodiments, the pharmaceutical composition comprises an excipient, wherein the excipient is present at a concentration of about 1 mmol/L to about 300 mmol/L. In some embodiments, the pharmaceutical composition comprises an excipient, wherein the excipient is present at a concentration of about 50 mmol/L to about 300 mmol/L. In some embodiments, the pharmaceutical composition comprises an excipient, wherein the excipient is present at a concentration of about 100 mmol/L to about 300 mmol/L. In some embodiments, the pharmaceutical composition comprises an excipient, wherein the excipient is present at a concentration of about 100 mmol/L to about 250 mmol/L. In some embodiments, the pharmaceutical composition comprises an excipient, wherein the excipient is present at a concentration of about 100 mmol/L to about 220 mmol/L. In some embodiments, the pharmaceutical composition comprises an excipient, wherein the excipient is present at a concentration of about 110 mmol/L to about 220 mmol/L. In some embodiments, the pharmaceutical composition comprises an excipient, wherein the excipient is present at a concentration of about 120 mmol/L to about 220 mmol/L. In some embodiments, the pharmaceutical composition comprises an excipient, wherein the excipient is present at a concentration of about 130 mmol/L to about 220 mmol/L. In some embodiments, the pharmaceutical composition comprises an excipient, wherein the excipient is present at a concentration of about 140 mmol/L to about 220 mmol/L. In some embodiments, the pharmaceutical composition comprises an excipient, wherein the excipient is present at a concentration of about 150 mmol/L to about 220 mmol/L. In some embodiments, the pharmaceutical composition comprises an excipient, wherein the excipient is present at a concentration of about 160 mmol/L to about 220 mmol/L. In some embodiments, the pharmaceutical composition comprises an excipient, wherein the excipient is present at a concentration of about 170 mmol/L to about 220 mmol/L. In some embodiments, the pharmaceutical composition comprises an excipient, wherein the excipient is present at a concentration of about 180 mmol/L to about 220 mmol/L. In some embodiments, the pharmaceutical composition comprises an excipient, wherein the excipient is present at a concentration of about 190 mmol/L to about 210 mmol/L. In some embodiments, the pharmaceutical composition comprises an excipient, wherein the excipient is present at a concentration of about 200 mmol/L.

In some embodiments, the pharmaceutical composition comprises an excipient, wherein the excipient is present at a concentration of about 100 mmol/L to about 200 mmol/L. In some embodiments, the pharmaceutical composition comprises an excipient, wherein the excipient is present at a concentration of about 110 mmol/L to about 200 mmol/L. In some embodiments, the pharmaceutical composition comprises an excipient, wherein the excipient is present at a concentration of about 120 mmol/L to about 200 mmol/L. In some embodiments, the pharmaceutical composition comprises an excipient, wherein the excipient is present at a concentration of about 130 mmol/L to about 200 mmol/L. In some embodiments, the pharmaceutical composition comprises an excipient, wherein the excipient is present at a concentration of about 140 mmol/L to about 200 mmol/L. In some embodiments, the pharmaceutical composition comprises an excipient, wherein the excipient is present at a concentration of about 150 mmol/L to about 200 mmol/L. In some embodiments, the pharmaceutical composition comprises an excipient, wherein the excipient is present at a concentration of about 160 mmol/L to about 200 mmol/L. In some embodiments, the pharmaceutical composition comprises an excipient, wherein the excipient is present at a concentration of about 170 mmol/L to about 200 mmol/L. In some embodiments, the pharmaceutical composition comprises an excipient, wherein the excipient is present at a concentration of about 180 mmol/L to about 200 mmol/L. In some embodiments, the pharmaceutical composition comprises an excipient, wherein the excipient is present at a concentration of about 170 mmol/L to about 190 mmol/L. In some embodiments, the pharmaceutical composition comprises an excipient, wherein the excipient is present at a concentration of about 180 mmol/L.

In some embodiments, the pharmaceutical composition comprises an excipient, wherein the excipient is present at a concentration of about 100 mmol/L to about 190 mmol/L. In some embodiments, the pharmaceutical composition comprises an excipient, wherein the excipient is present at a concentration of about 100 mmol/L to about 180 mmol/L. In some embodiments, the pharmaceutical composition comprises an excipient, wherein the excipient is present at a concentration of about 100 mmol/L to about 170 mmol/L. In some embodiments, the pharmaceutical composition comprises an excipient, wherein the excipient is present at a concentration of about 100 mmol/L to about 160 mmol/L. In some embodiments, the pharmaceutical composition comprises an excipient, wherein the excipient is present at a concentration of about 120 mmol/L to about 160 mmol/L. In some embodiments, the pharmaceutical composition comprises an excipient, wherein the excipient is present at a concentration of about 130 mmol/L to about 150 mmol/L. In some embodiments, the pharmaceutical composition comprises an excipient, wherein the excipient is present at a concentration of about 140 mmol/L.

In some embodiments, the pharmaceutical composition comprises an excipient, wherein the excipient is present at a concentration of about 100 mmol/L to about 150 mmol/L. In some embodiments, the pharmaceutical composition comprises an excipient, wherein the excipient is present at a concentration of about 110 mmol/L to about 150 mmol/L. In some embodiments, the pharmaceutical composition comprises an excipient, wherein the excipient is present at a concentration of about 120 mmol/L to about 140 mmol/L. In some embodiments, the pharmaceutical composition comprises an excipient, wherein the excipient is present at a concentration of about 130 mmol/L.

In some embodiments, the pharmaceutical composition comprises an excipient, wherein the excipient is present at a concentration of about 100 mmol/L to about 150 mmol/L. In some embodiments, the pharmaceutical composition comprises an excipient, wherein the excipient is present at a concentration of about 100 mmol/L to about 140 mmol/L. In some embodiments, the pharmaceutical composition comprises an excipient, wherein the excipient is present at a concentration of about 110 mmol/L to about 130 mmol/L. In some embodiments, the pharmaceutical composition comprises an excipient, wherein the excipient is present at a concentration of about 120 mmol/L.

In some embodiments, the pharmaceutical composition comprises an excipient, wherein the excipient is present at a concentration of about 1 mmol/L to about 100 mmol/L. In some embodiments, the pharmaceutical composition comprises an excipient, wherein the excipient is present at a concentration of about 1 mmol/L to about 90 mmol/L. In some embodiments, the pharmaceutical composition comprises an excipient, wherein the excipient is present at a concentration of about 1 mmol/L to about 80 mmol/L. In some embodiments, the pharmaceutical composition comprises an excipient, wherein the excipient is present at a concentration of about 1 mmol/L to about 70 mmol/L. In some embodiments, the pharmaceutical composition comprises an excipient, wherein the excipient is present at a concentration of about 30 mmol/L to about 70 mmol/L. In some embodiments, the pharmaceutical composition comprises an excipient, wherein the excipient is present at a concentration of about 40 mmol/L to about 60 mmol/L. In some embodiments, the pharmaceutical composition comprises an excipient, wherein the excipient is present at a concentration of about 50 mmol/L.

In some embodiments, the pharmaceutical composition comprises an excipient, wherein the excipient is present at a concentration of about 1 mmol/L to about 40 mmol/L. In some embodiments, the pharmaceutical composition comprises an excipient, wherein the excipient is present at a concentration of about 10 mmol/L to about 30 mmol/L. In some embodiments, the pharmaceutical composition comprises an excipient, wherein the excipient is present at a concentration of about 20 mmol/L.

In some embodiments, the excipient is present at a concentration of about 600 mmol/L or less. In some embodiments, the excipient is present at a concentration of about 500 mmol/L or less. In some embodiments, the excipient is present at a concentration of about 400 mmol/L or less. In some embodiments, the excipient is present at a concentration of about 300 mmol/L or less. In some embodiments, the excipient is present at a concentration of about 250 mmol/L or less. In some embodiments, the excipient is present at a concentration of about 220 mmol/L or less. In some embodiments, the excipient is present at a concentration of about 200 mmol/L or less. In some embodiments, the excipient is present at a concentration of about 180 mmol/L or less. In some embodiments, the excipient is present at a concentration of about 160 mmol/L or less. In some embodiments, the excipient is present at a concentration of about 140 mmol/L or less. In some embodiments, the excipient is present at a concentration of about 120 mmol/L or less. In some embodiments, the excipient is present at a concentration of about 100 mmol/L or less. In some embodiments, the excipient is present at a concentration of about 50 mmol/L or less. In some embodiments, the excipient is present at a concentration of about 20 mmol/L or less.

In some embodiments, the pharmaceutical composition comprises an excipient, wherein the excipient is present at a concentration of about 10 mmol/L. In some embodiments, the pharmaceutical composition comprises an excipient, wherein the excipient is present at a concentration of about 20 mmol/L. In some embodiments, the pharmaceutical composition comprises an excipient, wherein the excipient is present at a concentration of about 30 mmol/L. In some embodiments, the pharmaceutical composition comprises an excipient, wherein the excipient is present at a concentration of about 40 mmol/L. In some embodiments, the pharmaceutical composition comprises an excipient, wherein the excipient is present at a concentration of about 50 mmol/L. In some embodiments, the pharmaceutical composition comprises an excipient, wherein the excipient is present at a concentration of about 75 mmol/L. In some embodiments, the pharmaceutical composition comprises an excipient, wherein the excipient is present at a concentration of about 100 mmol/L. In some embodiments, the pharmaceutical composition comprises an excipient, wherein the excipient is present at a concentration of about 110 mmol/L. In some embodiments, the pharmaceutical composition comprises an excipient, wherein the excipient is present at a concentration of about 120 mmol/L. In some embodiments, the pharmaceutical composition comprises an excipient, wherein the excipient is present at a concentration of about 130 mmol/L. In some embodiments, the pharmaceutical composition comprises an excipient, wherein the excipient is present at a concentration of about 140 mmol/L. In some embodiments, the pharmaceutical composition comprises an excipient, wherein the excipient is present at a concentration of about 150 mmol/L. In some embodiments, the pharmaceutical composition comprises an excipient, wherein the excipient is present at a concentration of about 160 mmol/L. In some embodiments, the pharmaceutical composition comprises an excipient, wherein the excipient is present at a concentration of about 170 mmol/L. In some embodiments, the pharmaceutical composition comprises an excipient, wherein the excipient is present at a concentration of about 180 mmol/L. In some embodiments, the pharmaceutical composition comprises an excipient, wherein the excipient is present at a concentration of about 190 mmol/L. In some embodiments, the pharmaceutical composition comprises an excipient, wherein the excipient is present at a concentration of about 200 mmol/L. In some embodiments, the pharmaceutical composition comprises an excipient, wherein the excipient is present at a concentration of about 210 mmol/L. In some embodiments, the pharmaceutical composition comprises an excipient, wherein the excipient is present at a concentration of about 220 mmol/L. In some embodiments, the pharmaceutical composition comprises an excipient, wherein the excipient is present at a concentration of about 250 mmol/L. In some embodiments, the pharmaceutical composition comprises an excipient, wherein the excipient is present at a concentration of about 300 mmol/L. In some embodiments, the pharmaceutical composition comprises an excipient, wherein the excipient is present at a concentration of about 400 mmol/L. In some embodiments, the pharmaceutical composition comprises an excipient, wherein the excipient is present at a concentration of about 500 mmol/L. In some embodiments, the pharmaceutical composition comprises an excipient, wherein the excipient is present at a concentration of about 600 mmol/L.

In some embodiments, the pharmaceutical composition comprises an excipient, wherein the excipient is an amino acid. In some embodiments, the excipient is histidine, glycine, arginine, proline, or glutamate, or a pharmaceutically acceptable salt thereof, or any combination thereof. In some embodiments, the excipient is a combination of any two or more of histidine, glycine, arginine, proline, or glutamate, or pharmaceutically acceptable salts thereof.

In some embodiments, the pharmaceutical composition comprises an excipient, wherein the excipient is glycine, arginine, or proline, or a pharmaceutically acceptable salt thereof. In some embodiments, the excipient is glycine, or a pharmaceutically acceptable salt thereof. In some embodiments, the excipient is glutamate, or a pharmaceutically acceptable salt thereof. In some embodiments, the excipient is arginine, or a pharmaceutically acceptable salt thereof. In some embodiments, the excipient is histidine, or a pharmaceutically acceptable salt thereof. In some embodiments, the excipient is proline, or a pharmaceutically acceptable salt thereof.

In some embodiments, the excipient is a buffering agent. In some embodiments, the buffering agent is histidine.

In some embodiments, the excipient is a viscosity reducing agent. In some embodiments, the viscosity reducing agent is histidine, glycine, arginine, proline, or glutamate, or a pharmaceutically acceptable salt thereof, or any combination thereof.

In some embodiments, the pharmaceutical composition comprises histidine, or a pharmaceutically acceptable salt thereof. Histidine is an essential amino acid that can be represented by the formula:

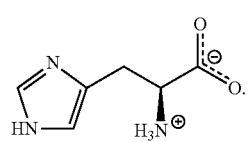

Histidine, as used herein, includes the free base form of histidine, as well as any and all salts thereof. In some embodiments, histidine includes a pharmaceutically acceptable salt thereof, e.g., histidine hydrochloride. In some embodiments, the pharmaceutically acceptable salt of histidine is histidine hydrochloride. Histidine, as used herein, also includes all enantiomers (e.g., L-histidine and S-histidine), and any combination of enantiomers (e.g., 50% L-histidine and 50% S-histidine; 90%-100% L-histidine and 10%-0% S-histidine, etc.). In some embodiments, the term "histidine" includes greater than 99% L-histidine and less than 1% S-histidine. In some embodiments, the term "histidine" includes an enantiomerically pure L-histidine. In some embodiments, histidine is a pharmaceutical grade histidine.

In some embodiments, the pharmaceutical composition comprises histidine, or a pharmaceutically acceptable salt thereof. In some embodiments, the pharmaceutical composition comprises histidine, or a pharmaceutically acceptable salt thereof, at a concentration of about 1 mmol/L to about 600 mmol/L. In some embodiments, the pharmaceutical composition comprises histidine, or a pharmaceutically acceptable salt thereof, at a concentration of about 1 mmol/L to about 300 mmol/L. In some embodiments, the pharmaceutical composition comprises histidine, or a pharmaceutically acceptable salt thereof, at a concentration of about 50 mmol/L to about 300 mmol/L. In some embodiments, the pharmaceutical composition comprises histidine, or a pharmaceutically acceptable salt thereof, at a concentration of about 100 mmol/L to about 300 mmol/L. In some embodiments, the pharmaceutical composition comprises histidine, or a pharmaceutically acceptable salt thereof, at a concentration of about 100 mmol/L to about 250 mmol/L. In some embodiments, the pharmaceutical composition comprises histidine, or a pharmaceutically acceptable salt thereof, at a concentration of about 100 mmol/L to about 220 mmol/L. In some embodiments, the pharmaceutical composition comprises histidine, or a pharmaceutically acceptable salt thereof, at a concentration of about 110 mmol/L to about 220 mmol/L. In some embodiments, the pharmaceutical composition comprises histidine, or a pharmaceutically acceptable salt thereof, at a concentration of about 120 mmol/L to about 220 mmol/L. In some embodiments, the pharmaceutical composition comprises histidine, or a pharmaceutically acceptable salt thereof, at a concentration of about 130 mmol/L to about 220 mmol/L. In some embodiments, the pharmaceutical composition comprises histidine, or a pharmaceutically acceptable salt thereof, at a concentration of about 140 mmol/L to about 220 mmol/L. In some embodiments, the pharmaceutical composition comprises histidine, or a pharmaceutically acceptable salt thereof, at a concentration of about 150 mmol/L to about 220 mmol/L. In some embodiments, the pharmaceutical composition comprises histidine, or a pharmaceutically acceptable salt thereof, at a concentration of about 160 mmol/L to about 220 mmol/L. In some embodiments, the pharmaceutical composition comprises histidine, or a pharmaceutically acceptable salt thereof, at a concentration of about 170 mmol/L to about 220 mmol/L. In some embodiments, the pharmaceutical composition comprises histidine, or a pharmaceutically acceptable salt thereof, at a concentration of about 180 mmol/L to about 220 mmol/L. In some embodiments, the pharmaceutical composition comprises histidine, or a pharmaceutically acceptable salt thereof, at a concentration of about 190 mmol/L to about 210 mmol/L. In some embodiments, the pharmaceutical composition comprises histidine, or a pharmaceutically acceptable salt thereof, at a concentration of about 200 mmol/L.

In some embodiments, the pharmaceutical composition comprises histidine, or a pharmaceutically acceptable salt thereof, at a concentration of about 100 mmol/L to about 200 mmol/L. In some embodiments, the pharmaceutical composition comprises histidine, or a pharmaceutically acceptable salt thereof, at a concentration of about 110 mmol/L to about 200 mmol/L. In some embodiments, the pharmaceutical composition comprises histidine, or a pharmaceutically acceptable salt thereof, at a concentration of about 120 mmol/L to about 200 mmol/L. In some embodiments, the pharmaceutical composition comprises histidine, or a pharmaceutically acceptable salt thereof, at a concentration of about 130 mmol/L to about 200 mmol/L. In some embodiments, the pharmaceutical composition comprises histidine, or a pharmaceutically acceptable salt thereof, at a concentration of about 140 mmol/L to about 200 mmol/L. In some embodiments, the pharmaceutical composition comprises histidine, or a pharmaceutically acceptable salt thereof, at a concentration of about 150 mmol/L to about 200 mmol/L. In some embodiments, the pharmaceutical composition comprises histidine, or a pharmaceutically acceptable salt thereof, at a concentration of about 160 mmol/L to about 200 mmol/L. In some embodiments, the pharmaceutical composition comprises histidine, or a pharmaceutically acceptable salt thereof, at a concentration of about 170 mmol/L to about 190 mmol/L. In some embodiments, the pharmaceutical composition comprises histidine, or a pharmaceutically acceptable salt thereof, at a concentration of about 180 mmol/L.

In some embodiments, the pharmaceutical composition comprises histidine, or a pharmaceutically acceptable salt thereof, at a concentration of about 100 mmol/L to about 190 mmol/L. In some embodiments, the pharmaceutical composition comprises histidine, or a pharmaceutically acceptable salt thereof, at a concentration of about 100 mmol/L to about 180 mmol/L. In some embodiments, the pharmaceutical composition comprises histidine, or a pharmaceutically acceptable salt thereof, at a concentration of about 100 mmol/L to about 170 mmol/L. In some embodiments, the pharmaceutical composition comprises histidine, or a pharmaceutically acceptable salt thereof, at a concentration of about 100 mmol/L to about 160 mmol/L. In some embodiments, the pharmaceutical composition comprises histidine, or a pharmaceutically acceptable salt thereof, at a concentration of about 120 mmol/L to about 160 mmol/L. In some embodiments, the pharmaceutical composition comprises histidine, or a pharmaceutically acceptable salt thereof, at a concentration of about 130 mmol/L to about 150 mmol/L. In some embodiments, the pharmaceutical composition comprises histidine, or a pharmaceutically acceptable salt thereof, at a concentration of about 140 mmol/L.

In some embodiments, the pharmaceutical composition comprises histidine, or a pharmaceutically acceptable salt thereof, at a concentration of about 100 mmol/L to about 150 mmol/L. In some embodiments, the pharmaceutical composition comprises histidine, or a pharmaceutically acceptable salt thereof, at a concentration of about 110 mmol/L to about 150 mmol/L. In some embodiments, the pharmaceutical composition comprises histidine, or a pharmaceutically acceptable salt thereof, at a concentration of about 120 mmol/L to about 140 mmol/L. In some embodiments, the pharmaceutical composition comprises histidine, or a pharmaceutically acceptable salt thereof, at a concentration of about 130 mmol/L.

In some embodiments, the pharmaceutical composition comprises histidine, or a pharmaceutically acceptable salt thereof, at a concentration of about 100 mmol/L to about 150 mmol/L. In some embodiments, the pharmaceutical composition comprises histidine, or a pharmaceutically acceptable salt thereof, at a concentration of about 100 mmol/L to about 140 mmol/L. In some embodiments, the pharmaceutical composition comprises histidine, or a pharmaceutically acceptable salt thereof, at a concentration of about 110 mmol/L to about 130 mmol/L. In some embodiments, the pharmaceutical composition comprises histidine, or a pharmaceutically acceptable salt thereof, at a concentration of about 120 mmol/L.

In some embodiments, the pharmaceutical composition comprises histidine, or a pharmaceutically acceptable salt thereof, at a concentration of about 1 mmol/L to about 100 mmol/L. In some embodiments, the pharmaceutical composition comprises histidine, or a pharmaceutically acceptable salt thereof, at a concentration of about 1 mmol/L to about 90 mmol/L. In some embodiments, the pharmaceutical composition comprises histidine, or a pharmaceutically acceptable salt thereof, at a concentration of about 1 mmol/L to about 80 mmol/L. In some embodiments, the pharmaceutical composition comprises histidine, or a pharmaceutically acceptable salt thereof, at a concentration of about 1 mmol/L to about 70 mmol/L. In some embodiments, the pharmaceutical composition comprises histidine, or a pharmaceutically acceptable salt thereof, at a concentration of about 30 mmol/L to about 70 mmol/L. In some embodiments, the pharmaceutical composition comprises histidine, or a pharmaceutically acceptable salt thereof, at a concentration of about 40 mmol/L to about 60 mmol/L. In some embodiments, the pharmaceutical composition comprises histidine, or a pharmaceutically acceptable salt thereof, at a concentration of about 50 mmol/L.

In some embodiments, the pharmaceutical composition comprises histidine, or a pharmaceutically acceptable salt thereof, at a concentration of about 1 mmol/L to about 40 mmol/L. In some embodiments, the pharmaceutical composition comprises histidine, or a pharmaceutically acceptable salt thereof, at a concentration of about 10 mmol/L to about 30 mmol/L. In some embodiments, the pharmaceutical composition comprises histidine, or a pharmaceutically acceptable salt thereof, at a concentration of about 20 mmol/L.

In some embodiments, the histidine, or a pharmaceutically acceptable salt thereof, is present at a concentration of about 600 mmol/L or less. In some embodiments, the histidine, or a pharmaceutically acceptable salt thereof, is present at a concentration of about 500 mmol/L or less. In some embodiments, the histidine, or a pharmaceutically acceptable salt thereof, is present at a concentration of about 400 mmol/L or less. In some embodiments, the histidine, or a pharmaceutically acceptable salt thereof, is present at a concentration of about 300 mmol/L or less. In some embodiments, the histidine, or a pharmaceutically acceptable salt thereof, is present at a concentration of about 250 mmol/L or less. In some embodiments, the histidine, or a pharmaceutically acceptable salt thereof, is present at a concentration of about 220 mmol/L or less. In some embodiments, the histidine, or a pharmaceutically acceptable salt thereof, is present at a concentration of about 200 mmol/L or less. In some embodiments, the histidine, or a pharmaceutically acceptable salt thereof, is present at a concentration of about 180 mmol/L or less. In some embodiments, the histidine, or a pharmaceutically acceptable salt thereof, is present at a concentration of about 160 mmol/L or less. In some embodiments, the histidine, or a pharmaceutically acceptable salt thereof, is present at a concentration of about 140 mmol/L or less. In some embodiments, the histidine, or a pharmaceutically acceptable salt thereof, is present at a concentration of about 120 mmol/L or less. In some embodiments, the histidine, or a pharmaceutically acceptable salt thereof, is present at a concentration of about 100 mmol/L or less. In some embodiments, the histidine, or a pharmaceutically acceptable salt thereof, is present at a concentration of about 50 mmol/L or less. In some embodiments, the histidine, or a pharmaceutically acceptable salt thereof, is present at a concentration of about 20 mmol/L or less.

In some embodiments, the pharmaceutical composition comprises histidine, or a pharmaceutically acceptable salt thereof, at a concentration of about 10 mmol/L. In some embodiments, the pharmaceutical composition comprises histidine, or a pharmaceutically acceptable salt thereof, at a concentration of about 20 mmol/L. In some embodiments, the pharmaceutical composition comprises histidine, or a pharmaceutically acceptable salt thereof, at a concentration of about 30 mmol/L. In some embodiments, the pharmaceutical composition comprises histidine, or a pharmaceutically acceptable salt thereof, at a concentration of about 40 mmol/L. In some embodiments, the pharmaceutical composition comprises histidine, or a pharmaceutically acceptable salt thereof, at a concentration of about 50 mmol/L. In some embodiments, the pharmaceutical composition comprises histidine, or a pharmaceutically acceptable salt thereof, at a concentration of about 75 mmol/L. In some embodiments, the pharmaceutical composition comprises histidine, or a pharmaceutically acceptable salt thereof, at a concentration of about 100 mmol/L. In some embodiments, the pharmaceutical composition comprises histidine, or a pharmaceutically acceptable salt thereof, at a concentration of about 110 mmol/L. In some embodiments, the pharmaceutical composition comprises histidine, or a pharmaceutically acceptable salt thereof, at a concentration of about 120 mmol/L. In some embodiments, the pharmaceutical composition comprises histidine, or a pharmaceutically acceptable salt thereof, at a concentration of about 130 mmol/L. In some embodiments, the pharmaceutical composition comprises histidine, or a pharmaceutically acceptable salt thereof, at a concentration of about 140 mmol/L. In some embodiments, the pharmaceutical composition comprises histidine, or a pharmaceutically acceptable salt thereof, at a concentration of about 150 mmol/L. In some embodiments, the pharmaceutical composition comprises histidine, or a pharmaceutically acceptable salt thereof, at a concentration of about 160 mmol/L. In some embodiments, the pharmaceutical composition comprises histidine, or a pharmaceutically acceptable salt thereof, at a concentration of about 170 mmol/L. In some embodiments, the pharmaceutical composition comprises histidine, or a pharmaceutically acceptable salt thereof, at a concentration of about 180 mmol/L. In some embodiments, the pharmaceutical composition comprises histidine, or a pharmaceutically acceptable salt thereof, at a concentration of about 190 mmol/L. In some embodiments, the pharmaceutical composition comprises histidine, or a pharmaceutically acceptable salt thereof, at a concentration of about 200 mmol/L. In some embodiments, the pharmaceutical composition comprises histidine, or a pharmaceutically acceptable salt thereof, at a concentration of about 210 mmol/L. In some embodiments, the pharmaceutical composition comprises histidine, or a pharmaceutically acceptable salt thereof, at a concentration of about 220 mmol/L. In some embodiments, the pharmaceutical composition comprises histidine, or a pharmaceutically acceptable salt thereof, at a concentration of about 250 mmol/L. In some embodiments, the pharmaceutical composition comprises histidine, or a pharmaceutically acceptable salt thereof, at a concentration of about 300 mmol/L. In some embodiments, the pharmaceutical composition comprises histidine, or a pharmaceutically acceptable salt thereof, at a concentration of about 400 mmol/L. In some embodiments, the pharmaceutical composition comprises histidine, or a pharmaceutically acceptable salt thereof, at a concentration of about 500 mmol/L. In some embodiments, the pharmaceutical composition comprises histidine, or a pharmaceutically acceptable salt thereof, at a concentration of about 600 mmol/L.

In some embodiments, pharmaceutical composition comprises glycine, or a pharmaceutically acceptable salt thereof. Glycine is an amino acid that can be represented by the formula:

$$H_2N\diagup\diagdown\diagup^O_{OH}$$

Glycine, as used herein, includes the free base form of glycine, as well as any and all salts thereof. In some embodiments, glycine includes a pharmaceutically acceptable salt thereof, e.g., glycine hydrochloride. In some embodiments, the pharmaceutically acceptable salt of glycine is glycine hydrochloride. Glycine, as used herein, also includes all enantiomers (e.g., L-glycine and S-glycine), and any combination of enantiomers (e.g., 50% L-glycine and 50% S-glycine; 90%-100% L-glycine and 10%-0% S-glycine, etc.). In some embodiments, the term "glycine" includes greater than 99% L-glycine and less than 1% S-glycine. In some embodiments, the term "glycine" includes an enantiomerically pure L-glycine. In some embodiments, glycine is a pharmaceutical grade glycine.

In some embodiments, the pharmaceutical composition comprises glycine, or a pharmaceutically acceptable salt thereof. In some embodiments, the pharmaceutical composition comprises glycine, or a pharmaceutically acceptable salt thereof, at a concentration of about 1 mmol/L to about 600 mmol/L. In some embodiments, the pharmaceutically composition comprises glycine, or a pharmaceutically acceptable salt thereof, at a concentration of about 1 mmol/L to about 300 mmol/L. In some embodiments, the pharmaceutical composition comprises glycine, or a pharmaceutically acceptable salt thereof, at a concentration of about 50 mmol/L to about 300 mmol/L. In some embodiments, the pharmaceutical composition comprises glycine, or a pharmaceutically acceptable salt thereof, at a concentration of about 100 mmol/L to about 300 mmol/L. In some embodiments, the pharmaceutical composition comprises glycine, or a pharmaceutically acceptable salt thereof, at a concentration of about 100 mmol/L to about 250 mmol/L. In some embodiments, the pharmaceutical composition comprises glycine, or a pharmaceutically acceptable salt thereof, at a concentration of about 100 mmol/L to about 220 mmol/L. In some embodiments, the pharmaceutical composition comprises glycine, or a pharmaceutically acceptable salt thereof, at a concentration of about 110 mmol/L to about 220 mmol/L. In some embodiments, the pharmaceutical composition comprises glycine, or a pharmaceutically acceptable salt thereof, at a concentration of about 120 mmol/L to about 220 mmol/L. In some embodiments, the pharmaceutical composition comprises glycine, or a pharmaceutically acceptable salt thereof, at a concentration of about 130 mmol/L to about 220 mmol/L. In some embodiments, the pharmaceutical composition comprises glycine, or a pharmaceutically acceptable salt thereof, at a concentration of about 140 mmol/L to about 220 mmol/L. In some embodiments, the pharmaceutical composition comprises glycine, or a pharmaceutically acceptable salt thereof, at a concentration of about 150 mmol/L to about 220 mmol/L. In some embodiments, the pharmaceutical composition comprises glycine, or a pharmaceutically acceptable salt thereof, at a concentration of about 160 mmol/L to about 220 mmol/L. In some embodiments, the pharmaceutical composition comprises glycine, or a pharmaceutically acceptable salt thereof, at a concentration of about 170 mmol/L to about 220 mmol/L. In some embodiments, the pharmaceutical composition comprises glycine, or a pharmaceutically acceptable salt thereof, at a concentration of about 180 mmol/L to about 220 mmol/L. In some embodiments, the pharmaceutical composition comprises glycine, or a pharmaceutically acceptable salt thereof, at a concentration of about 190 mmol/L to about 210 mmol/L. In some embodiments, the pharmaceutical composition comprises glycine, or a pharmaceutically acceptable salt thereof, at a concentration of about 200 mmol/L.

In some embodiments, the pharmaceutical composition comprises glycine, or a pharmaceutically acceptable salt thereof, at a concentration of about 100 mmol/L to about 200 mmol/L. In some embodiments, the pharmaceutical composition comprises glycine, or a pharmaceutically acceptable salt thereof, at a concentration of about 110 mmol/L to about 200 mmol/L. In some embodiments, the pharmaceutical composition comprises glycine, or a pharmaceutically acceptable salt thereof, at a concentration of about 120 mmol/L to about 200 mmol/L. In some embodiments, the pharmaceutical composition comprises glycine, or a pharmaceutically acceptable salt thereof, at a concentration of about 130 mmol/L to about 200 mmol/L. In some embodiments, the pharmaceutical composition comprises glycine, or a pharmaceutically acceptable salt thereof, at a concentration of about 140 mmol/L to about 200 mmol/L. In some embodiments, the pharmaceutical composition comprises glycine, or a pharmaceutically acceptable salt thereof, at a concentration of about 150 mmol/L to about 200 mmol/L. In some embodiments, the pharmaceutical composition comprises glycine, or a pharmaceutically acceptable salt thereof, at a concentration of about 160 mmol/L to about 200 mmol/L. In some embodiments, the pharmaceutical composition comprises glycine, or a pharmaceutically acceptable salt thereof, at a concentration of about 170 mmol/L to about 190 mmol/L. In some embodiments, the pharmaceutical composition comprises glycine, or a pharmaceutically acceptable salt thereof, at a concentration of about 180 mmol/L.

In some embodiments, the pharmaceutical composition comprises glycine, or a pharmaceutically acceptable salt thereof, at a concentration of about 100 mmol/L to about 190 mmol/L. In some embodiments, the pharmaceutical composition comprises glycine, or a pharmaceutically acceptable salt thereof, at a concentration of about 100 mmol/L to about 180 mmol/L. In some embodiments, the pharmaceutical composition comprises glycine, or a pharmaceutically acceptable salt thereof, at a concentration of about 100 mmol/L to about 170 mmol/L. In some embodiments, the pharmaceutical composition comprises glycine, or a pharmaceutically acceptable salt thereof, at a concentration of about 100 mmol/L to about 160 mmol/L. In some embodiments, the pharmaceutical composition comprises glycine, or a pharmaceutically acceptable salt thereof, at a concentration of about 120 mmol/L to about 160 mmol/L. In some embodiments, the pharmaceutical composition comprises glycine, or a pharmaceutically acceptable salt thereof, at a concentration of about 130 mmol/L to about 150 mmol/L. In some embodiments, the pharmaceutical composition comprises glycine, or a pharmaceutically acceptable salt thereof, at a concentration of about 140 mmol/L.

In some embodiments, the pharmaceutical composition comprises glycine, or a pharmaceutically acceptable salt thereof, at a concentration of about 100 mmol/L to about 150 mmol/L. In some embodiments, the pharmaceutical composition comprises glycine, or a pharmaceutically acceptable salt thereof, at a concentration of about 110 mmol/L to about 150 mmol/L. In some embodiments, the pharmaceutical composition comprises glycine, or a pharmaceutically acceptable salt thereof, at a concentration of about 120 mmol/L to about 140 mmol/L. In some embodiments, the pharmaceutical composition comprises glycine, or a pharmaceutically acceptable salt thereof, at a concentration of about 130 mmol/L.

In some embodiments, the pharmaceutical composition comprises glycine, or a pharmaceutically acceptable salt thereof, at a concentration of about 100 mmol/L to about 150 mmol/L. In some embodiments, the pharmaceutical composition comprises glycine, or a pharmaceutically acceptable salt thereof, at a concentration of about 100 mmol/L to about 140 mmol/L. In some embodiments, the pharmaceutical composition comprises glycine, or a pharmaceutically acceptable salt thereof, at a concentration of about 110 mmol/L to about 130 mmol/L. In some embodiments, the pharmaceutical composition comprises glycine, or a pharmaceutically acceptable salt thereof, at a concentration of about 120 mmol/L.

In some embodiments, the pharmaceutical composition comprises glycine, or a pharmaceutically acceptable salt thereof, at a concentration of about 1 mmol/L to about 100 mmol/L. In some embodiments, the pharmaceutical composition comprises glycine, or a pharmaceutically acceptable salt thereof, at a concentration of about 1 mmol/L to about 90 mmol/L. In some embodiments, the pharmaceutical composition comprises glycine, or a pharmaceutically acceptable salt thereof, at a concentration of about 1 mmol/L to about 80 mmol/L. In some embodiments, the pharmaceutical composition comprises glycine, or a pharmaceutically acceptable salt thereof, at a concentration of about 1 mmol/L to about 70 mmol/L. In some embodiments, the pharmaceutical composition comprises glycine, or a pharmaceutically acceptable salt thereof, at a concentration of about 30 mmol/L to about 70 mmol/L. In some embodiments, the pharmaceutical composition comprises glycine, or a pharmaceutically acceptable salt thereof, at a concentration of about 40 mmol/L to about 60 mmol/L. In some embodiments, the pharmaceutical composition comprises glycine, or a pharmaceutically acceptable salt thereof, at a concentration of about 50 mmol/L.

In some embodiments, the pharmaceutical composition comprises glycine, or a pharmaceutically acceptable salt thereof, at a concentration of about 1 mmol/L to about 40 mmol/L. In some embodiments, the pharmaceutical composition comprises glycine, or a pharmaceutically acceptable salt thereof, at a concentration of about 10 mmol/L to about 30 mmol/L. In some embodiments, the pharmaceutical composition comprises glycine, or a pharmaceutically acceptable salt thereof, at a concentration of about 20 mmol/L.

In some embodiments, the glycine, or a pharmaceutically acceptable salt thereof, is present at a concentration of about 600 mmol/L or less. In some embodiments, the glycine, or a pharmaceutically acceptable salt thereof, is present at a concentration of about 500 mmol/L or less. In some embodiments, the glycine, or a pharmaceutically acceptable salt thereof, is present at a concentration of about 400 mmol/L or less. In some embodiments, the glycine, or a pharmaceutically acceptable salt thereof, is present at a concentration of about 300 mmol/L or less. In some embodiments, the glycine, or a pharmaceutically acceptable salt thereof, is present at a concentration of about 250 mmol/L or less. In some embodiments, the glycine, or a pharmaceutically acceptable salt thereof, is present at a concentration of about 220 mmol/L or less. In some embodiments, the glycine, or a pharmaceutically acceptable salt thereof, is present at a concentration of about 200 mmol/L or less. In some embodiments, the glycine, or a pharmaceutically acceptable salt thereof, is present at a concentration of about 180 mmol/L or less. In some embodiments, the glycine, or a pharmaceutically acceptable salt thereof, is present at a concentration of about 160 mmol/L or less. In some embodiments, the glycine, or a pharmaceutically acceptable salt thereof, is present at a concentration of about 140 mmol/L or less. In some embodiments, the glycine, or a pharmaceutically acceptable salt thereof, is present at a concentration of about 120 mmol/L or less. In some embodiments, the glycine, or a pharmaceutically acceptable salt thereof, is present at a concentration of about 100 mmol/L or less. In some embodiments, the glycine, or a pharmaceutically acceptable salt thereof, is present at a concentration of about 50 mmol/L or less. In some embodiments, the glycine, or a pharmaceutically acceptable salt thereof, is present at a concentration of about 20 mmol/L or less.

In some embodiments, the pharmaceutical composition comprises glycine, or a pharmaceutically acceptable salt thereof, at a concentration of about 10 mmol/L. In some embodiments, the pharmaceutical composition comprises glycine, or a pharmaceutically acceptable salt thereof, at a concentration of about 20 mmol/L. In some embodiments, the pharmaceutical composition comprises glycine, or a pharmaceutically acceptable salt thereof, at a concentration of about 30 mmol/L. In some embodiments, the pharmaceutical composition comprises glycine, or a pharmaceutically acceptable salt thereof, at a concentration of about 40 mmol/L. In some embodiments, the pharmaceutical composition comprises glycine, or a pharmaceutically acceptable salt thereof, at a concentration of about 50 mmol/L. In some embodiments, the pharmaceutical composition comprises glycine, or a pharmaceutically acceptable salt thereof, at a concentration of about 75 mmol/L. In some embodiments, the pharmaceutical composition comprises glycine, or a pharmaceutically acceptable salt thereof, at a concentration of about 100 mmol/L. In some embodiments, the pharmaceutical composition comprises glycine, or a pharmaceutically acceptable salt thereof, at a concentration of about 110 mmol/L. In some embodiments, the pharmaceutical composition comprises glycine, or a pharmaceutically acceptable salt thereof, at a concentration of about 120 mmol/L. In some embodiments, the pharmaceutical composition comprises glycine, or a pharmaceutically acceptable salt thereof, at a concentration of about 130 mmol/L. In some embodiments, the pharmaceutical composition comprises glycine, or a pharmaceutically acceptable salt thereof, at a concentration of about 140 mmol/L. In some embodiments, the pharmaceutical composition comprises glycine, or a pharmaceutically acceptable salt thereof, at a concentration of about 150 mmol/L. In some embodiments, the pharmaceutical composition comprises glycine, or a pharmaceutically acceptable salt thereof, at a concentration of about 160 mmol/L. In some embodiments, the pharmaceutical composition comprises glycine, or a pharmaceutically acceptable salt thereof, at a concentration of about 170 mmol/L. In some embodiments, the pharmaceutical composition comprises glycine, or a pharmaceutically acceptable salt thereof, at a concentration of about 180 mmol/L. In some embodiments, the pharmaceutical composition comprises glycine, or a pharmaceutically acceptable salt thereof, at a concentration of about 190 mmol/L. In some embodiments, the pharmaceutical composition comprises glycine, or a pharmaceutically acceptable salt thereof, at a concentration of about 200 mmol/L. In some embodiments, the pharmaceutical composition comprises glycine, or a pharmaceutically acceptable salt thereof, at a concentration of about 210 mmol/L. In some embodiments, the pharmaceutical composition comprises glycine, or a pharmaceutically acceptable salt thereof, at a concentration of about 220 mmol/L. In some embodiments, the pharmaceutical composition comprises glycine, or a pharmaceutically acceptable salt thereof, at a concentration of about 250 mmol/L. In some embodiments, the pharmaceutical composition comprises glycine, or a pharmaceutically acceptable salt thereof, at a concentration of about 300 mmol/L. In some embodiments, the pharmaceutical composition comprises glycine, or a pharmaceutically acceptable salt thereof, at a concentration of about 400 mmol/L. In some embodiments, the pharmaceutical composition comprises glycine, or a pharmaceutically acceptable salt thereof, at a concentration of about 500 mmol/L. In some embodiments, the pharmaceutical composition comprises glycine, or a pharmaceutically acceptable salt thereof, at a concentration of about 600 mmol/L.

In some embodiments, the pharmaceutical composition comprises arginine, or a pharmaceutically acceptable salt thereof. Arginine is a conditionally non-essential amino acid that can be represented by the formula:

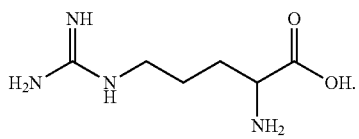

Arginine, as used herein, includes the free base form of arginine, as well as any and all salts thereof. In some embodiments, arginine includes a pharmaceutically acceptable salt thereof, e.g., arginine hydrochloride. In some embodiments, the pharmaceutically acceptable salt of arginine is arginine hydrochloride.

Arginine, as used herein, also includes all enantiomers (e.g., L-arginine and S-arginine), and any combination of enantiomers (e.g., 50% L-arginine and 50% S-arginine; 90%-100% L-arginine and 10%-0% S-arginine, etc.). In some embodiments, the term "arginine" includes greater than 99% L-arginine and less than 1% S-arginine. In some embodiments, the term "arginine" includes an enantiomerically pure L-arginine. In some embodiments, arginine is a pharmaceutical grade arginine.

In some embodiments, the pharmaceutical composition comprises arginine, or a pharmaceutically acceptable salt thereof. In some embodiments, the pharmaceutical composition comprises arginine, or a pharmaceutically acceptable salt thereof, at a concentration of about 1 mmol/L to about 600 mmol/L. In some embodiments, the pharmaceutical composition comprises arginine, or a pharmaceutically acceptable salt thereof, at a concentration of about 1 mmol/L to about 300 mmol/L. In some embodiments, the pharmaceutical composition comprises arginine, or a pharmaceutically acceptable salt thereof, at a concentration of about 50 mmol/L to about 300 mmol/L. In some embodiments, the pharmaceutical composition comprises arginine, or a pharmaceutically acceptable salt thereof, at a concentration of about 100 mmol/L to about 300 mmol/L. In some embodiments, the pharmaceutical composition comprises arginine, or a pharmaceutically acceptable salt thereof, at a concentration of about 100 mmol/L to about 250 mmol/L. In some embodiments, the pharmaceutical composition comprises arginine, or a pharmaceutically acceptable salt thereof, at a concentration of about 100 mmol/L to about 220 mmol/L. In some embodiments, the pharmaceutical composition comprises arginine, or a pharmaceutically acceptable salt thereof, at a concentration of about 110 mmol/L to about 220 mmol/L. In some embodiments, the pharmaceutical composition comprises arginine, or a pharmaceutically acceptable salt thereof, at a concentration of about 120 mmol/L to about 220 mmol/L. In some embodiments, the pharmaceutical composition comprises arginine, or a pharmaceutically acceptable salt thereof, at a concentration of about 130 mmol/L to about 220 mmol/L. In some embodiments, the pharmaceutical composition comprises arginine, or a pharmaceutically acceptable salt thereof, at a concentration of about 140 mmol/L to about 220 mmol/L. In some embodiments, the pharmaceutical composition comprises arginine, or a pharmaceutically acceptable salt thereof, at a concentration of about 150 mmol/L to about 220 mmol/L. In some embodiments, the pharmaceutical composition comprises arginine, or a pharmaceutically acceptable salt thereof, at a concentration of about 160 mmol/L to about 220 mmol/L. In some embodiments, the pharmaceutical composition comprises arginine, or a pharmaceutically acceptable salt thereof, at a concentration of about 170 mmol/L to about 220 mmol/L. In some embodiments, the pharmaceutical composition comprises arginine, or a pharmaceutically acceptable salt thereof, at a concentration of about 180 mmol/L to about 220 mmol/L. In some embodiments, the pharmaceutical composition comprises arginine, or a pharmaceutically acceptable salt thereof, at a concentration of about 190 mmol/L to about 210 mmol/L. In some embodiments, the pharmaceutical composition comprises arginine, or a pharmaceutically acceptable salt thereof, at a concentration of about 200 mmol/L.

In some embodiments, the pharmaceutical composition comprises arginine, or a pharmaceutically acceptable salt thereof, at a concentration of about 100 mmol/L to about 200 mmol/L. In some embodiments, the pharmaceutical composition comprises arginine, or a pharmaceutically acceptable salt thereof, at a concentration of about 110 mmol/L to about 200 mmol/L. In some embodiments, the pharmaceutical composition comprises arginine, or a pharmaceutically acceptable salt thereof, at a concentration of about 120 mmol/L to about 200 mmol/L. In some embodiments, the pharmaceutical composition comprises arginine, or a pharmaceutically acceptable salt thereof, at a concentration of about 130 mmol/L to about 200 mmol/L. In some embodiments, the pharmaceutical composition comprises arginine, or a pharmaceutically acceptable salt thereof, at a concentration of about 140 mmol/L to about 200 mmol/L. In some embodiments, the pharmaceutical composition comprises arginine, or a pharmaceutically acceptable salt thereof, at a concentration of about 150 mmol/L to about 200 mmol/L. In some embodiments, the pharmaceutical composition comprises arginine, or a pharmaceutically acceptable salt thereof, at a concentration of about 160 mmol/L to about 200 mmol/L. In some embodiments, the pharmaceutical composition comprises arginine, or a pharmaceutically acceptable salt thereof, at a concentration of about 170 mmol/L to about 190 mmol/L. In some embodiments, the pharmaceutical composition comprises arginine, or a pharmaceutically acceptable salt thereof, at a concentration of about 180 mmol/L.

In some embodiments, the pharmaceutical composition comprises arginine, or a pharmaceutically acceptable salt thereof, at a concentration of about 100 mmol/L to about 190 mmol/L. In some embodiments, the pharmaceutical composition comprises arginine, or a pharmaceutically acceptable salt thereof, at a concentration of about 100 mmol/L to about 180 mmol/L. In some embodiments, the pharmaceutical composition comprises arginine, or a pharmaceutically acceptable salt thereof, at a concentration of about 100 mmol/L to about 170 mmol/L. In some embodiments, the pharmaceutical composition comprises arginine, or a pharmaceutically acceptable salt thereof, at a concentration of about 100 mmol/L to about 160 mmol/L. In some embodiments, the pharmaceutical composition comprises arginine, or a pharmaceutically acceptable salt thereof, at a concentration of about 120 mmol/L to about 160 mmol/L. In some embodiments, the pharmaceutical composition comprises arginine, or a pharmaceutically acceptable salt thereof, at a concentration of about 130 mmol/L to about 150 mmol/L. In some embodiments, the pharmaceutical composition comprises arginine, or a pharmaceutically acceptable salt thereof, at a concentration of about 140 mmol/L.

In some embodiments, the pharmaceutical composition comprises arginine, or a pharmaceutically acceptable salt thereof, at a concentration of about 100 mmol/L to about 150 mmol/L. In some embodiments, the pharmaceutical composition comprises arginine, or a pharmaceutically acceptable salt thereof, at a concentration of about 110 mmol/L to about 150 mmol/L. In some embodiments, the pharmaceutical composition comprises arginine, or a pharmaceutically acceptable salt thereof, at a concentration of about 120 mmol/L to about 140 mmol/L. In some embodiments, the pharmaceutical composition comprises arginine, or a pharmaceutically acceptable salt thereof, at a concentration of about 130 mmol/L.

In some embodiments, the pharmaceutical composition comprises arginine, or a pharmaceutically acceptable salt thereof, at a concentration of about 100 mmol/L to about 150 mmol/L. In some embodiments, the pharmaceutical composition comprises arginine, or a pharmaceutically acceptable salt thereof, at a concentration of about 100 mmol/L to about 140 mmol/L. In some embodiments, the pharmaceutical composition comprises arginine, or a pharmaceutically acceptable salt thereof, at a concentration of about 110 mmol/L to about 130 mmol/L. In some embodiments, the pharmaceutical composition comprises arginine, or a pharmaceutically acceptable salt thereof, at a concentration of about 120 mmol/L.

In some embodiments, the pharmaceutical composition comprises arginine, or a pharmaceutically acceptable salt thereof, at a concentration of about 1 mmol/L to about 100 mmol/L. In some embodiments, the pharmaceutical composition comprises arginine, or a pharmaceutically acceptable salt thereof, at a concentration of about 1 mmol/L to about 90 mmol/L. In some embodiments, the pharmaceutical composition comprises arginine, or a pharmaceutically acceptable salt thereof, at a concentration of about 1 mmol/L to about 80 mmol/L. In some embodiments, the pharmaceutical composition comprises arginine, or a pharmaceutically acceptable salt thereof, at a concentration of about 1 mmol/L to about 70 mmol/L. In some embodiments, the pharmaceutical composition comprises arginine, or a pharmaceutically acceptable salt thereof, at a concentration of about 30 mmol/L to about 70 mmol/L. In some embodiments, the pharmaceutical composition comprises arginine, or a pharmaceutically acceptable salt thereof, at a concentration of about 40 mmol/L to about 60 mmol/L. In some embodiments, the pharmaceutical composition comprises arginine, or a pharmaceutically acceptable salt thereof, at a concentration of about 50 mmol/L.

In some embodiments, the pharmaceutical composition comprises arginine, or a pharmaceutically acceptable salt thereof, at a concentration of about 1 mmol/L to about 40 mmol/L. In some embodiments, the pharmaceutical composition comprises arginine, or a pharmaceutically acceptable salt thereof, at a concentration of about 10 mmol/L to about 30 mmol/L. In some embodiments, the pharmaceutical composition comprises arginine, or a pharmaceutically acceptable salt thereof, at a concentration of about 20 mmol/L.

In some embodiments, the arginine, or a pharmaceutically acceptable salt thereof, is present at a concentration of about 600 mmol/L or less. In some embodiments, the arginine, or a pharmaceutically acceptable salt thereof, is present at a concentration of about 500 mmol/L or less. In some embodiments, the arginine, or a pharmaceutically acceptable salt thereof, is present at a concentration of about 400 mmol/L or less. In some embodiments, the arginine, or a pharmaceutically acceptable salt thereof, is present at a concentration of about 300 mmol/L or less. In some embodiments, the arginine, or a pharmaceutically acceptable salt thereof, is present at a concentration of about 250 mmol/L or less. In some embodiments, the arginine, or a pharmaceutically acceptable salt thereof, is present at a concentration of about 220 mmol/L or less. In some embodiments, the arginine, or a pharmaceutically acceptable salt thereof, is present at a concentration of about 200 mmol/L or less. In some embodiments, the arginine, or a pharmaceutically acceptable salt thereof, is present at a concentration of about 180 mmol/L or less. In some embodiments, the arginine, or a pharmaceutically acceptable salt thereof, is present at a concentration of about 160 mmol/L or less. In some embodiments, the arginine, or a pharmaceutically acceptable salt thereof, is present at a concentration of about 140 mmol/L or less. In some embodiments, the arginine, or a pharmaceutically acceptable salt thereof, is present at a concentration of about 120 mmol/L or less. In some embodiments, the arginine, or a pharmaceutically acceptable salt thereof, is present at a concentration of about 100 mmol/L or less. In some embodiments, the arginine, or a pharmaceutically acceptable salt thereof, is present at a concentration of about 50 mmol/L or less. In some embodiments, the arginine, or a pharmaceutically acceptable salt thereof, is present at a concentration of about 20 mmol/L or less.

In some embodiments, the pharmaceutical composition comprises arginine, or a pharmaceutically acceptable salt thereof, at a concentration of about 10 mmol/L. In some embodiments, the pharmaceutical composition comprises arginine, or a pharmaceutically acceptable salt thereof, at a concentration of about 20 mmol/L. In some embodiments, the pharmaceutical composition comprises arginine, or a pharmaceutically acceptable salt thereof, at a concentration of about 30 mmol/L. In some embodiments, the pharmaceutical composition comprises arginine, or a pharmaceutically acceptable salt thereof, at a concentration of about 40 mmol/L. In some embodiments, the pharmaceutical composition comprises arginine, or a pharmaceutically acceptable salt thereof, at a concentration of about 50 mmol/L. In some embodiments, the pharmaceutical composition comprises arginine, or a pharmaceutically acceptable salt thereof, at a concentration of about 75 mmol/L. In some embodiments, the pharmaceutical composition comprises arginine, or a pharmaceutically acceptable salt thereof, at a concentration of about 100 mmol/L. In some embodiments, the pharmaceutical composition comprises arginine, or a pharmaceutically acceptable salt thereof, at a concentration of about 110 mmol/L. In some embodiments, the pharmaceutical composition comprises arginine, or a pharmaceutically acceptable salt thereof, at a concentration of about 120 mmol/L. In some embodiments, the pharmaceutical composition comprises arginine, or a pharmaceutically acceptable salt thereof, at a concentration of about 130 mmol/L. In some embodiments, the pharmaceutical composition comprises arginine, or a pharmaceutically acceptable salt thereof, at a concentration of about 140 mmol/L. In some embodiments, the pharmaceutical composition comprises arginine, or a pharmaceutically acceptable salt thereof, at a concentration of about 150 mmol/L. In some embodiments, the pharmaceutical composition comprises arginine, or a pharmaceutically acceptable salt thereof, at a concentration of about 160 mmol/L. In some embodiments, the pharmaceutical composition comprises arginine, or a pharmaceutically acceptable salt thereof, at a concentration of about 170 mmol/L. In some embodiments, the pharmaceutical composition comprises arginine, or a pharmaceutically acceptable salt thereof, at a concentration of about 180 mmol/L. In some embodiments, the pharmaceutical composition comprises arginine, or a pharmaceutically acceptable salt thereof, at a concentration of about 190 mmol/L. In some embodiments, the pharmaceutical composition comprises arginine, or a pharmaceutically acceptable salt thereof, at a concentration of about 200 mmol/L. In some embodiments, the pharmaceutical composition comprises arginine, or a pharmaceutically acceptable salt thereof, at a concentration of about 210 mmol/L. In some embodiments, the pharmaceutical composition comprises arginine, or a pharmaceutically acceptable salt thereof, at a concentration of about 220 mmol/L. In some embodiments, the pharmaceutical composition comprises arginine, or a pharmaceutically acceptable salt thereof, at a concentration of about 250 mmol/L. In some embodiments, the pharmaceutical composition comprises arginine, or a pharmaceutically acceptable salt thereof, at a concentration of about 300 mmol/L. In some embodiments, the pharmaceutical composition comprises arginine, or a pharmaceutically acceptable salt thereof, at a concentration of about 400 mmol/L. In some embodiments, the pharmaceutical composition comprises arginine, or a pharmaceutically acceptable salt thereof, at a concentration of about 500 mmol/L. In some embodiments, the pharmaceutical composition comprises arginine, or a pharmaceutically acceptable salt thereof, at a concentration of about 600 mmol/L.

In some embodiments, the viscosity reducing agent is proline, or a pharmaceutically acceptable salt thereof. Proline is an amino acid that can be represented by the formula:

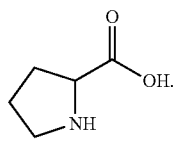

Proline, as used herein, includes the free base form of proline, as well as any and all salts thereof. In some embodiments, proline includes a pharmaceutically acceptable salt thereof, e.g., proline hydrochloride. In some embodiments, the pharmaceutically acceptable salt of proline is proline hydrochloride. Proline, as used herein, also includes all enantiomers (e.g., L-proline and S-proline), and any combination of enantiomers (e.g., 50% L-proline and 50% S-proline; 90%-100% L-proline and 10%-0% S-proline, etc.). In some embodiments, the term "proline" includes greater than 99% L-proline and less than 1% S-proline. In some embodiments, the term "proline" includes an enantiomerically pure L-proline. In some embodiments, proline is a pharmaceutical grade proline.

In some embodiments, the pharmaceutical composition comprises proline, or a pharmaceutically acceptable salt thereof. In some embodiments, the pharmaceutical composition comprises proline, or a pharmaceutically acceptable salt thereof, at a concentration of about 1 mmol/L to about 600 mmol/L. In some embodiments, the pharmaceutical composition comprises proline, or a pharmaceutically acceptable salt thereof, at a concentration of about 1 mmol/L to about 300 mmol/L. In some embodiments, the pharmaceutical composition comprises proline, or a pharmaceutically acceptable salt thereof, at a concentration of about 50 mmol/L to about 300 mmol/L. In some embodiments, the pharmaceutical composition comprises proline, or a pharmaceutically acceptable salt thereof, at a concentration of about 100 mmol/L to about 300 mmol/L. In some embodiments, the pharmaceutical composition comprises proline, or a pharmaceutically acceptable salt thereof, at a concentration of about 100 mmol/L to about 250 mmol/L. In some embodiments, the pharmaceutical composition comprises proline, or a pharmaceutically acceptable salt thereof, at a concentration of about 100 mmol/L to about 220 mmol/L. In some embodiments, the pharmaceutical composition comprises proline, or a pharmaceutically acceptable salt thereof, at a concentration of about 110 mmol/L to about 220 mmol/L. In some embodiments, the pharmaceutical composition comprises proline, or a pharmaceutically acceptable salt thereof, at a concentration of about 120 mmol/L to about 220 mmol/L. In some embodiments, the pharmaceutical composition comprises proline, or a pharmaceutically acceptable salt thereof, at a concentration of about 130 mmol/L to about 220 mmol/L. In some embodiments, the pharmaceutical composition comprises proline, or a pharmaceutically acceptable salt thereof, at a concentration of about 140 mmol/L to about 220 mmol/L. In some embodiments, the pharmaceutical composition comprises proline, or a pharmaceutically acceptable salt thereof, at a concentration of about 150 mmol/L to about 220 mmol/L. In some embodiments, the pharmaceutical composition comprises proline, or a pharmaceutically acceptable salt thereof, at a concentration of about 160 mmol/L to about 220 mmol/L. In some embodiments, the pharmaceutical composition comprises proline, or a pharmaceutically acceptable salt thereof, at a concentration of about 170 mmol/L to about 220 mmol/L. In some embodiments, the pharmaceutical composition comprises proline, or a pharmaceutically acceptable salt thereof, at a concentration of about 180 mmol/L to about 220 mmol/L. In some embodiments, the pharmaceutical composition comprises proline, or a pharmaceutically acceptable salt thereof, at a concentration of about 190 mmol/L to about 210 mmol/L. In some embodiments, the pharmaceutical composition comprises proline, or a pharmaceutically acceptable salt thereof, at a concentration of about 200 mmol/L.

In some embodiments, the pharmaceutical composition comprises proline, or a pharmaceutically acceptable salt thereof, at a concentration of about 100 mmol/L to about 200 mmol/L. In some embodiments, the pharmaceutical composition comprises proline, or a pharmaceutically acceptable salt thereof, at a concentration of about 110 mmol/L to about 200 mmol/L. In some embodiments, the pharmaceutical composition comprises proline, or a pharmaceutically acceptable salt thereof, at a concentration of about 120 mmol/L to about 200 mmol/L. In some embodiments, the pharmaceutical composition comprises proline, or a pharmaceutically acceptable salt thereof, at a concentration of about 130 mmol/L to about 200 mmol/L. In some embodiments, the pharmaceutical composition comprises proline, or a pharmaceutically acceptable salt thereof, at a concentration of about 140 mmol/L to about 200 mmol/L. In some embodiments, the pharmaceutical composition comprises proline, or a pharmaceutically acceptable salt thereof, at a concentration of about 150 mmol/L to about 200 mmol/L. In some embodiments, the pharmaceutical composition comprises proline, or a pharmaceutically acceptable salt thereof, at a concentration of about 160 mmol/L to about 200 mmol/L. In some embodiments, the pharmaceutical composition comprises proline, or a pharmaceutically acceptable salt thereof, at a concentration of about 170 mmol/L to about 190 mmol/L. In some embodiments, the pharmaceutical composition comprises proline, or a pharmaceutically acceptable salt thereof, at a concentration of about 180 mmol/L.

In some embodiments, the pharmaceutical composition comprises proline, or a pharmaceutically acceptable salt thereof, at a concentration of about 100 mmol/L to about 190 mmol/L. In some embodiments, the pharmaceutical composition comprises proline, or a pharmaceutically acceptable salt thereof, at a concentration of about 100 mmol/L to about 180 mmol/L. In some embodiments, the pharmaceutical composition comprises proline, or a pharmaceutically acceptable salt thereof, at a concentration of about 100 mmol/L to about 170 mmol/L. In some embodiments, the pharmaceutical composition comprises proline, or a pharmaceutically acceptable salt thereof, at a concentration of about 100 mmol/L to about 160 mmol/L. In some embodiments, the pharmaceutical composition comprises proline, or a pharmaceutically acceptable salt thereof, at a concentration of about 120 mmol/L to about 160 mmol/L. In some embodiments, the pharmaceutical composition comprises proline, or a pharmaceutically acceptable salt thereof, at a concentration of about 130 mmol/L to about 150 mmol/L. In some embodiments, the pharmaceutical composition comprises proline, or a pharmaceutically acceptable salt thereof, at a concentration of about 140 mmol/L.

In some embodiments, the pharmaceutical composition comprises proline, or a pharmaceutically acceptable salt thereof, at a concentration of about 100 mmol/L to about 150 mmol/L. In some embodiments, the pharmaceutical composition comprises proline, or a pharmaceutically acceptable salt thereof, at a concentration of about 110 mmol/L to about 150 mmol/L. In some embodiments, the pharmaceutical composition comprises proline, or a pharmaceutically acceptable salt thereof, at a concentration of about 120 mmol/L to about 140 mmol/L. In some embodiments, the pharmaceutical composition comprises proline, or a pharmaceutically acceptable salt thereof, at a concentration of about 130 mmol/L.

In some embodiments, the pharmaceutical composition comprises proline, or a pharmaceutically acceptable salt thereof, at a concentration of about 100 mmol/L to about 150 mmol/L. In some embodiments, the pharmaceutical composition comprises proline, or a pharmaceutically acceptable salt thereof, at a concentration of about 100 mmol/L to about 140 mmol/L. In some embodiments, the pharmaceutical composition comprises proline, or a pharmaceutically acceptable salt thereof, at a concentration of about 110 mmol/L to about 130 mmol/L. In some embodiments, the pharmaceutical composition comprises proline, or a pharmaceutically acceptable salt thereof, at a concentration of about 120 mmol/L.

In some embodiments, the pharmaceutical composition comprises proline, or a pharmaceutically acceptable salt thereof, at a concentration of about 1 mmol/L to about 100 mmol/L. In some embodiments, the pharmaceutical composition comprises proline, or a pharmaceutically acceptable salt thereof, at a concentration of about 1 mmol/L to about 90 mmol/L. In some embodiments, the pharmaceutical composition comprises proline, or a pharmaceutically acceptable salt thereof, at a concentration of about 1 mmol/L to about 80 mmol/L. In some embodiments, the pharmaceutical composition comprises proline, or a pharmaceutically acceptable salt thereof, at a concentration of about 1 mmol/L to about 70 mmol/L. In some embodiments, the pharmaceutical composition comprises proline, or a pharmaceutically acceptable salt thereof, at a concentration of about 30 mmol/L to about 70 mmol/L. In some embodiments, the pharmaceutical composition comprises proline, or a pharmaceutically acceptable salt thereof, at a concentration of about 40 mmol/L to about 60 mmol/L. In some embodiments, the pharmaceutical composition comprises proline, or a pharmaceutically acceptable salt thereof, at a concentration of about 50 mmol/L.

In some embodiments, the pharmaceutical composition comprises proline, or a pharmaceutically acceptable salt thereof, at a concentration of about 1 mmol/L to about 40 mmol/L. In some embodiments, the pharmaceutical composition comprises proline, or a pharmaceutically acceptable salt thereof, at a concentration of about 10 mmol/L to about 30 mmol/L. In some embodiments, the pharmaceutical composition comprises proline, or a pharmaceutically acceptable salt thereof, at a concentration of about 20 mmol/L.

In some embodiments, the proline, or a pharmaceutically acceptable salt thereof, is present at a concentration of about 600 mmol/L or less. In some embodiments, the proline, or a pharmaceutically acceptable salt thereof, is present at a concentration of about 500 mmol/L or less. In some embodiments, the proline, or a pharmaceutically acceptable salt thereof, is present at a concentration of about 400 mmol/L or less. In some embodiments, the proline, or a pharmaceutically acceptable salt thereof, is present at a concentration of about 300 mmol/L or less. In some embodiments, the proline, or a pharmaceutically acceptable salt thereof, is present at a concentration of about 250 mmol/L or less. In some embodiments, the proline, or a pharmaceutically acceptable salt thereof, is present at a concentration of about 220 mmol/L or less. In some embodiments, the proline, or a pharmaceutically acceptable salt thereof, is present at a concentration of about 200 mmol/L or less. In some embodiments, the proline, or a pharmaceutically acceptable salt thereof, is present at a concentration of about 180 mmol/L or less. In some embodiments, the proline, or a pharmaceutically acceptable salt thereof, is present at a concentration of about 160 mmol/L or less. In some embodiments, the proline, or a pharmaceutically acceptable salt thereof, is present at a concentration of about 140 mmol/L or less. In some embodiments, the proline, or a pharmaceutically acceptable salt thereof, is present at a concentration of about 120 mmol/L or less. In some embodiments, the proline, or a pharmaceutically acceptable salt thereof, is present at a concentration of about 100 mmol/L or less. In some embodiments, the proline, or a pharmaceutically acceptable salt thereof, is present at a concentration of about 50 mmol/L or less. In some embodiments, the proline, or a pharmaceutically acceptable salt thereof, is present at a concentration of about 20 mmol/L or less.

In some embodiments, the pharmaceutical composition comprises proline, or a pharmaceutically acceptable salt thereof, at a concentration of about 10 mmol/L. In some embodiments, the pharmaceutical composition comprises proline, or a pharmaceutically acceptable salt thereof, at a concentration of about 20 mmol/L. In some embodiments, the pharmaceutical composition comprises proline, or a pharmaceutically acceptable salt thereof, at a concentration of about 30 mmol/L. In some embodiments, the pharmaceutical composition comprises proline, or a pharmaceutically acceptable salt thereof, at a concentration of about 40 mmol/L. In some embodiments, the pharmaceutical composition comprises proline, or a pharmaceutically acceptable salt thereof, at a concentration of about 50 mmol/L. In some embodiments, the pharmaceutical composition comprises proline, or a pharmaceutically acceptable salt thereof, at a concentration of about 75 mmol/L. In some embodiments, the pharmaceutical composition comprises proline, or a pharmaceutically acceptable salt thereof, at a concentration of about 100 mmol/L. In some embodiments, the pharmaceutical composition comprises proline, or a pharmaceutically acceptable salt thereof, at a concentration of about 110 mmol/L. In some embodiments, the pharmaceutical composition comprises proline, or a pharmaceutically acceptable salt thereof, at a concentration of about 120 mmol/L. In some embodiments, the pharmaceutical composition comprises proline, or a pharmaceutically acceptable salt thereof, at a concentration of about 130 mmol/L. In some embodiments, the pharmaceutical composition comprises proline, or a pharmaceutically acceptable salt thereof, at a concentration of about 140 mmol/L. In some embodiments, the pharmaceutical composition comprises proline, or a pharmaceutically acceptable salt thereof, at a concentration of about 150 mmol/L. In some embodiments, the pharmaceutical composition comprises proline, or a pharmaceutically acceptable salt thereof, at a concentration of about 160 mmol/L. In some embodiments, the pharmaceutical composition comprises proline, or a pharmaceutically acceptable salt thereof, at a concentration of about 170 mmol/L. In some embodiments, the pharmaceutical composition comprises proline, or a pharmaceutically acceptable salt thereof, at a concentration of about 180 mmol/L. In some embodiments, the pharmaceutical composition comprises proline, or a pharmaceutically acceptable salt thereof, at a concentration of about 190 mmol/L. In some embodiments, the pharmaceutical composition comprises proline, or a pharmaceutically acceptable salt thereof, at a concentration of about 200 mmol/L. In some embodiments, the pharmaceutical composition comprises proline, or a pharmaceutically acceptable salt thereof, at a concentration of about 210 mmol/L. In some embodiments, the pharmaceutical composition comprises proline, or a pharmaceutically acceptable salt thereof, at a concentration of about 220 mmol/L. In some embodiments, the pharmaceutical composition comprises proline, or a pharmaceutically acceptable salt thereof, at a concentration of about 250 mmol/L. In some embodiments, the pharmaceutical composition comprises proline, or a pharmaceutically acceptable salt thereof, at a concentration of about 300 mmol/L. In some embodiments, the pharmaceutical composition comprises proline, or a pharmaceutically acceptable salt thereof, at a concentration of about 400 mmol/L. In some embodiments, the pharmaceutical composition comprises proline, or a pharmaceutically acceptable salt thereof, at a concentration of about 500 mmol/L. In some embodiments, the pharmaceutical composition comprises proline, or a pharmaceutically acceptable salt thereof, at a concentration of about 600 mmol/L.

In some embodiments, the pharmaceutical composition comprises histidine buffer, and additionally comprises proline.

In some embodiments, the excipient is glutamate, or a pharmaceutically acceptable salt thereof. Glutamate is an amino acid that can be represented by the formula:

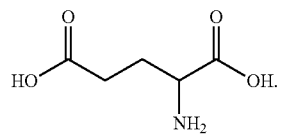

Glutamate, as used herein, includes the free base form of glutamate, as well as any and all salts thereof. In some embodiments, glutamate includes a pharmaceutically acceptable salt thereof, e.g., glutamate hydrochloride. In some embodiments, the pharmaceutically acceptable salt of glutamate is glutamate hydrochloride. Glutamate, as used herein, also includes all enantiomers (e.g., L-glutamate and S-glutamate), and any combination of enantiomers (e.g., 50% L-glutamate and 50% S-glutamate; 90%-100% L-glutamate and 10%-0% S-glutamate, etc.). In some embodiments, the term "glutamate" includes greater than 99% L-glutamate and less than 1% S-glutamate. In some embodiments, the term "glutamate" includes an enantiomerically pure L-glutamate. In some embodiments, glutamate is a pharmaceutical grade glutamate.

In some embodiments, the pharmaceutical composition comprises glutamate, or a pharmaceutically acceptable salt thereof. In some embodiments, the pharmaceutical composition comprises glutamate, or a pharmaceutically acceptable salt thereof, at a concentration of about 1 mmol/L to about 600 mmol/L. In some embodiments, the pharmaceutical composition comprises glutamate, or a pharmaceutically acceptable salt thereof, at a concentration of about 1 mmol/L to about 300 mmol/L. In some embodiments, the pharmaceutical composition comprises glutamate, or a pharmaceutically acceptable salt thereof, at a concentration of about 50 mmol/L to about 300 mmol/L. In some embodiments, the pharmaceutical composition comprises glutamate, or a pharmaceutically acceptable salt thereof, at a concentration of about 100 mmol/L to about 300 mmol/L. In some embodiments, the pharmaceutical composition comprises glutamate, or a pharmaceutically acceptable salt thereof, at a concentration of about 100 mmol/L to about 250 mmol/L. In some embodiments, the pharmaceutical composition comprises glutamate, or a pharmaceutically acceptable salt thereof, at a concentration of about 100 mmol/L to about 220 mmol/L. In some embodiments, the pharmaceutical composition comprises glutamate, or a pharmaceutically acceptable salt thereof, at a concentration of about 110 mmol/L to about 220 mmol/L. In some embodiments, the pharmaceutical composition comprises glutamate, or a pharmaceutically acceptable salt thereof, at a concentration of about 120 mmol/L to about 220 mmol/L. In some embodiments, the pharmaceutical composition comprises glutamate, or a pharmaceutically acceptable salt thereof, at a concentration of about 130 mmol/L to about 220 mmol/L. In some embodiments, the pharmaceutical composition comprises glutamate, or a pharmaceutically acceptable salt thereof, at a concentration of about 140 mmol/L to about 220 mmol/L. In some embodiments, the pharmaceutical composition comprises glutamate, or a pharmaceutically acceptable salt thereof, at a concentration of about 150 mmol/L to about 220 mmol/L. In some embodiments, the pharmaceutical composition comprises glutamate, or a pharmaceutically acceptable salt thereof, at a concentration of about 160 mmol/L to about 220 mmol/L. In some embodiments, the pharmaceutical composition comprises glutamate, or a pharmaceutically acceptable salt thereof, at a concentration of about 170 mmol/L to about 220 mmol/L. In some embodiments, the pharmaceutical composition comprises glutamate, or a pharmaceutically acceptable salt thereof, at a concentration of about 180 mmol/L to about 220 mmol/L. In some embodiments, the pharmaceutical composition comprises glutamate, or a pharmaceutically acceptable salt thereof, at a concentration of about 190 mmol/L to about 210 mmol/L. In some embodiments, the pharmaceutical composition comprises glutamate, or a pharmaceutically acceptable salt thereof, at a concentration of about 200 mmol/L.

In some embodiments, the pharmaceutical composition comprises glutamate, or a pharmaceutically acceptable salt thereof, at a concentration of about 100 mmol/L to about 200 mmol/L. In some embodiments, the pharmaceutical composition comprises glutamate, or a pharmaceutically acceptable salt thereof, at a concentration of about 110 mmol/L to about 200 mmol/L. In some embodiments, the pharmaceutical composition comprises glutamate, or a pharmaceutically acceptable salt thereof, at a concentration of about 120 mmol/L to about 200 mmol/L. In some embodiments, the pharmaceutical composition comprises glutamate, or a pharmaceutically acceptable salt thereof, at a concentration of about 130 mmol/L to about 200 mmol/L. In some embodiments, the pharmaceutical composition comprises glutamate, or a pharmaceutically acceptable salt thereof, at a concentration of about 140 mmol/L to about 200 mmol/L. In some embodiments, the pharmaceutical composition comprises glutamate, or a pharmaceutically acceptable salt thereof, at a concentration of about 150 mmol/L to about 200 mmol/L. In some embodiments, the pharmaceutical composition comprises glutamate, or a pharmaceutically acceptable salt thereof, at a concentration of about 160 mmol/L to about 200 mmol/L. In some embodiments, the pharmaceutical composition comprises glutamate, or a pharmaceutically acceptable salt thereof, at a concentration of about 170 mmol/L to about 190 mmol/L. In some embodiments, the pharmaceutical composition comprises glutamate, or a pharmaceutically acceptable salt thereof, at a concentration of about 180 mmol/L.

In some embodiments, the pharmaceutical composition comprises glutamate, or a pharmaceutically acceptable salt thereof, at a concentration of about 100 mmol/L to about 190 mmol/L. In some embodiments, the pharmaceutical composition comprises glutamate, or a pharmaceutically acceptable salt thereof, at a concentration of about 100 mmol/L to about 180 mmol/L. In some embodiments, the pharmaceutical composition comprises glutamate, or a pharmaceutically acceptable salt thereof, at a concentration of about 100 mmol/L to about 170 mmol/L. In some embodiments, the pharmaceutical composition comprises glutamate, or a pharmaceutically acceptable salt thereof, at a concentration of about 100 mmol/L to about 160 mmol/L. In some embodiments, the pharmaceutical composition comprises glutamate, or a pharmaceutically acceptable salt thereof, at a concentration of about 120 mmol/L to about 160 mmol/L. In some embodiments, the pharmaceutical composition comprises glutamate, or a pharmaceutically acceptable salt thereof, at a concentration of about 130 mmol/L to about 150 mmol/L. In some embodiments, the pharmaceutical composition comprises glutamate, or a pharmaceutically acceptable salt thereof, at a concentration of about 140 mmol/L.

In some embodiments, the pharmaceutical composition comprises glutamate, or a pharmaceutically acceptable salt thereof, at a concentration of about 100 mmol/L to about 150 mmol/L. In some embodiments, the pharmaceutical composition comprises glutamate, or a pharmaceutically acceptable salt thereof, at a concentration of about 110 mmol/L to about 150 mmol/L. In some embodiments, the pharmaceutical composition comprises glutamate, or a pharmaceutically acceptable salt thereof, at a concentration of about 120 mmol/L to about 140 mmol/L. In some embodiments, the pharmaceutical composition comprises glutamate, or a pharmaceutically acceptable salt thereof, at a concentration of about 130 mmol/L.

In some embodiments, the pharmaceutical composition comprises glutamate, or a pharmaceutically acceptable salt thereof, at a concentration of about 100 mmol/L to about 150 mmol/L. In some embodiments, the pharmaceutical composition comprises glutamate, or a pharmaceutically acceptable salt thereof, at a concentration of about 100 mmol/L to about 140 mmol/L. In some embodiments, the pharmaceutical composition comprises glutamate, or a pharmaceutically acceptable salt thereof, at a concentration of about 110 mmol/L to about 130 mmol/L. In some embodiments, the pharmaceutical composition comprises glutamate, or a pharmaceutically acceptable salt thereof, at a concentration of about 120 mmol/L.

In some embodiments, the pharmaceutical composition comprises glutamate, or a pharmaceutically acceptable salt thereof, at a concentration of about 1 mmol/L to about 100 mmol/L. In some embodiments, the pharmaceutical composition comprises glutamate, or a pharmaceutically acceptable salt thereof, at a concentration of about 1 mmol/L to about 90 mmol/L. In some embodiments, the pharmaceutical composition comprises glutamate, or a pharmaceutically acceptable salt thereof, at a concentration of about 1 mmol/L to about 80 mmol/L. In some embodiments, the pharmaceutical composition comprises glutamate, or a pharmaceutically acceptable salt thereof, at a concentration of about 1 mmol/L to about 70 mmol/L. In some embodiments, the pharmaceutical composition comprises glutamate, or a pharmaceutically acceptable salt thereof, at a concentration of about 30 mmol/L to about 70 mmol/L. In some embodiments, the pharmaceutical composition comprises glutamate, or a pharmaceutically acceptable salt thereof, at a concentration of about 40 mmol/L to about 60 mmol/L. In some embodiments, the pharmaceutical composition comprises glutamate, or a pharmaceutically acceptable salt thereof, at a concentration of about 50 mmol/L.

In some embodiments, the pharmaceutical composition comprises glutamate, or a pharmaceutically acceptable salt thereof, at a concentration of about 1 mmol/L to about 40 mmol/L. In some embodiments, the pharmaceutical composition comprises glutamate, or a pharmaceutically acceptable salt thereof, at a concentration of about 10 mmol/L to about 30 mmol/L. In some embodiments, the pharmaceutical composition comprises glutamate, or a pharmaceutically acceptable salt thereof, at a concentration of about 20 mmol/L.

In some embodiments, the glutamate, or a pharmaceutically acceptable salt thereof, is present at a concentration of about 600 mmol/L or less. In some embodiments, the glutamate, or a pharmaceutically acceptable salt thereof, is present at a concentration of about 500 mmol/L or less. In some embodiments, the glutamate, or a pharmaceutically acceptable salt thereof, is present at a concentration of about 400 mmol/L or less. In some embodiments, the glutamate, or a pharmaceutically acceptable salt thereof, is present at a concentration of about 300 mmol/L or less. In some embodiments, the glutamate, or a pharmaceutically acceptable salt thereof, is present at a concentration of about 250 mmol/L or less. In some embodiments, the glutamate, or a pharmaceutically acceptable salt thereof, is present at a concentration of about 220 mmol/L or less. In some embodiments, the glutamate, or a pharmaceutically acceptable salt thereof, is present at a concentration of about 200 mmol/L or less. In some embodiments, the glutamate, or a pharmaceutically acceptable salt thereof, is present at a concentration of about 180 mmol/L or less. In some embodiments, the glutamate, or a pharmaceutically acceptable salt thereof, is present at a concentration of about 160 mmol/L or less. In some embodiments, the glutamate, or a pharmaceutically acceptable salt thereof, is present at a concentration of about 140 mmol/L or less. In some embodiments, the glutamate, or a pharmaceutically acceptable salt thereof, is present at a concentration of about 120 mmol/L or less. In some embodiments, the glutamate, or a pharmaceutically acceptable salt thereof, is present at a concentration of about 100 mmol/L or less. In some embodiments, the glutamate, or a pharmaceutically acceptable salt thereof, is present at a concentration of about 50 mmol/L or less. In some embodiments, the glutamate, or a pharmaceutically acceptable salt thereof, is present at a concentration of about 20 mmol/L or less.

In some embodiments, the pharmaceutical composition comprises glutamate, or a pharmaceutically acceptable salt thereof, at a concentration of about 10 mmol/L. In some embodiments, the pharmaceutical composition comprises glutamate, or a pharmaceutically acceptable salt thereof, at a concentration of about 20 mmol/L. In some embodiments, the pharmaceutical composition comprises glutamate, or a pharmaceutically acceptable salt thereof, at a concentration of about 30 mmol/L. In some embodiments, the pharmaceutical composition comprises glutamate, or a pharmaceutically acceptable salt thereof, at a concentration of about 40 mmol/L. In some embodiments, the pharmaceutical composition comprises glutamate, or a pharmaceutically acceptable salt thereof, at a concentration of about 50 mmol/L. In some embodiments, the pharmaceutical composition comprises glutamate, or a pharmaceutically acceptable salt thereof, at a concentration of about 75 mmol/L. In some embodiments, the pharmaceutical composition comprises glutamate, or a pharmaceutically acceptable salt thereof, at a concentration of about 100 mmol/L. In some embodiments, the pharmaceutical composition comprises glutamate, or a pharmaceutically acceptable salt thereof, at a concentration of about 110 mmol/L. In some embodiments, the pharmaceutical composition comprises glutamate, or a pharmaceutically acceptable salt thereof, at a concentration of about 120 mmol/L. In some embodiments, the pharmaceutical composition comprises glutamate, or a pharmaceutically acceptable salt thereof, at a concentration of about 130 mmol/L. In some embodiments, the pharmaceutical composition comprises glutamate, or a pharmaceutically acceptable salt thereof, at a concentration of about 140 mmol/L. In some embodiments, the pharmaceutical composition comprises glutamate, or a pharmaceutically acceptable salt thereof, at a concentration of about 150 mmol/L. In some embodiments, the pharmaceutical composition comprises glutamate, or a pharmaceutically acceptable salt thereof, at a concentration of about 160 mmol/L. In some embodiments, the pharmaceutical composition comprises glutamate, or a pharmaceutically acceptable salt thereof, at a concentration of about 170 mmol/L. In some embodiments, the pharmaceutical composition comprises glutamate, or a pharmaceutically acceptable salt thereof, at a concentration of about 180 mmol/L. In some embodiments, the pharmaceutical composition comprises glutamate, or a pharmaceutically acceptable salt thereof, at a concentration of about 190 mmol/L. In some embodiments, the pharmaceutical composition comprises glutamate, or a pharmaceutically acceptable salt thereof, at a concentration of about 200 mmol/L. In some embodiments, the pharmaceutical composition comprises glutamate, or a pharmaceutically acceptable salt thereof, at a concentration of about 210 mmol/L. In some embodiments, the pharmaceutical composition comprises glutamate, or a pharmaceutically acceptable salt thereof, at a concentration of about 220 mmol/L. In some embodiments, the pharmaceutical composition comprises glutamate, or a pharmaceutically acceptable salt thereof, at a concentration of about 250 mmol/L. In some embodiments, the pharmaceutical composition comprises glutamate, or a pharmaceutically acceptable salt thereof, at a concentration of about 300 mmol/L. In some embodiments, the pharmaceutical composition comprises glutamate, or a pharmaceutically acceptable salt thereof, at a concentration of about 400 mmol/L. In some embodiments, the pharmaceutical composition comprises glutamate, or a pharmaceutically acceptable salt thereof, at a concentration of about 500 mmol/L. In some embodiments, the pharmaceutical composition comprises glutamate, or a pharmaceutically acceptable salt thereof, at a concentration of about 600 mmol/L.

In some embodiments, the pharmaceutical composition comprises histidine buffer and additionally comprises glutamate.

In some aspects, anti-TSLP-R antibody compositions of the present disclosure comprise an uncharged excipient. In some aspects, the uncharged excipient can assist in the prevention of denaturation or otherwise assist in stabilizing the antibody, or antigen-binding fragment thereof. Examples of excipients are known in the art. Examples can be taken, e.g., from the handbook: Gennaro, Alfonso R.: "Remington's Pharmaceutical Sciences", Mack Publishing Company, Easton, Pa., 1990. In some embodiments, the uncharged excipient is fructose, glucose, mannose, sorbose, xylose, lactose, maltose, sucrose, dextran, pullulan, dextrin, cyclodextrins, soluble starch, trehalose, sorbitol, erythritol, isomalt, lactitol, maltitol, xylitol, glycerol, lactitol, hydroxyethyl starch, water-soluble glucans, or a combination thereof. In some aspects, the uncharged excipient is sucrose. In some aspects, the uncharged excipient is trehaolse. In some aspects, the uncharged excipient is mannitol.

In some embodiments, the pharmaceutical composition comprises an excipient, wherein the excipient is glycine, glutamate, arginine, histidine, or proline, or a pharmaceutically acceptable salt thereof, or any combination thereof, wherein the pharmaceutical composition additionally comprises an excipient, wherein the excipient is sodium chloride and/or sucrose.

In some embodiments, the pharmaceutical composition comprises an excipient, wherein the excipient is sodium chloride and/or sucrose.

In some embodiments, the pharmaceutical composition comprises sodium chloride, wherein the sodium chloride is present at a concentration of about 1 mmol/L to about 200 mmol/L. In some embodiments, the pharmaceutical composition comprises sodium chloride, wherein the sodium chloride is present at a concentration of about 10 mmol/L to about 150 mmol/L. In some embodiments, the pharmaceutical composition comprises sodium chloride, wherein the sodium chloride is present at a concentration of about 25 mmol/L to about 125 mmol/L. In some embodiments, the pharmaceutical composition comprises sodium chloride, wherein the sodium chloride is present at a concentration of about 50 mmol/L to about 120 mmol/L.

In some embodiments, the pharmaceutical composition comprises sodium chloride, wherein the sodium chloride is present at a concentration of about 10 mmol/L. In some embodiments, the pharmaceutical composition comprises sodium chloride, wherein the sodium chloride is present at a concentration of about 20 mmol/L. In some embodiments, the pharmaceutical composition comprises sodium chloride, wherein the sodium chloride is present at a concentration of about 30 mmol/L. In some embodiments, the pharmaceutical composition comprises sodium chloride, wherein the sodium chloride is present at a concentration of about 40 mmol/L. In some embodiments, the pharmaceutical composition comprises sodium chloride, wherein the sodium chloride is present at a concentration of about 50 mmol/L. In some embodiments, the pharmaceutical composition comprises sodium chloride, wherein the sodium chloride is present at a concentration of about 60 mmol/L. In some embodiments, the pharmaceutical composition comprises sodium chloride, wherein the sodium chloride is present at a concentration of about 70 mmol/L. In some embodiments, the pharmaceutical composition comprises sodium chloride, wherein the sodium chloride is present at a concentration of about 80 mmol/L. In some embodiments, the pharmaceutical composition comprises sodium chloride, wherein the sodium chloride is present at a concentration of about 90 mmol/L. In some embodiments, the pharmaceutical composition comprises sodium chloride, wherein the sodium chloride is present at a concentration of about 100 mmol/L. In some embodiments, the pharmaceutical composition comprises sodium chloride, wherein the sodium chloride is present at a concentration of about 110 mmol/L. In some embodiments, the pharmaceutical composition comprises sodium chloride, wherein the sodium chloride is present at a concentration of about 120 mmol/L. In some embodiments, the pharmaceutical composition comprises sodium chloride, wherein the sodium chloride is present at a concentration of about 130 mmol/L. In some embodiments, the pharmaceutical composition comprises sodium chloride, wherein the sodium chloride is present at a concentration of about 140 mmol/L. In some embodiments, the pharmaceutical composition comprises sodium chloride, wherein the sodium chloride is present at a concentration of about 150 mmol/L. In some embodiments, the pharmaceutical composition comprises sodium chloride, wherein the sodium chloride is present at a concentration of about 160 mmol/L. In some embodiments, the pharmaceutical composition comprises sodium chloride, wherein the sodium chloride is present at a concentration of about 170 mmol/L. In some embodiments, the pharmaceutical composition comprises sodium chloride, wherein the sodium chloride is present at a concentration of about 180 mmol/L. In some embodiments, the pharmaceutical composition comprises sodium chloride, wherein the sodium chloride is present at a concentration of about 190 mmol/L. In some embodiments, the pharmaceutical composition comprises sodium chloride, wherein the sodium chloride is present at a concentration of about 200 mmol/L.

In some embodiments, the pharmaceutical composition comprises sucrose, wherein the sucrose is present at a concentration of about 1% (w/v) to about 15% (w/v). In some embodiments, the pharmaceutical composition comprises sucrose, wherein the sucrose is present at a concentration of about 1% (w/v) to about 10% (w/v). In some embodiments, the pharmaceutical composition comprises sucrose, wherein the sucrose is present at a concentration of about 1% (w/v) to about 5% (w/v). In some embodiments, the pharmaceutical composition comprises sucrose, wherein the sucrose is present at a concentration of about 2% (w/v) to about 4% (w/v).

In some embodiments, the pharmaceutical composition comprises sucrose, wherein the sucrose is at a concentration of about 1%, about 2%, about 3%, about 4%, about 5%, about 6%, about 7%, about 8%, about 9%, about 10%, about 11%, about 12%, about 13%, about 14%, or about 15% (w/v). In some embodiments, the pharmaceutical composition comprises sucrose, wherein the sucrose is at a concentration of about 1% (w/v). In some embodiments, the pharmaceutical composition comprises sucrose, wherein the sucrose is at a concentration of about 2% (w/v). In some embodiments, the pharmaceutical composition comprises sucrose, wherein the sucrose is at a concentration of about 3% (w/v). In some embodiments, the pharmaceutical composition comprises sucrose, wherein the sucrose is at a concentration of about 4% (w/v). In some embodiments, the pharmaceutical composition comprises sucrose, wherein the sucrose is at a concentration of about 5% (w/v). In some embodiments, the pharmaceutical composition comprises sucrose, wherein the sucrose is at a concentration of about 6% (w/v). In some embodiments, the pharmaceutical composition comprises sucrose, wherein the sucrose is at a concentration of about 7% (w/v). In some embodiments, the pharmaceutical composition comprises sucrose, wherein the sucrose is at a concentration of about 8% (w/v). In some embodiments, the pharmaceutical composition comprises sucrose, wherein the sucrose is at a concentration of about 9% (w/v). In some embodiments, the pharmaceutical composition comprises sucrose, wherein the sucrose is at a concentration of about 10% (w/v). In some embodiments, the pharmaceutical composition comprises sucrose, wherein the sucrose is at a concentration of about 11% (w/v). In some embodiments, the pharmaceutical composition comprises sucrose, wherein the sucrose is at a concentration of about 12% (w/v). In some embodiments, the pharmaceutical composition comprises sucrose, wherein the sucrose is at a concentration of about 13% (w/v). In some embodiments, the pharmaceutical composition comprises sucrose, wherein the sucrose is at a concentration of about 14% (w/v). In some embodiments, the pharmaceutical composition comprises sucrose, wherein the sucrose is at a concentration of about 15% (w/v).

In some embodiments, the pharmaceutical composition is described in Table 5.

TABLE 5

| Formulation ID | TRAB-1 (mg/mL) | Buffer | Excipients | Surfactant | Formulation pH | ID |
|---|---|---|---|---|---|---|
| A01 | 200 | 20 mM Sodium Acetate | — | — | 4.5 | A01 |
| A02 | | | | | 5.0 | A02 |
| A03 | | | | | 5.5 | A03 |
| A04 | | 20 mM Sodium Succinate | | | 5.0 | A06 |
| A05 | | | | | 5.5 | A05 |
| A06 | | | | | 6.0 | A06 |
| A07 | | 20 mM Histidine | | | 5.5 | A07 |
| A08 | | | | | 6.0 | A08 |
| A09 | | | | | 6.5 | A09 |
| A10 | | 20 mM Sodium Phosphate | | | 6.5 | A10 |
| A11 | | | | | 7.0 | A11 |
| A12 | | | | | 7.5 | A12 |
| B01 | | | 140 mM Arg HCl | 0.02% (w/v) PS80 | 5.7 | B01 |
| B02 | 150 | | | | | B02 |
| C01 | 200 | 20 mM Histidine | 120 mM Arg HCl | 0.04% (w/v) PS80 | | C01 |
| C02 | | | | 0.02% (w/v) PS80 | | C02 |
| C03 | | | 120 mM Glutamate | | | C03 |
| C04 | | | 120 mM NaCl | | | C04 |
| C05 | | | 180 mM Proline | | | C05 |
| C06 | | | 180 mM Glycine | | | C06 |
| C07 | | | 50 mM NaCl, 3% Sucrose | | | C07 |
| C08 | 150 | | 130 mM Arg HCl | | | C08 |
| C09 | | | 200 mM Proline | | | C09 |
| C10 | | | 50 mM NaCl, 4% Sucrose | | | C10 |
| D01 | 200 | | 180 mM Glycine | 0.03% (w/v) PS80 | | D01 |
| D02 | 150 | | | | | D02 |
| D03 | | | | 0.02% (w/v) PS80 | | D03 |
| E01 | 200 | | 120 mM Arg HCl | 0.03% (w/v) PS80 | | E01 |
| E02 | 150 | | | 0.04% (w/v) PS80 | | E02 |
| E03 | | | | 0.03% (w/v) PS80 | | E03 |
| E04 | | | | 0.02% (w/v) PS80 | | E04 |
| F01 | 200 | | 180 mM Proline | 0.03% (w/v) PS80 | | F01 |
| F02 | 150 | | | | | F02 |
| F03 | | | | 0.02% (w/v) PS80 | | F03 |

In some embodiments, the pharmaceutical composition comprises: (i) an anti-TSLP-R antibody, or antigen-binding fragment thereof, at a concentration of 180 mg/mL to 220 mg/mL; (ii) sodium acetate buffer at a concentration of 18 mmol/L to 22 mmol/L; and (iii) a pH of 4.4 to 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium acetate buffer at a concentration of 18 mmol/L to 22 mmol/L; and (iii) a pH of 4.4 to 4.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium acetate buffer at a concentration of 18 mmol/L to 22 mmol/L; and (iii) a pH of 4.9 to 5.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium acetate buffer at a concentration of 18 mmol/L to 22 mmol/L; and (iii) a pH of 5.4 to 5.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium acetate buffer at a concentration of about 20 mmol/L; and (iii) a pH of about 4.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium acetate buffer at a concentration of about 20 mmol/L; and (iii) a pH of about 5.0, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium acetate buffer at a concentration of about 20 mmol/L; and (iii) a pH of about 5.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium succinate buffer at a concentration of 18 mmol/L to 22 mmol/L; and (iii) a pH of 4.9 to 6.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium succinate buffer at a concentration of 18 mmol/L to 22 mmol/L; and (iii) a pH of 4.9 to 5.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium succinate buffer at a concentration of 18 mmol/L to 22 mmol/L; and (iii) a pH of 5.4 to 5.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium succinate buffer at a concentration of 18 mmol/L to 22 mmol/L; and (iii) a pH of 5.9 to 6.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium succinate buffer at a concentration of about 20 mmol/L; and (iii) a pH of about 5.0, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium succinate buffer at a concentration of about 20 mmol/L; and (iii) a pH of about 5.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium succinate buffer at a concentration of about 20 mmol/L; and (iii) a pH of about 6.0, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; and (iii) a pH of 6.4 to 7.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; and (iii) a pH of 6.4 to 6.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; and (iii) a pH of 6.9 to 7.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; and (iii) a pH of 7.4 to 7.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium phosphate buffer at a concentration of about 20 mmol/L; and (iii) a pH of about 6.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium phosphate buffer at a concentration of about 20 mmol/L; and (iii) a pH of about 7.0, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium phosphate buffer at a concentration of about 20 mmol/L; and (iii) a pH of about 7.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; and (iii) a pH of 5.4 to 6.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; and (iii) a pH of 5.4 to 5.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; and (iii) a pH of 5.9 to 6.1, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; and (iii) a pH of 6.4 to 6.6, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; and (iii) a pH of about 5.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; and (iii) a pH of about 6.0, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; and (iii) a pH of about 6.5, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, a pharmaceutical composition is provided, the pharmaceutical composition comprising: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises: (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

In some embodiments, the pharmaceutical composition comprises the anti-TSLP-R antibody, or antigen-binding fragment thereof, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises the anti-TSLP-R antibody, or antigen-binding fragment thereof, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises:

an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5; and (ii) a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable heavy chain polypeptide having a sequence of SEQ ID NO: 5.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the anti-TSLP-R antibody, or antigen-binding fragment thereof, comprises: (i) a variable heavy chain polypeptide having a sequence of SEQ ID NO: 5; and (ii) a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 1 mg/mL to about 300 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 50 mg/mL to about 250 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 100 mg/mL to about 200 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 150 mg/mL to about 200 mg/mL.

In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 25 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 50 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 100 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 125 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 150 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 175 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 200 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 225 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 250 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 275 mg/mL. In some embodiments, the pharmaceutical composition comprises: an anti-TSLP-R antibody, or antigen-binding fragment thereof; a pharmaceutically acceptable buffer; glycine, or a pharmaceutically acceptable salt thereof; and a surfactant, wherein the concentration of the antibody, or antigen-binding fragment thereof, is present at a concentration from about 300 mg/mL.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; glycine, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is histidine buffer. In some embodiments, the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 700 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 60 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 60 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 50 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 40 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 30 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 25 mmol; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 20 mmol; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the glycine, or pharmaceutically acceptable salt thereof, is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 50 mmol/L to about 300 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 100 mmol/L to about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 120 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) glycine, or a pharmaceutically acceptable salt thereof, at a concentration of about 130 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 140 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 150 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 160 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 170 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 180 mmol/L to about 200 mmol/L; and (iv) a surfactant at a concentration of about 0.001% to about 1% (w/v).

In some embodiments, the glycine, or pharmaceutically acceptable salt thereof, is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) glycine, or a pharmaceutically acceptable salt thereof, at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) glycine, or a pharmaceutically acceptable salt thereof, at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 300 mmol/L; and (iv) a surfactant at a concentration of about 0.001% to about 1% (w/v).

In some embodiments, the glycine, or a pharmaceutically acceptable salt thereof, is glycine hydrochloride. In some embodiments, the glycine hydrochloride is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) glycine hydrochloride at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) glycine hydrochloride at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine hydrochloride at a concentration of about 300 mmol/L; and (iv) a surfactant at a concentration of about 0.001% to about 1% (w/v).

In some embodiments, the surfactant is a polysorbate or a poloxamer. In some embodiments, the polysorbate is polysorbate 20 (PS20) or polysorbate 80 (PS80).

In some embodiments, the polysorbate is polysorbate 20 (PS20). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS20 at a concentration of about 0.001% to about 1% (w/v).

In some embodiments, the polysorbate is polysorbate 80 (PS80). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.001% to about 1% (w/v).

In some embodiments, the poloxamer is poloxamer 188. In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) poloxamer 188 at a concentration of about 0.001% to about 1% (w/v).

In some embodiments, the surfactant is present at a concentration of about 0.001% to about 1%, about 0.01% to about 0.5%, about 0.01% to about 0.1%, or about 0.02% to about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.01% to about 0.5% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.01% to about 0.1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.02% to about 0.05% (w/v).

In some embodiments, the surfactant is present at a concentration of about 0.01%, about 0.02%, about 0.03%, about 0.04%, or about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.01% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.02% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) a surfactant at a concentration of about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.01% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.02% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or pharmaceutically acceptable salt thereof, at a concentration of about 1 mmol/L to about 600 mmol/L; and (iv) PS80 at a concentration of about 0.05% (w/v).

In some embodiments, the pH of the pharmaceutical composition is from about 4.9 to about 6.6. In some embodiments, the pH of the pharmaceutical composition is from about 5.0 to about 6.5. In some embodiments, the pH of the pharmaceutical composition is about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.6.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.7.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.8.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.9.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) glycine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) glycine, or a pharmaceutically acceptable salt thereof, at a concentration of about 150 mmol/L to about 200 mmol/L; (iv) polysorbate 80 at a concentration of about 0.01% to about 0.2% (w/v); and (v) a pH of about 5.7.

In some embodiments, the pharmaceutical composition comprises: (i) an anti-TSLP-R antibody, or antigen-binding fragment thereof, at a concentration of 135 mg/mL to 220 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) glycine, or a pharmaceutically acceptable salt thereof, at a concentration of about 160 mmol/L to about 200 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, a pharmaceutical composition is provided, the pharmaceutical composition comprising: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises: (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

In some embodiments, the pharmaceutical composition comprises the anti-TSLP-R antibody, or antigen-binding fragment thereof, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises the anti-TSLP-R antibody, or antigen-binding fragment thereof, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5; and (ii) a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable heavy chain polypeptide having a sequence of SEQ ID NO: 5.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the anti-TSLP-R antibody, or antigen-binding fragment thereof, comprises: (i) a variable heavy chain polypeptide having a sequence of SEQ ID NO: 5; and (ii) a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 1 mg/mL to about 300 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 50 mg/mL to about 250 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 100 mg/mL to about 200 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 150 mg/mL to about 200 mg/mL.

In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 25 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 50 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 100 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 125 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 150 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 175 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 200 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 225 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 250 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 275 mg/mL. In some embodiments, the pharmaceutical composition comprises: an anti-TSLP-R antibody, or antigen-binding fragment thereof; a pharmaceutically acceptable buffer; arginine, or a pharmaceutically acceptable salt thereof; and a surfactant, wherein the concentration of the antibody, or antigen-binding fragment thereof, is present at a concentration from about 300 mg/mL.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; arginine, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

In some embodiments, the pharmaceutically acceptable buffer is sodium phosphate.

In some embodiments, the pharmaceutical composition comprises: (i) an anti-TSLP-R antibody, or antigen-binding fragment thereof, at a concentration of 135 mg/mL to 220 mg/mL; (ii) sodium phosphate buffer at a concentration of 18 mmol/L to 22 mmol/L; (iii) arginine, or a pharmaceutically acceptable salt thereof, at a concentration of 125 mmol/L to 155 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises histidine, and additionally comprises arginine.

In some embodiments, the pharmaceutical composition comprises: (i) an anti-TSLP-R antibody, or antigen-binding fragment thereof, at a concentration of 135 mg/mL to 220 mg/mL; (ii) sodium phosphate buffer at a concentration of 18 mmol/L to 22 mmol/L; (iii) arginine hydrochloride at a concentration of 125 mmol/L to 155 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; (iii) arginine, or a pharmaceutically acceptable salt thereof, at a concentration of 125 mmol/L to 155 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) sodium phosphate buffer at a concentration of 18 mmol/L to 22 mmol/L; (iii) arginine, or a pharmaceutically acceptable salt thereof, at a concentration of 125 mmol/L to 155 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) sodium phosphate buffer at a concentration of 18 mmol/L to 22 mmol/L; (iii) arginine hydrochloride at a concentration of 125 mmol/L to 155 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) sodium phosphate buffer at a concentration of 18 mmol/L to 22 mmol/L; (iii) arginine hydrochloride at a concentration of 125 mmol/L to 155 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium phosphate buffer at a concentration of about 20 mmol/L; (iii) arginine, or a pharmaceutically acceptable salt thereof, at a concentration of about 140 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) sodium phosphate buffer at a concentration of about 20 mmol/L; (iii) arginine, or a pharmaceutically acceptable salt thereof, at a concentration of about 140 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) sodium phosphate buffer at a concentration of about 20 mmol/L; (iii) arginine hydrochloride at a concentration of about 140 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) sodium phosphate buffer at a concentration of about 20 mmol/L; (iii) arginine hydrochloride at a concentration of about 140 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is histidine buffer. In some embodiments, the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 700 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 60 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 60 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 50 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 40 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 30 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 25 mmol; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 20 mmol; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the arginine, or pharmaceutically acceptable salt thereof, is present at a concentration of about 1 mmol/L to about 600 mmol/L, about 50 mmol/L to about 300 mmol/L, about 100 mmol/L to about 250 mmol/L, about 100 mmol/L to about 200 mmol/L, about 100 mmol/L to about 190 mmol/L, about 100 mmol/L to about 180 mmol/L, about 100 mmol/L to about 175 mmol/L, about 100 mmol/L to about 150 mmol/L, about 100 mmol/L to about 130 mmol/L, or about 110 mmol/L to about 130 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 50 mmol/L to about 300 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 175 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L to about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 110 mmol/L to about 130 mmol/L; and (iv) a surfactant at a concentration of about 0.001% to about 1% (w/v).

In some embodiments, the arginine, or pharmaceutically acceptable salt thereof, is present at a concentration of about 50 mmol/L, about 75 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 110 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 300 mmol/L; and (iv) a surfactant at a concentration of about 0.001% to about 1% (w/v).

In some embodiments, the arginine, or a pharmaceutically acceptable salt thereof, is arginine hydrochloride.

In some embodiments, the arginine hydrochloride is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 300 mmol/L; and (iv) a surfactant at a concentration of about 0.001% to about 1% (w/v).

In some embodiments, the surfactant is a polysorbate or a poloxamer. In some embodiments, the polysorbate is polysorbate 20 (PS20) or polysorbate 80 (PS80).

In some embodiments, the polysorbate is polysorbate 20 (PS20). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS20 at a concentration of about 0.001% to about 1% (w/v).

In some embodiments, the polysorbate is polysorbate 80 (PS80). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.001% to about 1% (w/v).

In some embodiments, the poloxamer is poloxamer 188. In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) poloxamer 188 at a concentration of about 0.001% to about 1% (w/v).

In some embodiments, the surfactant is present at a concentration of about 0.001% to about 1%, about 0.01% to about 0.5%, about 0.01% to about 0.1%, or about 0.02% to about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.01% to about 0.5% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.01% to about 0.1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.02% to about 0.05% (w/v).

In some embodiments, the surfactant is present at a concentration of about 0.01%, about 0.02%, about 0.03%, about 0.04%, or about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.01% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.02% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) a surfactant at a concentration of about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.01% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.02% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; and (iv) PS80 at a concentration of about 0.05% (w/v).

In some embodiments, the pH of the pharmaceutical composition is from about 4.9 to about 6.6. In some embodiments, the pH of the pharmaceutical composition is from about 5.0 to about 6.5. In some embodiments, the pH of the pharmaceutical composition is about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of 1 mmol/L to about 600 mmol/L; (iv) a surfactant at a concentration of about 0.01% to about 0.5% (w/v); and (v) a pH of about 5.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.6.

In some embodiments, the pharmaceutical composition comprises: (i) an anti-TSLP-R antibody, or antigen-binding fragment thereof, at a concentration of about 1 mg/mL to (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.7.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.8.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.9.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride a concentration of 1 mmol/L to about 600 mmol/L; (iv) a surfactant at a concentration of about 0.01% to about 0.5% (w/v); and (v) a pH of about 5.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.6.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride a concentration of about 1 mmol/L to about 600 mmol/L; (iv) a surfactant at a concentration of about 0.01% to about 0.5% (w/v); and (v) a pH of about 5.7.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.8.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 5.9.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine hydrochloride at a concentration of about 1 mmol/L to about 600 mmol/L; (iv) a surfactant at a concentration of about 0.01% to about 0.5% (w/v); and (v) a pH of about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) arginine, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) arginine, or a pharmaceutically acceptable salt thereof, at a concentration of about 100 mmol/L to about 150 mmol/L; (iv) a surfactant at a concentration of about 0.01% to about 0.2% (w/v); and (v) a pH of about 5.7.

In some embodiments, the pharmaceutical composition comprises: (i) an anti-TSLP-R antibody, or antigen-binding fragment thereof, at a concentration of about 150 mg/mL to about 250 mg/mL; (ii) histidine buffer at a concentration of about 10 mmol/L to about 30 mmol/L; (iii) arginine hydrochloride at a concentration of about 100 mmol/L to about 150 mmol/L; (iv) a surfactant at a concentration of about 0.01% to about 0.05% (w/v); and (v) a pH of about 5.7.

In some embodiments, the pharmaceutical composition comprises: (i) an anti-TSLP-R antibody, or antigen-binding fragment thereof, at a concentration of 135 mg/mL to 220 mg/mL; (ii) histidine buffer at a concentration of 18 mmol/L to 22 mmol/L; (iii) arginine, or a pharmaceutically acceptable salt thereof, at a concentration of 105 mmol/L to 145 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 220 mg/mL; (ii) histidine buffer at a concentration of 18 mmol/L to 22 mmol/L; (iii) arginine hydrochloride at a concentration of 105 mmol/L to 145 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) arginine, or a pharmaceutically acceptable salt thereof, at a concentration of about 105 mmol/L to 135 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.036% (w/v) to 0.044% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine, or a pharmaceutically acceptable salt thereof, at a concentration of 115 mmol/L to 145 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 130 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.036% (w/v) to 0.044% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine hydrochloride at a concentration of 105 mmol/L to 135 mmol/L; (iv) polysorbate 80 at a concentration of 0.036% (w/v) to 0.044% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine hydrochloride at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine hydrochloride at a concentration of 105 mmol/L to 135 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine hydrochloride at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine hydrochloride at a concentration of 117 mmol/L to 143 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine hydrochloride at a concentration of about 130 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine hydrochloride at a concentration of 105 mmol/L to 135 mmol/L; (iv) polysorbate 80 at a concentration of 0.036% (w/v) to 0.044% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine hydrochloride at a concentration of about 120 mmol/L; (iv) polysorbate 80 at a concentration of about 0.04% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) arginine hydrochloride at a concentration of 105 mmol/L to 135 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO:

11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) arginine hydrochloride at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) arginine hydrochloride at a concentration of 105 mmol/L to 135 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine hydrochloride at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) arginine hydrochloride at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, a pharmaceutical composition is provided, the pharmaceutical composition comprising: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises: (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

In some embodiments, the pharmaceutical composition comprises the anti-TSLP-R antibody, or antigen-binding fragment thereof, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 90% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 91% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 92% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 93% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 94% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 95% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 96% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 97% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 98% identical to the sequence of SEQ ID NO: 5, provided that the heavy chain polypeptide comprises the amino acid sequences of SEQ ID NO: 7, SEQ ID NO: 8, and SEQ ID NO: 9. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence that is at least 99% identical to the sequence of SEQ ID NO: 5, provided that the heavy chain polypeptide comprises the amino acid sequences of SEQ ID NO: 7, SEQ ID NO: 8, and SEQ ID NO: 9.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises the anti-TSLP-R antibody, or antigen-binding fragment thereof, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 90% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 91% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 92% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 93% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 94% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 95% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 96% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 97% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 98% identical to the sequence of SEQ ID NO: 6, provided that the light chain polypeptide comprises the amino acid sequences of SEQ ID NO: 10, SEQ ID NO: 11, and SEQ ID NO: 12. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence that is at least 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5; and (ii) a variable light chain polypeptide having a sequence that is at least 90%, 91%, 92%, 93%, 94%, 95%, 96%, 97%, 98%, or 99% identical to the sequence of SEQ ID NO: 6.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises: (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable heavy chain polypeptide having a sequence of SEQ ID NO: 5.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the anti-TSLP-R antibody, or antigen-binding fragment thereof, comprises: (i) a variable heavy chain polypeptide having a sequence of SEQ ID NO: 5; and (ii) a variable light chain polypeptide having a sequence of SEQ ID NO: 6.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 1 mg/mL to about 300 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 50 mg/mL to about 250 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 100 mg/mL to about 200 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 150 mg/mL to about 200 mg/mL.

In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 25 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 50 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 100 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 125 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 150 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 175 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 200 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 225 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 250 mg/mL. In some embodiments, the pharmaceutical composition comprises: an anti-TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 275 mg/mL. In some embodiments, the pharmaceutical composition comprises: an anti- TSLP-R antibody, or antigen-binding fragment thereof; a pharmaceutically acceptable buffer; proline, or a pharmaceutically acceptable salt thereof; and a surfactant, wherein the concentration of the antibody, or antigen-binding fragment thereof, is present at a concentration from about 300 mg/mL.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; proline, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

In some embodiments, the pharmaceutical composition comprises: (i) an anti-TSLP-R antibody, or antigen-binding fragment thereof, at a concentration of about 1 mg/mL to about 300 mg/mL; (ii) a pharmaceutically acceptable buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v), wherein the pharmaceutically acceptable buffer is histidine buffer. In some embodiments, the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 700 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 60 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 60 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 50 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 10 mmol/L to about 40 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 30 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 15 mmol/L to about 25 mmol; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 20 mmol; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the proline, or pharmaceutically acceptable salt thereof, is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 50 mmol/L to about 300 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline, or a pharmaceutically acceptable salt thereof, at a concentration of about 100 mmol/L to about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 120 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 140 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 150 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 160 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 170 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline, or a pharmaceutically acceptable salt thereof, at a concentration of about 180 mmol/L to about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 110 mmol/L to about 130 mmol/L; and (iv) a surfactant at a concentration of about 0.001% to about 1% (w/v).

In some embodiments, the proline, or pharmaceutically acceptable salt thereof, is present at a concentration of about 50 mmol/L, about 75 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline, or a pharmaceutically acceptable salt thereof, at a concentration of about 110 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline, or a pharmaceutically acceptable salt thereof, at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 300 mmol/L; and (iv) a surfactant at a concentration of about 0.001% to about 1% (w/v).

In some embodiments, the proline, or a pharmaceutically acceptable salt thereof, is proline hydrochloride.

In some embodiments, the proline hydrochloride is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 50 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 75 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 100 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 120 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 130 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline hydrochloride at a concentration of about 140 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 150 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 160 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 170 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 180 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 190 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to (iii) proline hydrochloride at a concentration of about 200 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 250 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline hydrochloride at a concentration of about 300 mmol/L; and (iv) a surfactant at a concentration of about 0.001% to about 1% (w/v).

In some embodiments, the surfactant is a polysorbate or a poloxamer. In some embodiments, the polysorbate is polysorbate 20 (PS20) or polysorbate 80 (PS80).

In some embodiments, the polysorbate is polysorbate 20 (PS20). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS20 at a concentration of about 0.001% to about 1% (w/v).

In some embodiments, the polysorbate is polysorbate 80 (PS80). In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS80 at a concentration of about 0.001% to about 1% (w/v).

In some embodiments, the poloxamer is poloxamer 188. In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) poloxamer 188 at a concentration of about 0.001% to about 1% (w/v).

In some embodiments, the surfactant is present at a concentration of about 0.001% to about 1%, about 0.01% to about 0.5%, about 0.01% to about 0.1%, or about 0.02% to about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.01% to about 0.5% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.01% to about 0.1% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.02% to about 0.05% (w/v).

In some embodiments, the surfactant is present at a concentration of about 0.01%, about 0.02%, about 0.03%, about 0.04%, or about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.01% (w/v).

In some embodiments, the pharmaceutical composition comprises: (i) an anti-TSLP-R antibody, or antigen-binding fragment thereof, at a concentration of about 1 mg/mL to (iii) proline, or pharmaceutically acceptable salt thereof, at a concentration of about 1 mmol/L to about 600 mmol/L; and (iv) a surfactant at a concentration of about 0.02% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) a surfactant at a concentration of about 0.05% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS80 at a concentration of about 0.01% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS80 at a concentration of about 0.02% (w/v).

In some embodiments, the pharmaceutical composition comprises: (i) an anti-TSLP-R antibody, or antigen-binding fragment thereof, at a concentration of about 1 mg/mL to (iii) proline, or pharmaceutically acceptable salt thereof, at a concentration of about 1 mmol/L to about 600 mmol/L; and (iv) PS80 at a concentration of about 0.03% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS80 at a concentration of about 0.04% (w/v).

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or pharmaceutically acceptable salt thereof, at a concentration of about 1 mmol/L to about 600 mmol/L; and (iv) PS80 at a concentration of about 0.05% (w/v).

In some embodiments, the pH of the pharmaceutical composition is from about 4.9 to about 6.6. In some embodiments, the pH of the pharmaceutical composition is from about 5.0 to about 6.5. In some embodiments, the pH of the pharmaceutical composition is about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.6.

In some embodiments, the pharmaceutical composition comprises: (i) an anti-TSLP-R antibody, or antigen-binding fragment thereof, at a concentration of about 1 mg/mL to (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.7.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.8.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 5.9.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.0.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.1.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.2.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.3.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.4.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; (iv) a surfactant at a concentration of about 0.01% to about 0.5% (w/v); and (v) a pH of about 6.5.

In some embodiments, the pharmaceutical composition comprises: (i) an anti-TSLP-R antibody, or antigen-binding fragment thereof, at a concentration of about 1 mg/mL to about 300 mg/mL; (ii) histidine buffer at a concentration of about 5 mmol/L to about 100 mmol/L; (iii) proline, or a pharmaceutically acceptable salt thereof, at a concentration of about 1 mmol/L to about 600 mmol/L; and (iv) a surfactant at a concentration of about 0.001% to about 1% (w/v).

In some embodiments, the pharmaceutical composition comprises: (i) an anti-TSLP-R antibody, or antigen-binding fragment thereof, at a concentration of about 150 mg/mL to about 250 mg/mL; (ii) histidine buffer at a concentration of about 10 mmol/L to about 20 mmol/L; (iii) proline, or a pharmaceutically acceptable salt thereof, at a concentration of about 150 mmol/L to about 220 mmol/L; (iv) a surfactant at a concentration of about 0.01% to about 0.2% (w/v); and (v) a pH of about 5.7.

In some embodiments, the pharmaceutical composition comprises: (i) an anti-TSLP-R antibody, or antigen-binding fragment thereof, at a concentration of 135 mg/mL to 220 mg/mL; (ii) histidine buffer at a concentration of 18 mmol/L to 22 mmol/L; (iii) proline, or a pharmaceutically acceptable salt thereof, at a concentration of 160 mmol/L to 220 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) anti-TSLP-R antibody, or antigen-binding fragment thereof, at a concentration of about 135 mg/mL to about 165 mg/mL; (ii) histidine buffer at a concentration of about 18 mmol/L to about 22 mmol/L; (iii) proline, or a pharmaceutically acceptable salt thereof, at a concentration of about 160 mmol/L to about 200 mmol/L; (iv) polysorbate 80 at a concentration of about 0.01% to about 0.05% (w/v), and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) proline, or a pharmaceutically acceptable salt thereof, at a concentration of 200 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 200 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.027% (w/v) to 0.033% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) glutamate, or a pharmaceutically acceptable salt thereof, at a concentration of 105 mmol/L to 135 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) glutamate, or a pharmaceutically acceptable salt thereof, at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) sodium chloride at a concentration of 105 mmol/L to 135 mmol/L; (iv) polysorbate 80 at a concentration of 0.018% (w/v) to 0.022% (w/v); and (v) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) sodium chloride at a concentration of about 120 mmol/L; (iv) polysorbate 80 at a concentration of about 0.02% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) sodium chloride at a concentration of 45 mmol/L to 55 mmol/L; (iv) sucrose at a concentration of 2% (w/v) to 5% (w/v); (v) polysorbate 80 at a concentration of 0.01% (w/v) to 0.05% (w/v); and (vi) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 180 mg/mL to 220 mg/mL; (ii) histidine buffer at a concentration of 18 mmol/L to 22 mmol/L; (iii) sodium chloride at a concentration of 45 mmol/L to 55 mmol/L; (iv) sucrose at a concentration of 2.7% (w/v) to 3.3% (w/v); (v) polysorbate 80 at a concentration of 0.018% (w/v) to 0.022% (w/v); and (vi) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 200 mg/mL; (ii) histidine buffer at a concentration of about 20 mmol/L; (iii) sodium chloride at a concentration of about 50 mmol/L; (iv) sucrose at a concentration of about 3% (w/v); (v) polysorbate 80 at a concentration of about 0.02% (w/v); and (vi) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of 135 mg/mL to 165 mg/mL; (ii) histidine buffer at a concentration of 18 mmol/L to 22 mmol/L; (iii) sodium chloride at a concentration of 45 mmol/L to 55 mmol/L; (iv) sucrose at a concentration of 3.6% (w/v) to 4.4% (w/v); (v) polysorbate 80 at a concentration of 0.018% (w/v) to 0.022% (w/v); and (vi) a pH of 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a concentration of about 150 mg/mL; (ii) histidine buffer at a concentration of about 20 mmol/L; (iii) sodium chloride at a concentration of about 50 mmol/L; (iv) sucrose at a concentration of about 4% (w/v); (v) polysorbate 80 at a concentration of about 0.02% (w/v); and (vi) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; and optionally: (ii) a pharmaceutically acceptable buffer at a concentration of about 5 mmol/L to about 100 mmol/L; (iii) an excipient at a concentration of about 1 mmol/L to about 600 mmol/L; and (iv) a surfactant at a concentration of about 0.001% to about 1% (w/v). In some embodiments, the pharmaceutical composition of claim 154, comprises: (i) an anti-TSLP-R antibody, or antigen-binding fragment thereof, in an amount of 25 mg to 600 mg; (ii) histidine buffer at a concentration of about 10 mmol/L to about 30 mmol/L; (iii) proline, or a pharmaceutically acceptable salt thereof, at a concentration of about 150 mmol/L to about 200 mmol/L; (iv) polysorbate 80 at a concentration of about 0.01% to about 0.05% (w/v); and (v) a pH of about 5.7.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) glycine, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) glycine, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) arginine, or a pharmaceutically acceptable salt thereof, at a concentration of 105 mmol/L to 135 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) arginine, or a pharmaceutically acceptable salt thereof, at a concentration of about 120 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of 18 mmol/L to 22 mmol/L; (iii) proline, or a pharmaceutically acceptable salt thereof, at a concentration of 160 mmol/L to 200 mmol/L; (iv) polysorbate 80 at a concentration of 0.01% (w/v) to 0.05% (w/v); and (v) a pH of about 5.6 to 5.8, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the pharmaceutical composition comprises: (i) an anti-TSLP-R antibody, or antigen-binding fragment thereof, at a dose of about 0.03 mg/kg to about 10 mg/kg; (ii) histidine buffer at a concentration of about 20 mmol/L; (iii) proline, or a pharmaceutically acceptable salt thereof, at a concentration of about 180 mmol/L; (iv) polysorbate 80 at a concentration of about 0.03% (w/v); and (v) a pH of about 5.7, wherein the anti-TSLP-R antibody, or antigen-binding fragment thereof, comprises: (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

In some embodiments, the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 450 mg, about 475 mg, about 500 mg, about 525 mg, about 550 mg, about 575 mg, about 600 mg, or about 625 mg; and the pharmaceutical composition is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.

In some embodiments, the antibody, or antigen-binding fragment thereof, is present in an of about 25 mg, about 50 mg, about 100 mg, about 150 mg, about 200 mg, about 250 mg, or about 300 mg; and the pharmaceutical composition is administered about every 8 weeks.

In some embodiments, the antibody, or antigen-binding fragment thereof, is present in an of about 25 mg, about 50 mg, about 100 mg, about 150 mg, about 200 mg, about 250 mg, or about 300 mg; and the pharmaceutical composition is administered about every 12 weeks.

In some embodiments, the antibody, or antigen-binding fragment thereof, is present in an amount of about 200 mg, about 250 mg, about 300 mg, about 350 mg, about 400 mg, about 500 mg, or about 600 mg; and the pharmaceutical composition is administered about every 24 weeks.

In some embodiments, the pharmaceutical composition is suitable for intravenous, subcutaneous, or intramuscular administration. In some embodiments, the pharmaceutical composition is suitable for intravenous administration. In some embodiments, the pharmaceutical composition is suitable for subcutaneous administration. In some embodiments, the pharmaceutical composition is suitable for intramuscular administration.

In some embodiments, the pharmaceutical composition is a liquid pharmaceutical composition. In some embodiments, the pharmaceutical composition is a lyophilized pharmaceutical composition. In some embodiments, the pharmaceutical composition is a lyophilized pharmaceutical composition that can be dissolved to form a liquid composition. In some embodiments, the pharmaceutical composition is a lyophilized pharmaceutical composition that can be dissolved in a liquid to make a liquid pharmaceutical composition suitable for intravenous, subcutaneous, or intramuscular administration. In some embodiments, the pharmaceutical composition is a lyophilized pharmaceutical composition that can be dissolved in a liquid to make a liquid pharmaceutical composition suitable for intravenous administration. In some embodiments, the pharmaceutical composition is a lyophilized pharmaceutical composition that can be dissolved in a liquid to make a liquid pharmaceutical composition suitable for subcutaneous administration. In some embodiments, the pharmaceutical composition is a lyophilized pharmaceutical composition that can be dissolved in a liquid to make a liquid pharmaceutical composition suitable for intramuscular administration.

In some embodiments, the lyophilized pharmaceutical composition can be dissolved in a liquid to make a liquid pharmaceutical composition, wherein the pH of the liquid pharmaceutical composition is from about 5.0 to from about 6.5. In some embodiments, the lyophilized pharmaceutical composition can be dissolved in a liquid to make a liquid pharmaceutical composition, wherein the pH of the liquid pharmaceutical composition is about 5.0, 5.1, 5.2, 5.3, 5.4, 5.5, 5.6, 5.7, 5.8, 5.9, 6.0, 6.1, 6.2, 6.3, 6.4, or 6.5. In some embodiments, the lyophilized pharmaceutical composition can be dissolved in a liquid to make a liquid pharmaceutical composition, wherein the pH of the liquid pharmaceutical composition is about 5.0. In some embodiments, the lyophilized pharmaceutical composition can be dissolved in a liquid to make a liquid pharmaceutical composition, wherein the pH of the liquid pharmaceutical composition is about 5.1. In some embodiments, the lyophilized pharmaceutical composition can be dissolved in a liquid to make a liquid pharmaceutical composition, wherein the pH of the liquid pharmaceutical composition is about 5.2. In some embodiments, the lyophilized pharmaceutical composition can be dissolved in a liquid to make a liquid pharmaceutical composition, wherein the pH of the liquid pharmaceutical composition is about 5.3. In some embodiments, the lyophilized pharmaceutical composition can be dissolved in a liquid to make a liquid pharmaceutical composition, wherein the pH of the liquid pharmaceutical composition is about 5.4. In some embodiments, the lyophilized pharmaceutical composition can be dissolved in a liquid to make a liquid pharmaceutical composition, wherein the pH of the liquid pharmaceutical composition is about 5.5. In some embodiments, the lyophilized pharmaceutical composition can be dissolved in a liquid to make a liquid pharmaceutical composition, wherein the pH of the liquid pharmaceutical composition is about 5.6. In some embodiments, the lyophilized pharmaceutical composition can be dissolved in a liquid to make a liquid pharmaceutical composition, wherein the pH of the liquid pharmaceutical composition is about 5.7. In some embodiments, the lyophilized pharmaceutical composition can be dissolved in a liquid to make a liquid pharmaceutical composition, wherein the pH of the liquid pharmaceutical composition is about 5.8. In some embodiments, the lyophilized pharmaceutical composition can be dissolved in a liquid to make a liquid pharmaceutical composition, wherein the pH of the liquid pharmaceutical composition is about 5.9. In some embodiments, the lyophilized pharmaceutical composition can be dissolved in a liquid to make a liquid pharmaceutical composition, wherein the pH of the liquid pharmaceutical composition is about 6.0. In some embodiments, the lyophilized pharmaceutical composition can be dissolved in a liquid to make a liquid pharmaceutical composition, wherein the pH of the liquid pharmaceutical composition is about 6.1. In some embodiments, the lyophilized pharmaceutical composition can be dissolved in a liquid to make a liquid pharmaceutical composition, wherein the pH of the liquid pharmaceutical composition is about 6.2. In some embodiments, the lyophilized pharmaceutical composition can be dissolved in a liquid to make a liquid pharmaceutical composition, wherein the pH of the liquid pharmaceutical composition is about 6.3. In some embodiments, the lyophilized pharmaceutical composition can be dissolved in a liquid to make a liquid pharmaceutical composition, wherein the pH of the liquid pharmaceutical composition is about 6.4. In some embodiments, the lyophilized pharmaceutical composition can be dissolved in a liquid to make a liquid pharmaceutical composition, wherein the pH of the liquid pharmaceutical composition is about 6.5.

In some embodiments, any pharmaceutical composition described herein can further comprise a liposome, vesicle, synthetic vesicle, exosome, synthetic exosome, dendrimer, or nanoparticle. In some embodiments, the composition as described herein further comprises sterile saline, sterile saline formulated with a buffering solution, or sterile phosphate buffered saline. In some embodiments, the composition as described herein further comprises any chemical stabilizer known in the art, or any combination thereof. In some embodiments, the composition as described herein further comprises auxiliary substances, such as wetting or emulsifying agents, pH buffering substances, and the like. In some embodiments, the composition as described herein further comprises isotonic agents, for example, sugars.

In some embodiments, the composition as described herein further comprises agents for delaying absorption that can include, but are not limited to, aluminum monostearate. In some embodiments, the composition as described herein further comprises a coating to maintain proper fluidity. In some embodiments, the composition as described herein can further comprise sterile aqueous solutions, sterile aqueous dispersions, or sterile powders for the extemporaneous preparation of sterile injectable solutions or dispersions. In some embodiments, the composition is sterile, fluid, and easily administered by a syringe. In some embodiments, the compositions are provided in lyophilized preparations. In some embodiments, the lyophilized preparations can be diluted for immediate or future use. In some embodiments, the composition is a formulation of therapeutic and diagnostic agents that is prepared by mixing with acceptable carriers, excipients, or stabilizers in the form of, e.g., lyophilized powders or aqueous solutions.

In some embodiments, the composition as described herein is stable under the conditions of manufacture and storage. In some embodiments, the composition remains stable and active even when subjected to freeze/thaw cycling and when stored in containers made of various materials, including glass. In some embodiments, the pharmaceutical composition is stable for 3 or more freeze/thaw cycles between about −70° C. and room temperature. In some embodiments, the pharmaceutical composition is stable for 5 or more freeze/thaw cycles between about −70° C. and room temperature. In some embodiments, the pharmaceutical composition is stable under agitation conditions. In some embodiments, the pharmaceutical composition is stable against agitation conditions. In some embodiments, the pharmaceutical composition is stable in agitation conditions at room temperature.

In some embodiments, the pharmaceutical composition is stable at −20° C. for 12 or more weeks. In some embodiments, the pharmaceutical composition is stable at about 2° C. to about 8° C. for 1 or more day. In some embodiments, the pharmaceutical composition is stable at about 2° C. to about 8° C. for 6 or more weeks. In some embodiments, the pharmaceutical composition is stable at about 2° C. to about 8° C. for 12 or more weeks.

In some embodiments, the liquid or dissolved lyophilized powder formulation of the pharmaceutical composition is clear in appearance. In some embodiments, the liquid or dissolved lyophilized powder formulation of the pharmaceutical composition is slightly yellow in appearance. In some embodiments, the liquid or dissolved lyophilized powder formulation of the pharmaceutical composition is slightly opalescent in appearance. In some embodiments, the liquid or dissolved lyophilized powder formulation of the pharmaceutical composition is free of visible particles. In some embodiments, the liquid or dissolved lyophilized powder formulation of the pharmaceutical composition is free of visible particles comprising high molecular weight molecules. In some embodiments, the liquid or dissolved lyophilized powder formulation of the pharmaceutical composition is free of low molecular weight molecule degradants of the anti-TSLP-R antibody, or fragment thereof.

In some embodiments, the liquid or dissolved lyophilized powder formulation of the pharmaceutical composition is free of degradation products. In some embodiments, the liquid or dissolved lyophilized powder formulation of the pharmaceutical composition is consistently free of degradation products over time. In some embodiments, the liquid or dissolved lyophilized powder formulation of the pharmaceutical composition is consistently free of oxidation products. In some embodiments, the liquid or dissolved lyophilized powder formulation of the pharmaceutical composition is consistently free of tryptophan oxidation products. In some embodiments, the liquid or dissolved lyophilized powder formulation of the pharmaceutical composition is consistently free of AGE products. In some embodiments, the liquid or dissolved lyophilized powder formulation of the pharmaceutical composition is consistently free of adduct degradation. In some embodiments, the color of the liquid or dissolved lyophilized powder formulation of the pharmaceutical composition is consistent over time.

Degradation products, such as tryptophan oxidants, AGE products, and adduct degradation, may chance the color of a formulation; therefore, is critical that the color of a formulation remains consistent over time (Ambrogelly, A.

The Different Colors of mAbs in Solution. Antibodies (Basel). 2021 June; 10(2): 21). In some embodiments, the liquid or dissolved lyophilized powder formulation of the pharmaceutical composition is free of degradation products and is clear in appearance after between about 1 day and about 12 weeks at about −20° C., at about 2° C. to 8° C., or at about 40° C. In some embodiments, the liquid or dissolved lyophilized powder formulation of the pharmaceutical composition is free of degradation products and is clear in appearance after about 1 day, about 1 week, about 2 weeks, about 4 weeks, about 6 weeks, or about 12 weeks at about −20° C., about 2° C. to 8° C., or about 40° C. In some embodiments, the liquid or dissolved lyophilized powder formulation of the pharmaceutical composition is free of degradation products and is clear in appearance after about 1, 2, 3, 4, 5, or more freeze/thaw cycles between about −70° C. and about 25° C. In some embodiments, the liquid or dissolved lyophilized powder formulation of the pharmaceutical composition is free of degradation products and is clear in appearance after about 3 or more freeze/thaw cycles between about −70° C. and about 25° C. In some embodiments, the liquid or dissolved lyophilized powder formulation of the pharmaceutical composition is free of degradation products and is clear in appearance after about 5 or more freeze/thaw cycles between about −70° C. and about 25° C. In some embodiments, the liquid or dissolved lyophilized powder formulation of the pharmaceutical composition is free of degradation products and is clear in appearance after agitation conditions at room temperature. In some embodiments, the liquid or dissolved lyophilized powder formulation of the pharmaceutical composition is free of degradation products and is free of degradation products and is clear in appearance after agitation conditions at room temperature after about 1, 2, 3, or more days. In some embodiments, the liquid or dissolved lyophilized powder formulation of the pharmaceutical composition is free of degradation products and is clear in appearance after agitation conditions at room temperature after about 1 or more days. In some embodiments, the liquid or dissolved lyophilized powder formulation of the pharmaceutical composition is free of degradation products and is clear in appearance after agitation conditions at room temperature after about 3 or more days.

A chance in color of a formulation can indicate the presence of degradation products over time. It is important that degradation products are minimized in antibody formulations; therefore, it is important that the color does not substantially change (Ambrogelly, A. The Different Colors of mAbs in Solution. Antibodies (Basel). 2021 June; 10(2): 21). A substantial color change can be yellow, yellow brown, red, pink, or brown. In some embodiments, the liquid or dissolved lyophilized powder formulation of the pharmaceutical composition is mostly free of degradation products and is slightly yellow in appearance after between about 1 day and 12 weeks at about −20° C., about 2° C. to 8° C., or about 40° C. In some embodiments, the liquid or dissolved lyophilized powder formulation of the pharmaceutical composition is mostly free of degradation products and is slightly yellow in appearance after about 1 day, about 1 week, about 2 weeks, about 4 weeks, about 6 weeks, or about 12 weeks at about −20° C., about 2° C. to 8° C., or about 40° C. In some embodiments, the liquid or dissolved lyophilized powder formulation of the pharmaceutical composition is mostly free of degradation products and is slightly yellow in appearance after about 1, 2, 3, 4, 5, or more freeze/thaw cycles between about −70° C. and about 25° C. In some embodiments, the liquid or dissolved lyophilized powder formulation of the pharmaceutical composition is mostly free of degradation products and is slightly yellow in appearance after about 3 or more freeze/thaw cycles between about −70° C. and about 25° C. In some embodiments, the liquid or dissolved lyophilized powder formulation of the pharmaceutical composition is mostly free of degradation products and is slightly yellow in appearance after about 5 or more freeze/thaw cycles between about −70° C. and about 25° C. In some embodiments, the liquid or dissolved lyophilized powder formulation of the pharmaceutical composition is mostly free of degradation products and is slightly yellow in appearance after about 1, 2, 3, or more days under agitation conditions at room temperature.

Opalescence indicates physical instability of a formulation because of the presence of aggregates or liquid-liquid phase separation in solution and has been reported for monoclonal antibody (mAb) formulations. Increased solution opalescence can be attributed to attractive protein-protein interactions (PPIs). It is critical that aggregates or liquid-liquid phase separation in formulations is minimal and that the opalescence of the formulation does not exceed slight opalescence (Raut, A. S., Kalonia, D. S. J Pharm Sci. 2015 April; 104(4):1263-74). In some embodiments, the liquid or dissolved lyophilized powder formulation of the pharmaceutical composition is slightly opalescent in appearance after between about 1 day and 12 weeks at about −20° C., about 2° C. to 8° C., or about 40° C. In some embodiments, the liquid or dissolved lyophilized powder formulation of the pharmaceutical composition is slightly opalescent in appearance after about 1 day, about 1 week, about 2 weeks, about 4 weeks, about 6 weeks, or about 12 weeks at about −20° C., about 2° C. to 8° C., or about 40° C. In some embodiments, the liquid or dissolved lyophilized powder formulation of the pharmaceutical composition is slightly opalescent in appearance after about 1, 2, 3, 4, 5, or more freeze/thaw cycles between about −70° C. and about 25° C. In some embodiments, the liquid or dissolved lyophilized powder formulation of the pharmaceutical composition is slightly opalescent in appearance after about 3 or more freeze/thaw cycles between about −70° C. and about 25° C. In some embodiments, the liquid or dissolved lyophilized powder formulation of the pharmaceutical composition is slightly opalescent in appearance after about 5 or more freeze/thaw cycles between about −70° C. and about 25° C. In some embodiments, the liquid or dissolved lyophilized powder formulation of the pharmaceutical composition is slightly opalescent in appearance after about 1, 2, 3, or more days under agitation conditions at room temperature.

Visible and subvisible particulates in antibody products may pose safety and immunogenicity risks to patients and therefore it is important that formulations are free of visible and subvisible particles (Guidance for industry: Q8 (R2) pharmaceutical development. US Food and Drug Administration Center for Drug Evaluation and Research, 2009). In some embodiments, the liquid or dissolved lyophilized powder formulation of the pharmaceutical composition is free of visible particles comprising high molecular weight molecules after between about 1 day and 12 weeks at about −20° C., about 2° C. to 8° C., or about 40° C. In some embodiments, the liquid or dissolved lyophilized powder formulation of the pharmaceutical composition is free of visible particles comprising high molecular weight molecules after about 1 day, about 1 week, about 2 weeks, about 4 weeks, about 6 weeks, or about 12 weeks at about −20° C., about 2° C. to 8° C., or about 40° C. In some embodiments, the liquid or dissolved lyophilized powder formulation of the pharmaceutical composition is free of visible particles comprising high molecular weight molecules after about 1, 2, 3, 4, 5, or more freeze/thaw cycles between about −70° C. and about 25° C. In some embodiments, the liquid or dissolved lyophilized powder formulation of the pharmaceutical composition is free of visible particles comprising high molecular weight molecules after about 3 or more freeze/thaw cycles between about −70° C. and about 25° C. In some embodiments, the liquid or dissolved lyophilized powder formulation of the pharmaceutical composition is free of visible particles comprising high molecular weight molecules after about 5 or more freeze/thaw cycles between about −70° C. and about 25° C. In some embodiments, the liquid or dissolved lyophilized powder formulation of the pharmaceutical composition is free of visible particles comprising high molecular weight molecules after about 1, 2, 3, or more days under agitation conditions at room temperature.

In some embodiments, the formulation prevents or inhibits, the formation of high molecular weight species (HMWS), which is a sign of aggregation, or the formation of low molecular weight species (LMWS), which is a sign of degradation. The species can be measured by any method, including, but not limited to, SEC (size exclusion chromatography). In some embodiments, the presence of monomer species (intact antibody) is at least 95% after 1 month, 3 months, 6 months, or 9 months at 5° C. In some embodiments, the presence of monomer species (intact antibody) is at least 96% after 1 month, 3 months, 6 months, or 9 months at 5° C. In some embodiments, the presence of monomer species (intact antibody) is at least 97% after 1 month, 3 months, 6 months, or 9 months at 5° C. In some embodiments, the presence of monomer species (intact antibody) is at least 98% after 1 month, 3 months, 6 months, or 9 months at 5° C. In some embodiments, the presence of monomer species (intact antibody) is at least 99% after 1 month, 3 months, 6 months, or 9 months at 5° C. In some embodiments, the presence of monomer species (intact antibody) is at least 95% after 1 month, 3 months, 6 months, or 9 months at 25° C. In some embodiments, the presence of monomer species (intact antibody) is at least 96% after 1 month, 3 months, 6 months, or 9 months at 25° C. In some embodiments, the presence of monomer species (intact antibody) is at least 97% after 1 month, 3 months, 6 months, or 9 months at 25° C. In some embodiments, the presence of monomer species (intact antibody) is at least 98% after 1 month, 3 months, 6 months, or 9 months at 25° C. In some embodiments, the presence of monomer species (intact antibody) is at least 99% after 1 month, 3 months, 6 months, or 9 months at 25° C. In some embodiments, the presence of monomer species (intact antibody) is at least 95% after 0.25 month, 0.5 month or 1 month at 40° C. In some embodiments, the presence of monomer species (intact antibody) is at least 96% after 0.25 month, 0.5 month or 1 month at 40° C. In some embodiments, the presence of monomer species (intact antibody) is at least 97% after 0.25 month, 0.5 month or 1 month at 40° C. In some embodiments, the presence of monomer species (intact antibody) is at least 96% after 0.25 month, 0.5 month or 1 month at 40° C. In some embodiments, the presence of monomer species (intact antibody) is at least 98% after 0.25 month, 0.5 month or 1 month at 40° C. In some embodiments, the presence of monomer species (intact antibody) is at least 99% after 0.25 month, 0.5 month or 1 month at 40° C. In some embodiments, the presence of monomer species (intact antibody) is at least 97% after 0.25 month, 0.5 month or 1 month at 40° C.

In some embodiments, the amount of the HMWS is less than or about, 1% or 2% as measured by, for example, as SEC, after 1 month, 3 months, 6 months, or 9 months at 5° C. In some embodiments, the amount of the HMWS is less than or about, 1% or 2% as measured by, for example, as SEC, after 1 month, 3 months, 6 months, or 9 months at 25° C. In some embodiments, the amount of the HMWS is less than or about, 1% or 2% as measured by, for example, as SEC, after 1 month, 3 months, 6 months, or 9 months at 40° C.

In some embodiments, the amount of the LMWS is less than or about, 1% or 2% as measured by, for example, as SEC, after 1 month, 3 months, 6 months, or 9 months at 5° C. In some embodiments, the amount of the HMWS is less than or about, 1% or 2% as measured by, for example, as SEC, after 1 month, 3 months, 6 months, or 9 months at 25° C. In some embodiments, the amount of the HMWS is less than or about, 1% or 2% as measured by, for example, as SEC, after 0.25 months, 0.5 months, 1 month, 3 months, 6 months, or 9 months at 40° C.

Although the months listed in the preceding paragraphs are included in a list, they are simply provided in a list for ease of drafting and it should be understood that they also include them singularly. For example, it should be understood that the phrase "In some embodiments, the presence of monomer species (intact antibody) is at least 95% after 1 month, 3 months, 6 months, or 9 months at 5° C." would be understood to mean after 1 month not in a list, which would read as "In some embodiments, the presence of monomer species (intact antibody) is at least 95% after 1 month." This is just one example to demonstrate how the list should be interpreted and is not intended to limited to this one example.

In some embodiments, the liquid or dissolved lyophilized powder formulation of the pharmaceutical composition is free of low molecular weight molecule degradants after between about 1 day and 12 weeks at about −20° C., about 2° C. to 8° C., or about 40° C. In some embodiments, the liquid or dissolved lyophilized powder formulation of the pharmaceutical composition is free of low molecular weight molecule degradants after about 1 day, about 1 week, about 2 weeks, about 4 weeks, about 6 weeks, or about 12 weeks at about −20° C., about 2° C. to 8° C., or about 40° C. In some embodiments, the liquid or dissolved lyophilized powder formulation of the pharmaceutical composition is free of low molecular weight molecule degradants after about 1, 2, 3, 4, 5, or more freeze/thaw cycles between about −70° C. and about 25° C. In some embodiments, the liquid or dissolved lyophilized powder formulation of the pharmaceutical composition is free of low molecular weight molecule degradants after about 3 or more freeze/thaw cycles between about −70° C. and about 25° C. In some embodiments, the liquid or dissolved lyophilized powder formulation of the pharmaceutical composition is free of low molecular weight molecule degradants after about 5 or more freeze/thaw cycles between about −70° C. and about 25° C. In some embodiments, the liquid or dissolved lyophilized powder formulation of the pharmaceutical composition is free of low molecular weight molecule degradants after about 1, 2, 3, or more days under agitation conditions at room temperature.

In some embodiments, the pharmaceutical composition comprises an anti-TSLP-R antibody, or fragment thereof, at a purity of about 90.0%, 91.0%, 92.0%, 93.0%, 94.0%, 95.0%, 96.0%, 97.0%, 98.0%, 98.5%, 99.0%, 99.5%, 99.6%, 99.7%, 99.8%, or 99.9% or greater. In some embodiments, the pharmaceutical composition comprises an anti-TSLP-R antibody, or fragment thereof, at a purity of about 90.0%, 91.0%, 92.0%, 93.0%, 94.0%, 95.0%, 96.0%, 97.0%, 98.0%, 98.5%, 99.0%, 99.5%, 99.6%, 99.7%, 99.8%, or 99.9% or greater, under non-reducing conditions. In some embodiments, the pharmaceutical composition comprises an anti-TSLP-R antibody, or fragment thereof, at a purity of about 90.0%, 91.0%, 92.0%, 93.0%, 94.0%, 95.0%, 96.0%, 97.0%, 98.0%, 98.5%, 99.0%, 99.5%, 99.6%, 99.7%, 99.8%, or 99.9% or greater, under reducing conditions.

In some embodiments, the pharmaceutical composition comprises an anti-TSLP-R antibody, or fragment thereof, at a purity of about 90.0% purity to about 95% purity, about 90.0% purity to about 100% purity, about 95.0% purity to about 100% purity, about 96.0% purity to about 100% purity, about 97.0% purity to about 100% purity, about 98.0% purity to about 100% purity, about 99.0% purity to about 100% purity, or about 99.5% purity to about 100% purity. In some embodiments, the pharmaceutical composition comprises an anti-TSLP-R antibody, or fragment thereof, at a purity of about 90.0% purity to about 95% purity, about 90.0% purity to about 100% purity, about 95.0% purity to about 100% purity, about 96.0% purity to about 100% purity, about 97.0% purity to about 100% purity, about 98.0% purity to about 100% purity, about 99.0% purity to about 100% purity, or about 99.5% purity to about 100% purity under non-reducing conditions. In some embodiments, the pharmaceutical composition comprises an anti-TSLP-R antibody, or fragment thereof, at a purity of about 90.0% purity to about 95% purity, about 90.0% purity to about 100% purity, about 95.0% purity to about 100% purity, about 96.0% purity to about 100% purity, about 97.0% purity to about 100% purity, about 98.0% purity to about 100% purity, about 99.0% purity to about 100% purity, or about 99.5% purity to about 100% purity under reducing conditions.

In some embodiments, the purity is not significantly reduced after between about 1 day and 12 weeks at about −20° C., about 2° C. to 8° C., or about 40° C. In some embodiments, the purity is not significantly reduced after about 1 day, about 1 week, about 2 weeks, about 4 weeks, about 6 weeks, or about 12 weeks at about −20° C., about 2° C. to 8° C., or about 40° C. In some embodiments, the purity is not significantly reduced after about 1, 2, 3, 4, 5, or more freeze/thaw cycles between about −70° C. and about 25° C. In some embodiments, the purity is not significantly reduced after about 3 or more freeze/thaw cycles between about −70° C. and about 25° C. In some embodiments, the purity is not significantly reduced after about 5 or more freeze/thaw cycles between about −70° C. and about 25° C. In some embodiments, the purity is not significantly reduced after about 1, 2, 3, or more days under agitation conditions at room temperature.

In some embodiments, the composition further comprises preservatives. Examples of preservatives include, but not limited to, chlorobutanol, potassium sorbate, sorbic acid, sulfur dioxide, propyl gallate, the parabens, ethyl vanillin, glycerin, phenol, and parachlorophenol, or any other suitable preservative known in the art, or any combination thereof. In some embodiments, the preservative is to prevent the growth of microorganisms. In some embodiments, the composition is preserved against the contaminating action of microorganisms, such as bacteria and fungi. In some embodiments, the composition comprises antibacterial and antifungal agents, which can include, but are not limited to, parabens, chlorobutanol, phenol, sorbic acid, thimerosal, and the like.

In some embodiments, the pharmaceutical composition comprises any of the preceding embodiments.

Kits

Kits are also provided which are useful for carrying out the methods described herein.

In some embodiments, a kit is provided, wherein the kit comprises any of the pharmaceutical compositions, as disclosed herein, and instructions for use. In some embodiments, a kit is provided, wherein the kit comprises any of the pharmaceutical compositions, as disclosed herein, in a container, and instructions for use. In some embodiments, a kit is provided, wherein the kit comprises any of the pharmaceutical compositions, as disclosed herein, in a container, wherein the container is a pre-filled syringe, and instructions for use. In some embodiments, a kit is provided, wherein the kit comprises any of the pharmaceutical compositions, as disclosed herein, in a container, wherein the container is a plastic vial or glass vial, and instructions for use.

The kit includes a container holding antibodies, or antigen-binding fragments thereof, which binds an epitope of TSLP-R protein and instructions for using the antibodies, or antigen-binding fragments thereof, for the purpose of binding to TSLP-R protein to form an immunological complex and detecting the formation of the immunological complex such that the presence or absence of the immunological complex correlates with presence or absence of TSLP-R protein in the sample.

The present kits comprise a first container containing or packaged in association with the above-described antibodies, or fragments thereof. The kit may also comprise another container containing or packaged in association solutions necessary or convenient for carrying out the methods disclosed herein. The containers can be made of glass, plastic or foil and can be a vial, bottle, pouch, tube, bag, etc. The kit may also contain written information, such as procedures for carrying out the methods disclosed herein, or analytical information, such as the amount of reagent contained in the first container. The container may be in another container apparatus, e.g., a box or a bag, along with the written information. Examples of containers include multiwell plates which allow simultaneous detection of TSLP-R protein in multiple samples.

Yet another aspect provided for herein is a kit for detecting TSLP-R protein in a biological sample. The kit includes a container holding antibodies, or fragments thereof, which binds an epitope of TSLP-R protein and instructions for using the antibodies, or fragments thereof, for the purpose of binding to TSLP-R protein to form an immunological complex and detecting the formation of the immunological complex such that the presence or absence of the immunological complex correlates with presence or absence of TSLP-R protein in the sample. Examples of containers include multi-well plates which allow simultaneous detection of TSLP-R protein in multiple samples.

In some embodiments, antibodies, or fragments thereof, that bind to a TSLP-R protein are provided. In some embodiments, the antibody, or fragment thereof, is isolated. In some embodiments, the antibody, or fragment thereof, binds to a TSLP-R protein that is properly folded. In some embodiments, the antibody, or fragment thereof, binds to a TSLP-R protein in a cell membrane. In some embodiments, the antibody, or fragment thereof, binds to a TSLP-R protein that is in a cell membrane in an intact cell. In some embodiments, the antibody, or fragment thereof, inhibits or neutralizes the function of a TSLP-R protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody, or fragment thereof. In some embodiments, the antibody, or fragment thereof, inhibits the internalization of the TSLP-R protein.

The antibodies, or fragments thereof, can be provided in a kit, such as those provided herein. The antibodies, or fragments thereof, can be used or administered alone or in admixture with another therapeutic, analgesic, or diagnostic agent, such as provided for herein. In some embodiments, the methods comprise administering an antibody, or fragment thereof, such as those provided herein.

Dosing, Routes of Administration, and Methods of Use

The term "subject" as used throughout includes any organism, such as an animal, including a mammal. A subject can be also be referred to as a patient. The term animal refers to any vertebrate or invertebrate animal. Vertebrate animals include mammals, birds, reptiles, fish, and amphibians. The term "mammal" includes, but is not limited to mice, rats, other rodents, rabbits, dogs, cats, pigs, cattle, sheep, horses, and primates such as humans and monkeys. In some embodiments, the patient or subject is a human adult, adolescent, child or infant. In some embodiments, the patient or subject is an adolescent (i.e., 12-17 years old). In some embodiments, the patient or subject is younger than 2 years old. In some embodiments, the patient or subject is 18 years old, or older. In some embodiments, the patient or subject is between the age of 18 and 75.

As used herein, a subject that is "in need thereof" refers to a subject that has been identified as requiring treatment for the condition that is to be treated and is treated with the specific intent of treating such condition. The conditions can be, for example, any of the conditions described herein.

The term "disease" is used in this disclosure to mean, and is used interchangeably with, the terms disorder, condition, or illness, unless otherwise indicated.

As used herein, the terms "inhibit," "treat," and their conjugates means to provide a treatment. The term "treatment" includes eliciting a clinically significant response without excessive levels of side effects. The term further includes a postponement of or slowing of the development of the symptoms associated with a disease or disorder and/or a reduction in the severity of the symptoms of such disease or disorder. The terms further include preventing additional symptoms, ameliorating or preventing the underlying causes of such symptoms, and improving or ameliorating existing uncontrolled or unwanted symptoms, or otherwise obtaining beneficial or desired clinical results. Thus, the terms denote that a beneficial result has been conferred on, for example, a vertebrate subject with a disorder, disease, or symptom, or with the potential to develop such a disorder, disease, or symptom. For the purposes of this disclosure, beneficial or desired clinical results include, but are not limited to, improvement or amelioration of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; remission (whether partial or total), whether detectable or undetectable, or enhancement or improvement of the condition, disorder or disease; and prevention of disorder or disease manifestation. Treatment includes eliciting a clinically significant response without excessive levels of side effects. Treatment also includes prolonging survival as compared to expected survival if not receiving treatment.

The terms "prophylaxis," "prophylactic measures," and "preventative measures" refer to actions taken to prevent a disease or to delay the onset of a disease, especially by specified means or against a specified disease. The terms "prevent a disease," "disease prevention," and the like refer to prophylactic or preventative measures prior to overt disease or disorder onset to inhibit the full development or manifestation of a disease, or to minimize the extent of the disease, or to slow its course of development.

The phrases "delay the onset of the disease," "delay disease onset," and the like refer to prophylactic or preventative measures prior to overt disease or disorder onset to slow its course of development or to delay disease onset compared to expected onset if not receiving prophylactic or preventative measures.

The terms "administer," "administering," or "administration" as used herein refer to either directly administering a compound or agent.

As used herein, the terms "therapeutically effective amount," "therapeutically effective dose" and "effective amount" are used interchangeably in this disclosure and refer to an amount of the antibody, or antigen-binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention, or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The term "route of administration" refers to the location an agent is taken up into the body and the method by which the agent is administered to said location. Exemplary routes of administration include, but are not limited to, by mouth (oral), by injection, by inhalation, by insufflation (blowing into a body cavity), or by topical administration. Routes of administration may be combined, if desired. Oral administration includes the administration of any liquid, pill, capsule, or tablet that can be swallowed, chewed, or dissolved in the mouth. Alternatively, oral administration can refer to drinking or ingesting an agent that was added to a drink or food.

The term "injection" refers to administering a fluid, such as a medicament, into a part of the body by using a needle. An injection can have a systemic or a local effect. An injection can be used for intraarterial, intraarticular, intracameral, intracerebral, intradermal, intramedullary, intramuscular, intraocular/intravitreal, intraperitoneal, intrathecal/intraspinal, intravenous, intraventricular, subcutaneous, suprachoroidal, or retroorbital administration, or for administration to any location within the body that can be punctured with a needle or a microneedle. An injection can also be an infusion, which refers to the continuous delivery of an agent through an intravenous or subcutaneous injection. In some embodiments, the anti-TSLP-R antibody, or antigen-binding fragment thereof, is injected.

The terms "dose" and "dosage" refer to the physical form in which a drug is produced and dispensed, such as a tablet, a capsule, or an injectable. Doses can be administered one time, e.g., by continuous infusion, or by doses can be administered on a schedule, e.g., every 4 hours, daily, 1-7 times per week, weekly, bi-weekly, monthly, bimonthly, quarterly, semiannually, annually etc.

The terms "in combination with" and "co-administration" as used herein means two or more agents can be administered to an animal or subject together in a mixture, concurrently as single agents or sequentially as single agents in any order. Unless otherwise described, the terms as used herein refer to the administration of a TSLP-R antibody, or fragment thereof, and the administration of a second therapeutic agent. Agents can be administered by the same or different route of administration or at the same or different time.

Toxicity and therapeutic efficacy of the antibody, or fragment thereof, administered alone or in combination with another agent, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index (LD50/EDO. In particular aspects, antibodies, or fragments thereof, exhibiting high therapeutic indices are desirable. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the pharmaceutical dosage form employed and the route of administration.

In some embodiments, a pharmaceutical composition comprising the anti-TSLP-R antibody, or antigen-binding fragment thereof, is administered to a subject in accordance with the Physicians' Desk Reference 2003 (Thomson Healthcare; 57th edition (Nov. 1, 2002)). Treatment of individuals may comprise the administration of a therapeutically effective amount of the antibodies, or fragments thereof, as described herein.

Pharmaceutical compositions can be administered with medical devices known in the art. For example, a pharmaceutical composition of the present disclosure can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556, each of which is hereby incorporated by reference in its entirety.

The pharmaceutical compositions may also be administered by infusion. Examples of well-known implants and modules for administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody, or fragment thereof, in a local rather than systemic manner, for example, via injection of the antibody, or fragment thereof, directly into an arthritic joint or pathogen-induced lesion characterized by immunopathology, often in a depot or sustained release formulation. Furthermore, one may administer the antibody, or fragment thereof, in a targeted drug delivery system, for example, in a liposome coated with a tissue-specific antibody, or fragment thereof, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, or fragment thereof, the level of symptoms, the immunogenicity of the therapeutic antibody, or fragment thereof, and the accessibility of the target cells in the biological matrix. Preferably, the administration regimen delivers sufficient therapeutic antibody, or fragment thereof, to effect improvement in the target disease state, while simultaneously minimizing undesired side effects. Accordingly, the amount of biologic delivered depends in part on the particular therapeutic antibody, or fragment thereof, and the severity of the condition being treated. Guidance in selecting appropriate doses of therapeutic antibodies, or fragments thereof, is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert, et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

In some embodiments, the antibodies, or fragments thereof, used are compatible with the recipient species such that the immune response to the MAbs does not result in an unacceptably short circulating half-life or induce an immune response to the MAbs in the subject. In some embodiments, a pharmaceutical composition comprising the anti-TSLP-R antibody, or antigen-binding fragment thereof, is administered to a subject in accordance with the Physicians' Desk Reference 2003 (Thomson Healthcare; 57th edition (Nov. 1, 2002)). Treatment of individuals may comprise the administration of a therapeutically effective amount of the antibodies, or fragments thereof, described herein.

The development of suitable dosing in a variety of treatment regimens for using the pharmaceutical compositions described herein is well-known to those of skill in the art. In some embodiments, the pharmaceutical composition comprises an active ingredient that is at least about 0.1%, 1%, 2%, 5%, 10%, 15%, 20%, 25%, 30%, 35%, 40%, 45%, 50%, 55%, 60%, 65%, 70%, 75%, 80%, or more of the weight or volume of the total formulation. In some embodiments, the pharmaceutical composition comprises an active ingredient that is at least about 0.1% or more of the weight or volume of the total formulation. In some embodiments, the pharmaceutical composition comprises an active ingredient that is at least about 1% or more of the weight or volume of the total formulation. In some embodiments, the pharmaceutical composition comprises an active ingredient that is at least about 2% or more of the weight or volume of the total formulation. In some embodiments, the pharmaceutical composition comprises an active ingredient that is at least about 5% or more of the weight or volume of the total formulation. In some embodiments, the pharmaceutical composition comprises an active ingredient that is at least about 10% or more of the weight or volume of the total formulation. In some embodiments, the pharmaceutical composition comprises an active ingredient that is at least about 15% or more of the weight or volume of the total formulation. In some embodiments, the pharmaceutical composition comprises an active ingredient that is at least about 20% or more of the weight or volume of the total formulation. In some embodiments, the pharmaceutical composition comprises an active ingredient that is at least about 25% or more of the weight or volume of the total formulation. In some embodiments, the pharmaceutical composition comprises an active ingredient that is at least about 30% or more of the weight or volume of the total formulation. In some embodiments, the pharmaceutical composition comprises an active ingredient that is at least about 35% or more of the weight or volume of the total formulation. In some embodiments, the pharmaceutical composition comprises an active ingredient that is at least about 40% or more of the weight or volume of the total formulation. In some embodiments, the pharmaceutical composition comprises an active ingredient that is at least about 45% or more of the weight or volume of the total formulation. In some embodiments, the pharmaceutical composition comprises an active ingredient that is at least about 50% or more of the weight or volume of the total formulation. In some embodiments, the pharmaceutical composition comprises an active ingredient that is at least about 55% or more of the weight or volume of the total formulation. In some embodiments, the pharmaceutical composition comprises an active ingredient that is at least about 60% or more of the weight or volume of the total formulation. In some embodiments, the pharmaceutical composition comprises an active ingredient that is at least about 65% or more of the weight or volume of the total formulation. In some embodiments, the pharmaceutical composition comprises an active ingredient that is at least about 70% or more of the weight or volume of the total formulation. In some embodiments, the pharmaceutical composition comprises an active ingredient that is at least about 75% or more of the weight or volume of the total formulation. In some embodiments, the pharmaceutical composition comprises an active ingredient that is at least about 80% or more of the weight or volume of the total formulation.

Naturally, the amount of active ingredient in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. Appropriate doses will depend on the subject being treated (e.g., human or nonhuman primate or other mammal), age and general condition of the subject to be treated, the severity of the condition being treated, the mode of administration, among other factors. An appropriate effective amount can be readily determined by one of skill in the art.

Determination of the appropriate dose can be made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies may be desirable.

Doses can be adjusted to optimize the effects in the subject. Additionally, a subject can be monitored for improvement of their condition prior to increasing the dosage.

In some embodiments, the pharmaceutical composition is in a container. In some embodiments, a pharmaceutical dosage form comprising the pharmaceutical composition of any of the previous embodiments is provided. In some embodiments, the pharmaceutical dosage form of the pharmaceutical composition is in a container. In some embodiments, the pharmaceutical dosage form of the pharmaceutical composition is in a container, wherein the container is a pre-filled syringe. In some embodiments, the pharmaceutical dosage form of the pharmaceutical composition is in a container, wherein the container is a plastic vial or glass vial. In some embodiments, the pharmaceutical dosage form of the pharmaceutical composition is in a container, wherein the container is a plastic vial. In some embodiments, the pharmaceutical dosage form of the pharmaceutical composition is in a container, wherein the container is a glass vial.

In some embodiments, the pharmaceutical dosage form comprises an anti-TSLP-R antibody, or the antigen-binding fragment thereof, wherein the antibody, or antigen-binding fragment thereof, is present at a concentration of about 200 mg/mL or less.

In some embodiments, the pharmaceutical dosage form comprises an anti-TSLP-R antibody, or antigen-binding fragment thereof, wherein the antibody, or antigen-binding fragment thereof, is present at a dose of about 0.01 mg/kg to about 15 mg/kg. In some embodiments, the pharmaceutical dosage form comprises an anti-TSLP-R antibody, or antigen-binding fragment thereof, wherein the antibody, or antigen-binding fragment thereof, is present at a dose of about 0.02 mg/kg to about 15 mg/kg. In some embodiments, the pharmaceutical dosage form comprises an anti-TSLP-R antibody, or antigen-binding fragment thereof, wherein the antibody, or antigen-binding fragment thereof, is present at a dose of about 0.03 mg/kg to about 10 mg/kg.

In some embodiments, the pharmaceutical dosage form comprises an anti-TSLP-R antibody, or antigen-binding fragment thereof, wherein the antibody, or antigen-binding fragment thereof, is present at a dose of 0.01 mg/kg to 15 mg/kg. some embodiments, the pharmaceutical dosage form comprises an anti-TSLP-R antibody, or antigen-binding fragment thereof, wherein the antibody, or antigen-binding fragment thereof, is present at a dose of 0.02 mg/kg to 15 mg/kg. some embodiments, the pharmaceutical dosage form comprises an anti-TSLP-R antibody, or antigen-binding fragment thereof, wherein the antibody, or antigen-binding fragment thereof, is present at a dose of 0.03 mg/kg to 10 mg/kg.

In some embodiments, the pharmaceutical dosage form comprises an anti-TSLP-R antibody, or antigen-binding fragment thereof, wherein the antibody, or antigen-binding fragment thereof, is present in an amount of about 10 mg to about 700 mg. In some embodiments, the pharmaceutical dosage form comprises an anti-TSLP-R antibody, or antigen-binding fragment thereof, wherein the antibody, or antigen-binding fragment thereof, is present in an amount of about 25 mg to about 600 mg.

In some embodiments, the pharmaceutical dosage form comprises an anti-TSLP-R antibody, or antigen-binding fragment thereof, wherein the antibody, or antigen-binding fragment thereof, is present in an amount of 10 mg to 700 mg. In some embodiments, the pharmaceutical dosage form comprises an anti-TSLP-R antibody, or antigen-binding fragment thereof, wherein the antibody, or antigen-binding fragment thereof, is present in an amount of 25 mg to 600 mg.

In some embodiments, the pharmaceutical dosage form comprises an anti-TSLP-R antibody, or antigen-binding fragment thereof, wherein the antibody, or antigen-binding fragment thereof, is present at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3.0 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4.0 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5.0 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6.0 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7.0 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8.0 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9.0 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10.0 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11.0 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12.0 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13.0 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14.0 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15.0 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, or about 15.9 mg/kg.

In some embodiments, the pharmaceutical dosage form comprises an anti-TSLP-R antibody, or antigen-binding fragment thereof, wherein the antibody, or antigen-binding fragment thereof, is present at a dose of 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11.0 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12.0 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13.0 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14.0 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15.0 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, or 15.9 mg/kg.

In some embodiments, the pharmaceutical dosage form comprises an anti-TSLP-R antibody, or antigen-binding fragment thereof, wherein the antibody, or antigen-binding fragment thereof, is present in an amount of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, or about 700 mg.

In some embodiments, the pharmaceutical dosage form comprises an anti-TSLP-R antibody, or antigen-binding fragment thereof, wherein the antibody, or antigen-binding fragment thereof, is present in an amount of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, or 700 mg.

In some embodiments, the pharmaceutical dosage form comprises an anti-TSLP-R antibody, or antigen-binding fragment thereof, wherein the antibody, or antigen-binding fragment thereof, is present in an amount of 25 mg, 50 mg, 100 mg, 150 mg, 200 mg, 250 mg, or 300 mg. In some embodiments, the pharmaceutical dosage form comprises an anti-TSLP-R antibody, or antigen-binding fragment thereof, wherein the antibody, or antigen-binding fragment thereof, is present in an amount of about 200 mg, about 250 mg, about 300 mg, about 350 mg, about 400 mg, about 500 mg, or about 600 mg.

In some embodiments, the pharmaceutical dosage form comprises an anti-TSLP-R antibody, or antigen-binding fragment thereof, present at a dose of about 0.03 mg/kg to about 10 mg/kg, is present in an amount of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, or 700 mg.

In some embodiments, the pharmaceutical dosage form comprises an anti-TSLP-R antibody, or antigen-binding fragment thereof, present at a dose of about 0.03 mg/kg to about 10 mg/kg, is present in an amount of 25 mg, 50 mg, 100 mg, 150 mg, 200 mg, 250 mg, or 300 mg.

In some embodiments, the pharmaceutical dosage form comprises an anti-TSLP-R antibody, or antigen-binding fragment thereof, present at a dose of about 0.03 mg/kg to about 10 mg/kg, is present in an amount of about 200 mg, about 250 mg, about 300 mg, about 350 mg, about 400 mg, about 500 mg, or about 600 mg.

The pharmaceutical compositions provided herein can be provided by continuous infusion, or by doses administered, e.g., monthly, bimonthly, quarterly, semiannually, etc. Doses may be provided, e.g., intravenously or subcutaneously. In some embodiments, the pharmaceutical composition is administered about every one week, about every two weeks, about every three weeks, about every four weeks, about every five weeks, about every six weeks, about every seven weeks, about every eight weeks, about every twelve weeks, or about every twenty-four weeks. In some embodiments, the pharmaceutical composition is administered about every two weeks. In some embodiments, the pharmaceutical composition is administered about every four weeks. In some embodiments, the pharmaceutical composition is administered about every eight weeks. In some embodiments, the pharmaceutical composition is administered about every twelve weeks. In some embodiments, the pharmaceutical composition is administered about every 24 weeks. In some embodiments, the pharmaceutical composition is administered on such a schedule for at least 4 weeks. In some embodiments, the pharmaceutical composition is administered on such a schedule for at least 8 weeks. In some embodiments, the pharmaceutical composition is administered on such a schedule for at least 12 weeks. In some embodiments, the pharmaceutical composition is administered on such a schedule for at least 24 weeks. In some embodiments, the pharmaceutical composition is administered on such a schedule for at least 32 weeks. In some embodiments, the pharmaceutical composition is administered on such a schedule for at least 36 weeks. In some embodiments, the pharmaceutical composition is administered on such a schedule for at least 40 weeks. In some embodiments, the pharmaceutical composition is administered on such a schedule for at least 42 weeks. In some embodiments, the pharmaceutical composition is administered on such a schedule for at least 48 weeks.

In some embodiments, the pharmaceutical composition is administered (e.g., infusion or subcutaneous injection) once. In some embodiments, the pharmaceutical composition is administered (e.g., infusion or subcutaneous injection) twice. In some embodiments, the pharmaceutical composition is administered (e.g., infusion or subcutaneous injection) three times. In some embodiments, the pharmaceutical composition is administered (e.g., infusion or subcutaneous injection) four times. In some embodiments, the pharmaceutical composition is administered (e.g., infusion or subcutaneous injection) more than four times.

In some embodiments, the pharmaceutical composition as disclosed herein comprises an active form of an anti-TSLP-R antibody. In some embodiments, the anti-TSLP-R antibody, or antigen-binding fragment thereof, binds an epitope on a TSLP-R protein, or other protein described herein, and displays in vitro and/or in vivo TSLP-R inhibiting or therapeutic activities.

In some embodiments, methods of detecting the presence or absence of a TSLP-R in a sample are provided, the method comprising contacting a sample with one or more antibodies, or fragments thereof, described herein detecting the binding to a TSLP-R antigen by the antibody, or fragment thereof. In some embodiments, the detection of the binding indicates the presence of the TSLP-R antigen; or the absence of the detection of the binding to the TSLP-R antigen indicates the absence of the TSLP-R antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody, or fragment thereof, that binds to an epitope on TSLP-R protein, are provided, the method comprising contacting a test antibody, or fragment thereof, with the epitope on TSLP-R protein and determining whether the test antibody, or fragment thereof, binds to the epitope. In some embodiments, the determining comprises determining whether the test antibody, or fragment thereof, binds to the protein and is competitively inhibited by an antibody, or fragment thereof, comprising a sequence as provided herein. In some embodiments, the determining comprises mutating one or more residues of epitope or protein and determining binding of the test antibody, or fragment thereof, to the mutated epitope, wherein if the mutation reduces binding of the test antibody, or fragment thereof, as compared to the non-mutated epitope, the test antibody, or fragment thereof, is deemed to bind to that epitope.

In some embodiments, the methods of identifying a test antibody, or fragment thereof, that binds to an epitope on TSLP-R protein, comprise contacting the cell with an antibody, or fragment thereof, as provided for herein, or a pharmaceutical composition comprising the same. In some embodiments, the contacting comprises administering to a subject the antibody, or fragment thereof, or a pharmaceutical composition comprising the same. In some embodiments, the antibody, or fragment thereof, has an IC50 of less than, or equal to, about 0.2 nm, 0.15 nm, 0.10 nm, 0.09 nm. In some embodiments, the IC50 is measured in an in vitro assay, such as an assay as provided for herein, such as illustrated in the Examples. In some embodiments, the IC50 is measured in a cell that is an A549 cell or a HOCF cell.

In some embodiments, methods of monitoring internalization of TSLP-R from the surface of a cell are provided. In some embodiments, the method comprising contacting the cell with an anti-TSLP-R antibody, or fragment thereof, as provided herein and detecting the presence of TSLP-R in the cell or on the surface of the cell. The differences in cell surface expression can be measured and the internalization can be monitored and measured. This can be used, for example, to measure the effect of another molecule, such as a test agent, to modulate internalization of TSLP-R protein. Thus, the antibodies, or fragments thereof, provided for herein can be used to identify test agents that modulate (increase or decrease) the internalization of TSLP-R protein. Test molecules that increase the internalization, which would be measured as a decrease in binding of an anti-TSLP-R antibody, or fragment thereof, to TSLP-R protein on the cell surface, can be identified according to the methods provided herein. Test molecules that decrease the internalization, which would be measured as an increase in binding of an anti-TSLP-R antibody, or fragment thereof, to TSLP-R protein on the cell surface, can be identified according to the methods provided herein. The surface expression can be measured by fluorescence, which can be done through a secondary antibody, or fragment thereof, that recognized the TSLP-R antibodies, or fragments thereof, or by labelling the anti-TSLP-R antibodies, or fragments thereof, provided for herein.

In some embodiments, a method of increasing the internalization of TSLP-R on a cell is provided, the method comprising contacting the cell with a pharmaceutical composition as disclosed herein. In some embodiments, a method of increasing the internalization of TSLP-R on a cell is provided, the method comprising contacting the cell with a pharmaceutical composition comprising the pharmaceutical dosage form as disclosed herein.

In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or dosage form of the pharmaceutical composition is administered by injection. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion.

In some embodiments, a method of inhibiting TSLP-R on a cell is provided, the method comprising contacting the cell with a pharmaceutical composition as disclosed herein. In some embodiments, a method of inhibiting TSLP-R on a cell is provided, the method comprising contacting the cell with a pharmaceutical composition comprising the pharmaceutical dosage form as disclosed herein.

In some embodiments, a method of inhibiting TSLP-R by at least 95%, 96%, 97%, 98%, 99%, or by 100% in a subject in need thereof is provided, the method comprising administering a pharmaceutical composition as disclosed herein. In some embodiments, a method of inhibiting TSLP-R by at least 95%, 96%, 97%, 98%, 99%, or by 100% in a subject in need thereof is provided, the method comprising administering a pharmaceutical dosage form of the pharmaceutical composition as disclosed herein. In some embodiments, TSLP-R is inhibited by at least 95%. In some embodiments, TSLP-R is inhibited by at least 96%. In some embodiments, TSLP-R is inhibited by at least 97%. In some embodiments, TSLP-R is inhibited by at least 98%. In some embodiments, TSLP-R is inhibited by at least 99%. In some embodiments, TSLP-R is inhibited by 100%.

As used herein, a TSLP-R associated pathology refers to conditions that are caused by the modulation of TSLP-R.

In some embodiments, the anti-TSLP-R antibodies, or antigen-binding fragments thereof, are capable of inhibiting TSLP-R function and are suitable both as therapeutic agents for treating TSLP-R-associated conditions in humans and animals. An antibody, or fragment thereof, capable treating a condition associated with TSLP-R activity or use to treat a TSLP-R related pathology, is intended to be provided to subjects in an amount sufficient to affect a reduction, resolution, or amelioration in the TSLP-R related symptom or pathology.

Accordingly, in some embodiments, methods of treating a subject with a TSLP-R mediated disorder are provided. In some embodiments, the method of treating a TSLP-R associated pathology in a subject in need thereof comprises administering a pharmaceutical composition comprising an antibody, or antigen-binding fragment thereof, as provided herein. In some embodiments, the methods of treating a TSLP-R associated pathology comprise administering a therapeutically or a prophylactically effective amount of one or more monoclonal antibodies, or antigen-binding fragments of the antibodies described herein to a susceptible subject or to one exhibiting a condition in which TSLP-R is known or suspected to have caused the pathology observed. Any active form of the antibody, or fragment thereof, can be administered, including, but not limited to scFV, Fab and F(ab')2 fragments and other forms of antibodies, or fragments thereof, provided for herein. In some embodiments, the method of treating a TSLP-R mediated pathology comprises administering an antibody, or antigen-binding fragment thereof, to the subject with such a condition, co-administered with other therapeutics. These can be administered simultaneously or sequentially.

In some embodiments, methods of treating a disease in a subject in need thereof are provided. In some embodiments, methods of treating a TSLP-R associated pathology are provided. In some embodiments, the method of treating a TSLP-R associated pathology in a subject in need thereof comprises administering to the subject a therapeutically effective amount of a pharmaceutical composition as disclosed herein. In some embodiments, the method of treating a TSLP-R associated pathology in a subject in need thereof comprises administering to the subject a therapeutically effective amount of a pharmaceutical dosage form of a pharmaceutical composition as disclosed herein.

In some embodiments, methods of delaying the onset of a disease in a subject in need thereof are provided. In some embodiments, methods of delaying the onset of a TSLP-R associated pathology are provided. In some embodiments, the method of delaying the onset of a TSLP-R associated pathology in a subject in need thereof comprises administering to the subject a therapeutically effective amount of a pharmaceutical composition as disclosed herein. In some embodiments, the method of delaying the onset of a TSLP-R associated pathology in a subject in need thereof comprises administering to the subject a therapeutically effective amount of a pharmaceutical dosage form of a pharmaceutical composition as disclosed herein.

In some embodiments, methods of preventing a disease in a subject in need thereof are provided. In some embodiments, methods of preventing a TSLP-R associated pathology are provided. In some embodiments, the method of preventing a TSLP-R associated pathology in a subject in need thereof comprises administering to the subject a therapeutically effective amount of a pharmaceutical composition as disclosed herein. In some embodiments, the method of preventing a TSLP-R associated pathology in a subject in need thereof comprises administering to the subject a therapeutically effective amount of a pharmaceutical dosage form of a pharmaceutical composition as disclosed herein.

In some embodiments, the subject in need thereof has a TSLP-R associated pathology, wherein the TSLP-R associated pathology comprises a pulmonary disease, a gastroenterological disease, an oncological disease, a dermatological disease, a nephrological disease, an allergy, or an immunological disease. In some embodiments, the TSLP-R associated pathology comprises an allergic inflammatory disease. In some embodiments, the TSLP-R associated pathology comprises asthma. In some embodiments, the TSLP-R associated pathology comprises systemic sclerosis.

In some embodiments, the pharmaceutical composition is administered by injection. In some embodiments, the pharmaceutical dosage form of the pharmaceutical composition is administered by injection. In some embodiments, the pharmaceutical composition administered by injection is administered with a needle or a microneedle. In some embodiments, the pharmaceutical dosage form of the pharmaceutical composition administered by injection is administered with a needle or a microneedle.

In some embodiments, the method of treating a TSLP-R associated pathology in a subject in need thereof comprises administering an antibody, or fragment thereof, described herein or a pharmaceutical composition described herein to a subject to treat, inhibit, or amelioratea pulmonary disease, a gastroenterological disease, an oncological disease, a dermatological disease, a nephrological disease, an allergy, or an immunological disease.

In some embodiments, the methods provided for herein are for treating asthma. In some embodiments, the methods provided for herein are for treating sclerosis, such as systemic sclerosis.

In some embodiments, the method of treating a TSLP-R associated pathology in a subject in need thereof comprises administering an antibody, or fragment thereof, described herein or a pharmaceutical composition described herein to a subject to treat, inhibit, or ameliorate an allergic inflammatory disease. In some embodiments, the method of treating a TSLP-R associated pathology in a subject in need thereof comprises administering an antibody, or fragment thereof, described herein or a pharmaceutical composition described herein to a subject to treat, inhibit, or ameliorate asthma. In some embodiments, the method of treating a TSLP-R associated pathology in a subject in need thereof comprises administering an antibody, or fragment thereof, described herein or a pharmaceutical composition described herein to a subject to treat, inhibit, or ameliorate systemic sclerosis.

In some embodiments, the method of treating a TSLP-R associated pathology in a subject in need thereof comprises administering an antibody, or fragment thereof, described herein or a pharmaceutical composition described herein to a subject to treat, inhibit, or ameliorate a TSLP-R associated pathology.

In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks. In some embodiments, the method of treating a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the anti-TSLP-R antibody, or antigen-binding fragment thereof, is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; at least 2 administrations or at least 3 administrations of the anti-TSLP-R antibody, or antigen-binding fragment thereof, are administered; and the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks. In some embodiments, the method of delaying the onset of a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the anti-TSLP-R antibody, or antigen-binding fragment thereof, is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; at least 2 administrations or at least 3 administrations of the anti-TSLP-R antibody, or antigen-binding fragment thereof, are administered; and the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the anti-TSLP-R antibody, or antigen-binding fragment thereof, is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; at least 2 administrations or at least 3 administrations of the anti-TSLP-R antibody, or antigen-binding fragment thereof, are administered; and the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered intravenously. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of preventing a TSLP-R associated pathology in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of treating a TSLP-R associated pathology comprises increasing the internalization of TSLP-R on a cell. In some embodiments, the method of delaying the onset of a TSLP-R associated pathology comprises increasing the internalization of TSLP-R on a cell. In some embodiments, the method of preventing a TSLP-R associated pathology comprises increasing the internalization of TSLP-R on a cell.

In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of increasing the internalization of TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of treating a TSLP-R associated pathology comprises inhibiting TSLP-R on a cell. In some embodiments, the method of delaying the onset of a TSLP-R associated pathology comprises inhibiting TSLP-R on a cell. In some embodiments, the method of preventing a TSLP-R associated pathology comprises inhibiting TSLP-R on a cell.

In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of inhibiting TSLP-R on a cell comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of treating a TSLP-R associated pathology comprises inhibiting TSLP-R by at least 95%, 96%, 97%, 98%, 99%, or by 100% in a subject in need thereof. In some embodiments, the method of delaying the onset of a TSLP-R associated pathology comprises inhibiting TSLP-R by at least 95%, 96%, 97%, 98%, 99%, or by 100% in a subject in need thereof. In some embodiments, the method of preventing a TSLP-R associated pathology comprises inhibiting TSLP-R by at least 95%, 96%, 97%, 98%, 99%, or by 100% in a subject in need thereof.

In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered with a needle or a microneedle.

In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered intravenously. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or pharmaceutical dosage form of the pharmaceutical composition is administered by injection is administered subcutaneously. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the injection of the pharmaceutical composition or pharmaceutical dosage form of the pharmaceutical composition is an infusion.

In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after administration of the pharmaceutical composition or the pharmaceutical dosage form has ceased. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration after at least 1 administration of the pharmaceutical composition or the pharmaceutical dosage form. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition or the pharmaceutical dosage form is administered to the subject about every 4 weeks; and the subject has a decrease in blood eosinophil concentration following 3 administrations of the pharmaceutical composition or the pharmaceutical dosage form. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the treatment results in an improvement of or reduction in severity of a symptom of the disease. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the improvement of or reduction in severity of a symptom of the disease is sustained at least 1, 2, 3, 4, 5, 6, 7, 8, 9, 10, 11, 12, 13, 14, 15, 16, 17, or 18 months after discontinuation of antibody administration. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the pharmaceutical composition is administered as a first dose and a subsequence dose, or subsequent doses. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 4 weeks. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 8 weeks. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 12 weeks. In some embodiments, the method of inhibiting TSLP-R by at least 95%, 96%, 97%, 98%, 99%, or by 100% in a subject in need thereof comprises administering a therapeutically effective amount of the pharmaceutical composition as disclosed herein, or the pharmaceutical dosage form of the pharmaceutical composition as disclosed herein, to a subject in need thereof, wherein the subsequent dose, or subsequence doses, are administered once every 24 weeks.

Although the present disclosure has been described in considerable detail with reference to certain preferred embodiments thereof, other versions are possible. Therefore, the spirit and scope of the appended claims should not be limited to the description and the preferred versions contained within this specification.

ENUMERATED EMBODIMENTS

1. A pharmaceutical composition comprising:
   (i) an anti-TSLP-R antibody, or antigen-binding fragment thereof, at a concentration of about 1 mg/mL to about 300 mg/mL;
   (ii) a pharmaceutically acceptable buffer at a concentration of about 5 mmol/L to about 100 mmol/L;
   (iii) an excipient at a concentration of about 1 mmol/L to about 600 mmol/L; and
   (iv) a surfactant at a concentration of about 0.001% to about 1% (w/v).
2. The pharmaceutical composition of embodiment 1, wherein the anti-TSLP-R antibody, or antigen-binding fragment thereof, comprises:
   (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and
   (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.
3. The pharmaceutical composition of any one of embodiments 1-2, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.
4. The pharmaceutical composition of any one of embodiments 1-3, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.
5. The pharmaceutical composition of any one of embodiments 1-4, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.
6. The pharmaceutical composition of any one of embodiments 1-5, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.
7. The pharmaceutical composition of any one of embodiments 1-6, wherein the anti-TSLP-R antibody, or antigen-binding fragment thereof, comprises:
   (i) a variable heavy chain polypeptide having a sequence that is at least 90%, 91%, 92%, 93%, 94%, 95%, 96%, 97%, 98%, or 99% identical to the sequence of SEQ ID NO: 5; and
   (ii) a variable light chain polypeptide having a sequence that is at least 90%, 91%, 92%, 93%, 94%, 95%, 96%, 97%, 98%, or 99% identical to the sequence of SEQ ID NO: 6.
8. The pharmaceutical composition of any one of embodiments 1-7, wherein the anti-TSLP-R antibody, or antigen-binding fragment thereof, comprises:
   (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and
   (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.
9. The pharmaceutical composition of any one of embodiments 1-8, wherein the anti-TSLP-R antibody, or antigen-binding fragment thereof, comprises a variable heavy chain polypeptide having a sequence of SEQ ID NO: 5.
10. The pharmaceutical composition of any one of embodiments 1-9, wherein the anti-TSLP-R antibody, or antigen-binding fragment thereof, comprises a variable light chain polypeptide having a sequence of SEQ ID NO: 6.
11. The pharmaceutical composition of any one of embodiments 1-10, wherein the anti-TSLP-R antibody, or antigen-binding fragment thereof, comprises:
    (i) a variable heavy chain polypeptide having a sequence of SEQ ID NO: 5; and
    (ii) a variable light chain polypeptide having a sequence of SEQ ID NO: 6.
12. The pharmaceutical composition of any one of embodiments 1-11, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL.

13. The pharmaceutical composition of any one of embodiments 1-12, wherein the antibody, or antigen-binding fragment thereof, is present at a concentration of about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL.

14. The pharmaceutical composition of any one of embodiments 1-13, wherein the antibody, or antigen-binding fragment thereof, is present at a concentration of about 150 mg/mL.

15. The pharmaceutical composition of any one of embodiments 1-13, wherein the antibody, or antigen-binding fragment thereof, is present at a concentration of about 200 mg/mL.

16. The pharmaceutical composition of any one of embodiments 1-15, wherein the pharmaceutically acceptable buffer is one or more chosen from histidine buffer, phosphoric acid buffer, citric acid buffer, acetic acid buffer, succinic acid buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

17. The pharmaceutical composition of embodiment 16, wherein the pharmaceutically acceptable buffer is a histidine buffer.

18. The pharmaceutical composition of embodiment 17, wherein the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

19. The pharmaceutical composition of any one of embodiments 17 or 18, wherein the histidine buffer is present at a concentration of about 20 mmol/L.

20. The pharmaceutical composition of any one of embodiments 1-19, wherein the excipient is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.

21. The pharmaceutical composition of any one of embodiments 1-20, wherein the excipient is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

22. The pharmaceutical composition of any one of embodiments 1-21, wherein the excipient is a viscosity reducing agent.

23. The pharmaceutical composition of any one of embodiments 1-22, wherein the excipient is an amino acid chosen from glycine, glutamate, arginine, histidine, proline, or a pharmaceutically acceptable salt thereof.

24. The pharmaceutical composition of any one of embodiments 1-23, wherein the excipient is glycine, arginine, or proline, or a pharmaceutically acceptable salt thereof.

25. The pharmaceutical composition of any one of embodiments 23-24, wherein the excipient is glycine, or a pharmaceutically acceptable salt thereof.

26. The pharmaceutical composition of embodiment 25, wherein the pharmaceutically acceptable salt of glycine is glycine hydrochloride.

27. The pharmaceutical composition of any one of embodiments 23-24, wherein the excipient is arginine, or a pharmaceutically acceptable salt thereof.

28. The pharmaceutical composition of embodiment 27, wherein the pharmaceutically acceptable salt of arginine is arginine hydrochloride.

29. The pharmaceutical composition of any one of embodiments 23-28, wherein the excipient is proline, or a pharmaceutically acceptable salt thereof.

30. The pharmaceutical composition of embodiment 27, wherein the pharmaceutically acceptable salt of proline is proline hydrochloride.

31. The pharmaceutical composition of any one of embodiments 1-21, wherein the excipient is sodium chloride and/or sucrose.

32. The pharmaceutical composition of embodiment 31, wherein the sucrose is present at a concentration of about 1% to about 15%, about 1% to about 10%, about 1% to about 5%, or about 2% to about 4% (w/v).

33. The pharmaceutical composition of any one of embodiments 31-32, wherein the sucrose is at a concentration of about 1%, about 2%, about 3%, about 4%, about 5%, about 6%, about 7%, about 8%, about 9%, about 10%, about 11%, about 12%, about 13%, about 14%, or about 15% (w/v).

34. The pharmaceutical composition of embodiment 31, wherein the sodium chloride is present at a concentration of about 1 mmol/L to about 200 mmol/L, about 10 mmol/L to about 150 mmol/L, about 25 mmol/L to about 125 mmol/L, or about 50 mmol/L to about 120 mmol/L.

35. The pharmaceutical composition of any one of embodiments 31 or 34, wherein the sodium chloride is present at a concentration of about 10 mmol/L, about 20 mmol/L, about 30 mmol/L, about 40 mmol/L, about 50 mmol/L, about 60 mmol/L, about 70 mmol/L, about 80 mmol/L, about 90 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, or about 200 mmol/L.

36. The pharmaceutical composition of any one of embodiments 1-35, wherein the surfactant is a polysorbate or a poloxamer.

37. The pharmaceutical composition of embodiment 36, wherein the polysorbate is polysorbate 20 (PS20), or polysorbate 80 (PS80).

38. The pharmaceutical composition of embodiment 36, wherein the poloxamer is poloxamer 188.

39. The pharmaceutical composition of any one of embodiments 1-38, wherein the surfactant is present at a concentration of about 0.001% to about 1%, about 0.01% to about 0.5%, about 0.01% to about 0.1%, or about 0.02% to about 0.05% (w/v).

40. The pharmaceutical composition of any one of embodiments 1-39, wherein the surfactant is present at a concentration of about 0.01%, about 0.02%, about 0.03%, about 0.04%, or about 0.05% (w/v).

41. The pharmaceutical compositions of any one of embodiments 1-40, wherein the pH of the pharmaceutical composition is from about 5.0 to about 6.5.

42. The pharmaceutical compositions of any one of embodiments 1-41, wherein the pH of the pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

43. A pharmaceutical composition comprising:
   (i) an anti-TSLP-R antibody, or antigen-binding fragment thereof, at a concentration of about 1 mg/mL to about 300 mg/mL;
   (ii) a pharmaceutically acceptable buffer at a concentration of about 5 mmol/L to about 100 mmol/L;
   (iii) glycine, or a pharmaceutically acceptable salt thereof, at a concentration of about 1 mmol/L to about 600 mmol/L; and
   (iv) a surfactant at a concentration of about 0.001% to about 1% (w/v).

44. The pharmaceutical composition of embodiment 43, wherein the anti-TSLP-R antibody, or antigen-binding fragment thereof, comprises:
   (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and
   (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

45. The pharmaceutical composition of any one of embodiments 43-44, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

46. The pharmaceutical composition of any one of embodiments 43-45, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

47. The pharmaceutical composition of any one of embodiments 43-46, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

48. The pharmaceutical composition of any one of embodiments 43-47, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

49. The pharmaceutical composition of any one of embodiments 43-48, wherein the anti-TSLP-R antibody, or antigen-binding fragment thereof, comprises:
   (i) a variable heavy chain polypeptide having a sequence that is at least 90%, 91%, 92%, 93%, 94%, 95%, 96%, 97%, 98%, or 99% identical to the sequence of SEQ ID NO: 5; and
   (ii) a variable light chain polypeptide having a sequence that is at least 90%, 91%, 92%, 93%, 94%, 95%, 96%, 97%, 98%, or 99% identical to the sequence of SEQ ID NO: 6.

50. The pharmaceutical composition of any one of embodiments 43-49, wherein the anti-TSLP-R antibody, or antigen-binding fragment thereof, comprises:
   (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and
   (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

51. The pharmaceutical composition of any one of embodiments 43-50, wherein the anti-TSLP-R antibody, or antigen-binding fragment thereof, comprises a variable heavy chain polypeptide having a sequence of SEQ ID NO: 5.

52. The pharmaceutical composition of any one of embodiments 43-51, wherein the anti-TSLP-R antibody, or antigen-binding fragment thereof, comprises a variable light chain polypeptide having a sequence of SEQ ID NO: 6.

53. The pharmaceutical composition of any one of embodiments 43-52, wherein the anti-TSLP-R antibody, or antigen-binding fragment thereof, comprises:
   (i) a variable heavy chain polypeptide having a sequence of SEQ ID NO: 5; and
   (ii) a variable light chain polypeptide having a sequence of SEQ ID NO: 6.

54. The pharmaceutical composition of embodiment 43, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL.

55. The pharmaceutical composition of embodiment 43, wherein the antibody, or antigen-binding fragment thereof, is present at a concentration of about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL.

56. The pharmaceutical composition of embodiment 43, wherein the antibody, or antigen-binding fragment thereof, is present at a concentration of about 150 mg/mL.

57. The pharmaceutical composition of embodiment 43, wherein the antibody, or antigen-binding fragment thereof, is present at a concentration of about 200 mg/mL.

58. The pharmaceutical composition of embodiment 43, wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

59. The pharmaceutical composition of embodiment 43, wherein the pharmaceutically acceptable buffer is a histidine buffer.

60. The pharmaceutical composition of embodiment 59, wherein the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

61. The pharmaceutical composition of any one of embodiments 59 or 60, wherein the histidine buffer is present at a concentration of about 20 mmol/L.

62. The pharmaceutical composition of embodiment 43, wherein the glycine, or pharmaceutically acceptable salt thereof, is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.

63. The pharmaceutical composition of any one of embodiments 43 or 62, wherein the glycine, or pharmaceutically acceptable salt thereof, is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

64. The pharmaceutical composition of any one of embodiments 43 or 62, wherein the glycine, or pharmaceutically acceptable salt thereof, is present at a concentration of about 180 mmol/L.

65. The pharmaceutical composition of any one of embodiments 43 or 63-64, wherein the glycine, or a pharmaceutically acceptable salt thereof, is glycine hydrochloride.

66. The pharmaceutical composition of embodiment 43, wherein the surfactant is a polysorbate or a poloxamer.

67. The pharmaceutical composition of embodiment 43, wherein the polysorbate is polysorbate 20 (PS20) or polysorbate 80 (PS80).

68. The pharmaceutical composition of any one of embodiments 43 or 67, wherein the polysorbate is polysorbate 80 (PS80).

69. The pharmaceutical composition of embodiment 43, wherein the poloxamer is poloxamer 188.

70. The pharmaceutical composition of embodiment 43, wherein the surfactant is present at a concentration of about 0.001% to about 1%, about 0.01% to about 0.5%, about 0.01% to about 0.1%, or about 0.02% to about 0.05% (w/v).

71. The pharmaceutical composition of embodiment 43, wherein the surfactant is present at a concentration of about 0.01%, about 0.02%, about 0.03%, about 0.04%, or about 0.05% (w/v).

72. The pharmaceutical composition of embodiment 43, wherein the surfactant is PS80, and wherein PS80 is present at a concentration of about 0.03% (w/v).

73. The pharmaceutical compositions of any one of embodiments 43-69, wherein the pH of the pharmaceutical composition is from about 5.0 to about 6.5.

74. The pharmaceutical compositions of any one of embodiments 43-69, wherein the pH of the pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

75. The pharmaceutical composition of embodiment 43, comprising:
  (i) an anti-TSLP-R antibody, or antigen-binding fragment thereof, at a concentration of about 150 mg/mL to about 250 mg/mL;
  (ii) histidine buffer at a concentration of about 10 mmol/L to about 30 mmol/L;
  (iii) glycine, or a pharmaceutically acceptable salt thereof, at a concentration of about 150 mmol/L to about 200 mmol/L;
  (iv) polysorbate 80 at a concentration of about 0.01% to about 0.05% (w/v); and
  (v) a pH of about 5.7.

76. A pharmaceutical composition comprising:
  (i) an anti-TSLP-R antibody, or antigen-binding fragment thereof, at a concentration of about 1 mg/mL to about 300 mg/mL;
  (ii) a pharmaceutically acceptable buffer at a concentration of about 5 mmol/L to about 100 mmol/L;
  (iii) arginine, or a pharmaceutically acceptable salt thereof, at a concentration of about 1 mmol/L to about 600 mmol/L; and
  (iv) a surfactant at a concentration of about 0.001% to about 1% (w/v).

77. The pharmaceutical composition of embodiment 76, wherein the anti-TSLP-R antibody, or antigen-binding fragment thereof, comprises:
  (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and
  (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

78. The pharmaceutical composition of any one of embodiments 76-77, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

79. The pharmaceutical composition of any one of embodiments 76-78, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

80. The pharmaceutical composition of any one of embodiments 76-79, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

81. The pharmaceutical composition of any one of embodiments 76-80, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

82. The pharmaceutical composition of any one of embodiments 76-81, wherein the anti-TSLP-R antibody, or antigen-binding fragment thereof, comprises:
    (i) a variable heavy chain polypeptide having a sequence that is at least 90%, 91%, 92%, 93%, 94%, 95%, 96%, 97%, 98%, or 99% identical to the sequence of SEQ ID NO: 5; and
    (ii) a variable light chain polypeptide having a sequence that is at least 90%, 91%, 92%, 93%, 94%, 95%, 96%, 97%, 98%, or 99% identical to the sequence of SEQ ID NO: 6.

83. The pharmaceutical composition of any one of embodiments 76-82, wherein the anti-TSLP-R antibody, or antigen-binding fragment thereof, comprises:
    (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and
    (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

84. The pharmaceutical composition of any one of embodiments 76-83, wherein the anti-TSLP-R antibody, or antigen-binding fragment thereof, comprises a variable heavy chain polypeptide having a sequence of SEQ ID NO: 5.

85. The pharmaceutical composition of any one of embodiments 76-84, wherein the anti-TSLP-R antibody, or antigen-binding fragment thereof, comprises a variable light chain polypeptide having a sequence of SEQ ID NO: 6.

86. The pharmaceutical composition of any one of embodiments 76-85, wherein the anti-TSLP-R antibody, or antigen-binding fragment thereof, comprises:
    (i) a variable heavy chain polypeptide having a sequence of SEQ ID NO: 5; and
    (ii) a variable light chain polypeptide having a sequence of SEQ ID NO: 6.

87. The pharmaceutical composition of embodiment 76, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL.

88. The pharmaceutical composition of embodiment 76, wherein the antibody, or antigen-binding fragment thereof, is present at a concentration of about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL.

89. The pharmaceutical composition of embodiment 76, wherein the antibody, or antigen-binding fragment thereof, is present at a concentration of about 150 mg/mL.

90. The pharmaceutical composition of embodiment 76, wherein the antibody, or antigen-binding fragment thereof, is present at a concentration of about 200 mg/mL.

91. The pharmaceutical composition of embodiment 76, wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.

92. The pharmaceutical composition of embodiment 76, wherein the pharmaceutically acceptable buffer is a histidine buffer.

93. The pharmaceutical composition of embodiment 92, wherein the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.

94. The pharmaceutical composition of embodiment 92, wherein the histidine buffer is present at a concentration of about 20 mmol/L.

95. The pharmaceutical composition of embodiment 76, wherein the arginine, or pharmaceutically acceptable salt thereof, is present at a concentration of about 1 mmol/L to about 600 mmol/L, about 50 mmol/L to about 300 mmol/L, about 100 mmol/L to about 250 mmol/L, about 100 mmol/L to about 200 mmol/L, about 100 mmol/L to about 190 mmol/L, about 100 mmol/L to about 180 mmol/L, about 100 mmol/L to about 175 mmol/L, about 100 mmol/L to about 150 mmol/L, about 100 mmol/L to about 130 mmol/L, or about 110 mmol/L to about 130 mmol/L.

96. The pharmaceutical composition of any one of embodiments 76 or 95, wherein the arginine, or pharmaceutically acceptable salt thereof, is present at a concentration of about 50 mmol/L, about 75 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.

97. The pharmaceutical composition of any one of embodiments 76 or 95-96, wherein the arginine, or pharmaceutically acceptable salt thereof, is present at a concentration of about 120 mmol/L.

98. The pharmaceutical composition of any one of embodiments 76 or 95-96, wherein the arginine, or a pharmaceutically acceptable salt thereof, is arginine hydrochloride.

99. The pharmaceutical composition of embodiment 76, wherein the surfactant is a polysorbate or a poloxamer.

100. The pharmaceutical composition of embodiment 76, wherein the polysorbate is polysorbate 20 (PS20) or polysorbate 80 (PS80).

101. The pharmaceutical composition of any one of embodiments 76 or 100, wherein the polysorbate is polysorbate 80 (PS80).

102. The pharmaceutical composition of embodiment 76, wherein the poloxamer is poloxamer 188.

103. The pharmaceutical composition of embodiment 76, wherein the surfactant is present at a concentration of about 0.001% to about 1%, about 0.01% to about 0.5%, about 0.01% to about 0.1%, or about 0.02% to about 0.05% (w/v).

104. The pharmaceutical composition of embodiment 76, wherein the surfactant is present at a concentration of about 0.01%, about 0.02%, about 0.03%, about 0.04%, or about 0.05% (w/v).

105. The pharmaceutical composition of embodiment 76, wherein the surfactant is PS80, and wherein PS80 is present at a concentration of about 0.03% (w/v).

106. The pharmaceutical compositions of any one of embodiments 76-105, wherein the pH of the pharmaceutical composition is from about 5.0 to about 6.5.

107. The pharmaceutical compositions of any one of embodiments 76-106, wherein the pH of the pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

108. The pharmaceutical composition of embodiment 76, comprising:
  (i) an anti-TSLP-R antibody, or antigen-binding fragment thereof, at a concentration of about 150 mg/mL to about 250 mg/mL;
  (ii) histidine buffer at a concentration of about 10 mmol/L to about 30 mmol/L;
  (iii) arginine, or a pharmaceutically acceptable salt thereof, at a concentration of about 100 mmol/L to about 150 mmol/L;
  (iv) polysorbate 80 at a concentration of about 0.01% to about 0.05% (w/v); and
  (v) a pH of about 5.7.

109. A pharmaceutical composition comprising:
  (i) an anti-TSLP-R antibody, or antigen-binding fragment thereof, at a concentration of about 1 mg/mL to about 300 mg/mL;
  (ii) a pharmaceutically acceptable buffer at a concentration of about 5 mmol/L to about 100 mmol/L;
  (iii) proline, or a pharmaceutically acceptable salt thereof, at a concentration of about 1 mmol/L to about 600 mmol/L; and
  (iv) a surfactant at a concentration of about 0.001% to about 1% (w/v).

110. The pharmaceutical composition of embodiment 109, wherein the anti-TSLP-R antibody, or antigen-binding fragment thereof, comprises:
  (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and
  (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

111. The pharmaceutical composition of any one of embodiments 109-110, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

112. The pharmaceutical composition of any one of embodiments 109-111, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

113. The pharmaceutical composition of any one of embodiments 109-112, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

114. The pharmaceutical composition of any one of embodiments 109-113, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

115. The pharmaceutical composition of any one of embodiments 109-114, wherein the anti-TSLP-R antibody, or antigen-binding fragment thereof, comprises:
  (i) a variable heavy chain polypeptide having a sequence that is at least 90%, 91%, 92%, 93%, 94%, 95%, 96%, 97%, 98%, or 99% identical to the sequence of SEQ ID NO: 5; and
  (ii) a variable light chain polypeptide having a sequence that is at least 90%, 91%, 92%, 93%, 94%, 95%, 96%, 97%, 98%, or 99% identical to the sequence of SEQ ID NO: 6.
116. The pharmaceutical composition of any one of embodiments 109-115, wherein the anti-TSLP-R antibody, or antigen-binding fragment thereof, comprises:
  (i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and
  (ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.
117. The pharmaceutical composition of any one of embodiments 109-116, wherein the anti-TSLP-R antibody, or antigen-binding fragment thereof, comprises a variable heavy chain polypeptide having a sequence of SEQ ID NO: 5.
118. The pharmaceutical composition of any one of embodiments 109-117, wherein the anti-TSLP-R antibody, or antigen-binding fragment thereof, comprises a variable light chain polypeptide having a sequence of SEQ ID NO: 6.
119. The pharmaceutical composition of any one of embodiments 109-118, wherein the anti-TSLP-R antibody, or antigen-binding fragment thereof, comprises:
  (i) a variable heavy chain polypeptide having a sequence of SEQ ID NO: 5; and
  (ii) a variable light chain polypeptide having a sequence of SEQ ID NO: 6.
120. The pharmaceutical composition of embodiment 109, wherein the concentration of the antibody, or antigen-binding fragment thereof, is present at a concentration from about 1 mg/mL to about 300 mg/mL, from about 50 mg/mL to about 250 mg/mL, from about 100 mg/mL to about 200 mg/mL, or from about 150 mg/mL to about 200 mg/mL.
121. The pharmaceutical composition of embodiment 109, wherein the antibody, or antigen-binding fragment thereof, is present at a concentration of about 25 mg/mL, about 50 mg/mL, about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL.
122. The pharmaceutical composition of embodiment 109, wherein the antibody, or antigen-binding fragment thereof, is present at a concentration of about 150 mg/mL.
123. The pharmaceutical composition of embodiment 109, wherein the antibody, or antigen-binding fragment thereof, is present at a concentration of about 200 mg/mL.
124. The pharmaceutical composition of embodiment 109, wherein the pharmaceutically acceptable buffer is phosphoric acid buffer, citric acid buffer, acetic acid buffer, succinic acid buffer, histidine buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.
125. The pharmaceutical composition of embodiment 109, wherein the pharmaceutically acceptable buffer is a histidine buffer.
126. The pharmaceutical composition of embodiment 125, wherein the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.
127. The pharmaceutical composition of embodiment 125, wherein the histidine buffer is present at a concentration of about 20 mmol/L.
128. The pharmaceutical composition of embodiment 109, wherein the proline, or pharmaceutically acceptable salt thereof, is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.
129. The pharmaceutical composition of any one of embodiments 108 or 127, wherein the proline, or pharmaceutically acceptable salt thereof, is present at a concentration of about 50 mmol/L, about 75 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.
130. The pharmaceutical composition of any one of embodiments 109 or 128-129, wherein the proline, or pharmaceutically acceptable salt thereof, is present at a concentration of about 180 mmol/L.
131. The pharmaceutical composition of any one of embodiments 109 or 128-129, wherein the proline, or a pharmaceutically acceptable salt thereof, is proline hydrochloride.
132. The pharmaceutical composition of embodiment 109, wherein the surfactant is a polysorbate or a poloxamer.
133. The pharmaceutical composition of embodiment 109, wherein the polysorbate is polysorbate 20 (PS20) or polysorbate 80 (PS80).
134. The pharmaceutical composition of any one of embodiments 109 or 133, wherein the polysorbate is polysorbate 80 (PS80).
135. The pharmaceutical composition of embodiment 109, wherein the poloxamer is poloxamer 188.
136. The pharmaceutical composition of embodiment 109, wherein the surfactant is present at a concentration of about 0.001% to about 1%, about 0.01% to about 0.5%, about 0.01% to about 0.1%, or about 0.02% to about 0.05% (w/v).
137. The pharmaceutical composition of embodiment 109, wherein the surfactant is present at a concentration of about 0.01%, about 0.02%, about 0.03%, about 0.04%, or about 0.05% (w/v).

138. The pharmaceutical composition of embodiment 109, wherein the surfactant is PS80, and wherein PS80 is present at a concentration of about 0.03% (w/v).

139. The pharmaceutical compositions of any one of embodiments 109-138, wherein the pH of the pharmaceutical composition is from about 5.0 to about 6.5.

140. The pharmaceutical compositions of any one of embodiments 109-139, wherein the pH of the pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

141. The pharmaceutical composition of embodiment 109, comprising:
   (i) an anti-TSLP-R antibody, or antigen-binding fragment thereof, at a concentration of about 150 mg/mL to about 250 mg/mL;
   (ii) histidine buffer at a concentration of about 10 mmol/L to about 30 mmol/L;
   (iii) proline, or a pharmaceutically acceptable salt thereof, at a concentration of about 150 mmol/L to about 200 mmol/L;
   (iv) polysorbate 80 at a concentration of about 0.01% to about 0.05% (w/v); and
   (v) a pH of about 5.7.

142. A pharmaceutical composition comprising:
   (i) an anti-TSLP-R antibody, or antigen-binding fragment thereof, at a concentration of 180 mg/mL to 220 mg/mL;
   (ii) histidine buffer at a concentration of 18 mmol/L to 22 mmol/L;
   (iii) glycine, or a pharmaceutically acceptable salt thereof, at a concentration of 160 mmol/L to 200 mmol/L;
   (iv) polysorbate 80 at a concentration of 0.01% (w/v) to 0.05% (w/v); and
   (v) a pH of 5.6 to 5.8, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

143. A pharmaceutical composition comprising:
   (i) an anti-TSLP-R antibody, or antigen-binding fragment thereof, at a concentration of about 200 mg/mL;
   (ii) histidine buffer at a concentration of about 20 mmol/L;
   (iii) glycine, or a pharmaceutically acceptable salt thereof, at a concentration of about 180 mmol/L;
   (iv) polysorbate 80 at a concentration of about 0.03% (w/v); and
   (v) a pH of about 5.7, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

144. A pharmaceutical composition comprising:
   (i) an anti-TSLP-R antibody, or antigen-binding fragment thereof, at a concentration of 180 mg/mL to 220 mg/mL;
   (ii) histidine buffer at a concentration of 18 mmol/L to 22 mmol/L;
   (iii) arginine, or a pharmaceutically acceptable salt thereof, at a concentration of 105 mmol/L to 135 mmol/L;
   (iv) polysorbate 80 at a concentration of 0.01% (w/v) to 0.05% (w/v); and
   (v) a pH of 5.6 to 5.8, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

145. A pharmaceutical composition comprising:
   (i) an anti-TSLP-R antibody, or antigen-binding fragment thereof, at a concentration of about 200 mg/mL;
   (ii) histidine buffer at a concentration of about 20 mmol/L;
   (iii) arginine, or a pharmaceutically acceptable salt thereof, at a concentration of about 120 mmol/L;
   (iv) polysorbate 80 at a concentration of about 0.03% (w/v); and
   (v) a pH of about 5.7, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

146. A pharmaceutical composition comprising:
   (i) an anti-TSLP-R antibody, or antigen-binding fragment thereof, at a concentration of 180 mg/mL to 220 mg/mL;
   (ii) histidine buffer at a concentration of 18 mmol/L to 22 mmol/L;
   (iii) proline, or a pharmaceutically acceptable salt thereof, at a concentration of 160 mmol/L to 200 mmol/L;
   (iv) polysorbate 80 at a concentration of 0.01% (w/v) to 0.05% (w/v); and
   (v) a pH of 5.6 to 5.8, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

147. A pharmaceutical composition comprising:
   (i) an anti-TSLP-R antibody, or antigen-binding fragment thereof, at a concentration of about 200 mg/mL;
   (ii) histidine buffer at a concentration of about 20 mmol/L;
   (iii) proline, or a pharmaceutically acceptable salt thereof, at a concentration of about 180 mmol/L;
   (iv) polysorbate 80 at a concentration of about 0.03% (w/v); and
   (v) a pH of about 5.7, wherein the anti-TSLP-R antibody, or antigen-binding fragment thereof, comprises:
      (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
      (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

148. The pharmaceutical composition of any one of embodiments 1-147, suitable for intravenous, subcutaneous, or intramuscular administration.

149. The pharmaceutical composition of any one of embodiments 1-148, wherein the pharmaceutical composition is a liquid pharmaceutical composition.

150. The pharmaceutical composition of any one of embodiments 1-147, wherein the pharmaceutical composition is a lyophilized pharmaceutical composition.

151. The pharmaceutical composition of any one of embodiments 1-147 or embodiment 150, wherein the pharmaceutical composition is a lyophilized pharmaceutical composition that can be dissolved in a liquid to make a liquid pharmaceutical composition suitable for intravenous, subcutaneous, or intramuscular administration.

152. The lyophilized pharmaceutical composition of any one of embodiments 150 or 151, wherein the lyophilized pharmaceutical composition can be dissolved in a liquid to make a liquid pharmaceutical composition, wherein the pH of the liquid pharmaceutical composition is from about 5.0 to about 6.5.

153. The lyophilized pharmaceutical composition of any one of embodiments 150-152, wherein the lyophilized pharmaceutical composition can be dissolved in a liquid to make a liquid pharmaceutical composition, wherein the pH of the liquid pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

154. A pharmaceutical composition comprising:
   (i) an anti-TSLP-R antibody, or antigen-binding fragment thereof, at a dose of about 0.03 mg/kg to about 10 mg/kg; and optionally:
   (ii) a pharmaceutically acceptable buffer at a concentration of about 5 mmol/L to about 100 mmol/L;
   (iii) an excipient at a concentration of about 1 mmol/L to about 600 mmol/L; and
   (iv) a surfactant at a concentration of about 0.001% to about 1% (w/v).

155. The pharmaceutical composition of embodiment 154, wherein the anti-TSLP-R antibody, or antigen-binding fragment thereof, comprises:
   (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; or variants of any of the foregoing; and
   (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12; or variants of any of the foregoing.

156. The pharmaceutical composition of any one of embodiments 154-155, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5.

157. The pharmaceutical composition of any one of embodiments 154-156, wherein the anti-TSLP-R antibody, or antigen-binding fragment thereof, comprises a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9.

158. The pharmaceutical composition of any one of embodiments 154-157, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6.

159. The pharmaceutical composition of any one of embodiments 154-158, wherein the anti-TSLP-R antibody, or antigen-binding fragment thereof, comprises a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

160. The pharmaceutical composition of any one of embodiments 154-159, wherein the anti-TSLP-R antibody, or antigen-binding fragment thereof, comprises:
(i) a variable heavy chain polypeptide having a sequence that is at least 90%, 91%, 92%, 93%, 94%, 95%, 96%, 97%, 98%, or 99% identical to the sequence of SEQ ID NO: 5; and
(ii) a variable light chain polypeptide having a sequence that is at least 90%, 91%, 92%, 93%, 94%, 95%, 96%, 97%, 98%, or 99% identical to the sequence of SEQ ID NO: 6.

161. The pharmaceutical composition of any one of embodiments 154-160, wherein the anti-TSLP-R antibody, or antigen-binding fragment thereof, comprises:
(i) a variable heavy chain polypeptide having a sequence that is at least 90%, 91%, 92%, 93%, 94%, 95%, 96%, 97%, 98%, or 99% identical to the sequence of SEQ ID NO: 5, provided that the heavy chain polypeptide comprises the amino acid sequences of SEQ ID NO: 7, SEQ ID NO: 8, and SEQ ID NO: 9; and
(ii) a variable light chain polypeptide having a sequence that is at least 90%, 91%, 92%, 93%, 94%, 95%, 96%, 97%, 98%, or 99% identical to the sequence of SEQ ID NO: 6, provided that the light chain polypeptide comprises the amino acid sequences of SEQ ID NO: 10, SEQ ID NO: 11, and SEQ ID NO: 12.

162. The pharmaceutical composition of any one of embodiments 154-161, wherein the anti-TSLP-R antibody, or antigen-binding fragment thereof, comprises a variable heavy chain polypeptide having a sequence of SEQ ID NO: 5.

163. The pharmaceutical composition of any one of embodiments 154-162, wherein the anti-TSLP-R antibody, or antigen-binding fragment thereof, comprises a variable light chain polypeptide having a sequence of SEQ ID NO: 6.

164. The pharmaceutical composition of any one of embodiments 154-163, wherein the anti-TSLP-R antibody, or antigen-binding fragment thereof, comprises:
(i) a variable heavy chain polypeptide having a sequence of SEQ ID NO: 5; and
(ii) a variable light chain polypeptide having a sequence of SEQ ID NO: 6.

165. The pharmaceutical composition of any one of embodiments 154-164, wherein the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg.

166. The pharmaceutical composition of any one of embodiments 154-165, wherein the pharmaceutical composition is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.

167. The pharmaceutical composition of any one of embodiments 154-166, wherein the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg; and the pharmaceutical composition is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.

168. The pharmaceutical composition of any one of embodiments 154-167, wherein the antibody, or antigen-binding fragment thereof, is present in an amount of about 25 mg, about 50 mg, about 100 mg, about 150 mg, about 200 mg, about 250 mg, or about 300 mg; and the pharmaceutical composition is administered about every 4 weeks.

169. The pharmaceutical composition of any one of embodiments 154-167, wherein the antibody, or antigen-binding fragment thereof, is present in an amount of about 25 mg, about 50 mg, about 100 mg, about 150 mg, about 200 mg, about 250 mg, or about 300 mg; and the pharmaceutical composition is administered about every 8 weeks.

170. The pharmaceutical composition of any one of embodiments 154-167, wherein the antibody, or antigen-binding fragment thereof, is present in an amount of about 25 mg, about 50 mg, about 100 mg, 150 mg, about 200 mg, about 250 mg, or about 300 mg; and the pharmaceutical composition is administered about every 12 weeks.

171. The pharmaceutical composition of any one of embodiments 154-167, wherein the antibody, or antigen-binding fragment thereof, is present in an amount of about 200 mg, about 250 mg, about 300 mg, about 350 mg, about 400 mg, about 500 mg, or about 600 mg; and the pharmaceutical composition is administered about every 24 weeks.
172. The pharmaceutical composition of any one of embodiments 154-171, wherein the pharmaceutically acceptable buffer is histidine buffer, phosphoric acid buffer, citric acid buffer, acetic acid buffer, succinic acid buffer, phosphate buffer, acetate buffer, citrate buffer, succinate buffer, ascorbic acid buffer, glutamic acid buffer, lactic acid buffer, maleic acid buffer, trometamol buffer, and gluconic acid buffer.
173. The pharmaceutical composition of embodiment 172, wherein the pharmaceutically acceptable buffer is a histidine buffer.
174. The pharmaceutical composition of embodiment 173, wherein the histidine buffer is present at a concentration of about 5 mmol/L to about 100 mmol/L, about 5 mmol/L to about 70 mmol/L, about 5 mmol/L to about 60 mmol/L, about 10 mmol/L to about 60 mmol/L, about 10 mmol/L to about 50 mmol/L, about 10 mmol/L to about 40 mmol/L, about 15 mmol/L to about 30 mmol/L, or about 15 mmol/L to about 25 mmol/L.
175. The pharmaceutical composition of any one of embodiments 173 or 174, wherein the histidine buffer is present at a concentration of about 20 mmol/L.
176. The pharmaceutical composition of any one of embodiments 154-175, wherein the excipient is present at a concentration of about 1 mmol/L to about 600 mmol/L, about 50 mmol/L to about 300 mmol/L, about 100 mmol/L to about 250 mmol/L, about 120 mmol/L to about 200 mmol/L, about 130 mmol/L to about 200 mmol/L, about 140 mmol/L to about 200 mmol/L, about 150 mmol/L to about 200 mmol/L, about 160 mmol/L to about 200 mmol/L, about 170 mmol/L to about 200 mmol/L, or about 180 mmol/L to about 200 mmol/L.
177. The pharmaceutical composition of any one of embodiments 154-176, wherein the excipient is present at a concentration of about 50 mmol/L, about 75 mmol/L, about 100 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 250 mmol/L, or about 300 mmol/L.
178. The pharmaceutical composition of any one of embodiments 154-177, wherein the excipient is a viscosity reducing agent.
179. The pharmaceutical composition of any one of embodiments 154-178, wherein the excipient is an amino acid chosen from glycine, glutamate, arginine, histidine, proline, or a pharmaceutically acceptable salt thereof.
180. The pharmaceutical composition of any one of embodiments 154-179, wherein the excipient is glycine, arginine, or proline, or a pharmaceutically acceptable salt thereof.
181. The pharmaceutical composition of any one of embodiments 179-180, wherein the excipient is glycine, or a pharmaceutically acceptable salt thereof.
182. The pharmaceutical composition of embodiment 181, wherein the pharmaceutically acceptable salt of glycine is glycine hydrochloride.
183. The pharmaceutical composition of any one of embodiments 154-180, wherein the excipient is arginine, or a pharmaceutically acceptable salt thereof.
184. The pharmaceutical composition of embodiment 183, wherein the pharmaceutically acceptable salt of arginine is arginine hydrochloride.
185. The pharmaceutical composition of any one of embodiments 154-180, wherein the excipient is proline, or a pharmaceutically acceptable salt thereof.
186. The pharmaceutical composition of embodiment 185, wherein the pharmaceutically acceptable salt of proline is proline hydrochloride.
187. The pharmaceutical composition of any one of embodiments 154-178, wherein the excipient is sodium chloride and/or sucrose.
188. The pharmaceutical composition of embodiment 187, wherein the sucrose is present at a concentration of about 1% to about 15%, about 1% to about 10%, about 1% to about 5%, or about 2% to about 4% (w/v).
189. The pharmaceutical composition of any one of embodiments 187-188, wherein the sucrose is at a concentration of about 1%, about 2%, about 3%, about 4%, about 5%, about 6%, about 7%, about 8%, about 9%, about 10%, about 11%, about 12%, about 13%, about 14%, or about 15% (w/v).
190. The pharmaceutical composition of embodiment 187, wherein the sodium chloride is present at a concentration of about 1 mmol/L to about 200 mmol/L, about 10 mmol/L to about 150 mmol/L, about 25 mmol/L to about 125 mmol/L, or about 50 mmol/L to about 120 mmol/L.
191. The pharmaceutical composition of any one of embodiments 187 or 190, wherein the sodium chloride is present at a concentration of about 10 mmol/L, about 20 mmol/L, about 30 mmol/L, about 40 mmol/L, about 50 mmol/L, about 60 mmol/L, about 70 mmol/L, about 80 mmol/L, about 90 mmol/L, about 100 mmol/L, about 110 mmol/L, about 120 mmol/L, about 130 mmol/L, about 140 mmol/L, about 150 mmol/L, about 160 mmol/L, about 170 mmol/L, about 180 mmol/L, about 190 mmol/L, or about 200 mmol/L.
192. The pharmaceutical composition of any one of embodiments 154-191, wherein the surfactant is a polysorbate or a poloxamer.
193. The pharmaceutical composition of embodiment 192, wherein the polysorbate is polysorbate 20 (PS20), or polysorbate 80 (PS80).
194. The pharmaceutical composition of embodiment 192, wherein the poloxamer is poloxamer 188.
195. The pharmaceutical composition of any one of embodiments 154-194, wherein the surfactant is present at a concentration of about 0.001% to about 1%, about 0.01% to about 0.5%, about 0.01% to about 0.1%, or about 0.02% to about 0.05% (w/v).
196. The pharmaceutical composition of any one of embodiments 154-195, wherein the surfactant is present at a concentration of about 0.01%, about 0.02%, about 0.03%, about 0.04%, or about 0.05% (w/v).
197. The pharmaceutical compositions of any one of embodiments 154-196, wherein the pH of the pharmaceutical composition is from about 5.0 to about 6.5.
198. The pharmaceutical compositions of any one of embodiments 154-197, wherein the pH of the pharmaceutical composition is about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

199. The pharmaceutical composition of embodiment 154, comprising:
  (i) an anti-TSLP-R antibody, or antigen-binding fragment thereof, in an amount of about 25 mg to about 600 mg;
  (ii) histidine buffer at a concentration of about 10 mmol/L to about 30 mmol/L;
  (iii) proline, or a pharmaceutically acceptable salt thereof, at a concentration of about 150 mmol/L to about 200 mmol/L;
  (iv) polysorbate 80 at a concentration of about 0.01% to about 0.05% (w/v); and
  (v) a pH of about 5.7.

200. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of 18 mmol/L to 22 mmol/L;
  (iii) glycine, or a pharmaceutically acceptable salt thereof, at a concentration of 160 mmol/L to 200 mmol/L;
  (iv) polysorbate 80 at a concentration of 0.01% (w/v) to 0.05% (w/v); and
  (v) a pH of 5.6 to 5.8,
  wherein the anti-TSLP-R antibody, or antigen-binding fragment thereof, comprises:
    (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
    (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

201. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of about 20 mmol/L;
  (iii) glycine, or a pharmaceutically acceptable salt thereof, at a concentration of about 180 mmol/L;
  (iv) polysorbate 80 at a concentration of about 0.03% (w/v); and
  (v) a pH of about 5.7, wherein the anti-TSLP-R antibody, or antigen-binding fragment thereof, comprises:
    (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
    (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

202. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of 18 mmol/L to 22 mmol/L;
  (iii) arginine, or a pharmaceutically acceptable salt thereof, at a concentration of 105 mmol/L to 135 mmol/L;
  (iv) polysorbate 80 at a concentration of 0.01% (w/v) to 0.05% (w/v); and
  (v) a pH of 5.6 to 5.8,
  wherein the anti-TSLP-R antibody, or antigen-binding fragment thereof, comprises:
    (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
    (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

203. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of about 20 mmol/L;
  (iii) arginine, or a pharmaceutically acceptable salt thereof, at a concentration of about 120 mmol/L;
  (iv) polysorbate 80 at a concentration of about 0.03% (w/v); and
  (v) a pH of about 5.7,
  wherein the anti-TSLP-R antibody, or antigen-binding fragment thereof, comprises:
    (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
    (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

204. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of 18 mmol/L to 22 mmol/L;
  (iii) proline, or a pharmaceutically acceptable salt thereof, at a concentration of 160 mmol/L to 200 mmol/L;
  (iv) polysorbate 80 at a concentration of 0.01% (w/v) to 0.05% (w/v); and (v) a pH of 5.6 to 5.8,
wherein the anti-TSLP-R antibody, or antigen-binding fragment thereof, comprises:
  (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
  (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

205. A pharmaceutical composition comprising:
  (i) an anti-TSLP-R antibody, or antigen-binding fragment thereof, at a dose of 0.03 mg/kg to 10 mg/kg;
  (ii) histidine buffer at a concentration of about 20 mmol/L;
  (iii) proline, or a pharmaceutically acceptable salt thereof, at a concentration of about 180 mmol/L;
  (iv) polysorbate 80 at a concentration of about 0.03% (w/v); and
  (v) a pH of about 5.7,
wherein the anti-TSLP-R antibody, or antigen-binding fragment thereof, comprises:
  (a) a heavy chain variable region comprising heavy chain CDR1, CDR2, and CDR3 sequences, wherein the heavy chain CDR1 sequence has the amino acid sequence of SEQ ID NO: 7, the heavy chain CDR2 has the amino acid sequence of SEQ ID NO: 8, and the heavy chain CDR3 sequence has the amino acid sequence of SEQ ID NO: 9; and
  (b) a light chain variable region comprising light chain CDR1, CDR2, and CDR3 sequences, wherein the light chain CDR1 sequence has the amino acid sequence of SEQ ID NO: 10, the light chain CDR2 has the amino acid sequence of SEQ ID NO: 11, and the light chain CDR3 sequence has the amino acid sequence of SEQ ID NO: 12.

206. The pharmaceutical composition of any one of embodiments 200-205, wherein the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg.

207. The pharmaceutical composition of any one of embodiments 200-206, wherein the pharmaceutical composition is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.

208. The pharmaceutical composition of any one of embodiments 200-207, wherein the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg; and the pharmaceutical composition is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.

209. The pharmaceutical composition of any one of embodiments 200-208, wherein the antibody, or antigen-binding fragment thereof, is present in an amount of about 25 mg, about 50 mg, about 100 mg, about 150 mg, about 200 mg, about 250 mg, or about 300 mg; and the pharmaceutical composition is administered about every 4 weeks.

210. The pharmaceutical composition of any one of embodiments 200-208, wherein the antibody, or antigen-binding fragment thereof, is present in an amount of about 25 mg, about 50 mg, about 100 mg, about 150 mg, about 200 mg, about 250 mg, or about 300 mg; and the pharmaceutical composition is administered about every 8 weeks.

211. The pharmaceutical composition of any one of embodiments 200-208, wherein the antibody, or antigen-binding fragment thereof, is present in an amount of about 25 mg, about 50 mg, about 100 mg, about 150 mg, about 200 mg, about 250 mg, or about 300 mg; and the pharmaceutical composition is administered about every 12 weeks.

212. The pharmaceutical composition of any one of embodiments 200-208, wherein the antibody, or antigen-binding fragment thereof, is present in an amount of about 200 mg, about 250 mg, about 300 mg, about 350 mg, about 400 mg, about 500 mg, or about 600 mg; and the pharmaceutical composition is administered about every 24 weeks.

213. A pharmaceutical dosage form comprising a pharmaceutical composition of any one of embodiments 1-212.

214. The pharmaceutical dosage form of embodiment 213, wherein the antibody, or antigen-binding fragment thereof, is present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg.

215. A pharmaceutical dosage form comprising the pharmaceutical composition of any one of embodiments 1-212 in a container.
216. The pharmaceutical dosage form of embodiment 215, wherein the container is a pre-filled syringe.
217. The pharmaceutical dosage form of embodiment 215, wherein the container is a plastic vial or glass vial.
218. A kit, comprising the pharmaceutical composition of any one of embodiments 1-212, and instructions for use.
219. A kit, comprising a dosage form comprising the pharmaceutical composition of any one of embodiments 1-212 in a container, and instructions for use.
220. A kit, comprising a dosage form comprising the pharmaceutical composition of any one of embodiments 1-212 in a container, wherein the container is a pre-filled syringe, and instructions for use.
221. A kit, comprising a dosage form comprising the pharmaceutical composition of any one of embodiments 1-212 in a container, wherein the container is a plastic vial or glass vial, and instructions for use.
222. A method of treating a disease in a subject in need thereof, the method comprising administering to the subject a therapeutically effective amount of the pharmaceutical composition of any one of embodiments 1-212.
223. A method of treating a disease in a subject in need thereof, the method comprising administering to the subject a therapeutically effective amount of the pharmaceutical dosage form of any one of embodiments 213-217.
224. A method of delaying the onset of a disease in a subject in need thereof, the method comprising administering to the subject a therapeutically effective amount of the pharmaceutical composition of any one of embodiments 1-212.
225. A method of delaying the onset of a disease in a subject in need thereof, the method comprising administering to the subject a therapeutically effective amount of the pharmaceutical dosage form of any one of embodiments 213-217.
226. A method of preventing a disease in a subject in need thereof, the method comprising administering to the subject a therapeutically effective amount of the pharmaceutical composition of any one of embodiments 1-212.
227. A method of preventing a disease in a subject in need thereof, the method comprising administering to the subject a therapeutically effective amount of the pharmaceutical dosage form of any one of embodiments 213-217.
228. The method of any one of embodiments 222-227, wherein the pharmaceutical composition or the pharmaceutical dosage form is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.
229. The method of any one of embodiments 222-228, wherein the pharmaceutical composition or the pharmaceutical dosage form comprises the antibody, or antigen-binding fragment thereof, present in an amount of about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, or about 625 mg; and the pharmaceutical composition or the pharmaceutical dosage form is administered about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks.
230. The method of any one of embodiments 222-229, wherein the pharmaceutical composition or the pharmaceutical dosage form comprises the antibody, or antigen-binding fragment thereof, present in an amount of about 25 mg, about 50 mg, about 100 mg, about 150 mg, about 200 mg, about 250 mg, or about 300 mg; and the pharmaceutical composition or the pharmaceutical dosage form is administered about every 4 weeks.
231. The method of any one of embodiments 222-229, wherein the pharmaceutical composition or the pharmaceutical dosage form comprises the antibody, or antigen-binding fragment thereof, present in an amount of about 25 mg, about 50 mg, about 100 mg, about 150 mg, about 200 mg, about 250 mg, or about 300 mg; and the pharmaceutical composition or the pharmaceutical dosage form is administered about every 8 weeks.
232. The method of any one of embodiments 222-229, wherein the pharmaceutical composition or the pharmaceutical dosage form comprises the antibody, or antigen-binding fragment thereof, present in an amount of about 25 mg, about 50 mg, about 100 mg, about 150 mg, about 200 mg, about 250 mg, or about 300 mg; and the pharmaceutical composition or the pharmaceutical dosage form is administered about every 12 weeks.
233. The method of any one of embodiments 222-229, wherein the pharmaceutical composition or the pharmaceutical dosage form comprises the antibody, or antigen-binding fragment thereof, present in an amount of about 200 mg, about 250 mg, about 300 mg, about 350 mg, about 400 mg, about 500 mg, or about 600 mg; and the pharmaceutical composition or the pharmaceutical dosage form is administered about every 24 weeks.
234. A method of increasing the internalization of TSLP-R on a cell, the method comprising contacting the cell with a pharmaceutical composition of any one of embodiments 1-212, or the pharmaceutical dosage form of any one of embodiments 213-217.
235. A method of inhibiting TSLP-R on a cell, the method comprising contacting the cell with a pharmaceutical composition of any one of embodiments 1-212, or the pharmaceutical dosage form of any one of embodiments 213-217.
236. A method of inhibiting TSLP-R by at least 95%, 96%, 97%, 98%, or 99% or by 100% in a subject in need thereof, the method comprising administering to the subject a pharmaceutical composition of any one of embodiments 1-212, or the pharmaceutical dosage form of any one of embodiments 213-217.
237. The method of any one of embodiments 234-236, wherein the subject in need thereof has a disease chosen from the list consisting of a pulmonary disease, a gastroenterological disease, an oncological disease, a dermatological disease, a nephrological disease, an allergy, or an immunological disease.
238. The method of any one of embodiments 234-237, wherein the pharmaceutical composition or the pharmaceutical dosage form is administered by injection.
239. The method of embodiment 238, wherein the pharmaceutical composition or the pharmaceutical dosage form is administered with a needle or a microneedle.
240. The method of any one of embodiments 222-239, wherein the subject has a continued decrease in blood eosinophil concentration after administration of the pharmaceutical composition or the pharmaceutical dosage form has ceased.
241. The method of any one of embodiments 222-240, wherein the subject has a continued decrease in blood eosinophil concentration after at least 1 administration of the pharmaceutical composition or the pharmaceutical dosage form.
242. The method of embodiment 241, wherein the subject has a continued decrease in blood eosinophil concentration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks after the at least 1 administration of the pharmaceutical composition or the pharmaceutical dosage form.
243. The method of any one of embodiments 241-242, wherein:
the pharmaceutical composition or the pharmaceutical dosage form is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks; and the subject has a decrease in blood eosinophil concentration following 2, 3, 4, 5, or more administrations of the pharmaceutical composition or the pharmaceutical dosage form.
244. The method of any one of embodiments 241-243, wherein:
the pharmaceutical composition or the pharmaceutical dosage form is administered to the subject about every 4 weeks; and
the subject has a decrease in blood eosinophil concentration following 3 administrations of the pharmaceutical composition or the pharmaceutical dosage form.
245. The method of any one of embodiments 241-244, wherein the subject has a decrease in blood eosinophil concentration that is sustained after administration of the pharmaceutical composition or the pharmaceutical dosage form has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.
246. The method of any one of embodiments 241-245, wherein the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.
247. The method of any one of embodiments 241-246 wherein the anti-TSLP-R antibody, or antigen-binding fragment thereof, is administered to the subject about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, about every 20 weeks, about every 21 weeks, about every 22 weeks, about every 23 weeks, or about every 24 weeks;
at least 2 administrations or at least 3 administrations of the anti-TSLP-R antibody, or antigen-binding fragment thereof, are administered; and
the subject has a sustained and measurable serum concentration of the anti-TSLP-R antibody, or antigen-binding fragment thereof after administration has ceased for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, or at least 52 weeks.

EXAMPLES

Various aspects of the present disclosure are illustrated with reference to the following non-limiting examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1: pH and Buffer Screening Studies

Formulations of pharmaceutical compositions comprising the anti-TSLP-R antibody TRAB-1 and varying buffer systems with varying pH were studied to evaluate protein stability in different pH/buffer systems under thermal stress. The conditions evaluated are summarized in Table 6. The formulations were evaluated for protein appearance, protein concentration, SEC-UPLC performance, charge variants (iCIEF), and purity (Caliper-SDS, NR and R conditions). Concentrations of TRAB-1 studied were 200 mg/mL TRAB-1. Each formulation was packaged in glass vials with a filling volume of 1 mL/2 mL vial. The formulations were additionally evaluated by DSC. Finally, pH and viscosity (25° C.) were measured. The TRAB-1 formulations A01 through A12 were screened for TRAB-1 protein stability under the conditions shown in Table 7. The measured concentrations and pH are summarized in Table 8. No significant change in protein concentration was observed between formulations after 2 weeks at 40° C.

TABLE 6

| pH/Buffer screening plan | | | |
|---|---|---|---|
| Formulation ID | TRAB-1 Conc. | Buffer | pH |
| A01 | 200 mg/mL | 20 mM Acetate | 4.5 |
| A02 | | | 5.0 |
| A03 | | | 5.5 |
| A04 | | 20 mM Succinate | 5.0 |
| A05 | | | 5.5 |
| A06 | | | 6.0 |
| A07 | | 20 mM Histidine | 5.5 |
| A08 | | | 6.0 |
| A09 | | | 6.5 |
| A10 | | 20 mM Phosphate | 6.5 |
| A11 | | | 7.0 |
| A12 | | | 7.5 |

TABLE 7

| Conditions Screened | | |
|---|---|---|
| Condition Code | Condition | Sampling Points |
| T0 | Store at 2~8° C. (average approximately 4° C.) | Time = 0 |
| 40C_1W | Incubate at 40° C. | 1 week |
| 40C_2W | | 2 weeks |
| 40C_4W | | 4 weeks |

TABLE 8

| Concentrations and pH as measured in treated formulations | | | | |
|---|---|---|---|---|
| Formulation ID | pH | Measured TRAB-1 conc. (mg/mL) | | |
| | T0 | T0 | 40C_1W | 40C_2W |
| A01 | 4.5 | 200.1 | 199.4 | 206.6 |
| A02 | 5.1 | 193.9 | 194.8 | 198.3 |
| A03 | 5.5 | 197.9 | 199.7 | 201.0 |
| A04 | 5.1 | 196.9 | 192.0 | 195.4 |
| A05 | 5.5 | 200.7 | 202.0 | 206.5 |
| A06 | 6.0 | 202.3 | 199.3 | 204.2 |
| A07 | 5.5 | 210.1 | 203.3 | 208.1 |
| A08 | 6.0 | 199.6 | 197.3 | 201.1 |
| A09 | 6.5 | 207.2 | 205.1 | 210.1 |
| A10 | 6.1 | 196.1 | 196.2 | 200.4 |
| A11 | 7.0 | 199.1 | 197.4 | 204.2 |
| A12 | 7.4 | 203.5 | 198.1 | 204.3 |

Tm onset, Tm1, Tm2, and Tm3 values measured by DSC are available in Table 9. The Tm onset values predict that TRAB-1 is thermally stable in all buffers that were tested. Higher Tm onset values indicate better protein structural stability in each formulation.

TABLE 9

| Tm Onset Values | | | | |
|---|---|---|---|---|
| Formulation ID | Tm Onset | Tm1 | Tm2 | Tm3 |
| A01 | 59.4 | 67.2 | 76.4 | 84.2 |
| A02 | 62.8 | 70.9 | 77.4 | 86.5 |
| A03 | 61.6 | 73.4 | 77.5 | 86.8 |
| A04 | 61.4 | 68.6 | 76.4 | 85.8 |
| A05 | 62.9 | 70.2 | 77.0 | 86.6 |
| A06 | 60.3 | 73.9 | 77.0 | 86.7 |
| A07 | 61.5 | 68.5 | 76.4 | 84.0 |
| A08 | 62.4 | 72.0 | 77.5 | 86.6 |
| A09 | 59.1 | 74.0 | 78.5 | 87.4 |
| A10 | 61.9 | 73.5 | 77.7 | 87.1 |
| A11 | 61.0 | 75.9 | 86.7 | NA |
| A12 | 61.8 | 74.9 | 86.3 | NA |

The viscosity of the formulations described in Table 6 was measured at 15° C. and 25° C. as shown in Table 10. Viscosity is inversely related to shear rate. Shear rate in a syringe (27G needle) is approximately 160,000 1/s. Although the measured viscosities of the TRAB-1 formulations (non-Newtonian fluids) cannot fully mimic the sheer rate in a syringe or in processing, it is highly unlikely that the TRAB-1 formulations will reach the shear rate. Viscosity was found to increase exponentially between 150 mg/mL and 200 mg/mL TRAB-1. Viscosity of 150 mg/mL TRAB-1 was below the acceptable maximum for subcutaneous injection (20 cP) at 150 mg/mL (Berteau et al., Med Devices (Auckl). 2015; 8:473-84) at both 15° C. and 25° C. However, at 200 mg/mL, viscosity of some TRAB-1 formulations was below the acceptable maximum for subcutaneous injection at 25° C. but not 15° C.

TABLE 10

Viscosity of TRAB-1

| Form. ID | TRAB-1 (mg/mL) | Viscosity at 10 s⁻¹ sheer rate (cP) 15° C. | Viscosity at 10 s⁻¹ sheer rate (cP) 25° C. | Viscosity at 1500 s⁻¹ sheer rate (cP) 15° C. | Viscosity at 1500 s⁻¹ sheer rate (cP) 25° C. |
| --- | --- | --- | --- | --- | --- |
| A01 | 200.1 | 88.7 | 24.2 | 15.5 | 11.0 |
| A02 | 193.9 | 60.1 | 28.6 | 13.9 | 9.6 |
| A03 | 197.9 | 82.9 | 32.2 | 16.6 | 11.4 |
| A04 | 196.9 | Not measured | Not measured | Not measured | Not measured |
| A05 | 200.7 | 72.1 | 25.7 | 17.9 | 11.8 |
| A06 | 202.3 | 78.8 | 26.4 | 19.4 | 12.8 |
| A07 | 210.1 | 81.6 | 19.3 | 19.1 | 12.6 |
| A08 | 199.6 | 86.1 | 28.0 | 21.7 | 14.1 |
| A09 | 207.2 | 79.1 | 18.0 | 24.5 | 15.9 |
| A10 | 196.1 | 77.7 | 48.9 | 22.6 | 14.3 |
| A11 | 199.1 | 84.9 | 72.1 | 25.6 | 16.0 |
| A12 | 203.5 | 91.2 | 85.9 | 30.3 | 19.0 |

Next, the TRAB-1 formulations A01 through A12 were screened for TRAB-1 protein stability under the conditions shown in Table 7. The appearance of the TRAB-1 formulations after 1 or 2 weeks at 40° C. are summarized in Table 11. Stronger opalescence was observed in TRAB-1 formulations that comprised succinate and phosphate buffers compared to acetate and histidine buffers.

TABLE 11

Protein appearance

| Formulation ID | Appearance T0 | Appearance 40C_1W | Appearance 40C_2W |
| --- | --- | --- | --- |
| A01 | SY, SO, FP | SY, SO, FP | SY, SO, FP |
| A02 | SY, SO, FP | SY, SO, FP | SY, SO, FP |
| A03 | SY, SO, FP | SY, SO, FP | SY, SO, FP |
| A04 | SY, SO, FP | SY, SO, FP | SY, SO, FP |
| A05 | SY, SO, FP | SY, SO, FP | SY, SO, FP |
| A06 | SY, SO, FP | SY, SO, FP | SY, SO, FP |
| A07 | SY, SO, FP | SY, SO, FP | SY, SO, FP |
| A08 | SY, SO, FP | SY, SO, FP | SY, SO, FP |
| A09 | SY, SO, FP | SY, SO, FP | SY, SO, FP |
| A10 | SY, SO, FP | SY, SO, FP | SY, SO, FP |
| A11 | SY, SO, FP | SY, SO, FP | SY, SO, FP |
| A12 | SY, SO, FP | SY, SO, FP | SY, SO, FP |

SY: Slightly Yellow.
SO: Slightly Opalescent.
FP: Free of visible Particles.

SEC-UPLC performance for formulations A01 through A12 are summarized in Table 12. SEC-UPLC performance was evaluated by percentages of TRAB-1 monomers (monomer %), high molecular weight particles (HMW %), and low molecular weight particles (LMW %). Overall, acetate and histidine with pH between 5.0 and 6.0 showed relatively better SEC performance after 40° C. over 2 weeks. Phosphate showed worse performance. Overall, aggregation was found to increase with solution pH and ionic strength at 40° C. after 2 weeks.

TABLE 12

SEC-UPLC analysis of treated TRAB-1 formulations

| Form. ID | Monomer % T0 | Monomer % 40C_1W | Monomer % 40C_2W | HMW % T0 | HMW % 40C_1W | HMW % 40C_2W | LMW % T0 | LMW % 40C_1W | LMW % 40C_2W |
| --- | --- | --- | --- | --- | --- | --- | --- | --- | --- |
| A01 | 97.4 | 97 | 96.3 | 2.6 | 2.6 | 2.8 | 0 | 0.4 | 1.0 |
| A02 | 96.4 | 96.4 | 96.1 | 3.3 | 3.5 | 3.7 | 0 | 0.2 | 0.3 |
| A03 | 97.9 | 97.3 | 97.1 | 2.1 | 2.6 | 2.8 | 0 | 0.1 | 0.2 |
| A04 | 98.2 | 97.4 | 97.0 | 1.8 | 2.5 | 2.7 | 0 | 0.2 | 0.4 |
| A05 | 97.8 | 97.2 | 96.9 | 2.2 | 2.7 | 3.0 | 0 | 0.1 | 0.2 |
| A06 | 97.5 | 96.8 | 96.5 | 2.5 | 3.1 | 3.4 | 0 | 0.1 | 0.2 |
| A07 | 97.9 | 97.5 | 97.2 | 2.1 | 2.5 | 2.6 | 0 | 0.1 | 0.2 |
| A08 | 97.6 | 97.2 | 96.8 | 2.4 | 2.8 | 3.0 | 0 | 0.1 | 0.2 |
| A09 | 97.3 | 96.6 | 96.2 | 2.7 | 3.3 | 3.6 | 0 | 0.1 | 0.2 |
| A10 | 97.2 | 95.9 | 95.2 | 2.8 | 4.0 | 4.6 | 0 | 0.1 | 0.2 |
| A11 | 96.9 | 95.4 | 94.5 | 3.1 | 4.5 | 5.3 | 0 | 0.1 | 0.3 |
| A12 | 96.6 | 94.7 | 93.7 | 3.4 | 5.1 | 6.0 | 0 | 0.2 | 0.3 |

Charge variants of TRAB-1 were evaluated by imaged capillary isoelectric focusing (iCIEF) and the results are summarized in Table 13. Less changes in charge variants were observed at pH 5.5-6.0 at 40° C. for 2 weeks, indicating that these formulations had better performance.

TABLE 13 iCIEF Analysis of TRAB-1 after Agitation, Freeze/Thaw, or Thermal Stress

| Form. ID | Main peak % | | | Acidic peak % | | | Basic peak % | | |
|---|---|---|---|---|---|---|---|---|---|
| | T0 | 40C_1W | 40C_2W | T0 | 40C_1W | 40C_2W | T0 | 40C_1W | 40C_2W |
| A01 | 57.6 | 51.0 | 45.8 | 34.5 | 39.6 | 43.6 | 7.9 | 9.4 | 10.7 |
| A02 | 57.4 | 52.3 | 47.2 | 35.2 | 39.4 | 44.2 | 7.4 | 8.3 | 8.6 |
| A03 | 58.0 | 53.0 | 48.6 | 35.3 | 39.8 | 44.0 | 6.7 | 7.2 | 7.4 |
| A04 | 57.4 | 50.5 | 44.8 | 35.3 | 41.8 | 47.1 | 7.3 | 7.7 | 8.2 |
| A05 | 57.3 | 51.9 | 47.5 | 35.6 | 40.7 | 44.8 | 7.1 | 7.4 | 7.1 |
| A06 | 57.7 | 53.3 | 49.4 | 35.3 | 39.3 | 42.9 | 7.0 | 7.3 | 7.7 |
| A07 | 57.2 | 53.9 | 50.1 | 36.1 | 38.5 | 42.6 | 6.6 | 7.7 | 7.3 |
| A08 | 57.0 | 54.4 | 50.3 | 35.9 | 38.2 | 42.1 | 7.0 | 7.4 | 7.6 |
| A09 | 56.3 | 52.0 | 49.0 | 36.6 | 39.9 | 42.8 | 7.2 | 8.1 | 8.2 |
| A10 | 56.7 | 50.5 | 45.1 | 36.5 | 41.5 | 46.0 | 6.8 | 8.0 | 8.9 |
| A11 | 57.0 | 48.2 | 39.8 | 35.9 | 43.3 | 50.5 | 7.2 | 8.5 | 9.7 |
| A12 | 57.0 | 41.0 | 32.7 | 36.1 | 49.5 | 57.4 | 6.8 | 9.5 | 9.9 |

Example 2: TRAB-1 Pre-Formulation Studies

Two formulations of pharmaceutical compositions comprising the anti-TSLP-R antibody TRAB-1 were studied. The formulations comprised 150 mg/mL or 200 mg/mL TRAB-1, 20 mM sodium phosphate, 140 mM L-arginine hydrochloride, and 0.02% (w/v) P80, at pH 5.7. Tm onset was measured to be 60.4° C. by differential scanning calorimetry (DSC). Tm onset values of >50° C. are considered thermally stable. The viscosity of the formulations was measured at 15° C. and 25° C. as shown in Table 14. Viscosity was found to increase exponentially between 150 mg/mL and 200 mg/mL TRAB-1. Viscosity of TRAB-1 at a concentration of 150 mg/mL was below the acceptable maximum for subcutaneous injection (20 cP) (Berteau et al., Med Devices (Auckl). 2015; 8:473-84) at both 15° C. and 25° C. Viscosity of TRAB-1 at a concentration of 200 mg/mL was below the acceptable maximum for subcutaneous injection at 25° C. but not 15° C.

TABLE 14

Viscosity, Osmolality and pH of TRAB-1

| Formulation ID | B02 | B01 |
|---|---|---|
| Target TRAB-1 (mg/mL) | 150 | 200 |
| Viscosity at 15° C. (cP) | 7.4 | 22.2 |
| Viscosity at 25° C. (cP) | 5.0 | 15.8 |
| Osmolality (mOsmol/kg) | 336 | 368 |
| pH | 5.7 | 5.7 |

The TRAB-1 formulations were next screened for protein stability under the conditions shown in Table 15. To test thermal stability, the TRAB-1 formulations exposed to 40° C., −20° C. or 2~8° C. for up to 12 weeks. Additionally, the TRAB-1 formulations were screened for stability under freeze/thawing conditions or under agitation conditions. TRAB-1 formulations at 2~0.8° C. prior to exposure to thermal, freeze/thaw, or agitation stress (T0) were used as controls.

TABLE 15

Conditions Screened

| Condition code | Condition | Sampling Points |
|---|---|---|
| T0 | Store at 2~8° C. | Time = 0 |
| 4C_1D | (average approximately 4° C.) | 1 day |
| 4C_6W | | 6 weeks |
| 4C_12W | | 12 weeks |
| 40C_2W | Incubate at 40° C. | 2 weeks |
| 40C_4W | | 4 weeks |
| −20C_12W | Freeze at −20° C. | 12 weeks |
| FT_3 | Freeze/thaw between −70° C. | 3 cycles |
| FT_5 | and room temperature | 5 cycles |
| Ag_1D | Agitation at 300 rpm and 25° C. | 1 day |
| Ag_3D | | 3 days |

The tested TRAB-1 formulations were screened for protein concentration (Table 16) and protein appearance (Table 17) following exposure to thermal, freeze/thaw, and agitation stressors.

No substantial changes were observed in protein concentration or appearance after freeze/thaw and agitation stress compared to the controls at T0. No substantial changes were observed in protein appearance after 40° C. for 2 weeks and 4 weeks.

TABLE 16

TRAB-1 Concentration Screen

| Formulation ID | Target TRAB-1 Conc. (mg/mL) | Actual TRAB-1 Concentration (mg/mL) | | | | | | | |
|---|---|---|---|---|---|---|---|---|---|
| | | T0 | 40C_2W | 40C_4W | 4C_1D | Ag_1D | Ag_3D | FT_3 | FT_5 |
| B02 | 150 | 150.3 | 150.7 | 152.0 | 150.7 | 150.1 | 149.9 | 149.3 | 149.8 |
| B01 | 200 | 206.7 | 223.3 | 223.6 | 210.6 | 204.2 | 211.7 | 199.9 | 215.2 |

TABLE 17

TRAB-1 Appearance Screen

| Form. ID | TRAB-1. (mg/mL) | T0 | 40C_2W | 40C_4W | 4C_1D | Ag_1D | Ag_3D | FT_3 | FT_5 |
|---|---|---|---|---|---|---|---|---|---|
| | | | | | Appearance | | | | |
| B02 | 150 | SY, SO, FP | SY, SO, FP | SY, SO, FP | SY, SO, FP | SY, SO, FP | SY, SO, FP | SY, SO, FP | SY, SO, FP |
| B01 | 200 | SY, SO, FP | SY, SO, FP | SY, SO, FP | SY, SO, FP | SY, SO, FP | SY, SO, FP | SY, SO, FP | SY, SO, FP |

FT: freeze/thaw between −70° C. and room temperature.
Agitation: agitation at 300 rpm and 25° C.
SY: Slightly Yellow.
SO: Slightly Opalescent.
FP: Free of visible Particles.

The presence of sub-visible particles in treated TRAB-1 formulations are summarized in Table 18. Compared with T0 controls, no substantial changes in sub-visible particles after 3 days agitation or 5 freeze/thaw cycles.

TABLE 18

Sub-visible Particles in TRAB-1 formulations after Agitation or Freeze/Thaw Stress

| Form. ID | TRAB-1 (mg/mL) | MFI (≥2 μm/10 μm/25 μm) | | |
|---|---|---|---|---|
| | | T0 | Ag_3D | FT_5 |
| B02 | 150 | 462/68/0 | 318/2/0 | 1342/61/4 |
| B01 | 200 | 390/25/0 | 161/5/4 | 428/32/5 |

Treated TRAB-1 formulations were evaluated for SEC-UPLC performance for formulations after 1 day or 3 days agitation, 3 or 5 freeze/thaw cycles, 2 or 4 weeks at 40° C., 6 or 12 weeks at 2~8° C., and 12 weeks at −20° C. The results are summarized in Table 19. SEC-UPLC performance was evaluated by percentages of TRAB-1 monomers (monomer %), high molecular weight particles (HMW %), and low molecular weight particles (LMW %). After 4 weeks at 40° C., a slight increase in aggregates were observed. No change was observed after agitation or freeze/thaw stress.

TABLE 19

SEC-UPLC analysis of TRAB-1 formulations

| | Formulation ID: | | | | | |
|---|---|---|---|---|---|---|
| | B02 | | | B01 | | |
| | TRAB-1 (mg/mL): | | | | | |
| | 150 | | | 200 | | |
| Condition | Monomer % | HMW % | LMW % | Monomer % | HMW % | LMW % |
| T0 | 98.4 | 1.6 | 0 | 98.3 | 1.7 | 0 |
| 40C_2W | 97.7 | 2.1 | 0.2 | 97.4 | 2.4 | 0.2 |
| 40C_4W | 97.2 | 2.4 | 0.4 | 96.9 | 2.7 | 0.4 |
| Ag_1D | 98.4 | 1.6 | 0 | 98.3 | 1.7 | 0 |
| Ag_3D | 98.4 | 1.6 | 0 | 98.2 | 1.7 | 0 |
| FT_3 | 98.4 | 1.6 | 0 | 98.2 | 1.8 | 0 |
| FT_5 | 98.4 | 1.6 | 0 | 98.2 | 1.7 | 0 |

Caliper-SDS was used to measure purity of TRAB-1 in treated samples under non-reducing (caliper-NR) and reducing (caliper-R) conditions. Non-reduced Caliper (GelChip) was used to measure the purity of the intact Mab. The results are summarized in Table 20. No substantial changes were observed in caliper purity % after 3 days agitation or 5 freeze thaw cycles. A reduction in purity was observed after 4 weeks at 40° C. The pI of TRAB-1 was found to be 9.1.

TABLE 20

Caliper-NR and Caliper-R Purity analysis of TRAB-1 formulations

| | Formulation ID: | |
|---|---|---|
| | B02 | B01 |
| | TRAB-1 (mg/mL): | |
| | 150 | 200 |
| Condition | Caliper-NR Purity % | Caliper-NR Purity % |
| T0 | 96.7 | 96.5 |
| 40C_2W | 94.8 | 94.7 |
| 40C_4W | 93.0 | 92.8 |
| Ag_3D | 96.5 | 96.5 |
| FT_5 | 96.6 | 96.7 |

Charge variants (the different charged isoforms of a molecule) were evaluated by imaged capillary isoelectric focusing (iCIEF), and the results are summarized in Tables 13. No substantial changes were observed in charge variant peaks under stress conditions with agitation or freeze/thaw. Charge variants were observed to shift with an increase in acidic species and decrease in the main peak when formulations were exposed to 40° C. for 2 and 4 weeks.

TABLE 21 iCIEF Analysis of TRAB-1 after Agitation, Freeze/Thaw, or Thermal Stress

| | Formulation ID | | | | | |
|---|---|---|---|---|---|---|
| | B02 | | | B01 | | |
| | TRAB-1 (mg/mL) | | | | | |
| | 150 | | | 200 | | |
| Condition | Main peak % | Acidic peak % | Basic peak % | Main peak % | Acidic peak % | Basic peak % |
| T0 | 58.2 | 34.9 | 6.9 | 57.8 | 35.4 | 6.8 |
| 40C_2W | 50.2 | 41.8 | 8.0 | 50.3 | 41.7 | 7.9 |
| 40C_4W | 43.4 | 47.9 | 8.8 | 44.2 | 47.6 | 8.1 |
| Ag_3D | 57.2 | 35.9 | 6.9 | 57.4 | 35.7 | 6.9 |
| FT_5 | 57.0 | 36.0 | 7.0 | 57.8 | 35.5 | 6.6 |

Example 3: TRAB-1 Formulation Studies

Various formulations of pharmaceutical compositions comprising the anti-TSLP-R antibody TRAB-1 were studied.

Ten formulations (Table 22; C01-C10) comprising 150 mg/mL or 200 mg/mL TRAB-1, 20 mM histidine buffer at pH 5.7, and various excipients and surfactants were screened for TRAB-1 stability. The excipients and surfactant combinations chosen for the study were: 120 mmol/L arginine hydrochloride with 0.04% (w/v) PS80 (C01); 120 mmol/L arginine hydrochloride with 0.02% (w/v) PS80 (C01); 120 mmol/L arginine hydrochloride with 0.02% (w/v) PS80 (C02); 120 mmol/L glutamate with 0.02% (w/v) PS80 (C03); 120 mmol/L sodium chloride with 0.02% (w/v) PS80 (C04); 180 mmol/L proline with 0.02% (w/v) PS80 (C05); 180 mmol/L glycine with 0.02% (w/v) PS80 (C06); 50 mmol/L sodium chloride with 3% (w/v) sucrose and 0.02% (w/v) PS80 (C07); 130 mmol/L arginine hydrochloride with 0.02% (w/v) PS80 (C08); 200 mmol/L proline with 0.02% (w/v) PS80 (C09); and 50 mmol/L sodium chloride with 4% (w/v) sucrose and 0.02% (w/v) PS80 (C10). Concentrations of TRAB-1 studied were 200 mg/mL TRAB-1 (C01-007) and 150 mg/mL TRAB-1 (C08-C10). Each formulation was packaged in glass vials with a filling volume of 1 mL in 2 mL vials. The TRAB-1 formulations C01-C10 were screened for TRAB-1 protein stability under the conditions shown in Table 23.

TABLE 22

Excipient Screening Study Design

| Formulation ID | Buffer | TRAB-1 conc. | Excipients and Surfactant (w/v)** |
|---|---|---|---|
| C01 | 20 mM | 200 | 120 mM Arg•HCl, 0.04% PS80 |
| C02 | Histidine | mg/mL | 120 mM Arg•HCl, 0.02% PS80 |
| C03 | pH at 5.7 | | 120 mM Glutamate, 0.02% PS80 |
| C04 | | | 120 mM NaCl, 0.02% PS80 |
| C05 | | | 180 mM Proline, 0.02% PS80 |
| C06 | | | 180 mM Glycine, 0.02% PS80 |
| C07 | | | 50 mM NaCl, 3% Sucrose, 0.02% PS80 |
| C08 | | 150 | 130 mM Arg•HCl, 0.02% PS80 |
| C09 | | mg/mL | 200 mM Proline, 0.02% PS80 |
| C10 | | | 50 mM NaCl, 4% Sucrose, 0.02% PS80 |

TABLE 23

Conditions Screened

| Condition Code | Condition | Sampling Points |
|---|---|---|
| T0 | Store at 2~8° C. (average approximately 4° C.) | Time = 0 |
| 40C_2W | Incubate at 40° C. | 2 weeks |
| 40C_4W | | 4 weeks |
| FT_3 | Freeze/thaw between −70° C. and room temperature | 3 cycles |
| FT_5 | | 5 cycles |
| Ag_1D | Agitation at 300 rpm and 25° C. | 1 day |
| Ag_3D | | 3 days |
| 40C_2W | Incubate at 40° C. | 2 weeks |
| 40C_4W | | 4 weeks |

Thermal stability was evaluated by the appearance, concentration, SEC-UPLC performance, and purity of TRAB-1 after 2 and 4 weeks at 40° C. Purity was measured with caliper-SDS and iCIEF. Additionally, the formulations were screened for the presence of sub-visible particles after 4 weeks at 40° C. Select formulations were additionally screened for TRAB-1 potency. Results were compared to controls stored at 2-8° C.

The formulations C01-C10 were screened for TRAB-1 appearance, concentration, and SEC-UPLC performance after 3 and 5 freeze thaw cycles between −70° C. and room temperature. The formulations subjected to 5 freeze/thaw cycles were additionally screened for the presence of sub-visible particles, and purity. Purity was measured with caliper-SDS and iCIEF. Results were compared to controls stored at 2-8° C.

The formulations C01-C10 were screened for TRAB-1 stability under agitation conditions. TRAB-1 appearance, concentration, and SEC-UPLC performance were evaluated after 1 day and 3 days agitation at 300 rpm and 25° C. The formulations subjected to three days of agitation were additionally screened for the presence of sub-visible particles, and purity. Purity was measured with caliper-SDS and iCIEF. Results were compared to controls stored at 2-8° C.

Results

The appearance of the TRAB-1 formulations after 1 day or 3 days agitation, 3 or 5 freeze/thaw cycles, and 2 or 4 weeks at 40° C. are summarized in Table 24. All formulations showed slightly yellow, slightly opalescent solutions without visible particles, except for F3. Formulations of TRAB-1 in glycine buffer (C06) remained clear, colorless, slightly opalescent and free of visible particles. Formulations of TRAB-1 in arginine buffer (C01, C02) had stronger opalescence compared to formulations of TRAB-1 in glycine buffer (C06). Stronger opalescence was observed in formulations F1, F2, F3, F4, F7, F8, and C10 compared with formulations F5, F6, and F9.

TABLE 24

TRAB-1 Appearance after Agitation, Freeze/Thaw, or Thermal Stress

| Form. ID | pH T0 | T0 | Ag_1D | Ag_3D | FT_3 | FT_5 | 40C_2W | 40C_4W |
|---|---|---|---|---|---|---|---|---|
| C01 | 5.6 | SY, SO+, FP | SY, SO+, FP | SY, SO+, FP | SY, SO+, FP | SY, SO+, FP | SY, SO+, FP | SY, SO+, FP |
| C02 | 5.7 | SY, SO+, FP | SY, SO+, FP | SY, SO+, FP | SY, SO+, FP | SY, SO+, FP | SY, SO+, FP | SY, SO+, FP |
| C03 | 5.8 | SY, SO+, FP | SY, SO+, FP | SY, SO+, FP | SY, SO+, FP | SY, SO+, FP | SY, SO+, FP | SY, SO+, EFP |
| C04 | 5.8 | SY, SO+, FP | SY, SO+, FP | SY, SO+, FP | SY, SO+, FP | SY, SO+, FP | SY, SO+, FP | SY, SO+, FP |
| C05 | 5.8 | SY, SO, FP | SY, SO, FP | SY, SO, FP | SY, SO, FP | SY, SO, FP | SY, SO, FP | SY, SO, FP |
| C06 | 5.9 | SY, SO, FP | SY, SO, FP | SY, SO, FP | SY, SO, FP | SY, SO, FP | SY, SO, FP | SY, SO, FP |
| C07 | 5.8 | SY, SO+, FP | SY, SO+, FP | SY, SO+, FP | SY, SO+, FP | SY, SO+, FP | SY, SO+, FP | SY, SO+, FP |

TABLE 24-continued

TRAB-1 Appearance after Agitation, Freeze/Thaw, or Thermal Stress

| Form. ID | pH T0 | Appearance T0 | Ag_1D | Ag_3D | FT_3 | FT_5 | 40C_2W | 40C_4W |
|---|---|---|---|---|---|---|---|---|
| C08 | 5.7 | SY, SO+, FP | SY, SO+, FP | SY, SO+, FP | SY, SO+, FP | SY, SO+, FP | SY, SO+, FP | SY, SO+, FP |
| C09 | 5.8 | SY, SO, FP | SY, SO, FP | SY, SO, FP | SY, SO, FP | SY, SO, FP | SY, SO, FP | SY, SO, FP |
| C10 | 5.8 | SY, SO+, FP | SY, SO+, FP | SY, SO+, FP | SY, SO+, FP | SY, SO+, FP | SY, SO+, FP | SY, SO+, FP |

SY: Slightly Yellow.
SO: Slightly Opalescence.
SO+: Stronger Opalescence.
FP: Free of visible Particles.
EFP: Essentially Free of visible Particles.

The concentration of the TRAB-1 are summarized in Table 25 for formulations C01-C10 after 1 day or 3 days agitation, 3 or 5 freeze/thaw cycles, and 2 or 4 weeks at 40° C. Compared with T0 controls, no substantial changes in TRAB-1 concentrations were observed between formulations C01-C10 after 1 day or 3 days agitation, 3 or 5 freeze/thaw cycles, and 2 or 4 weeks at 40° C.

TABLE 25

TRAB-1 Concentration after Agitation, Freeze/Thaw, or Thermal Stress

| Form. ID | Target TRAB-1 conc. (mg/mL) | Measured TRAB-1 Concentration (mg/mL) | | | | | | |
|---|---|---|---|---|---|---|---|---|
| | | T0 | Ag_1D | Ag_3D | FT_3 | FT_5 | 40C_2W | 40C_4W |
| C01 | 200 | 205.8 | 204.0 | 208.2 | 201.5 | 204.9 | 213.1 | 206.8 |
| C02 | | 212.0 | 205.7 | 210.7 | 204.3 | 206.0 | 208.0 | 210.5 |
| C03 | | 207.3 | 205.0 | 208.9 | 197.3 | 204.1 | 210.9 | 206.2 |
| C04 | | 203.9 | 201.1 | 207.4 | 198.3 | 204.8 | 209.1 | 209.8 |
| C05 | | 203.6 | 201.2 | 207.8 | 204.5 | 203.3 | 210.9 | 211.5 |
| C06 | | 204.3 | 201.3 | 209.6 | 203.8 | 203.8 | 209.5 | 208.9 |
| C07 | | 204.7 | 201.3 | 208.1 | 202.3 | 204.4 | 209.0 | 207.3 |
| C08 | 150 | 159.4 | 158.6 | 156.0 | 157.3 | 154.8 | 155.1 | 155.3 |
| C09 | | 156.9 | 156.2 | 155.4 | 152.6 | 152.2 | 154.2 | 155.5 |
| C10 | | 157.8 | 157.1 | 156.1 | 156.4 | 155.3 | 156.6 | 157.4 |

TABLE 26

TRAB-1 Osmolality, and Viscosity at T0

| Form. ID | Osmolality (mOsmol/kg) | Viscosity (cP, 25° C.) |
|---|---|---|
| C01 | 329 | 11.0 |
| C02 | 336 | 11.5 |
| C03 | 389 | 11.3 |
| C04 | 365 | 12.3 |
| C05 | 336 | 11.7 |
| C06 | 316 | 12.5 |
| C07 | 342 | 13.1 |
| C08 | 319 | 5.0 |
| C09 | 313 | 5.1 |
| C10 | 345 | 5.7 |

The presence of sub-visible particles in formulations C01-C10 after 1 day or 3 days agitation, 3 or 5 freeze/thaw cycles, and 2 or 4 weeks at 40° C. are summarized in Table 27. Compared with T0 controls, no substantial changes in TRAB-1 sub-visible particles were observed between formulations C01-C10 after 3 days agitation or 5 freeze/thaw cycles compared to the control (T0). A significant increase in sub-visible particles was observed for formulations C03, C04, and C07 after 4 weeks at 40° C. compared to the control (T0).

TABLE 27

Presence of Sub-visible Particles after Agitation, Freeze/Thaw, or Thermal Stress

| Form. ID | MFI (≥2 μm/10 μm/25 μm) | | | |
|---|---|---|---|---|
| | T0 | Ag_3D | FT_3 | FT_5 |
| C01 | 200/4/0 | 505/25/2 | 521/22/2 | 158/4/0 |
| C02 | 210/5/0 | 806/74/2 | 754/48/7 | 995/19/2 |
| C03 | 127/4/2 | 634/25/0 | 266/7/0 | 11239/290/10 |
| C04 | 158/0/0 | 855/27/5 | 195/0/0 | 8946/644/4 |
| C05 | 218/4/2 | 466/12/0 | 261/9/2 | 457/4/0 |
| C06 | 105/0/0 | 733/33/0 | 264/7/0 | 700/9/0 |
| C07 | 218/2/0 | 836/112/4 | 169/2/0 | 6560/89/0 |
| C08 | 235/2/0 | 1951/59/7 | 1715/35/2 | 295/20/0 |
| C09 | 318/10/0 | 605/10/0 | 1507/10/2 | 466/2/0 |
| C10 | 336/5/0 | 2226/50/10 | 901/20/2 | 489/0/0 |

SEC-UPLC performance for formulations C01-C10 after 1 day or 3 days agitation, 3 or 5 freeze/thaw cycles, and 2 or 4 weeks at 40° C. are summarized in Tables 28-30. SEC-UPLC performance was evaluated by percentages of TRAB-1 monomers (monomer %), high molecular weight particles (HMW %), and low molecular weight particles (LMW %). After 4 weeks at 40° C., a 1.1%-1.8% decrease in monomer % and 0.5%-1.4% increase in HMW % were observed in all formulations. Formulations of TRAB-1 in glycine buffer (C06) and formulations of TRAB-1 in arginine buffer (C01, C02) displayed better SEC-UPLC performance after 4 weeks at 40° C.

TABLE 28

Monomer % in TRAB-1 formulations after Agitation,
Freeze/Thaw, or Thermal Stress

| Form. ID | T0 | Ag_1D | Ag_3D | FT_3 | FT_5 | 40C_2W | 40C_4W |
|---|---|---|---|---|---|---|---|
| C01 | 98.2 | 98.2 | 98.2 | 98.0 | 98.2 | 97.4 (↓0.8) | 96.6 (↓1.6) |
| C02 | 98.3 | 98.2 | 98.2 | 98.2 | 98.2 | 97.4 (↓0.9) | 96.7 (↓1.6) |
| C03 | 98.1 | 98.0 | 98.0 | 98.0 | 98.1 | 97.0 (↓1.1) | 96.1 (↓2.0) |
| C04 | 98.1 | 98.0 | 98.0 | 98.0 | 98.0 | 97.1 (↓1.0) | 96.4 (↓1.7) |
| C05 | 98.2 | 98.2 | 98.1 | 98.2 | 98.2 | 97.4 (↓0.8) | 96.8 (↓1.4) |
| C06 | 98.3 | 98.3 | 98.2 | 98.3 | 98.2 | 97.4 (↓0.9) | 96.5 (↓1.8) |
| C07 | 98.1 | 98.1 | 98.0 | 98.1 | 98.1 | 97.1 (↓1.0) | 96.5 (↓1.6) |
| C08 | 98.3 | 98.3 | 98.3 | 98.2 | 98.3 | 97.7 (↓0.6) | 96.9 (↓1.4) |
| C09 | 98.3 | 98.3 | 98.3 | 98.3 | 98.3 | 97.7 (↓0.6) | 97.2 (↓1.1) |
| C10 | 98.1 | 98.1 | 98.1 | 98.1 | 98.1 | 97.4 (↓0.7) | 96.8 (↓1.3) |

TABLE 29

HMW % in TRAB-1 formulations after Agitation,
Freeze/Thaw, or Thermal Stress

| Form. ID | T0 | Ag_1D | Ag_3D | FT_3 | FT_5 | 40C_2W | 40C_4W |
|---|---|---|---|---|---|---|---|
| C01 | 1.7 | 1.7 | 1.7 | 1.9 | 1.7 | 2.3 (↑0.6) | 2.7 (↑1.0) |
| C02 | 1.6 | 1.7 | 1.7 | 1.7 | 1.7 | 2.2 (↑0.6) | 2.6 (↑1.0) |
| C03 | 1.8 | 1.9 | 1.9 | 1.9 | 1.8 | 2.7 (↑0.9) | 3.2 (↑1.4) |
| C04 | 1.8 | 1.9 | 2.0 | 1.9 | 1.9 | 2.6 (↑0.8) | 3.0 (↑1.2) |
| C05 | 1.7 | 1.7 | 1.8 | 1.8 | 1.7 | 2.3 (↑0.6) | 2.5 (↑0.8) |
| C06 | 1.6 | 1.6 | 1.7 | 1.7 | 1.7 | 2.3 (↑0.7) | 2.8 (↑1.2) |
| C07 | 1.8 | 1.9 | 1.9 | 1.8 | 1.8 | 2.6 (↑0.8) | 2.9 (↑1.1) |
| C08 | 1.6 | 1.6 | 1.6 | 1.7 | 1.6 | 2.0 | 2.3 (↑0.7) |
| C09 | 1.6 | 1.6 | 1.6 | 1.6 | 1.6 | 2.0 | 2.1 (↑0.5) |
| C10 | 1.8 | 1.8 | 1.8 | 1.8 | 1.8 | 2.3 (↑0.5) | 2.5 (↑0.7) |

TABLE 30

LMW % in TRAB-1 formulations after Agitation,
Freeze/Thaw, or Thermal Stress

| Form. ID | T0 | Ag_1D | Ag_3D | FT_3 | FT_5 | 40C_2W | 40C_4W |
|---|---|---|---|---|---|---|---|
| C01 | 0.1 | 0.1 | 0.1 | 0.1 | 0.1 | 0.3 | 0.7 (↑0.6) |
| C02 | 0.1 | 0.1 | 0.1 | 0.1 | 0.1 | 0.3 | 0.7 (↑0.6) |
| C03 | 0.1 | 0.1 | 0.1 | 0.1 | 0.1 | 0.3 | 0.7 (↑0.6) |
| C04 | 0.1 | 0.1 | 0.1 | 0.1 | 0.1 | 0.3 | 0.6 (↑0.5) |
| C05 | 0.1 | 0.1 | 0.1 | 0.1 | 0.0 | 0.3 | 0.6 (↑0.5) |
| C06 | 0.1 | 0.1 | 0.1 | 0.1 | 0.1 | 0.3 | 0.7 (↑0.6) |
| C07 | 0.1 | 0.1 | 0.1 | 0.1 | 0.1 | 0.3 | 0.6 (↑0.5) |
| C08 | 0.1 | 0.1 | 0.1 | 0.1 | 0.1 | 0.3 | 0.8 (↑0.7) |
| C09 | 0.1 | 0.1 | 0.1 | 0.1 | 0.1 | 0.3 | 0.7 (↑0.6) |
| C10 | 0.1 | 0.1 | 0.1 | 0.1 | 0.1 | 0.3 | 0.7 (↑0.6) |

TRAB-1 purity was evaluated for formulations C01-C10 by caliper-SDS under non-reducing (caliper-NR) and reducing (caliper-R) conditions after 3 days agitation, 5 freeze/thaw cycles, and 2 or 4 weeks at 40° C., and the results are summarized in Table 31 and Table 32. No substantial changes were observed in caliper purity % after 3 days agitation or 5 freeze thaw cycles. Purity consistently decreased between 2 and 4 weeks at 40° C. After 4 weeks at 40° C., a 3.2%-5.6% decrease in caliper-NR purity % and 0.5-1.6% decrease in caliper-R purity % were observed in all formulations.

TABLE 31

Caliper-NR-Purity % after Agitation, Freeze/Thaw, or Thermal Stress

| Form. ID | T0 | Ag_3D | FT_5 | 40C_2W | 40C_4W |
|---|---|---|---|---|---|
| C01 | 99.1 | 98.6 | 99.0 | 98.6 (↓0.5) | 95.3 (↓3.8) |
| C02 | 99.2 | 99.1 | 98.9 | 98.4 (↓0.8) | 94.7 (↓4.5) |
| C03 | 99.2 | 99.0 | 99.0 | 98.8 | 93.6 (↓5.6) |
| C04 | 99.3 | 99.0 | 98.8 (↓0.5) | 98.5 (↓0.8) | 96.1 (↓3.2) |
| C05 | 99.2 | 99.0 | 99.0 | 98.5 (↓0.7) | 95.0 (↓4.2) |
| C06 | 99.3 | 99.0 | 99.0 | 98.8 (↓0.5) | 94.9 (↓4.4) |
| C07 | 99.3 | 99.0 | 98.8 (↓0.5) | 98.5 (↓0.8) | 93.7 (↓5.6) |
| C08 | 99.1 | 98.9 | 99.0 | 98.4 (↓0.7) | 95.5 (↓3.6) |
| C09 | 99.3 | 99.0 | 99.1 | 98.5 (↓0.8) | 95.5 (↓3.8) |
| C10 | 99.1 | 99.1 | 99.0 | 98.6 (↓0.5) | 95.8 (↓3.3) |

TABLE 32

Caliper-R-Purity % after Agitation, Freeze/Thaw, or Thermal Stress

| Form. ID | T0 | Ag_3D | FT_5 | 40C_2W | 40C_4W |
|---|---|---|---|---|---|
| C01 | 99.3 | 98.4 (↓0.9) | 99.0 | 99.0 | 98.5 (↓0.8) |
| C02 | 99.3 | 99.3 | 99.2 | 98.8 (↓0.5) | 98.2 (↓1.1) |
| C03 | 99.0 | 99.2 | 99.2 | 99.0 | 98.2 (↓0.8) |
| C04 | 99.1 | 99.2 | 98.9 | 99.0 | 98.2 (↓0.9) |
| C05 | 98.9 | 98.9 | 99.2 | 99.1 | 97.8 (↓1.1) |
| C06 | 99.0 | 99.1 | 99.1 | 98.9 | 97.4 (↓1.6) |
| C07 | 99.2 | 99.2 | 98.7 | 99.1 | 98.5 (↓0.7) |
| C08 | 99.2 | 99.3 | 99.3 | 99.1 | 98.5 (↓0.7) |
| C09 | 99.2 | 99.2 | 98.9 | 98.9 | 98.7 (↓0.5) |
| C10 | 99.2 | 99.2 | 99.0 | 98.9 | 98.6 (↓0.6) |

Charge variants of TRAB-1 were evaluated for formulations C01-C10 by imaged capillary isoelectric focusing (iCIEF) after 3 days agitation, 5 freeze/thaw cycles, and 2 or 4 weeks at 40° C., and the results are summarized in Tables 33-35. Charge variants were observed to shift with an increase in acidic species when formulations were exposed to 3 days agitation, 5 freeze/thaw cycles, or 40° C. for 2 weeks.

TABLE 33 iCIEF Main Peak % after Agitation, Freeze/Thaw, or Thermal Stress

| Form. ID | T0 | Ag_3D | FT_5 | 40C_2W |
|---|---|---|---|---|
| C01 | 60.8 | 61.9 (↑1.1) | 61.6 (↑0.8) | 55.8 (↓5.0) |
| C02 | 62.1 | 58.2 (↓3.9) | 61.3 (↓0.8) | 57.8 (↓4.3) |
| C03 | 60.6 | 60.4 | 58.9 (↓1.7) | 51.9 (↓8.7) |
| C04 | 61.2 | 59.7 (↓1.5) | 61.0 | 52.3 (↓8.9) |
| C05 | 59.2 | 57.3 (↓1.9) | 59.5 | 53.0 (↓6.2) |
| C06 | 62.9 | 58.7 (↓4.2) | 60.2 (↓2.7) | 52.6 (↓10.3) |
| C07 | 61.1 | 60.1 (↓1.0) | 57.5 (↓3.6) | 51.6 (↓9.5) |
| C08 | 61.8 | 60.4 (↓1.4) | 61.3 (↓0.5) | 52.8 (↓9.0) |
| C09 | 60.7 | 59.2 (↓1.5) | 58.6 (↓2.1) | 52.9 (↓7.8) |
| C10 | 59.2 | 60.8 (↑1.6) | 58.9 | 55.7 (↓3.5) |

TABLE 34 iCIEF Acidic Peak % after Agitation, Freeze/Thaw, or Thermal Stress

| Form. ID | T0 | Ag_3D | FT_5 | 40C_2W |
|---|---|---|---|---|
| C01 | 32.5 | 32.9 | 32.2 | 37.4 (↑4.9) |
| C02 | 30.7 | 36.1 (↑5.4) | 32.2 (↑1.5) | 35.0 (↑4.3) |
| C03 | 33.3 | 33.9 (↑0.6) | 34.4 (↑1.1) | 40.8 (↑7.5) |
| C04 | 32.2 | 33.1 (↑0.9) | 33.1 (↑0.9) | 39.9 (↑7.7) |
| C05 | 34.1 | 36.5 (↑2.4) | 34.1 | 39.6 (↑5.5) |
| C06 | 29.2 | 35.6 (↑6.4) | 34.2 (↑5.0) | 39.7 (↑10.5) |
| C07 | 31.9 | 33.7 (↑1.8) | 36.1 (↑4.2) | 41.6 (↑9.7) |
| C08 | 31.5 | 33.3 (↑1.8) | 33.2 (↑1.7) | 39.5 (↑8.0) |
| C09 | 32.7 | 34.5 (↑1.8) | 34.8 (↑2.1) | 40.0 (↑7.3) |
| C10 | 34.2 | 33.7 (↓0.5) | 35.3 (↑1.1) | 37.1 (↑2.9) |

TABLE 35 iCIEF Basic Peak % after Agitation, Freeze/Thaw, or Thermal Stress

| Form. ID | T0 | Ag_3D | FT_5 | 40C_2W |
|---|---|---|---|---|
| C01 | 6.7 | 5.3 (↓1.4) | 6.2 (↓0.5) | 6.8 |

TABLE 35-continued iCIEF Basic Peak % after Agitation, Freeze/Thaw, or Thermal Stress

| Form. ID | T0 | Basic peak % Ag_3D | FT_5 | 40C_2W |
|---|---|---|---|---|
| C02 | 7.2 | 5.7 (↓1.5) | 6.5 (↓0.7) | 7.1 |
| C03 | 6.1 | 5.7 | 6.7 (↑0.6) | 7.3 (↑1.2) |
| C04 | 6.6 | 7.2 (↑0.6) | 5.9 (↓0.7) | 7.7 (↑1.1) |
| C05 | 6.7 | 6.2 (↓0.5) | 6.4 | 7.5 (↑0.8) |
| C06 | 7.9 | 5.7 (↓2.2) | 5.6 (↓2.3) | 7.7 |
| C07 | 7.0 | 6.2 (↓0.8) | 6.5 (↓0.5) | 6.7 |
| C08 | 6.7 | 6.3 | 5.6 (↓1.1) | 7.7 (↑1.0) |
| C09 | 6.6 | 6.3 | 6.6 | 7.1 (↑0.5) |
| C10 | 6.7 | 5.4 (↓1.3) | 5.8 (↓0.9) | 7.2 (↑0.5) |

Example 4: Antibody TRAB-1 is Stable in Formulation C06 and does not Form Significant Aggregates or Degradation Products The formulation of C06 comprising the antibody was further tested for stability at the different temperatures of 5° C., and/or 25° C. using GMP and non-GMP lots.

At 5 C, 25 C, and 40C, a non-GMP produced drug product formulation of C06 (pH of ~5.7) with a concentration of about 200 mg/ml of the antibody was tested for stability of the antibody for the time periods illustrated in the table below. It was found that even at temperatures up to 40C, the antibody was stable and was found to be stable with minimal high molecular aggregates or low molecular weight degradation products through the time periods tested. The data is summarized in the following tables.

Stability of non-GMP Drug Product containing TRAB-1 Antibody in C06 Formulation at 5 C.

| Test/Attribute | 0 months | 1 months | 3 months | 6 months | 9 months |
|---|---|---|---|---|---|
| Monomer % (SEC) | 99.6 | 99.7 | 99.3 | 99.2 | 99.1 |
| HMWS % (SEC) | 0.3 | 0.3 | 0.6 | 0.7 | 0.8 |
| LMWS % (SEC) | 0.1 | ND | 0.1 | 0.1 | 0.1 |

Stability of non-GMP Drug Product containing TRAB-1 Antibody in C06 Formulation at 25 C.

| Test/Attribute | 0 months | 1 months | 3 months | 6 months |
|---|---|---|---|---|
| Monomer % (SEC) | 99.6 | 99.3 | 98.5 | 97.8 |
| HMWS % (SEC) | 0.3 | 0.5 | 1.1 | 1.4 |
| LMWS % (SEC) | 0.1 | 0.2 | 0.4 | 0.7 |

Stability of non-GMP Drug Product containing TRAB-1 Antibody in C06 Formulation at 40 C.

| Test/Attribute | 0 mo | 0.25 month | 0.5 month | 1 month |
|---|---|---|---|---|
| Monomer % (SEC) | 99.6 | 98.9 | 98.6 | 98.0 |
| HMWS % (SEC) | 0.3 | 0.8 | 1.0 | 1.1 |
| LMWS % (SEC) | 0.1 | ND | ND | ND |

Stability of GMP Drug Product containing TRAB-1 Antibody in C06 Formulation at 5 C.

| Test/Attribute | 0 months | 1 months | 3 months | 6 months |
|---|---|---|---|---|
| Monomer % (SEC) | 99.3 | 99.3 | 99.2 | 99.1 |
| HMWS % (SEC) | 0.5 | 0.6 | 0.7 | 0.8 |
| LMWS % (SEC) | 0.1 | 0.1 | 0.1 | 0.1 |

Stability of GMP Drug Product containing TRAB-1 Antibody in C06 Formulation at 25 C.

| Test/Attribute | 0 months | 1 months | 3 months | 6 months |
|---|---|---|---|---|
| Monomer % (SEC) | 99.3 | 98.9 | 98.5 | 97.7 |
| HMWS % (SEC) | 0.5 | 0.9 | 1.3 | 1.7 |
| LMWS % (SEC) | 0.1 | 0.1 | 0.3 | 0.6 |

Stability of GMP Drug Product containing TRAB-1 Antibody in C06 Formulation at 40 C.

| Test/Attribute | 0 mo | 0.5 month | 1 month |
|---|---|---|---|
| Monomer % (SEC) | 99.3 | 98.2 | 97.3 |
| HMWS % (SEC) | 0.5 | 1.2 | 2.0 |

These data illustrate that under various conditions and time periods the antibody remains stable having at least 97% monomer (intact antibody) present even at high temperatures (40 C). Thus, the formulation inhibits or prevents the formation of aggregation or degradation products as observed by the minimal amounts of High Molecular Weight Species (HMWS) and Low Molecular Weight Species (LMWS) present as shown at the various time points tested. These results could not have been predicted or expected prior to this being demonstrated herein.

Example 5: In Vitro Studies

Ba/F3 cells were transfected with human TSLP-R/IL-7Rα and treated with either TRAB-1 antibody (the anti-TSLP-R antibody described herein), tezepelumab antibody (an anti-TSLP antibody), or IgG antibody. Cell proliferation rates in the Ba/F3 cells were monitored as a function of the concentration of the antibody concentration (FIG. 1A). IC50 and IC90 values are plotted in Table 36.

TABLE 36

IC50 and IC90 values from Ba/F3 cells transfected with human TSLP-R/IL-7Rα and treated with either TRAB-1 antibody or tezepelumab antibody

|  | IC50 (ng/mL) | IC90 (ng/mL) |
|---|---|---|
| TRAB-1 | 90.7 | 200 |
| Tezepelumab | 518 | 15300 |

Figure 1B:
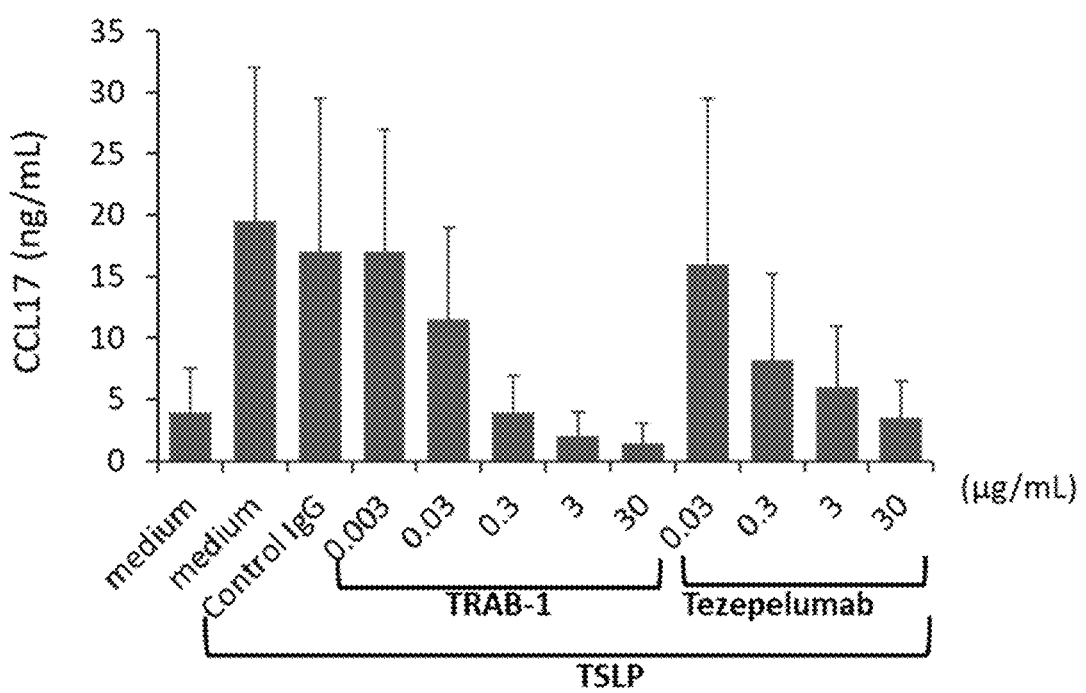

Dendritic cells were treated with TRAB-1 antibody, tezepelumab antibody, or IgG antibody. The CCL17 (ng/mL) production in the dendritic cells was monitored as a function of the concentration of the antibody concentration (FIG. 1B). IC50 and IC90 values are plotted in Table 37.

TABLE 37

IC50 and IC90 values from dendritic cells treated with either TRAB-1 antibody or tezepelumab antibody

|  | IC50 (ng/mL) | IC90 (ng/mL) |
|---|---|---|
| TRAB-1 | 16.1 | 163 |
| Tezepelumab | 67.0 | 855 |

IC90 values from these in vitro assays suggested a trough concentration of approximately 0.3 ng/mL. Together, these data depict that TRAB-1 produces potent suppression of TSLP/TSLP-R-mediated responses in vitro.

Example 6: Single Ascending Dose Studies in Healthy Volunteers

Single ascending dose (SAD) studies were performed in healthy volunteers. Healthy volunteer subjects (n=36) were treated with 0.03-10 mg/kg single doses of TRAB-1 either intravenously (IV) or subcutaneously (SC). The doses chosen for study were: 0.03 mg/kg IV; 0.1 mg/kg IV; 0.3 mg/kg IV; 1.0 mg/kg IV; 3 mg/kg IV; 10 mg/kg IV; and 1.0 mg/kg SC. No serious aversive events were observed in the group of healthy volunteers. The most common emergent adverse event in the treatment group was: dysmenorrhea (3, 8.3%), breast tenderness (3, 8.3%), and headache (1, 2.8%).

Figure 2A:
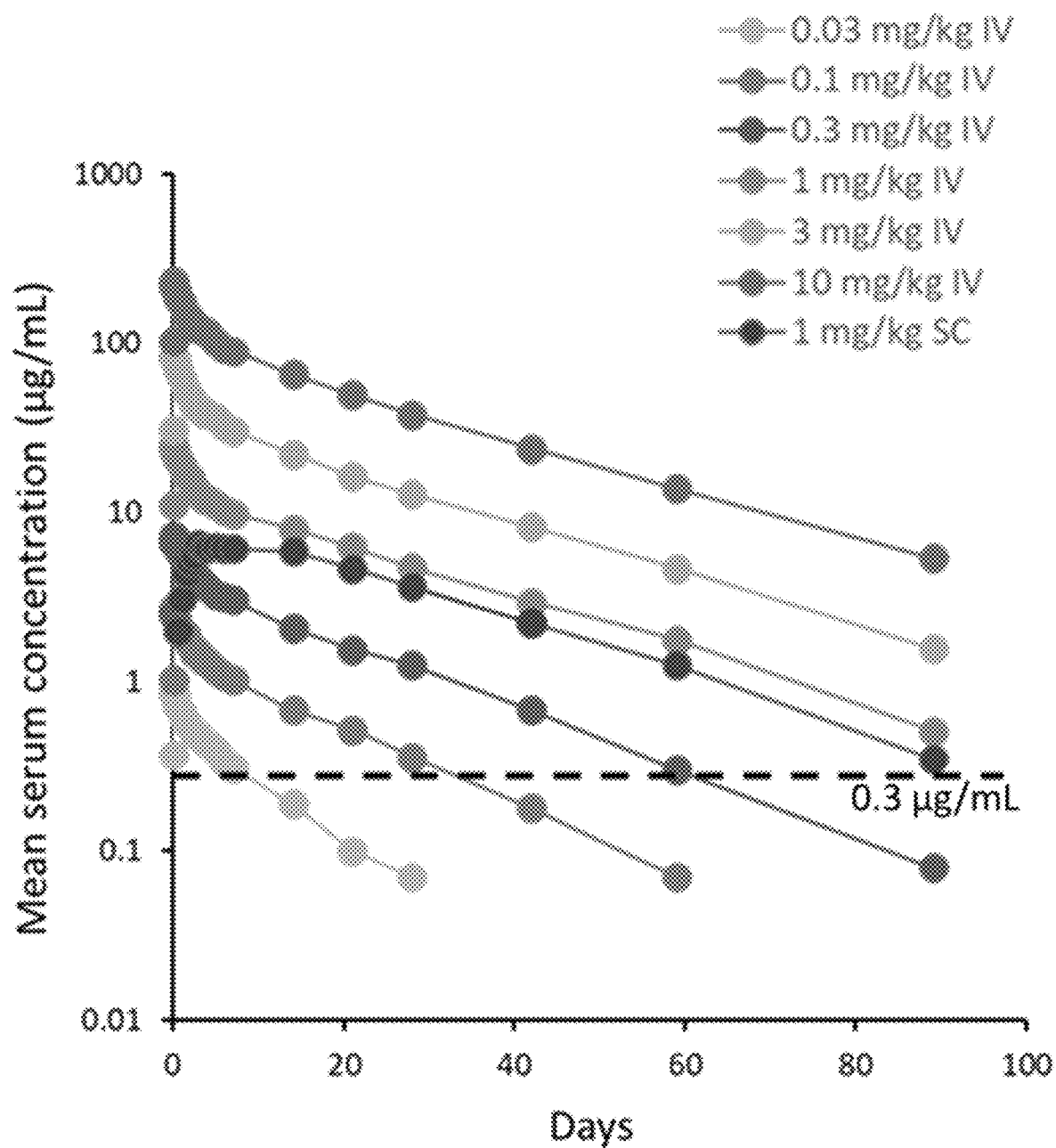
FIGS. 2A-2C: Data depicting that single ascending dose (SAD) studies in healthy volunteers demonstrated sustained pharmacokinetics (PK) effect over 60 days.
Figure 2B:
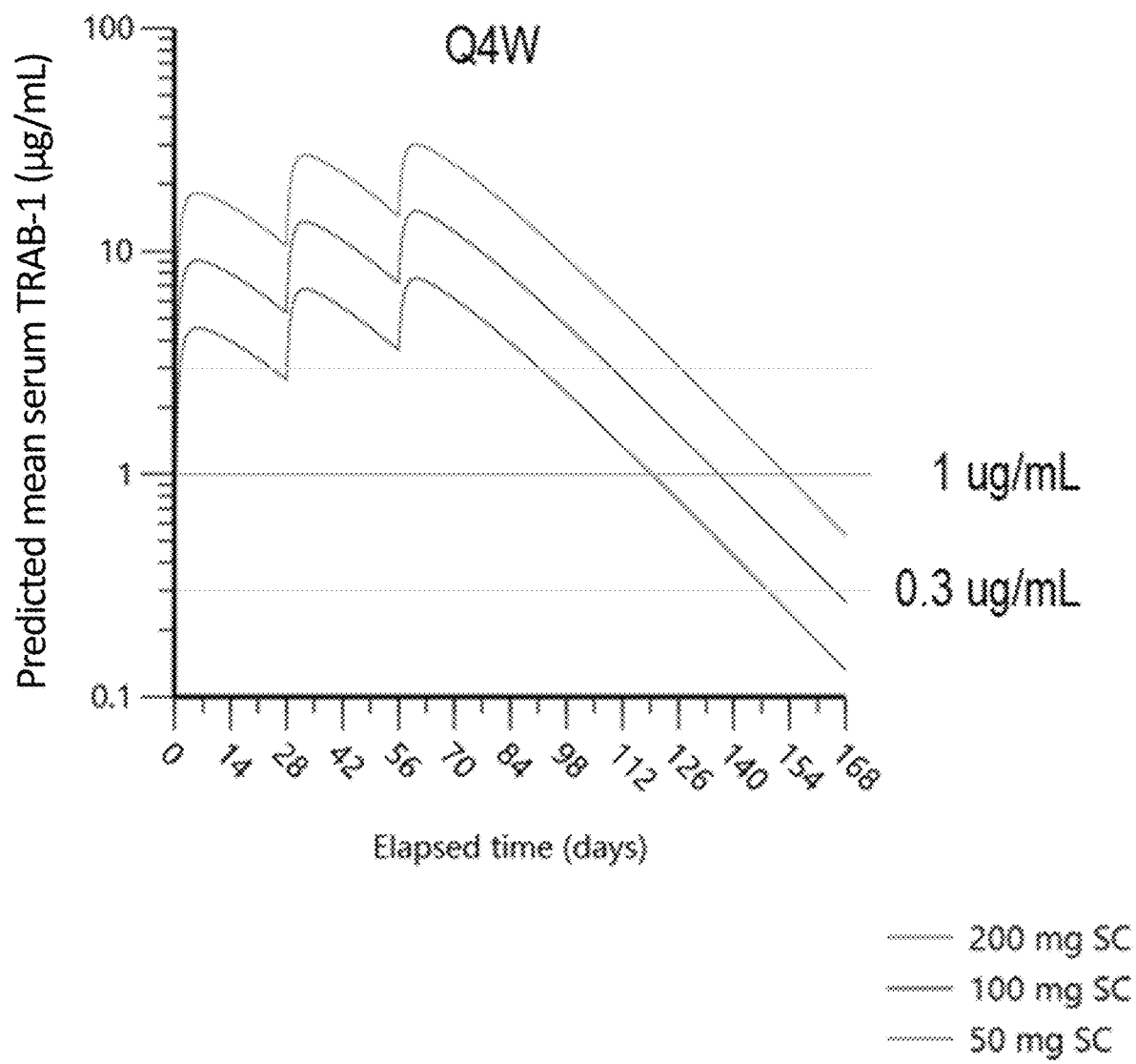
Figure 2C:
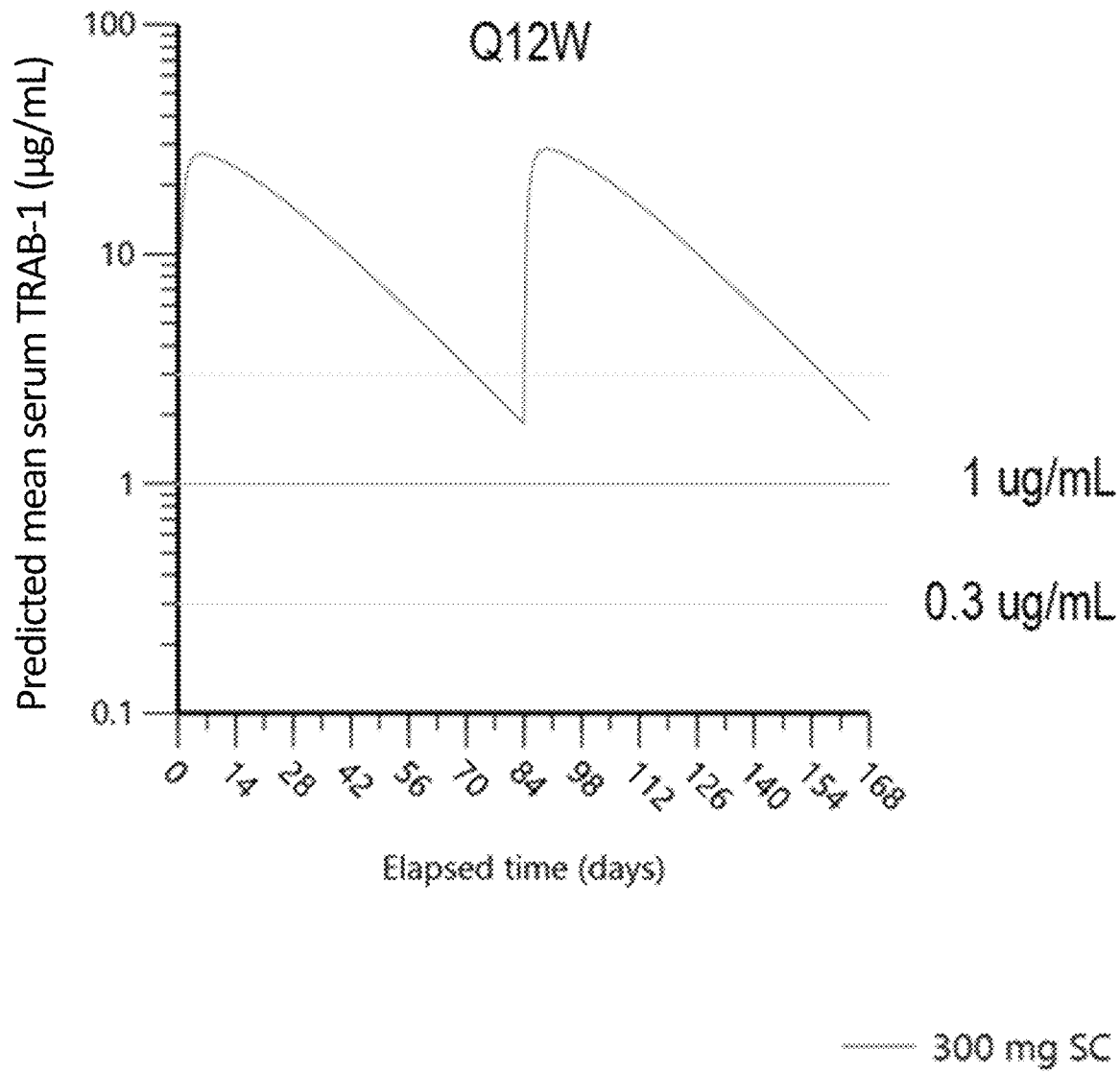

Mean serum concentration as a function of dose and route of administration of TRAB-1 was monitored over time (FIG. 2A). This data demonstrated sustained pharmacokinetics (PK) effect over 60 days. Dose-proportional pharmacokinetics were observed from 2 mg TRAB-1 to 700 mg TRAB-1. About 70% bioavailability was observed with sub-cutaneous administration. Doses of greater than or equal to 1.0 mg/kg resulted in exposure greater than or equal to the therapeutic target (0.3 µg/mL). Lower titer antidrug-antibodies (ADAs) were observed in 24% of subjects, with minimal impact on pharmacokinetics. The following dosing schedules were chosen for further study: every four weeks (Q4W), and every 12 weeks (Q12W). Predicted mean serum concentration of TRAB-1 over time, as a function of dose of TRAB-1 administered subcutaneously every 4 weeks, is shown in FIG. 2B. Predicted mean serum concentration of TRAB-1 over time, as a function of dose of TRAB-1 administered subcutaneously every 12 weeks, is shown in FIG. 2C.

Figure 3A:
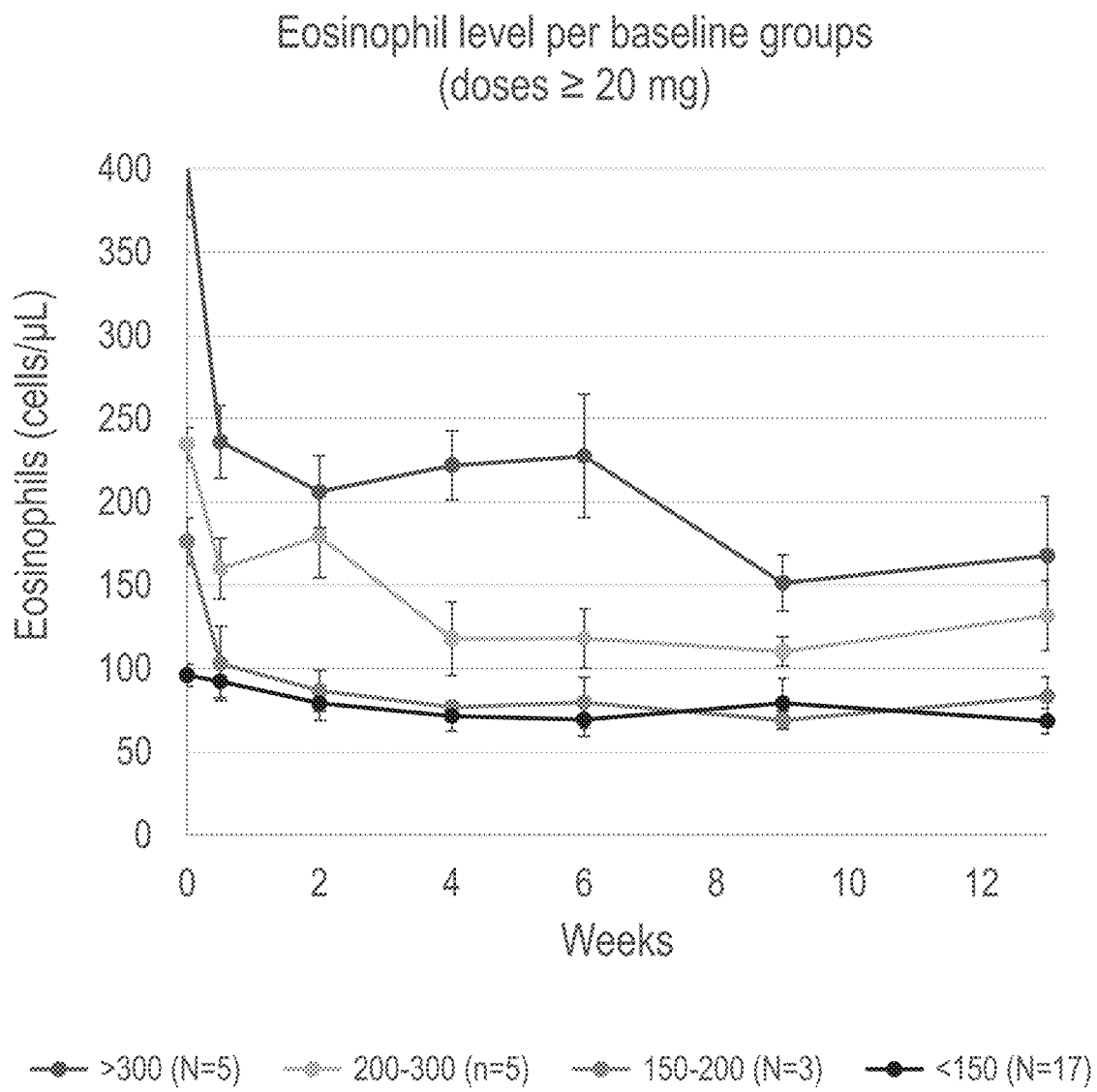
FIGS. 3A-3B: Data depicting that reduction of eosinophils was evident after a single dose of TRAB-1 in healthy volunteers.

Leukocyte differentials were measured from peripheral blood. Eosinophil concentrations in healthy volunteers treated with greater than or equal to 20 mg (0.3 mg/kg) of TRAB-1 were monitored as a function of time (FIG. 3A). Groups were selected based on eosinophil concentrations at day 0: <150 cells/µL (n=17); 150-200 cells/µL (n=3); 200-300 cells/µL (n=5); and >300 cell/µL (n=5).

Figure 3B:
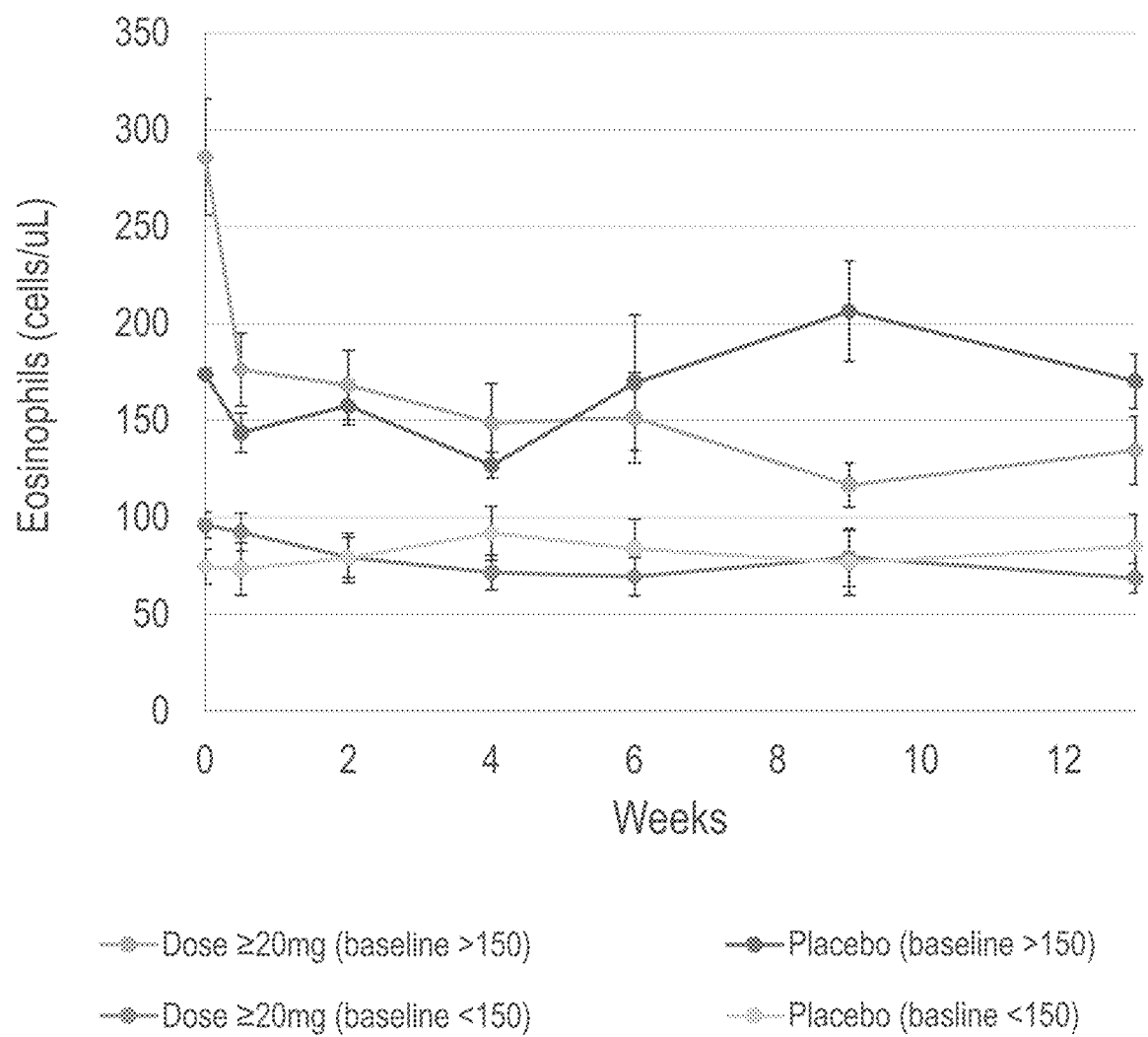

Eosinophil concentrations in healthy volunteers treated with greater than or equal to 20 mg (0.3 mg/kg) of TRAB-1 were monitored as a function of time and compared to the placebo group (FIG. 3B). Groups were selected based on eosinophil concentrations at day 0: <150 cells/µL (treatment: n=17; placebo: n=9); and >150 cells/µL (treatment: n=13; placebo: n=3). Data from one placebo subject, with high eosinophil baseline levels (646 cells/mL) was removed for being out of range. This data demonstrates that reduction of eosinophils was evident after a single dose of TRAB-1 in healthy volunteers.

Figure 4A:
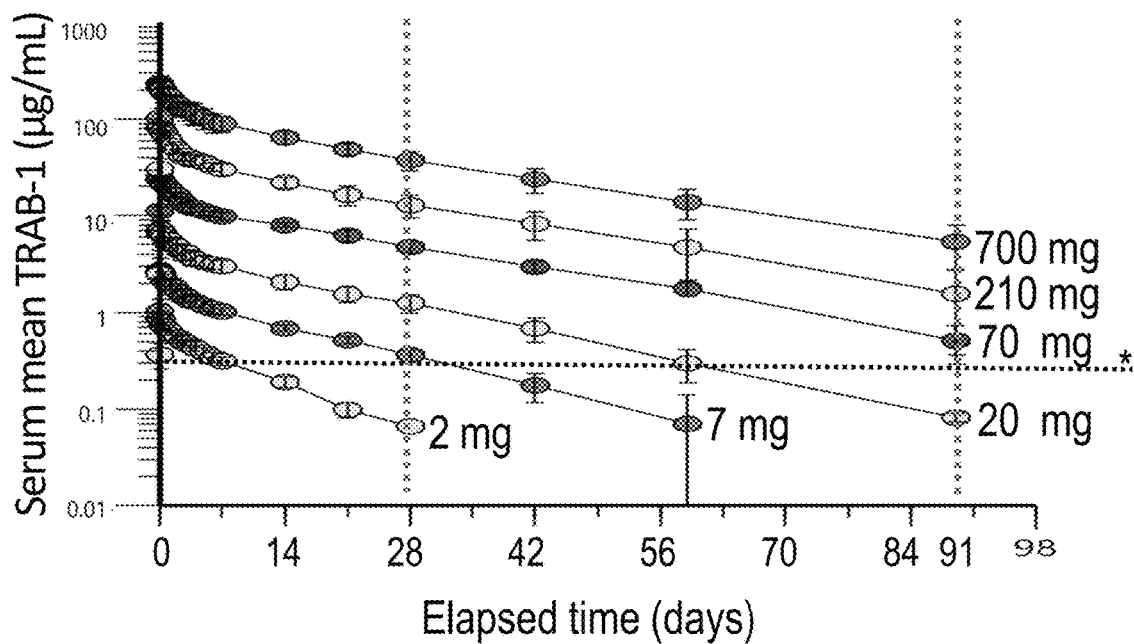
FIGS. 4A-4B: Data depicting an indication of pharmacokinetics/pharmacodynamics correlation in healthy volunteers treated with single ascending dose of TRAB-1.
Figure 4B:
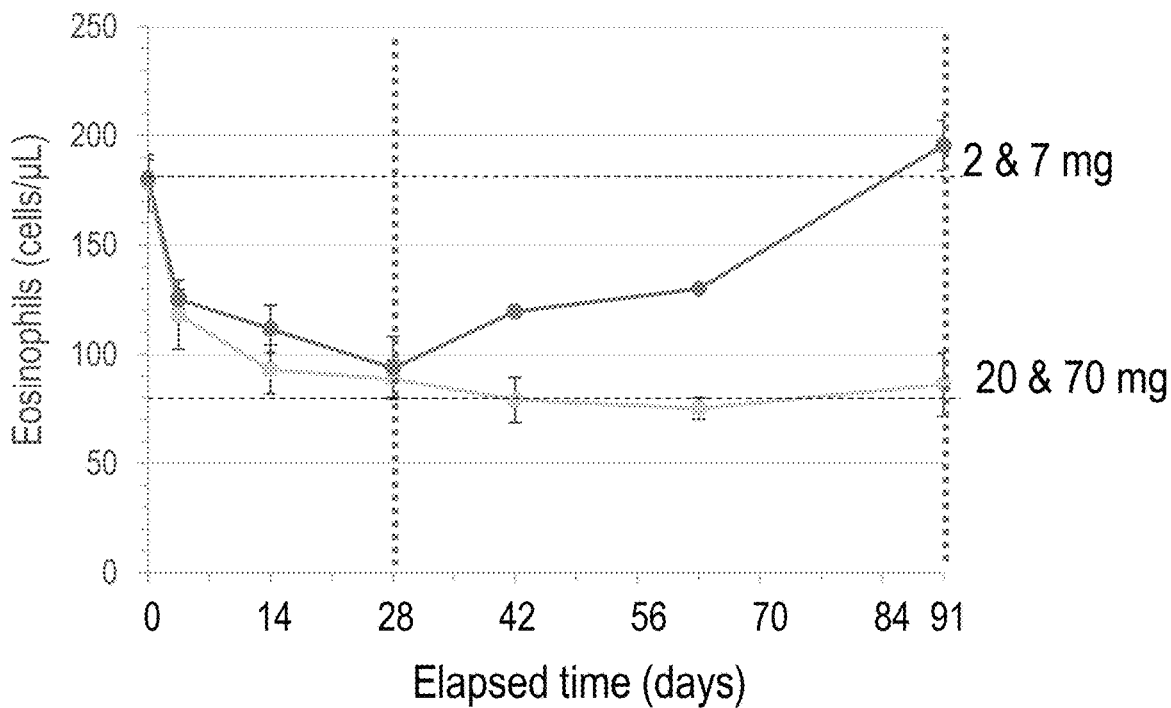

Pharmacokinetics curves depicting serum mean TRAB-1 were plotted as a function of time in healthy volunteers treated with 2 mg, 7 mg, 20 mg, 70 mg, 210 mg, or 700 mg of TRAB-1 (FIG. 4A). Subjects with the same baseline eosinophil levels (147-215 cells/µL) were compared across two dose groups (2 mg and 7 mg of TRAB-1, or 20 mg and 70 mg of TRAB-1), and the pharmacodynamics curves depicting eosinophils were plotted as a function of time (FIG. 4B). Low-doses were found to lose efficacy when serum concentrations of TRAB-1 dropped below the therapeutic threshold. Higher doses retained efficacy and TRAB-1 concentrations remained above the therapeutic threshold. These data depict that a pharmacokinetics/pharmacodynamics correlation in healthy volunteers treated with single ascending dose of TRAB-1 is indicated.

Example 7: Multiple Ascending Dose Studies in Asthmatic Subjects

Multiple ascending dose (MAD) studies were performed in asthmatic subjects treated with TRAB-1 or placebo. The studies were randomized and double-blind. Observation continued for either 4, 8, 12, or 24 weeks (as indicated herein) following the last dose. Safety, tolerability, immunogenicity, pharmacokinetics, and pharmacodynamics were assessed. The pharmacodynamics assessed included target engagement, blood eosinophils, and fractional exhaled Nitric Oxide (Fractional exhaled Nitric Oxide (FeNO)) levels. A pharmacokinetics-pharmacodynamics profile, including the long tail of the pharmacodynamics response, was assessed. Immunogenicity was used to confirm explore pharmacodynamics and anti-drug antibodies. Exploratory studies were also performed to assess mechanism of action. The exploratory studies were also performed to assess affected pathways (e.g., Th2 and Th1 response). For example, serum concentrations of cytokines downstream to TSLP-R were assessed in exploratory studies.

The following dosing schedules were studied: single dose (SD), every four weeks (Q4W), every 8 weeks (Q8W), every 12 weeks (Q12W), every 16 weeks (Q16W), and every 24 weeks (Q24W). The following doses were selected for study: 25 mg, 100 mg, 200 mg, and 300 mg. The pharmaceutical dosage range per weight selected for study was 0.03-10 mg/kg per pharmaceutical dosage. The routes of administration selected for study was subcutaneous injection (SC). The dosing schedule for each participant group is indicated in the following examples.

Abbreviations used in the examples are as follow: SD=single dose; Q4W=every 4 weeks; Q8W=every 8 weeks; Q12W=every 12 weeks; Q16W=every 16 weeks; Q24W=every 24 weeks; IV=intravenous; SC=subcutaneous The subjects were observed for treatment emergent aversive events and emergent adverse events. Mean serum concentration of TRAB-1 was monitored over time and was analyzed for dose-proportional pharmacokinetics. Bioavailability was measured. Antidrug-antibodies (ADAs) and their impact on pharmacokinetics was measured. Leukocyte differentials were measured from peripheral blood. Eosinophil concentrations in asthmatic subjects of TRAB-1 were monitored as a function of time and compared to the placebo group.

Pharmacokinetics and pharmacodynamics curves depicting serum mean TRAB-1 were monitored and plotted as a function of time in asthmatic subjects. Efficacy at low-doses and high doses were measured. The data was analyzed for a pharmacokinetics/pharmacodynamics correlation.

Receptor saturation is also measured.

Results

As discussed above, a randomized, double-blind, placebo-controlled multiple ascending-dose study was conducted to evaluate the safety, tolerability, pharmacokinetics (PK), and pharmacodynamics (PD) of TRAB-1 patients with asthma. The cohort received either a placebo for a total of 3 injections, or TRAB-1 by subcutaneous (SC) injection. Of the subjects administered TRAB-1, Group 1 was administered 100 mg TRAB-1 every 4 weeks for a total of 2 or 3 administrations, Group 2 was administered 200 mg TRAB-1 every 4 weeks for a total of 1, 2, or 3 administrations, a Group 3 was administered 300 mg TRAB-1 every 12 weeks for a total of 1 or 2 administrations, and a Group 4 was administered 25 mg TRAB-1 for a total of 1 administration. Groups were observed for up to 24 weeks. Demographics data for each cohort is available in Table 38.

TABLE 38

Subject Demographics

| TRAB-1 dosage and schedule | Group 1: 100 mg Q4W | Group 2: 200 mg Q4W | Group 3: 300 mg Q12W | Group 4: 25 mg | Placebo |
|---|---|---|---|---|---|
| n | 6 | 6 | 6 | 5 | 8 |
| Mean age | 35.7 | 37.7 | 32.7 | 49.4 | 37.0 |
| Gender N(%) | 1M:5F | 2M:4F | 4M:2F | 3M:2F | 5M:3F |
| Male | 1 (17%) | 2 (33%) | 4 (67%) | 3 (60%) | 5 (63%) |
| Female | 5 (83%) | 4 (67%) | 2 (33%) | 2 (40%) | 3 (38%) |
| Race N(%) | | | | | |
| Asian | 2 (33%) | — | 3 (30%) | — | — |
| African American/Black | — | 1 (17%) | — | — | 1 (13%) |
| White | 4 (67%) | 4 (67%) | 2 (33%) | 5 (100%) | 7 (88%) |
| Other or Mixed | — | 1 (17%) | 1 (17%) | — | — |
| Mean BMI | 26.6 | 25.2 | 25.2 | 26.8 | 25.6 |

Several subjects had mild, short-lived, and self-limited injection site reactions (ISR) TEAEs were observed in the groups administered 100 mg Q4W (83%; n=5/6), 200 mg Q4W (50%; n=3/6), and 300 mg Q12W (33%; n=2/6) of TRAB-1. All treatment emergent adverse events (TEAEs) that were observed are described in Table 39. All TEAEs were assigned a relatedness rating based on the likelihood of the TEAE being related to the treatment. All TEAEs were determined to be either possibly related to treatment (PR) or not related to treatment (NR). The TEAEs that were determined to be possibly related to treatment included respiratory infection, rhinitis, back stiffness, first degree heart block, and headaches. TEAEs that were determined to be not related to treatment included coryza (1 mild; 2 moderate) and blocked nose (2 mild). For Group 1, a total of 15 TEAEs (60% mild; 40% moderate) were observed, of which 2 mild TEAEs were determined to possibly be related to treatment, and 13 TEAEs were determined to be not related to treatment. For Group 2, a total of 8 TEAEs (63% mild; 38% moderate) were observed, of which 2 mild TEAEs were possibly be related to treatment, and 6 TEAEs were determined to be not related to treatment. For Group 3, a total of 3 TEAEs (100% mild) were observed, of which 2 were possibly be related to treatment, and 1 was determined to be not related to treatment. No TEAEs were observed for Group 4. For the placebo group, a total of 7 TEAEs (29% mild; 71% moderate) were observed, of which 1 mild TEAE was determined to possibly be related to treatment. No serious aversive events (SAEs) and no withdrawal symptoms were observed in any group. No treatments were not stopped for any individuals in any groups due to TEAEs. The most common TEAEs observed were headaches (HA) (see Table 40). For Group 1,3 individuals reported a total of 4 headaches, of which 1 (25%) was mild and possibly related to treatment, and 3 (75%) were moderate and determined to be not related to treatment. A single subject from the Group 3 experienced one mild headache that was determined to be possibly related to treatment.

TABLE 39

Treatment Emergent Adverse Events

| TRAB-1 dosage and schedule | Group 1: 100 mg Q4W N (%) | | Group 2: 200 mg Q4W N (%) | | Group 3: 300 mg Q12W N (%) | | Group 4: 25 mg N (%) | Placebo N (%) | |
|---|---|---|---|---|---|---|---|---|---|
| | N (%) | Related | N (%) | Related | N (%) | Related | N (%) | N (%) | Related |
| # of subjects with TEAEs | 5 (83%) | — | 3 (50%) | — | 2 (33%) | — | 0 (0%) | — | 5 (83%) |
| Total number of TEAEs | 15 | 2 PR 13 NR | 8 | 2 PR 6 NR | 3 | 1NR 2 PR | 0 | 1 PR 4 NR 2† | 15 |
| Mild (% of TEAEs) | 9 (60%) | 7 NR | 5 (63%) | 2 PR 3 NR | 3 (100%) | 1NR 2 PR | 0 (0%) | 1† | 9 (60%) |
| Moderate (% of TEAEs) | 6 (40%) | All NR | 3 (38%) | All NR | 0 (0%) | — | 0 (0%) | 3 NR 2† | 6 (40%) |
| Severe (% of TEAEs) | 0 (0%) | — | 0 (0%) | — | 0 (0%) | — | 0 (0%) | — | 0 (0%) |
| Withdrawal/IMP stopped | 0 (0%) | | 0 (0%) | | 0 (0%) | | 0 (0%) | 0 (0%) | |

\* Q4W = every 4 weeks;
Q12W = every 12 weeks;
PR = possibly related;
NR = not related;
† = Determination pending

TABLE 40

Distribution of TEAEs reported to be headaches

| TRAB-1 dosage and schedule | Group 1: 100 mg Q4W | | Group 2: 200 mg Q4W | Group 3: 300 mg Q12W | | Group 4: 25 mg | Placebo |
|---|---|---|---|---|---|---|---|
| | N (%) | Relatedness | N (%) | N (%) | Relatedness | N (%) | N (%) |
| # subjects with HA | 3 | — | 0 | 1 | — | 0 | 0 |
| # HAs reported | 4 | 3 NR, 1 PR | 0 (0%) | 1 | 1 PR | 0 (0%) | 0 (0%) |
| # Mild (% of HAs) | 1 (25%) | 1 PR | 0 (0%) | 1 (100%) | 1 PR | 0 (0%) | 0 (0%) |
| # Moderate (% of HAs) | 3 (75%) | All NR | 0 (0%) | 0 (0%) | — | 0 (0%) | 0 (0%) |

* Q4W = every 4 weeks;
Q12W = every 12 weeks;
HA = headache;
TEAE = treatment emergent adverse event No ADA positive samples were detected in samples tested from subjects receiving multiple doses of 100 mg or 200 mg TRAB-1.

Figure 5:
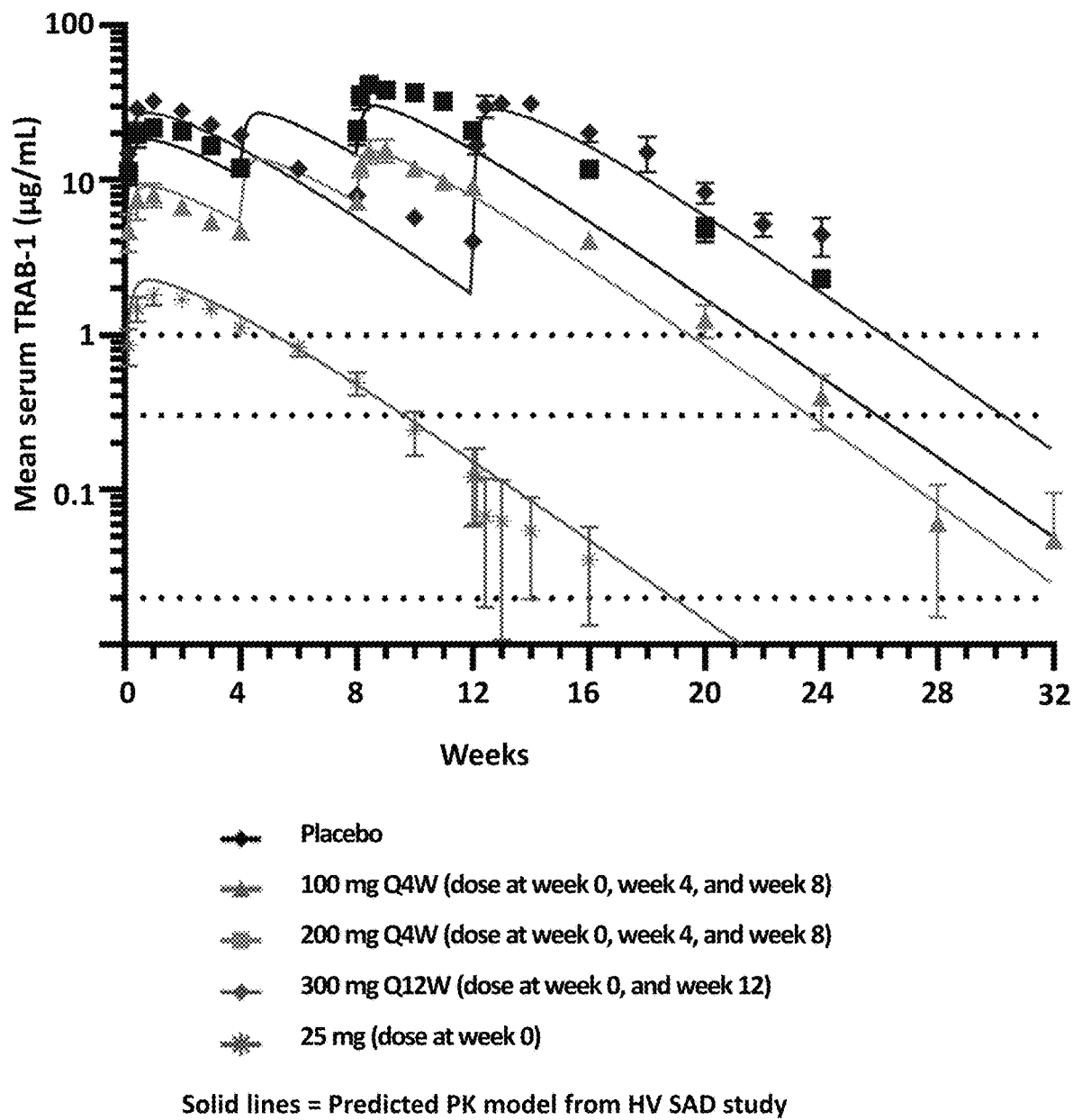
FIG. 5: Data depicting mean serum concentrations of TRAB-1 for up to 32 weeks in asthmatic subjects that had been administered or TRAB-1 by subcutaneous (SC) injection. Of the subjects administered TRAB-1: Group 1 was administered 100 mg TRAB-1 every 4 weeks for a total of 3 administrations and measurements were monitored for up to 32 week; Group 2 was administered 200 mg TRAB-1 for a total of 2 administrations and measurements were monitored for up to 24 weeks; and Group 3 was administered 300 mg TRAB-1 for a total of 1 administration and measurements were monitored for up to 24 weeks. The serum concentrations observed were compared to the concentrations predicted from the model shown in FIG. 2B, which are indicated by the solid lines.

Mean serum concentrations of TRAB-1 were monitored and plotted as a function of time (FIG. 5). Mean serum concentrations were obtained for Group 1 (100 mg TRAB-1) in subjects administered 3 administrations of TRAB-1. For Group 2 and Group 3, mean serum concentrations are shown for the subjects after a single administration of TRAB-1. The observed serum concentrations observed (FIG. 5) matched the predicted serum concentrations from the model as shown in FIG. 2B.

Figure 6:
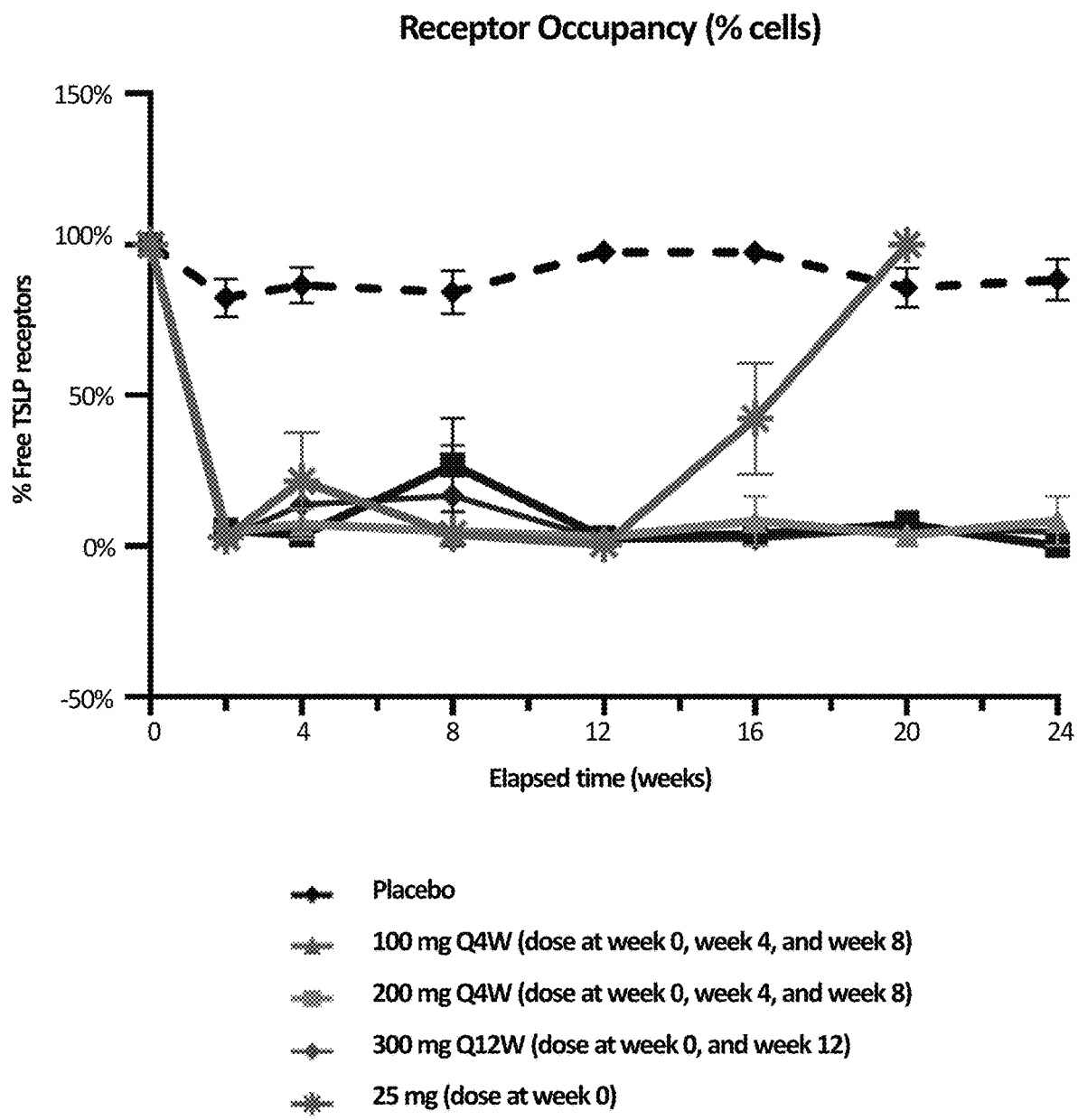
FIG. 6: Data depicting TSLP-R occupancy over time in asthmatic subjects that had been administered a placebo or TRAB-1 by subcutaneous (SC) injection. The placebo group was administered the placebo once and the percentage of free TSLP receptors was monitored over 24 weeks. For the subjects administered TRAB-1: Group 1 was administered 100 mg TRAB-1 every 4 weeks for a total of 2 or 3 administrations and receptor occupancy was monitored for up to 24 weeks; a Group 2 was administered 200 mg TRAB-1 for a total of 1, 2, or 3 administrations and receptor occupancy was monitored for up to 24 weeks; Group 3 was administered 300 mg TRAB-1 for a total of 1 or 2 administrations and receptor occupancy was monitored for up to 24 weeks; and Group 4 was administered a single dose of 25 mg TRAB-1 and receptor occupancy was monitored for up to 20 weeks.

TSLP-R occupancy was measured as a function of time (FIG. 6) in asthmatic subjects administered placebo, or TRAB-1. For the subjects administered TRAB-1: Group 1 was administered 100 mg TRAB-1 every 4 weeks for a total of 2 or 3 administrations and receptor occupancy was monitored over 24 weeks; a Group 2 was administered 200 mg TRAB-1 for a total of 1, 2, or 3 administrations and receptor occupancy was monitored over 24 weeks; Group 3 was administered 300 mg TRAB-1 and receptor occupancy was monitored over 24 weeks. Group 4 was administered 25 mg TRAB-1 and receptor occupancy was monitored over 24 weeks. Initial receptor occupancy was approximately 100% available receptors for all subjects prior to any injections. Receptor occupancy was observed for up to 24 weeks for Group 1, Group 2, and Group 3, and up to 20 weeks for Group 4 and the placebo group. After one dose, receptor occupancy decreased to approximately 0% free at 2 weeks for Group 1, Group 2, and Group 3, but remained elevated for the placebo group. Receptor occupancy remained approximately 0% free up to 24 weeks for Group 1, Group 2, and Group 3, and up to 12 weeks for Group 4. For the placebo group, receptor occupancy remained elevated (approximately 100% free receptors) through 24 weeks.

Figure 7A:
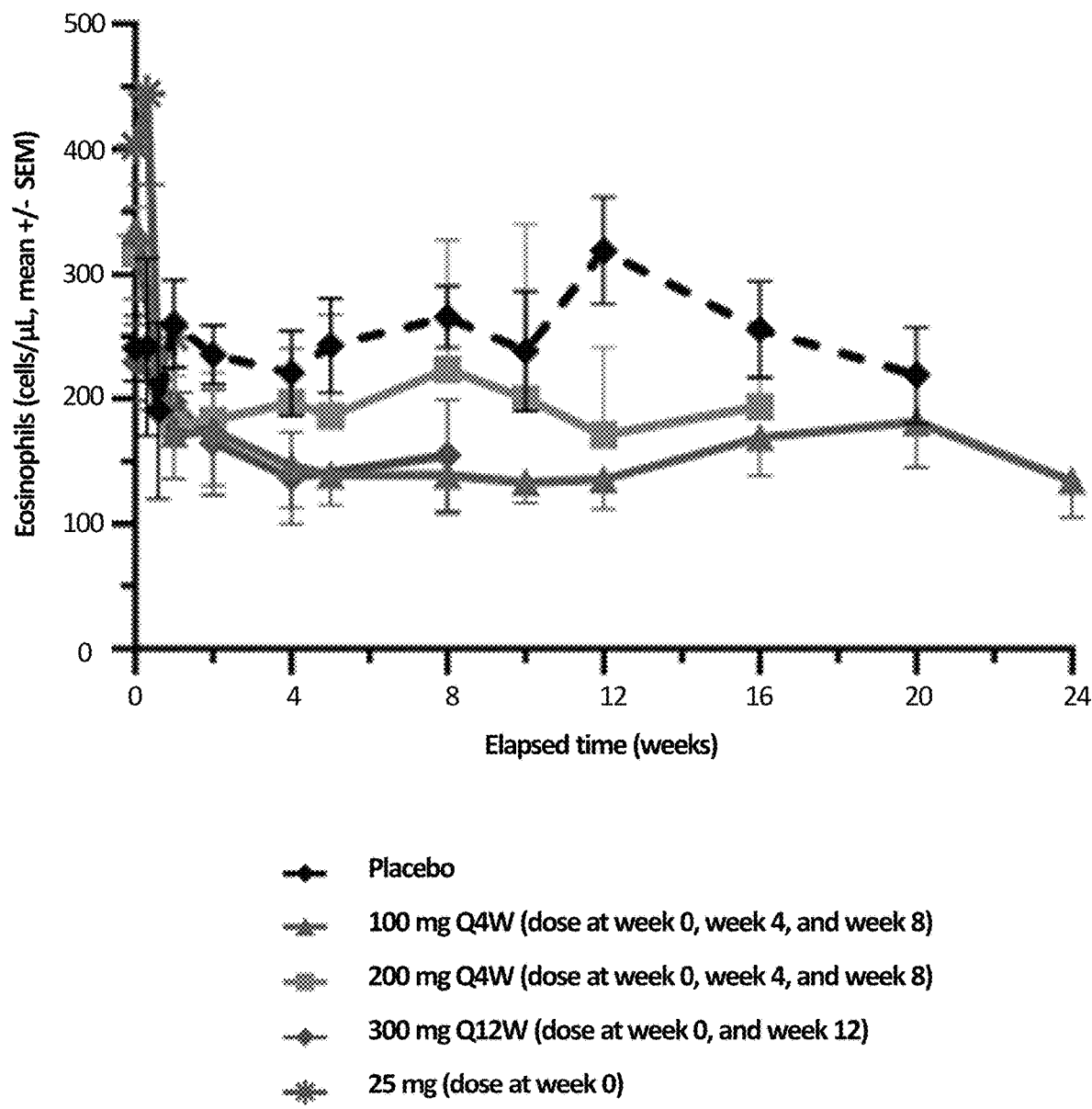
FIGS. 7A-7C: Data depicting blood eosinophil concentrations over time in asthmatic subjects that had been administered a placebo or TRAB-1 by subcutaneous (SC) injection. For the subjects administered TRAB-1: Group 1 was administered 100 mg TRAB-1 every 4 weeks for a total of 2 or 3 administrations and eosinophil concentrations was monitored for up to 24 weeks; Group 2 was administered 200 mg TRAB-1 for a total of 1, 2, or 3 administrations and eosinophil concentrations was monitored for up to 24 weeks; Group 3 was administered 300 mg TRAB-1 for a total of 1 or 2 administrations and eosinophil concentrations was monitored for up to 24 weeks; and Group 4 was administered a single dose of 25 mg TRAB-1 and receptor occupancy was monitored for up to 20 weeks.
Figure 7B:
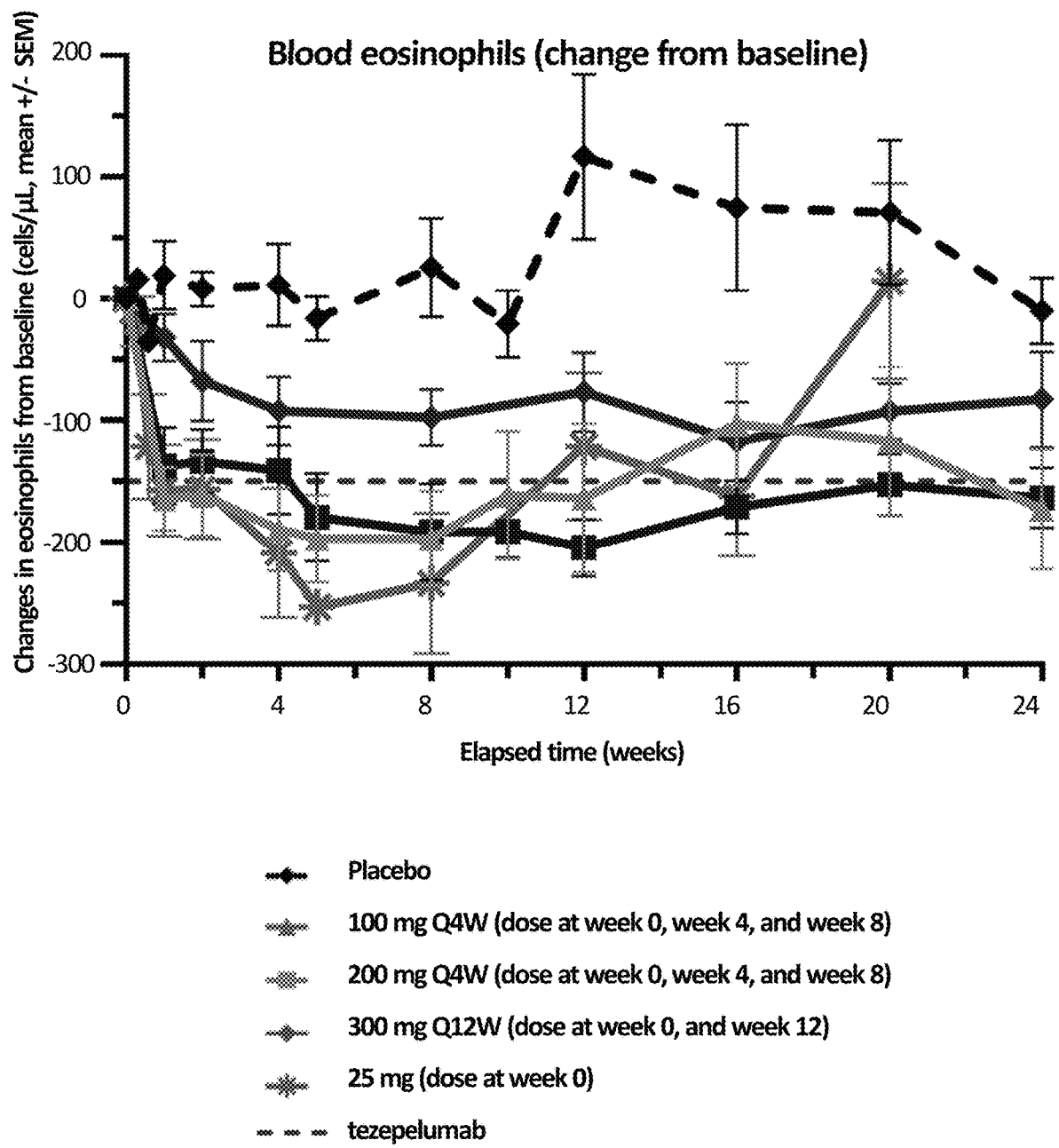
Figure 7C:
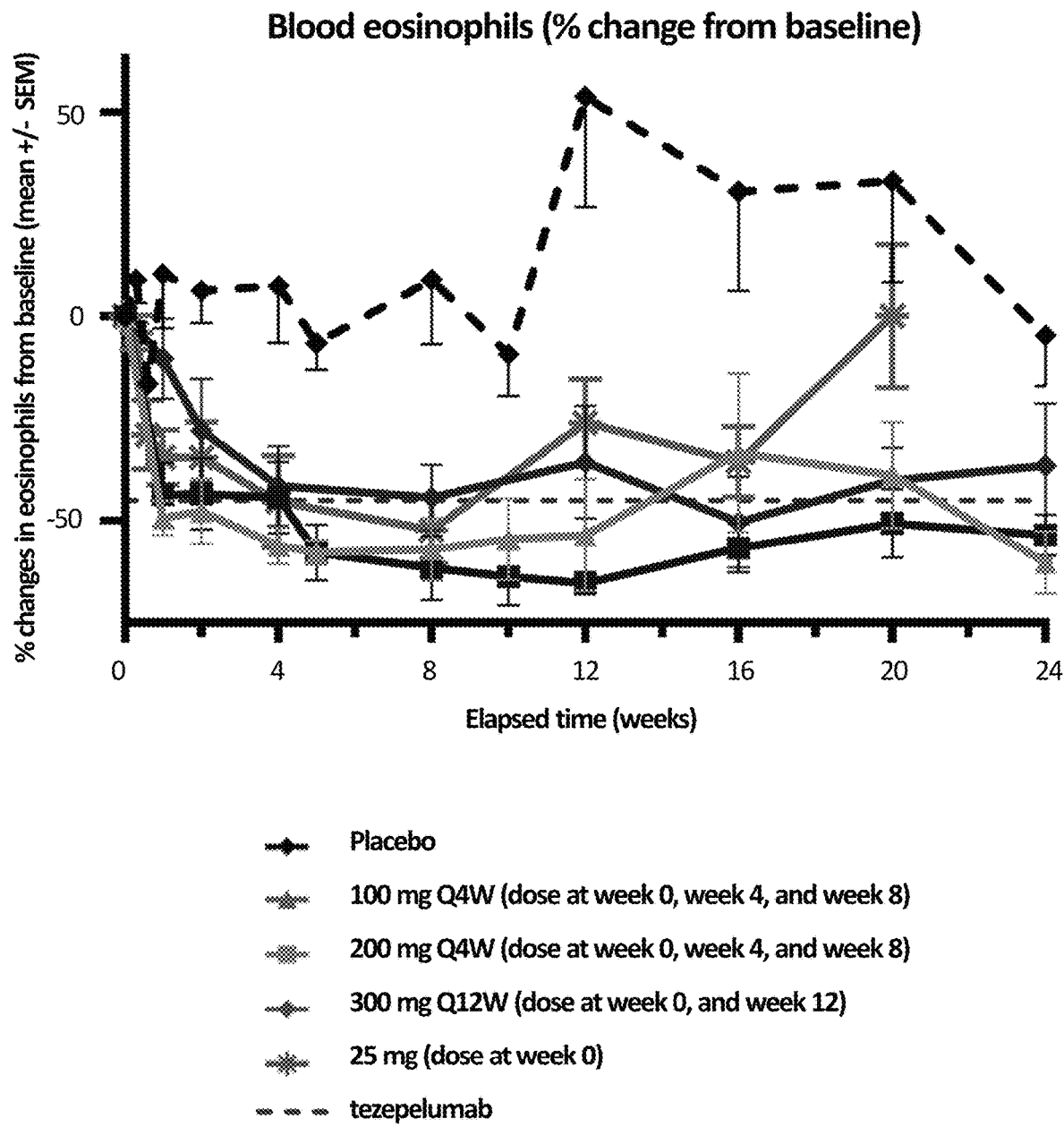

Eosinophil concentrations were monitored as a function of time in asthmatic subjects treated with TRAB-1 and compared to the placebo group (FIG. 7A). Group 1 was administered 100 mg TRAB-1 every 4 weeks for a total of 2 or 3 administrations and eosinophil concentration was monitored over 24 weeks; Group 2 was administered 200 mg TRAB-1 for a total of 1, 2, or 3 administrations and eosinophil concentration was monitored over 24 weeks; Group 3 was administered 300 mg TRAB-1 and eosinophil concentration was monitored over 24 weeks; and Group 4 was administered 25 mg TRAB-1 and eosinophil concentration was monitored over 20 weeks. Eosinophil concentrations were decreased at 1 week after 1 administration of Group 1, Group 2, Group 3, and Group 4. This data demonstrates that reduction of eosinophils was evident after in in asthmatic subjects administered 25 mg, 100 mg, 200 mg, or 300 mg of TRAB-1 after a single administration. At 12 weeks, a decrease in Eosinophils of approximately 164 cells/µL, 204 cells/µL, and 77 cells/µL were observed for Group 1, Group 2, and Group 3, respectively. These decreases were equivalent to an approximately a 54% decrease, 65% decrease, and 36% decrease compared to baseline (FIG. 7C), respectively. In comparison, approximately 150 cells/µL in eosinophils were observed in subjected administered 210 mg Tezepelumab (Teze Phase 3 study) after 12 weeks (Ly et al., J Clin Pharm 2021. Jul.; 61(7):901-912). This data demonstrates that reduction of eosinophils was evident in asthmatic subjects that received 100 mg or 200 mg of TRAB-1 every 4 weeks for a total of 1, 2, or 3 dosages.

Figure 8A:
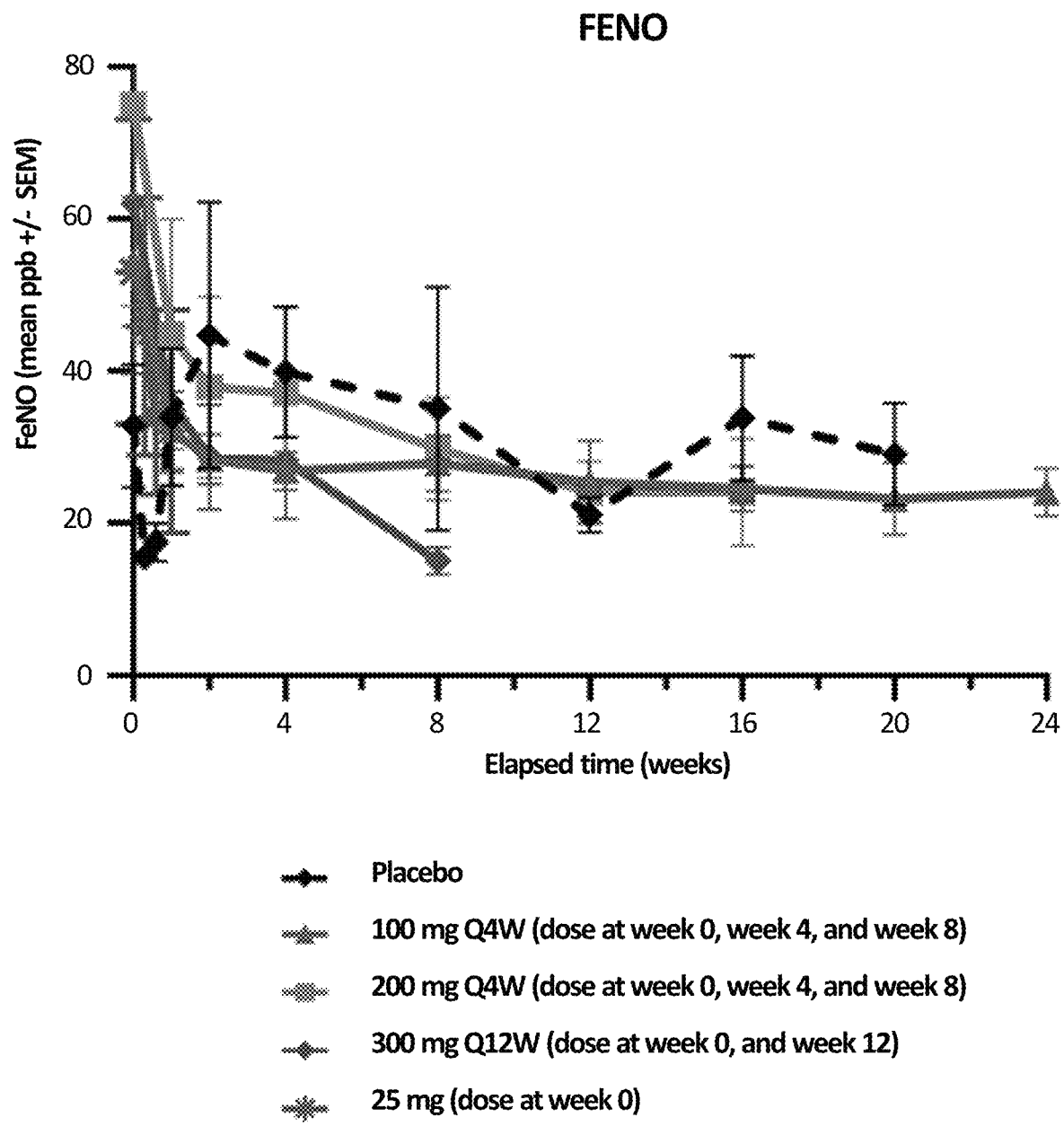
FIGS. 8A-8D: Data depicting fractional exhaled Nitric Oxide (FeNO) over time in asthmatic subjects that had been administered a placebo or TRAB-1 by subcutaneous (SC) injection. Of the subjects administered TRAB-1: Group 1 was administered 100 mg TRAB-1 every 4 weeks for a total of 2 or 3 administrations and FeNO was monitored for up to 32 weeks; a Group 2 was administered 200 mg TRAB-1 for a total of 1, 2, or 3 administrations and FeNO was monitored for up to 24 weeks; Group 3 was administered 300 mg TRAB-1 for a total of 1 or 2 administrations and FeNO was monitored for up to 24 weeks; and Group 4 was administered a single dose of 25 mg TRAB-1 and FeNO was monitored for up to 24 weeks.
Figure 8B:
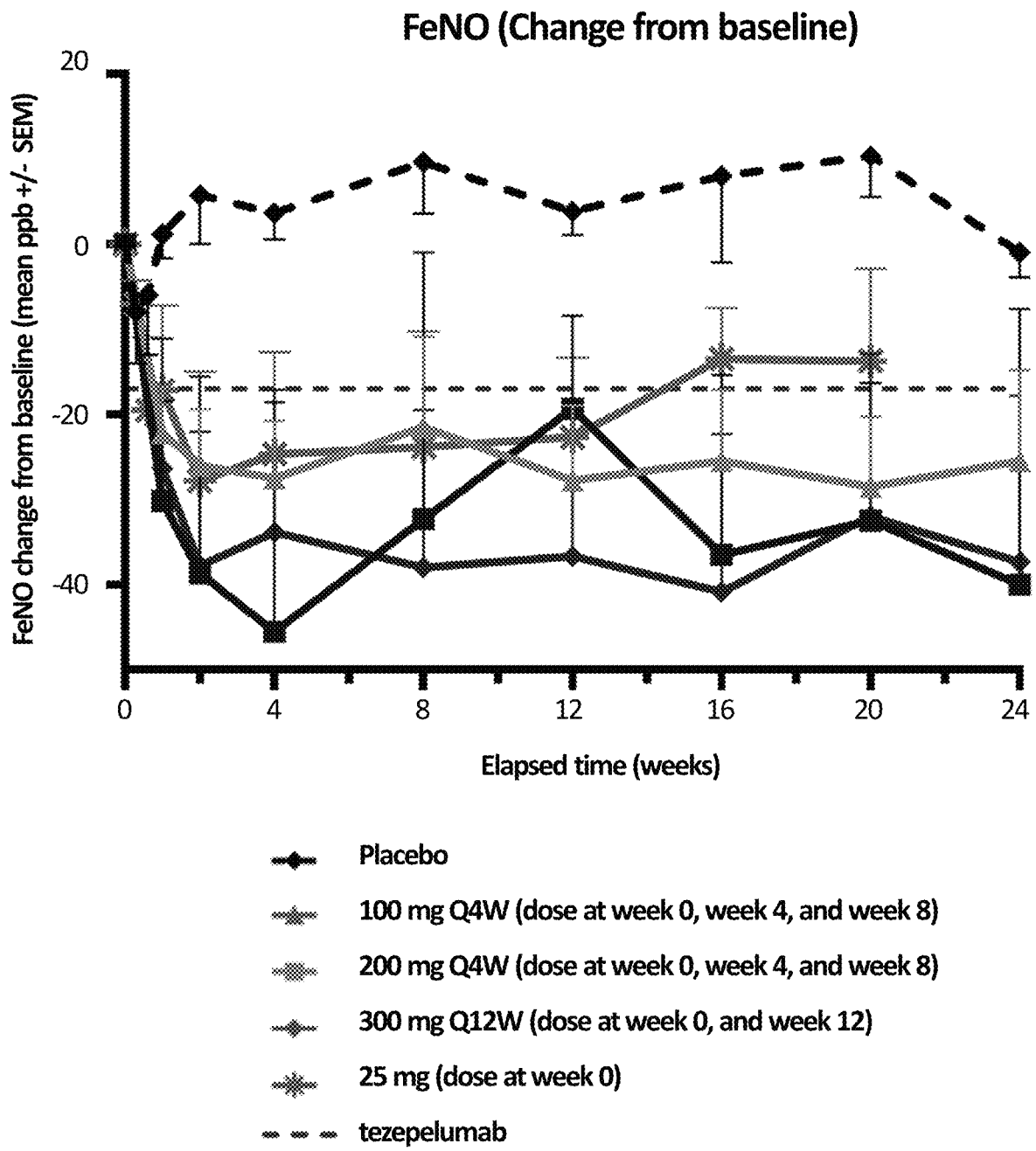
Figure 8C:
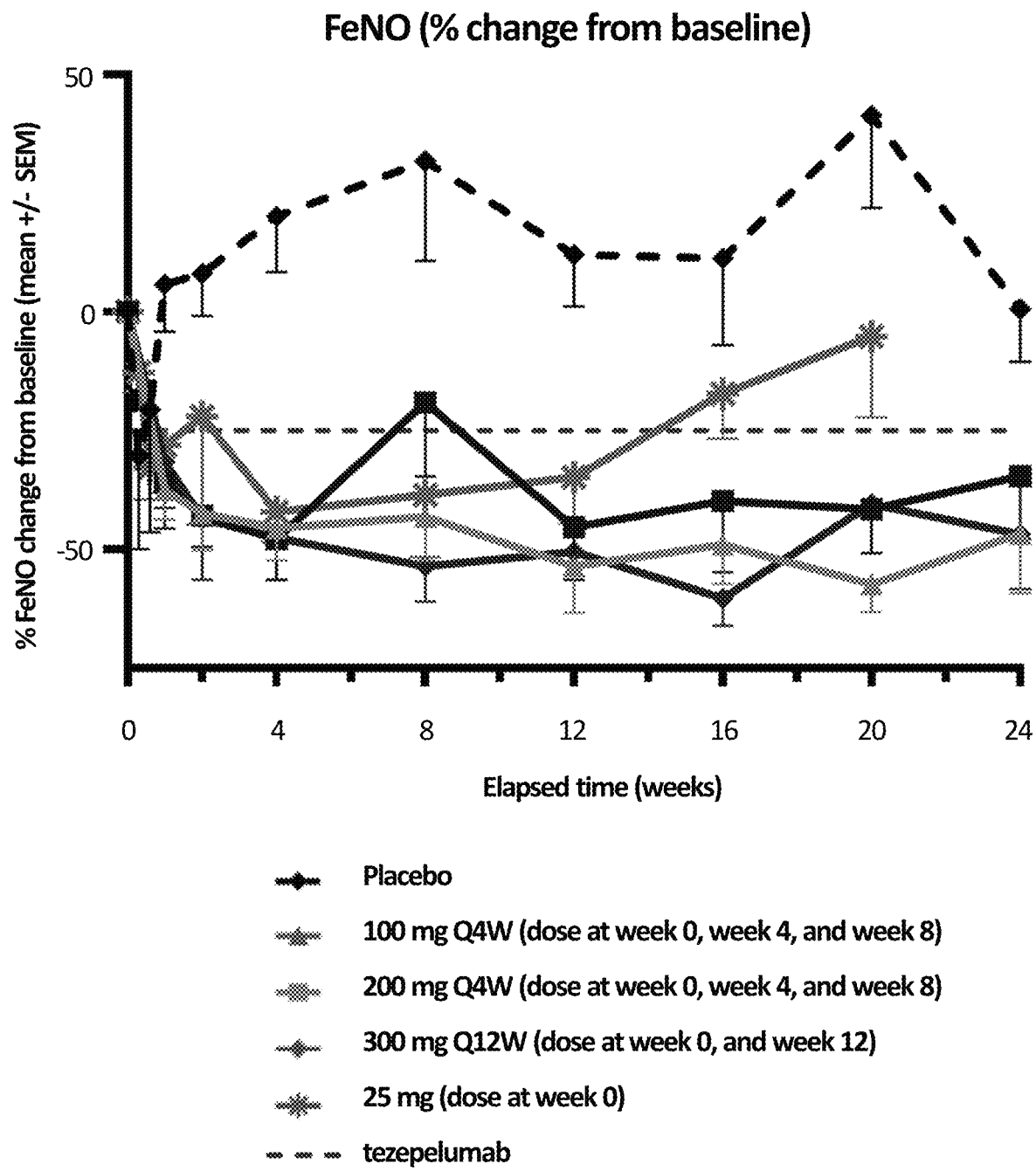
Figure 8D:
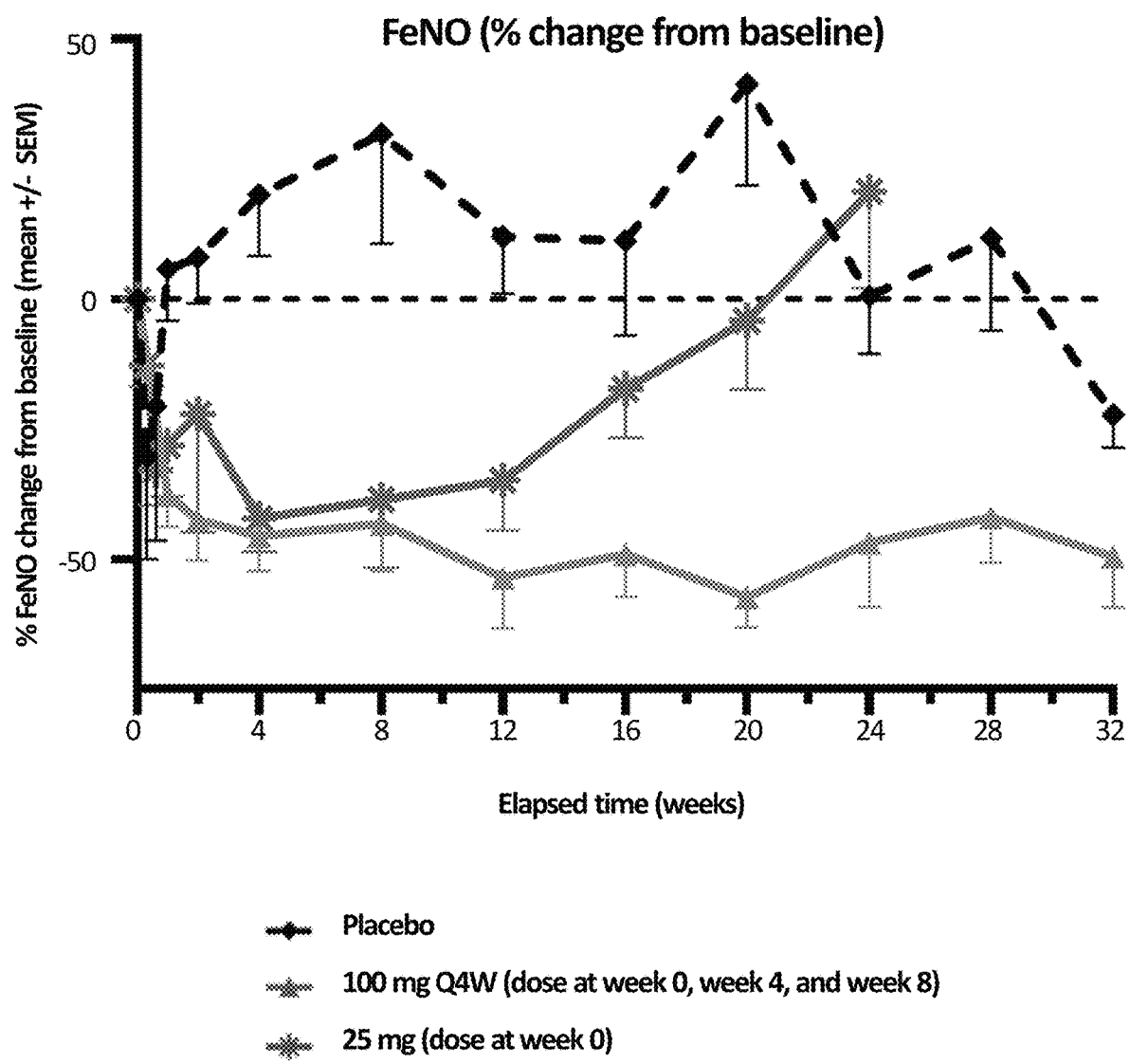

Fractional exhaled Nitric Oxide (FeNO) was monitored as a function of time (FIG. 8A) in asthmatic subjects administered placebo, or TRAB-1. Group 1 was administered 100 mg TRAB-1 every 4 weeks for a total of 3 administrations and FeNO was monitored over 32 weeks; a Group 2 was administered 200 mg TRAB-1 for a total of 1, 2, or 3 administrations and FeNO was monitored over 24 weeks; Group 3 was administered 300 mg TRAB-1 and FeNo was monitored over 2 4 weeks; and Group 4 was administered 25 mg TRAB-1 and FeNO was monitored over 24 weeks. FeNO were decreased at 4 weeks after 1 administration of Group 1, Group 2, Group 3, and Group 4. At 12 weeks, a decrease in FeNO of approximately 28 ppb, 19 ppb, and 37 ppb were observed in subjects in Group 1, Group 2, and Group 3, respectively (FIB. 8B). These decreases in FeNO were equivalent to an approximately a 54% decrease, 45% decrease, and 51% decrease compared to baseline (FIG. 8C), respectively. This data demonstrates that reduction of FeNO was evident after in the TRAB-1 in asthmatic subjects that received 100 mg of TRAB-1 every 4 weeks for a total of 3 dosages, up to 32 weeks after the administration of the first dosage and up to 24 weeks after the administration of the third dosage.

All available data on the effect of TRAB-1 on eosinophil levels and FeNO from the MAD study was used to generate a PK/PD model between TRAB-1 dose, TRAB-1 exposure (PK), and PD (FeNO or EOS) profiles in time. The maximum magnitude for response ($E_{max}$) was calculated to be a 42.6% reduction from baseline in eosinophil levels, and the concentration of TRAB-1 needed for a 50% response (EC50) on eosinophil levels was calculated to be 0.000514 µg/mL TRAB-1.

The $E_{max}$ for FeNO response was calculated to be a 43.4% reduction from baseline in FeNO, and the concentration of TRAB-1 needed for a 50% response (EC50) in FeNO was calculated to be 0.0514 µg/mL TRAB-1. In comparison, an approximately 27.8% decrease in FeNO with an EC50 of 2.5 µg/mL was observed in subjected administered 210 mg Tezepelumab (Teze Phase 3 study) after 12 weeks (Ly et al., J Clin Pharm 2021. Jul.; 61(7):901-912).

No subjects with clear loss of pharmacokinetics, FeNO, or eosinophil effect were observed.

Example 8: A Phase 1 First-In-Human Single Ascending-Dose Study with a Novel Antibody to the Human Thymic Stromal Lymphopoietin Receptor Thymic stromal lymphopoietin (TSLP) is an epithelial cell-derived cytokine that acts on multiple immune cell lineages, including dendritic cells, T cells, mast cells, and monocytes. Targeting upstream alarmins like TSLP has proven effective in the treatment of allergic/inflammatory diseases. TRAB-1 (previously known as ASP7266) is a novel recombinant fully human immunoglobulin G1 monoclonal antibody that targets the TSLP receptor. A randomized, double-blind, placebo-controlled single ascending-dose study was conducted to evaluate the safety, tolerability, pharmacokinetics (PK), and pharmacodynamics (PD) of TRAB-1 in healthy adult volunteers. Six cohorts received either placebo or TRAB-1 (0.03-10 mg/kg) by intravenous (IV) administration; one cohort received either placebo or TRAB-1 (1 mg/kg) by subcutaneous (SC) administration. All cohorts included 8 subjects (6 active, 2 placebo) each.

Fifty-six subjects (32 females, 24 males) aged 21 to 52 (average 32) were randomized. There was no dose-related increase in the incidence of treatment emergent adverse events (TEAEs). The most frequently TEAEs reported were headache and dysmenorrhea. One subject in the 1 mg/kg TRAB-1 IV cohort had a serious adverse event of nephrolithiasis which was deemed not related to study drug by the Investigator. No clinically relevant trends were observed in any of the clinical laboratory analyses or other safety assessments. None of the subjects who received TRAB-1 SC developed injection site AEs. A dose proportional increase in AUClast, AUCinf and Cmax were observed over the dose range of 0.03 to 10 mg/kg IV. The absolute bioavailability after a SC dose of 1 mg/kg TRAB-1 was 70%. Mean terminal t ½ after a single dose of 1 to 10 mg/kg IV or 1 mg/kg SC was approximately 20 days. Serum concentrations remained above the projected therapeutic level (>1 µg/mL, estimated from pre-clinical studies) for at least 90 days at doses >1 mg/kg. PK modelling suggests that sufficient exposure to maintain the desired PD effect could be achieved with dosing intervals of at least 8 weeks. Anti-drug antibodies were detected in 9/36 subjects given a single IV dose and in 3/6 subjects given a single SC dose. Titers ranged from 1 to 128 and did not appear to be either dose-related or significantly impact the PK profiles. TRAB-1 was well-tolerated, safe, and displayed linear and dose proportional PK. A low titer ADA response was detected in some subjects; however, there was no significant impact on either safety or PK. TRAB-1 has been advanced to Phase 1b development.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

Example 9: Pharmacokinetic/Pharmacodynamic Modeling of TRAB-1 on FeNO Based on MAD Data The relationship between the dosage of TRAB-1, the serum concentrations of TRAB-1 observed in patients immediately before the next dose was administered ($C_{trough}$), and the effect on FeNO was further evaluated over time in a PK/PD model. The threshold concentration of TRAB-1 needed for a 50% response ($EC_{50}$), 80% response ($EC_{80}$), and 90% response ($EC_{90}$) on FeNO were calculated to be 0.1386 µg/ml, 0.062 µg/ml, and 0.015 µg/ml based on all available data in the MAD study. The population of patients demonstrating a response above the threshold concentration of TRAB-1 needed for a 50% response ($EC_{50}$), 80% response ($EC_{80}$), and 90% response ($EC_{90}$) on FeNO was compared for the following dosing regimens: 20 mg, 40 mg, 75 mg, 100 mg, 150 mg, 200 mg, and 300 mg TRAB 1 given every 12 weeks (Q12W); 400 mg TRAB-1 given every 24 weeks (Q24W); and 100 mg TRAB-1 given every 4 weeks (Q4W).

Figure 9A:
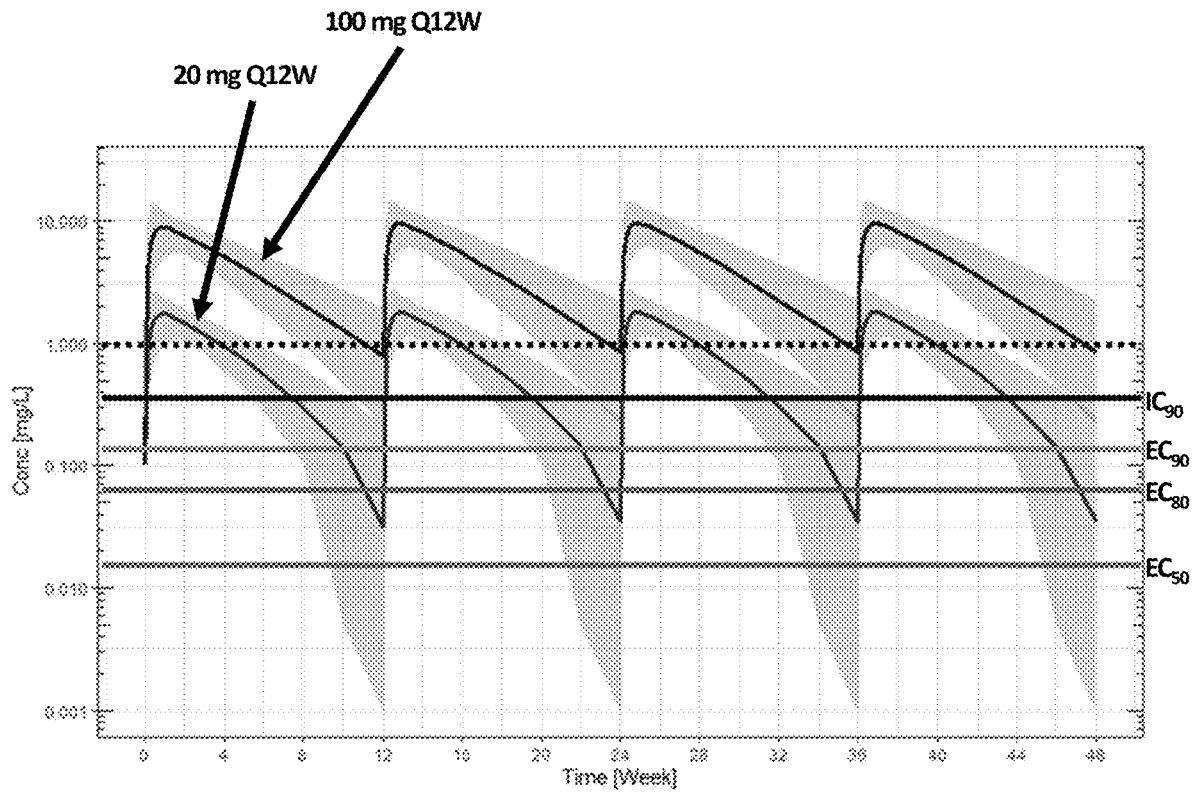
FIGS. 9A-9B: Graph depicting pharmacokinetic/pharmacodynamic model of TRAB-1 serum concentration in patients treated with varying regiments of TRAB-1

The 20 mg TRAB-1 Q12W dosing regimen was demonstrated to provide a trough exposure of greater than the $EC_{50}$ for FeNO in more than 60% of the population; of greater than the $EC_{80}$ for FeNO in 38.6% of the population; and of greater than the $EC_{90}$ for FeNO in 17.7% of the population (FIG. 9A). This data demonstrates that a dosing regimen of 20 mg TRAB-1 given every 12 weeks is a viable low dose regimen.

The 75 mg TRAB-1 Q12W and 100 mg TRAB-1 Q12W dosing regimens were demonstrated to provide trough exposures of greater than the EC90 for FeNO in more 94.6% and 97.9% of the population, respectively. In comparison, less than 5% of patients treated with 70 mg tezepelumab every 4 weeks achieved a trough exposure greater than the $EC_{90}$ for FeNO (Ly et al., J Clin Pharm 2021. Jul.; 61(7):901-912). Dosing regimens of 75 mg or more of TRAB-1 given every 12 weeks, and 100 mg of TRAB-1 given every 4 weeks, were demonstrated to produce near the maximum effect on FeNO in the majority of patients (Table 41A and Table 41B).

TABLE 41A

Proportion of patients above $EC_{50}$, $EC_{80}$, and $EC_{90}$ thresholds for FeNO response at varying dosage regimens for TRAB-1 antibody

| Threshold for FeNO response | Proportion above threshold at trough for given regimen | | | | |
|---|---|---|---|---|---|
| | 20 mg Q12W | 400 mg Q24W | 40 mg Q12W | 75 mg Q12W | 100 mg Q12W |
| $EC_{50}$ (0.0154 µg/mL) | 60.4% | 68.2% | 94.9% | 99.6% | 99.8% |
| $EC_{80}$ (0.0616 µg/mL) | 38.6% | 59.2% | 86.8% | 98.1% | 99.8% |

TABLE 41A-continued

Proportion of patients above EC$_{50}$, EC$_{80}$, and EC$_{90}$ thresholds for FeNO response at varying dosage regimens for TRAB-1 antibody

| Threshold for FeNO response | Proportion above threshold at trough for given regimen | | | | |
|---|---|---|---|---|---|
| | 20 mg Q12W | 400 mg Q24W | 40 mg Q12W | 75 mg Q12W | 100 mg Q12W |
| EC$_{90}$ (0.1386 µg/mL) | 17.7% | 48.0% | 73% | 94.6% | 97.9% |

TABLE 41B

Proportion of patients above EC$_{50}$, EC$_{80}$, and EC$_{90}$ thresholds for FeNO response at varying dosage regimens for TRAB-1 antibody

| Threshold for FeNO response | Proportion above threshold at trough for given regimen | | | |
|---|---|---|---|---|
| | 150 mg Q12W | 200 mg Q12W | 300 mg Q12W | 100 mg Q4W |
| EC50 (0.0154 µg/mL) | 99.8% | 100% | 100% | 100% |
| EC80 (0.0616 µg/mL) | 99.8% | 100% | 100% | 100% |
| EC90 (0.1386 µg/mL) | 99.6% | 99.7% | 99.8% | 100% |

In comparison, based on published data a dosing regimen of 280 mg tezepelumab given every 4 weeks (Q4W) is needed to produce near the maximum effect on FeNO in the majority of patients (Ly et al., J Clin Pharm 2021. Jul.; 61(7):901-912).

Figure 9B:
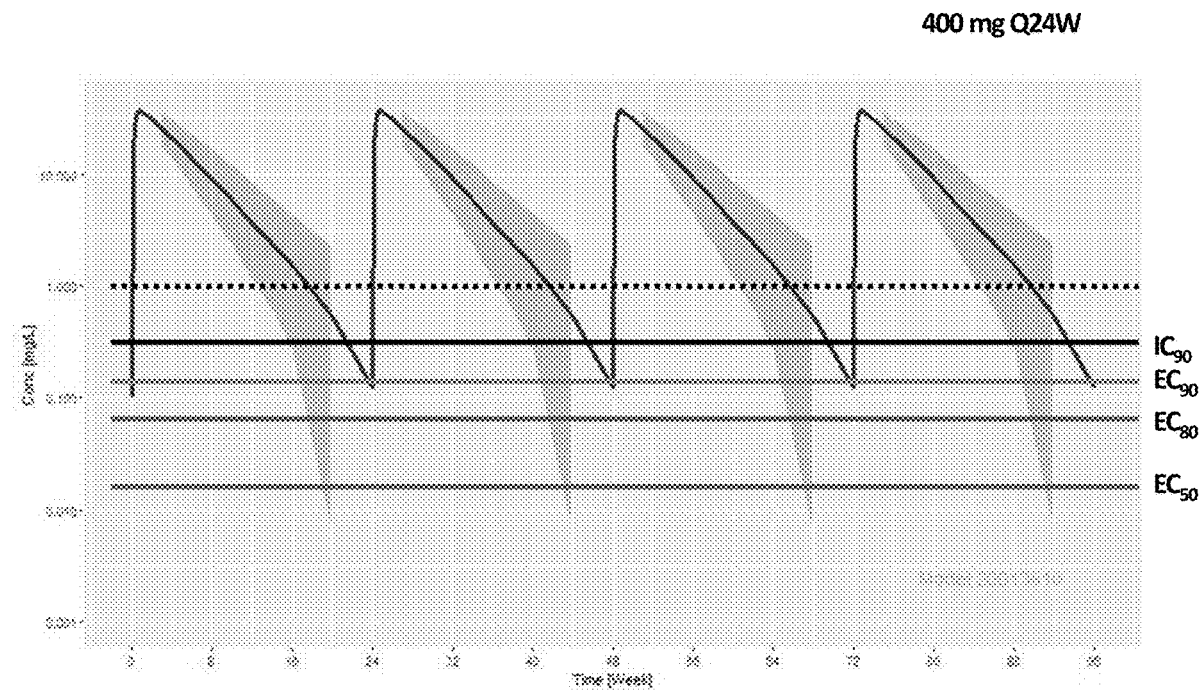

The 400 mg TRAB-1 Q24W dosing regimen was demonstrated to provide a trough exposure of greater than the EC$_{80}$ for FeNO in 59.2% of the population; and of greater than the EC$_{90}$ for FeNO in more 48% of the population (FIG. 9B).

This embodiments and data provided herein demonstrate that a dosing regimen of 400 mg TRAB-1 administered every 24 weeks to a subject can be used to achieve a consistent and durable therapeutic effect mediated by TRAB-1, such as for treating the indications and using the methods provided for herein. As provided for herein, although the composition may be administered every 24 weeks, other administration periods may be used with the same or different doses as provided for herein. For example, the PK/PD modeling based on the clinical data also demonstrates that dosing regimens of 100 mg of TRAB-1 given every 12 weeks or 200 of TRAB-1 given every 12 weeks can be therapeutically effective. In summary, it was demonstrated that TRAB-1 provided a greater effect on FeNO than what has been published regarding the effects of tezepelumab. This effect was achieved with lower dosages of TRAB-1 and less frequent dosing.

The present embodiments are not to be limited in scope by the specific embodiments described herein. Indeed, various modifications in addition to those described herein will become apparent to those skilled in the art from the foregoing description. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

SEQUENCE LISTING

```
Sequence total quantity: 12
SEQ ID NO: 1           moltype = AA   length = 448
FEATURE                Location/Qualifiers
source                 1..448
                       mol_type = protein
                       organism = synthetic construct
SEQUENCE: 1
EVQLLESGGG LVQPGGSLRL SCAASGFTFR SSAMHWVRQA PGKGLKWVSS VSGSGAGTYY   60
ADSVKGRFTI SRDNPKNTLY LQMNSLRAED TAVYYCVKEG GSRGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 2           moltype = DNA  length = 1347
FEATURE                Location/Qualifiers
source                 1..1347
                       mol_type = other DNA
                       organism = synthetic construct
SEQUENCE: 2
gaggtgcagc tgttggagtc tgggggaggc ttggtacagc cggggggttc cctgagactc   60
tcctgtgcag cctctggatt cacctttcgc agctctgcca tgcattgggt ccgccaggct  120
ccagggaagg gactgaaatg ggtctcaagt gttagtggca gtggtgctgg aacatactac  180
gcagactccg tgaagggccg gttcaccatc tccagagaca atcccaagaa tacactgtat  240
ctgcaaatga acagtctgag agccgaggac acggccgtat attattgtgt gaaagaaggg  300
ggcagccggg gttttgacta ctgggggcag ggaaccctgg tcaccgtctc ctcagcctcc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctta gtagcgtggt gaccgtgccc tccagcagct gggcaccca gacctacatc  600
tgcaacgtga atcacaagcc cagcaacacc aaggtggaca agaaagttga gcccaaatct  660
```

```
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc 1020
aaagggcagc cccgagaacc acaggtgtac accctgcccc catcccggga tgagctgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctacagcaag ctcaccgtgg acaagagcag gtggcagcag 1260
gggaacgtct tctcatgctc cgtgatgcat gaggctctgc acaaccacta cacgcagaag 1320
agcctctccc tgtctccggg taaatga                                    1347

SEQ ID NO: 3          moltype = AA  length = 214
FEATURE               Location/Qualifiers
source                1..214
                      mol_type = protein
                      organism = synthetic construct
SEQUENCE: 3
DIQMTQSPSS LSASVGDRVT ITCRASQDIS NYLAWFQQKP GKAPKSLIYT ASSLQSGVPS   60
KFSGSGSGTD FTLTISSLQP EDFATYYCQQ YNLYPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 4          moltype = DNA  length = 645
FEATURE               Location/Qualifiers
source                1..645
                      mol_type = other DNA
                      organism = synthetic construct
SEQUENCE: 4
gacatccaga tgacccagtc tccatcctca ctgtctgcat ctgtaggaga cagagtcacc   60
atcacttgtc gggcgagtca ggacattagc aattatttag cctggtttca gcagaaacca  120
gggaaagccc ctaagtccct gatctatact gcatccagtt tgcaaagtgg ggtcccatca  180
aagttcagcg gcagtggatc tgggacagat ttcactctca ccatcagcag cctgcagcct  240
gaagattttg caacttatta ctgccaacag tataatcttt atcctccgac gttcggccaa  300
gggaccaagg tggaaatcaa acggactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 5          moltype = AA  length = 118
FEATURE               Location/Qualifiers
source                1..118
                      mol_type = protein
                      organism = synthetic construct
SEQUENCE: 5
EVQLLESGGG LVQPGGSLRL SCAASGFTFR SSAMHWVRQA PGKGLKWVSS VSGSGAGTYY   60
ADSVKGRFTI SRDNPKNTLY LQMNSLRAED TAVYYCVKEG GSRGFDYWGQ GTLVTVSS   118

SEQ ID NO: 6          moltype = AA  length = 107
FEATURE               Location/Qualifiers
source                1..107
                      mol_type = protein
                      organism = synthetic construct
SEQUENCE: 6
DIQMTQSPSS LSASVGDRVT ITCRASQDIS NYLAWFQQKP GKAPKSLIYT ASSLQSGVPS   60
KFSGSGSGTD FTLTISSLQP EDFATYYCQQ YNLYPPTFGQ GTKVEIK               107

SEQ ID NO: 7          moltype = AA  length = 5
FEATURE               Location/Qualifiers
source                1..5
                      mol_type = protein
                      organism = synthetic construct
SEQUENCE: 7
SSAMH                                                               5

SEQ ID NO: 8          moltype = AA  length = 17
FEATURE               Location/Qualifiers
source                1..17
                      mol_type = protein
                      organism = synthetic construct
SEQUENCE: 8
SVSGSGAGTY YADSVKG                                                 17

SEQ ID NO: 9          moltype = AA  length = 9
FEATURE               Location/Qualifiers
source                1..9
```

```
                        mol_type = protein
                        organism = synthetic construct
SEQUENCE: 9
EGGSRGFDY                                                               9

SEQ ID NO: 10           moltype = AA  length = 11
FEATURE                 Location/Qualifiers
source                  1..11
                        mol_type = protein
                        organism = synthetic construct
SEQUENCE: 10
RASQDISNYL A                                                            11

SEQ ID NO: 11           moltype = AA  length = 7
FEATURE                 Location/Qualifiers
source                  1..7
                        mol_type = protein
                        organism = synthetic construct
SEQUENCE: 11
TASSLQS                                                                 7

SEQ ID NO: 12           moltype = AA  length = 9
FEATURE                 Location/Qualifiers
source                  1..9
                        mol_type = protein
                        organism = synthetic construct
SEQUENCE: 12
QQYNLYPPT                                                               9
```

What is claimed is:

1. A pharmaceutical composition comprising:
   (i) an anti-TSLP-R antibody, or antigen-binding fragment thereof, at a concentration of about 150 mg/mL to about 300 mg/mL;
   (ii) a pharmaceutically acceptable buffer at a concentration of about 5 mmol/L to about 100 mmol/L;
   (iii) glycine or a pharmaceutically acceptable salt thereof, at a concentration of 150 mmol/L to about 200 mmol/L; and
   (iv) a surfactant at a concentration of about 0.001% to about 1% (w/v);
   wherein the anti-TSLP-R antibody, or antigen-binding fragment thereof, comprises:
   (i) a heavy chain variable region comprising heavy chain CDR1, CDR2, and CDR3 sequences, wherein the heavy chain CDR1 sequence has the amino acid sequence of SEQ ID NO: 7; the heavy chain CDR2 has the amino acid sequence of SEQ ID NO: 8; and the heavy chain CDR3 sequence has the amino acid sequence of SEQ ID NO: 9; and
   (ii) a light chain variable region comprising light chain CDR1, CDR2, and CDR3 sequences, wherein the light chain CDR1 sequence has the amino acid sequence SEQ ID NO: 10; the light chain CDR2 sequence has the amino acid sequence of SEQ ID NO: 11; and the light chain CDR3 sequence has the amino acid sequence of SEQ ID NO: 12.

2. The pharmaceutical composition claim 1, wherein the anti-TSLP-R antibody, or antigen-binding fragment thereof, comprises a variable heavy chain polypeptide having a sequence that is at least 95% identical to the sequence of SEQ ID NO: 5, provided that the heavy chain variable region CDR1, CDR2, and CDR3 sequences comprise the sequences of SEQ ID NO: 7, SEQ ID NO: 8, and SEQ ID NO: 9, respectively.

3. The pharmaceutical composition of claim 1, wherein the anti-TSLP-R antibody, or antigen-binding fragment thereof, comprises a variable light chain polypeptide having a sequence that is at least 95% identical to the sequence of SEQ ID NO: 6, provided that the light chain variable region CDR1, CDR2, and CDR3 sequences comprise the sequences of SEQ ID NO: 10, SEQ ID NO: 11, and SEQ ID NO: 12, respectively.

4. The pharmaceutical composition of claim 1, wherein the anti-TSLP-R antibody, or antigen-binding fragment thereof, comprises:
   (i) a variable heavy chain polypeptide having a sequence that is at least 95% identical to the sequence of SEQ ID NO: 5, provided that the heavy chain variable region CDR1, CDR2, and CDR3 sequences comprise the sequences of SEQ ID NO: 7, SEQ ID NO: 8, and SEQ ID NO: 9, respectively; and
   (ii) a variable light chain polypeptide having a sequence that is at least 95% identical to the sequence of SEQ ID NO: 6, provided that the light chain variable region CDR1, CDR2, and CDR3 sequences comprise the sequences of SEQ ID NO: 10, SEQ ID NO: 11, and SEQ ID NO: 12, respectively.

5. The pharmaceutical composition of claim 1, wherein the anti-TSLP-R antibody, or antigen-binding fragment thereof, comprises a variable heavy chain polypeptide a sequence as set forth in SEQ ID NO: 5.

6. The pharmaceutical composition of claim 1, wherein the anti-TSLP-R antibody, or antigen-binding fragment thereof, comprises a variable light chain polypeptide sequence as set forth in SEQ ID NO: 6.

7. The pharmaceutical composition of claim 1, wherein the anti-TSLP-R antibody, or antigen-binding fragment thereof, comprises:
   (i) a variable heavy chain polypeptide sequence as set forth in SEQ ID NO: 5; and
   (ii) a variable light chain polypeptide sequence as set forth in SEQ ID NO: 6.

8. The pharmaceutical composition of claim 1, wherein the pharmaceutically acceptable buffer is histidine buffer at a concentration of 18 mmol/L to 22 mmol/L; glycine, or a pharmaceutically acceptable salt thereof, at a concentration of 160 mmol/L to 200 mmol/L; the surfactant is polysorbate 80 at a concentration of 0.01% (w/v) to 0.05% (w/v); and the pharmaceutical composition is at a pH of about 5.6 to 5.8.

9. The pharmaceutical composition of claim 1, wherein the pharmaceutically acceptable buffer is histidine buffer at a concentration of 20 mmol/L; glycine, or a pharmaceutically acceptable salt thereof, at a concentration of 180 mmol/L; the surfactant is polysorbate 80 at a concentration of 0.03% (w/v); and the pharmaceutical composition is at a pH of about 5.7.

10. The pharmaceutical composition of claim 1, wherein the pharmaceutical composition does not comprise arginine.

11. The pharmaceutical composition of claim 8, wherein the anti-TSLP-R antibody comprises a variable heavy chain polypeptide having the amino acid sequence as set forth in SEQ ID NO: 5 and a variable light chain polypeptide having the sequence as set forth in SEQ ID NO: 6.

12. The pharmaceutical composition of claim 9, wherein the anti-TSLP-R antibody comprises a variable heavy chain polypeptide having the amino acid sequence as set forth in SEQ ID NO: 5 and a variable light chain polypeptide having the sequence as set forth in SEQ ID NO: 6.

13. The pharmaceutical composition of claim 8, wherein the anti-TSLP-R antibody comprises a heavy chain having the amino acid sequence as set forth in SEQ ID NO: 1 and a light chain having the amino acid sequence as set forth in SEQ ID NO: 3.

14. The pharmaceutical composition of claim 9, wherein the anti-TSLP-R antibody comprises a heavy chain having the amino acid sequence as set forth in SEQ ID NO: 1 and a light chain having the amino acid sequence as set forth in SEQ ID NO: 3.

15. The pharmaceutical composition of claim 1, wherein the pharmaceutical composition comprises less than about 2% of high molecular weight species (HMWS) after 1 month at 5° C.

16. The pharmaceutical composition of claim 1, wherein the pharmaceutical composition comprises less than about 2% of high molecular weight species (HMWS) after 3 months at 5° C.

17. The pharmaceutical composition of claim 1, wherein the pharmaceutical composition comprises less than about 2% of high molecular weight species (HMWS) after 1 month at 25° C.

18. The pharmaceutical composition of claim 1, wherein the pharmaceutical composition comprises less than about 2% of high molecular weight species (HMWS) after 3 months at 25° C.

* * * * *